US008440457B2

(12) United States Patent
Jaatinen et al.

(10) Patent No.: US 8,440,457 B2
(45) Date of Patent: May 14, 2013

(54) METHOD OF PROFILING A CELL POPULATION

(75) Inventors: Taina Jaatinen, Helsinki (FI); Heidi Anderson, Helsinki (FI); Jukka Partanen, Helsinki (FI); Jarmo Laine, Helsinki (FI); Tero Satomaa, Helsinki (FI); Jari Natunen, Vantaa (FI); Maria Blomqvist, Itäsalmi (FI)

(73) Assignees: Suomen Punainen Risti, Veripalvelu, Helsinki (FI); Glykos Finland Oy, Helsinki (FI)

( * ) Notice: Subject to any disclaimer, the term of this patent is extended or adjusted under 35 U.S.C. 154(b) by 798 days.

(21) Appl. No.: 11/921,563

(22) PCT Filed: Jun. 6, 2006

(86) PCT No.: PCT/FI2006/050237
§ 371 (c)(1),
(2), (4) Date: Jun. 11, 2009

(87) PCT Pub. No.: WO2006/131599
PCT Pub. Date: Dec. 14, 2006

(65) Prior Publication Data
US 2010/0055678 A1    Mar. 4, 2010

(30) Foreign Application Priority Data

Jun. 6, 2005   (FI) .................................. 20055291
Aug. 31, 2005  (FI) .................................. 20055464
Mar. 1, 2006   (FI) .................................. 20060206

(51) Int. Cl.
*C12N 5/07* (2010.01)
*C12N 5/071* (2010.01)
*C12N 5/078* (2010.01)
*C12N 5/0789* (2010.01)

(52) U.S. Cl.
USPC ........................... 435/325; 435/366; 435/372

(58) Field of Classification Search ............... None
See application file for complete search history.

(56) References Cited

U.S. PATENT DOCUMENTS
2005/0272152 A1 * 12/2005 Xu et al. .................... 435/372

FOREIGN PATENT DOCUMENTS
WO    WO-2005/026720 A1    3/2005

OTHER PUBLICATIONS

Yasui et al., Stem Cells 21:143-151, 2003.*
Kawano et al., "Prediction of glycan structures form gene expression data based on glycosyltransferase reactions", Bioinformatics vol. 21 No. 21 2005, pp. 3976-3982.
He et al., "Differential Gene Expression Profiling of CD34+ CD133+ Umbilical Cord Blood Hematopoietic Stem Progenitor Cells", Stem Cells and Developement vol. 14 pp. 188-198 (2005).
Pomyje et al., "Expression of genes regulating angiogenesis in human circulating hematopoietic cord blood CD34+/CD133+ cells", European Journal of Haematology 2003, vol. 70, pp. 143-150.
Baal et al., "Expression of transcription factor Oct-4 and other embryonic genes in CD 133 positive cells from human umbilical cord blood", Thrombosis and Haemostasis, Oct. 2004, vol. 92, No. 4, pp. 767-775.
Georgantas et al., "Microarray and Serial Analysis of Gene Expression Analyses Identify Known and Novel Transcripts Overexpressed in Hematopoietic Stem Cells", Cancer Research, Jul. 1, 2004, vol. 64 pp. 4434-4441.
Pappu et al., "Alteration of Cell Surface Sialylation Regulates Antigen-Induced Naive CD8+ T Cell Responses", The Journal of Immunology Jul. 2004, vol. 173(1), pp. 275-284.
Numahata et al., "Sialosyl-Lex Expression Defines Invasive and Metastatic Properties of Bladder Carcinoma", American Cancer Society, Feb. 2002, vol. 94, No. 3, pp. 673-685.
Cheung et al., "Natural variation in human gene expression assessed in lymphoblastoid cells", Nature Genetics, Mar. 2003, vol. 33, pp. 422-425.
Jaatinen et al., "Global Gene Expression Profile of Human Cord Blood-Derived CD133+ Cells", Stem Cells 2006 vol. 24, pp. 631-641.
Toren et al., "CD133-Positive Hematopoietic Stem Cell "Stemness" Genes Contain Many Genes Mutated or Abnormally Expressed in Leukemia", Stem Cells, Sep. 2005, vol. 23, No. 8, pp. 1142-1153.

* cited by examiner

*Primary Examiner* — Daniel C Gamett
(74) *Attorney, Agent, or Firm* — Birch, Stewart, Kolasch & Birch, LLP

(57) ABSTRACT

The present invention relates to a method of profiling a cell population comprising a step of detecting the presence or absence of at least two biological markers in said cell population, wherein at least one of said markers is a cell surface marker, which is a sialylated N-glycan marker with structure NeuNAcα3Gal, and at least one of said markers is a mRNA marker related to glycoproteins and/or glycosynthase proteins. The invention also relates to method for purification of cord blood cell population and to a complete cell population from cord blood purified by said method.

14 Claims, 13 Drawing Sheets

(9 of 13 Drawing Sheet(s) Filed in Color)

A

B

CD34+ / 1. column    CD34+ / 2. column

METHOD OF PROFILING A CELL POPULATION

The present invention relates to a method of profiling a cell population comprising a step of detecting the presence or absence of at least two biological markers in said cell population, wherein at least one of said markers is a cell surface marker, which is a sialylated N-glycan marker with structure NeuNAcα3 Gal, and at least one of said markers is a mRNA marker related to glycoproteins and/or glycosynthase proteins. The invention also relates to method for purification of cord blood cell population and to a complete cell population from cord blood purified by said method.

BACKGROUND OF THE INVENTION

The present invention is based on scientific analysis of mRNA data from several samples of human cord blood and cross analysis between data from different sources. The mRNA data is also analyzed with regard to large amount of scientific literature about expression of proteins or mRNA in other related systems.

Preferred General Cell Types

The present invention is specifically directed to human cells, specifically to human cord blood cells. It is realized that use of mRNA and protein vary between species, so that making reliable parallels about exact roles of molecules in different species may not be possible. The present invention is preferably directed to native cells, meaning non-genetically modified cells. Genetic modifications are known-to alter cells in unpredictable ways, the unexpected changes in context of genetic transfection would require very broad control with regard to numerous biochemical systems existing in cells. The present invention is further directed in a preferred embodiment to fresh cells meaning non-cultivated cells as a cell population to be profiled by the method according to the invention.

Generally Non-Useful Bulk Genomics and Other Database Data or Combinations Thereof with Regard to Present Invention The inventors realize that data may already exist about now listed mRNA markers from various cell populations. However, this data do not necessarily indicate the usefulness of the data for any analytical method, since the amount of the data may be enormous and thus the usefulness of any specific single marker may be impossible to indicate. It is further realized that retrospective combinations of the database data does not allow determining usefulness of a marker, because such combinations would reveal endless number of targets for various uses without specific analysis and data to support the real usefulness of the data. It is further realized that single data point data include experimental variations and risks to such level that the scientist publishing the study may have not considered it useful for specific commercial application as such.

Preferred Markers and Marker Groups with Regard to Preferred Cell Populations

Hematopoietic Stem Cell Related Marker

The preferred hematopoietic stem cells related-markers include CD133, CD34, KIT, TIE1(TIE), ANGPT1, SCA-1, and MEIS1.

Background Related to ANGPT1

Angiopoiesis regulated genes has been studied in cord blood CD34+ cells. Potentially angiopoiesis related mRNAs TIE1, Ang-1 and Ang-2 have been detected enriched in doubly selected cord blood cell populations CD133+/CD34+ when compared to CD133−/CD34− cell line (Pomyje J. et al. Eur J. Haematol. (2003) 79 (3) 143-50). This work does not define the difference of the mRNA expression between CD34+ or CD34−, CD133+ and CD133− cells and other cell populations.

The present invention is specifically directed to ANGPT1 as a marker of CD133 positive complete cell populations, preferably complete blood derived cell populations, more preferably complete cell populations derived from cord blood.

TIE1

Presence of TIE1, among several other markers has been noted in magakaryocytes and CD34+ progenitor cells from cord blood (Blood (1996) 87 (6) 2212-20, Batard P et al.), it is further indicated to be associated with marker Flt3 (Blood (1997) 90, 111-125 Rappold, I et al.).

The present invention shows TIE1 as an important marker of CD133 cell populations and of complete cord blood cell populations, especially from complete CD133 cell populations and in combination with other important markers.

SCA-1

SCA-1 has been reported to be present in murine sinusoidal endothelial cells, it is also noted as a murine hematopoietic stem cell marker (Luna, G et al. Stem Cells Dev. (2004) 13 (5) 528-35; Liu Y J. Et al Blood (2004) 103 (12) 4449-56). In a review of both human and murine hematopoietic stem cells sca-1 and c-kit were indicated as marker of murine cells (Wognum A W. Et al. Arch. Med Res. (2003) 34 (6) 461-75).

The present invention is preferably directed to markers of human cells for which the background is not relevant. SCA-1 is preferred for all cells and methods according to the invention, most preferably for the preferred CD133 type cells.

MEIS1

This transcription factor has been reported to control expression of CD34 and FLT3 in human leukemia cells (AML) immortalized by Hoxa9 (Wang G G et. al. Blood (2005) Mar 8, publ. Ahead print). MEIS1 has been further detected in megakaryotes differentiated from CD34+ cord blood cells.

The present invention is preferably directed to native cells, meaning non-genetically modified cells, the present invention further directed in a preferred embodiment to fresh non-cultured cells.

MEIS1 is a preferred angiogenesis, especially capillary angiogenesis associated marker. MEIS1 is preferred for all cells and methods according to the invention, most preferably for the preferred CD133 type cells.

KIT (CD117)

KIT receptor tyrosine kinase has been reported from CD34+ cord blood cell populations by monoclonal antibodies 80-95% coexpressed with FLT3 (Rappold I et al. Blood (1997) 90 (1) 111-25). In another study CD34+ Kit+ and -cells were used in a transplantation model (Tanabe Y et al. BBRC (2004) 324 (2) 711-8). Kit protein expression was observed in a CD133 positive cord blood cell preparation but it was not indicated as an over expressed marker or otherwise useful marker (Ruziska K et al. (2004) Clin Chim. Acta. 343 (1-2) 85-92). In a review of both human and murine hematopoietic stem cells sca-1 and c-kit were indicated as marker of murine cells, and CD133 for human cells (Wognum A W. Et al. Arch. Med Res. (2003) 34 (6) 461-75).

The present invention shows KIT as an important marker of complete and/or homogenous cell populations, especially from complete, especially human, CD133 cell populations and in combination with other important markers.

Preferred Gene Clustering Methods Derived Markers

Three groups of similarly expressed markers were obtained. The preferred markers includes SPINK2, CD133, CD34, KIT, FLT3, LAPTM4B, EBPL, CRIM1, ANKRD28, DKC1, BAALC and JUP. The preferred subgroups are
group1: SPINK2, CD133, CD34, and KIT, more preferably SPINK2 and KIT, most preferably SPINK2;
group2: FLT3, LAPTM4B, EBPL and CRIM1;
group3: ANKRD28, DKC1, BAALC and JUP.

Ankyrin Repeat Domain 28, ANKRD28

ANKRD28 was cloned from human brain with no indication of function (Nagase T et al. DNA Res. (1997) 4 (2) 141-50). ANKRD28 mRNA appears to be novel marker for the preferred cell populations according to the invention, and for stem cell populations in general.

Baalc (Brain and Acute Leukemia Cytoplasmic)

Baalc has been reported in another context as development related protein from CD34+ bone marrow cells (Baldus, C D et al. (2003) 31 (11) 1051-6) and to be associated with mesoderm and muscle development (Satoskar A A et al Gene Expr Patterns (2005) 5 (4) 463-73).

Baalc (brain and acute leukemia cytoplasmic) mRNA appears to be novel marker for the preferred cell populations according to the invention.

Dyskeratosis Congenita 1 Dyskerin, DKC1

Mutation in DKC1 (dyskerin causes) rare X-linked form of disease dyskeratosis cognita, characterized with mucocutaneous abnormalities and bone marrow failure, premature ageing and a predispoposition for malignancy, patients have very short telomeres (Vulliamy T J et al. Blood molecular dis. (2001) 27 (2) 353-7). The disease resembles aplastic anemia and myeloplastic syndrome, stem cell transplantation may be a treatment (Bessler M et al. Curr Opin Pediatr. (2004) 16 (1) 23-8.

DKC1 mRNA appears to be novel marker for the preferred cell populations according to the invention, and for stem cell populations in general.

EBPL Emopamil Binding Protein Like

EBPL, emopamil binding protein-like has been indicated for sterol synthesis and X-chromosomal chondrodysplasia punctuata (Moebius F F, et al. Biochem J 374 229-37). EBPL mRNA appears to be novel marker for the preferred cell populations according to the invention, and for stem cell populations in general.

Serine protease Inhibitor, Kazal Type 2 (Acrosin-Trypsin Inhibitor), SPINK2

SPINK2 has been associated with defects in sperm development. SPINK2 mRNA appears to be novel marker for the preferred cell populations according to the invention, and for stem cell populations in general.

Cell Adhesion Related Molecules

The invention is further specifically directed to 12 mRNA-markers that encode adhesion related molecules and were up-regulated in CD133+ cells. The overexpression of these genes (CD34, COL5A1, DSG2, DST, IL-18, ITGA9, JUP, PKD2, SEPP1, TRO, VAV3, and VLA-4) was observed in CD133-type cells according to the invention. The invention is preferably directed to individual novel markers and subgroups thereof, the individual novel markers according to the invention includes COL5A1, DSG2, DST, IL-18, ITGA9, JUP, PKD2, SEPP1, TRO, VAV3, and VLA-4.

Part of the markers are especially preferred as cell adhesion supportive factors, especially in connection with cell junctions and cytoskeleton, these are referred as group 1 (of cell adhesion related molecules): DSG2, DST, JUP, PKD2, VAV3. Part of the molecules have roles as extracellular proteins supporting cell adhesion, referred under the embodiment as group 2, such as IL-18, COL5A1, SEPP1, The third preferred group includes cell adhesion receptors ITGA9, and VLA-4.

IL-18

IL-18 is cell adhesion related protein but as a cytokine not a direct cell adhesion receptor molecule.

High levels of IL-18 in neonatal cord blood have been associated with periventricular leukomalacia (neonatal white matter damage) which often leads to cerebral palsy (Minaga K. et al. (2002) 17 (3) 164-70).

The background data do not indicate expression of IL-18 by human cord blood cells, especially by the preferred subpopulations such as CD133+ cells, and for stem cell populations in general.

JUP (Plakoglobin, Gamma-Catenin)

Plakoglobin is expressed on protein level throughout zebrafish embryo development and it is observed in desmosomes during heart chamber development (Martin and Grealy (2004) 32 (15) 797-9). The protein is required for embryonic heart, neuroepithelium, skin and vasculature (Galliciano G L et al (2001) 128 (6) 929-41). JUP mRNA appears to be novel marker for the preferred cell populations according to the invention, and for stem cell populations in general.

JUP may function as intracellular protein and its role is especially related to cell junctions and support of cell adhesion.

Polycystin-2 PKD2

PKD2 mRNA appears to be novel marker for the preferred cell populations according to the invention, and for stem cell populations in general.

PKD2 may function as intracellular protein and its role is especially related to cell junctions and support of cell adhesion.

VAV3

VAV1-3 knock out indicate that especially VAV1 but also others are important for B and T-lymphocyte function (Fujikawa K et al. (2003) 198 (10) 1595-608). VAV3 mRNA appears to be novel marker for the preferred cell populations according to the invention, and for stem cell populations in general.

VAV3 may function as intracellular protein and its role is especially related to cell junctions and support of cell adhesion.

VLA4, (Very Late Activation Antigen 4), Integrin Alpha4Beta1

Several publications have indicated the presence of VLA4 in CD34 positive cord blood populations. The data do not indicate its presence in context of other preferred cell related adhesion molecules except CD34.

VLA4 has been further been analyzed in CD34 cell populations in comparison to CD133 cord blood population in cell growing system as a potential cell adhesion molecule. VLA4 was not analyzed to be a specifically enriched marker in native CD133+ cells but these were indicated as base line expression. The data of the abstract does not indicate usefulness of VLA4 as overexpressed specific marker in CD133 cells (Zhai Q L et al. Zhongguo Yi Xue Ke Xue Yuan Xue Bao (2002) 24 (1) 7-10.)

Preferred Receptor Molecules

The inventors revealed markers related to preferred receptor molecules. These includes preferred cell adhesion receptors (group 1 under the embodiment), regulatory receptors (group 2) and growth factor receptors (group 3).

Preferred cell adhesion receptors include ALCAM (Activated leukocyte cell adhesion molecule), ITGA9, and VLA-4.

Preferred growth and activating factor receptors include CRIM1 (cysteine-rich motor neuron 1), FLT-3, SCA-1, KIT, TIE1, LRP6 Low density lipoprotein receptor-related protein 6, TNFRSF21 (tumor necrosis factor receptor superfamily, member 21)

Preferred regulatory receptors include: PTPRD (Protein tyrosine phosphatase, receptor type, D), PILRB (paired immunoglobin-like type 2 receptor beta), ADAM28.

Soluble Regulatory Proteins Including Growth Factors and Cytokines

The inventors were able to define certain growth factors and cytokines being specifically associated with the preferred cell populations.

The invention is especially directed to growth factor and cytokine markers according to the invention including:
ANGPT1,
AREG Amphiregulin (schwannoma-derived growth factor),
IGFBP7 (Insulin-like growth factor binding protein 7,
    Angiomodulin/Mac25/tumor adhesion factor TAF,
    Insulin-like growth factor binding protein-related protein 1),
IL-18,
soluble ALCAM The invention is further directed IGFBP7 (Insulin-like growth factor binding protein 7) as a special growth factor regulating protein.

Cell Matrix Related Markers

The invention is further specifically directed to cell matrix related markers
col5a1, Collagen type V alpha 1, col5a1
MMP28, matrix metalloproteinase 28
LAPTM4B Expression of this mRNA has been reported from certain embryonal stem cell lines (Abeyta Hum. Mol Genet. 2004; 13:601-608), from HSCs and neuronal stem cells (Ivanova N B. Et al. Science. 2002; 298:601-604; Ramalho-Santos M. et al. Science. 2002; 298:597-600) and from hepatocellular carcinoma tissues (Liu X R. Et al World J Gastroenterol. 2004; 10:1555-1559).

The mRNA has not specified as a specific marker of the cell populations according to the present invention.

Transmembrane and/or Membrane Associated Proteins

The present invention is preferably directed to following markers related to transmembrane and/or membrane associated proteins, the corresponding Affymetrix probe set ID is indicated in Table 2:

ADAM28

ADAM28 mRNA appears to be novel marker for the preferred cell populations according to the invention, and for stem cell populations in general.

ALCAM, Activated Leukocyte Cell Adhesion Molecule (Mouse Dm-Grasp Protein; Rat MEMD protein, HB2, SB-10 Antigen, KG-CAM)

ALCAM has been indicated in context of mesenchymal stem cells. Prior art does not indicate ALCAM in cord blood, or in preferred cell populations derived from it nor in CD133 cells. ALCAM mRNA appears to be novel marker for the preferred cell populations according to the invention.

Amphiregulin AREG

Actually soluble glycoproteins growth factor at least in most cases, it is preferred also as a membrane associated protein, larger isoform is known.

AREG has been described from cord blood derived cultivated mast cells, but not from preferred cell populations according to the present invention (J Allergy Clin Immunol (2005) 115 (2) 287-94 Wang S w et al.).

AREG mRNA appears to be novel marker for the preferred cell populations according to the invention, and for stem cell populations in general.

ATP9A (ATPase, Class II, Type 9A)

ATP9A mRNA appears to be novel marker for the preferred cell populations according to the invention, and for stem cell populations in general.

CRHBP/CRH-BP, Corticotropin-Releasing Hormone-Binding Protein/ CRFBP/CRF-BP, Corticotropin-Releasing Factor-Binding Protein/

CRHBP mRNA appears to be novel marker for the preferred cell populations according to the invention, and for stem cell populations in general.

CRIM1

Crim1 expression has been shown from early condensing mesenchyme and distal comma shaped bodies of uretheric tree, and male-specifically from Sertoli cells of developing testis, being yet another spermatogenesis associated protein (Georgas K et al. (2000) 219 (4) 582-7). Crim1 gene expression has been further detected in endothelial of forming capillary structures and in endothelial cells of inner lining of blood vessels. The corresponding protein was shown to be glycosylated and accumulate close to cell-cell contacts (Glienke J et al. (2002) 199 (2) 165-74). Crim1 has been also studied from chick spinal cord (Kolle G. et al. Dev. Dyn (2003) 226(1) 107-11) and in murine ocular development (Lovicu F J et al. (2000) 94 (1-2) 261-5).

CRIM1 mRNA appears to be novel marker for the preferred human cell populations according to the invention, and for human stem cell populations in general.

C14rf1 Chromosome 14 Open Reading Frame 1

C14orf1 may be indicated in a CD34+ cultivated immortalized cancer cell lines having no relevance with regard to present cells (Genome Res. (2000) 10, 1546-60 Zhang Q-H et al.). C14orf1 mRNA appears to be novel marker for the preferred cell populations according to the invention.

CYYR1 (Cysteine and Tyrosine-Rich 1)

CYYR1 mRNA appears to be novel marker for the preferred cell populations according to the invention, and for stem cell populations in general.

Desmoglein 2, DSG2

DSG2 mRNA appears to be novel marker for the preferred cell populations according to the invention.

Epithelial Membrane Protein 1, EMP1

EMP1 belongs to peripheral myelin protein 22 (PMP22) family, it has been indicated from early neurons during neuritogenesis in mouse brain and in neuroectodermally differentiated P19 cells (Brain Res Dev Brain Res (1999) 166 (2) 169-80 Wulf and Suter).

EMP1 mRNA appears to be novel marker for the preferred human cell populations according to the invention, and for human stem cell populations in general

FLT3

FLT3 is a receptor tyrosine kinase binding flt-3 ligand, which is a growth factor type molecule used in hematopoietic cell cultures. A few background articles notes use of flt-3 ligand for proliferation of CD133+ cells from cord blood, this does not indicate FLT3 expression or it as a useful marker overexpressed in context of CD133, expression levels or it change were not indicated, the studies were directed to cultivated expanded cells and not to primary cell preferably directed by the invention (Thromb haemost. 820049 92 (4) 767-75 Baal N et al.; Stem Cells (2004) 22 (1) 100-8 Forraz N et al; Haematologia (2003) 88 (4) 388-95 Encabo A. et al; Transfusion (2003) 43 (3) 383-9 Encabo et al; J Heatother. Stem Cell Res. (2001) 10 (2) 273-81 Kobari L et al.; Cell Prolif. (2004) 37 (4) 295-306, McGuckin C P et al.). FLT3 has been widely studied in context of cord blood cells. It has been also used for selection of cell populations from cord blood. Specific overexpression in cord blood CD133+ cells has not been indicated.

FLVCR (Feline Leukemia Virus Subgroup C Cellular Receptor)
FLVCR mRNA appears to be novel marker for the preferred cell populations according to the invention, and for stem cell populations in general.

GPR125 (G Protein-Coupled Receptor 125)
GPR125 mRNA appears to be novel marker for the preferred cell populations according to the invention, and for stem cell populations in general.

IGFBP7 (Insulin-Like Growth Factor Binding Protein 7)
IGFBP7 mRNA and protein has been indicated from bone marrow stromal stem cells, implied as osteoprogenitor cells, and dental pulp stem cells (Shi, S et al. (2001) Bone 29 (6) 532-9). IGFBP7 mRNA appears to be novel marker for the preferred cell populations according to the invention.

Integrin 9Alpha, Alpha9Beta1 Integrin, ITG9A
ITG9A mRNA appears to be novel marker for the preferred cell populations according to the invention.

KIAA0286
KIAA0286 mRNA appears to be novel marker for the preferred cell populations according to the invention, and for stem cell populations in general.

KIAA0152
KIAA0152 mRNA appears to be novel marker for the preferred cell populations according to the invention, and for stem cell populations in general.

LRP6
LRP6 mRNA appears to be novel marker for the preferred cell populations according to the invention.

MMP28 Matrix Metalloproteinase 28
The invention is preferably directed to MMP28 as a membrane associated marker.
MMP28 mRNA appears to be novel marker for the preferred cell populations according to the invention, and for stem cell populations in general.

PILRB (Paired Immunoglobin-Like Type 2 Receptor Beta)
The protein has shown to be overexpressed in erythroid progenitor cells in comparison to bone marrow released peripheral blood CD34+ cells.

PON2, Paraoxonase2
PON2 mRNA appears to be novel marker for the preferred cell populations according to the invention, and for stem cell populations in general.

PTPRD (Protein Tyrosine Phosphatase, Receptor Type, D)
The literature background indicate absence of PTP delta from embryonic stem cells (Mol. Biol. Reprod. (1994) 19 (2) 105-8 Hendriks W et al.), absence of the type of PTP was further indicated from cultivated keratinocyte cell lines (J. Invest Deramtol. (1996) 106 (5) 972-6 Hendriks W et al.) PTPRD mRNA appears to be novel marker for the preferred cell populations according to the invention, and for stem cell populations in general.

SEPP1 (Selenoprotein P, Plasma, 1)
SEPP1 mRNA appears to be novel marker for the preferred cell populations according to the invention, and for stem cell populations in general.
The invention is specifically directed to SEPP1 as a membrane associated marker.

SLC16A14 (Solute Carrier Family 16 (Monocarboxylic Acid Transporters), Member 14)
SLC16A14 mRNA appears to be novel marker for the preferred cell populations according to the invention, and for stem cell populations in general.

SV2A
SV2A mRNA appears to be novel marker for the preferred cell populations according to the invention, and for stem cell populations in general.

TM7SF3 (Transmembrane 7 Superfamily Member 3)
TM7SF3 mRNA appears to be novel marker for the preferred cell populations according to the invention, and for stem cell populations in general.

Transmembrane 6 Superfamily Member 2 Isoform 2 TM6SF1
TM6SF1 mRNA appears to be novel marker for the preferred cell populations according to the invention, and for stem cell populations in general.

TNFRSF21 (Tumor Necrosis Factor Receptor Superfamily, Member 21)/Death Receptor 6, DR6
TNFRSF21 mRNA appears to be novel marker for the preferred cell populations according to the invention.

Trophinin, TRO
TRO mRNA appears to be novel marker for the preferred cell populations according to the invention, and for stem cell populations in general.

Vezatin
Vezatin mRNA appears to be novel marker for the preferred cell populations according to the invention, and for stem cell populations in general.

Transmembrane and/or Membrane Associated Glycoproteins
The preferred mRNAs corresponding to potential N-glycoproteins preferably include:
AREG, ALCAM, ITGA9, FLT3, PTPRD, TM7SF3, PON2, DST, ADAM28, CRHBP, DSG2, EMP1, FSTL1, GPR125, IGFBP7, KIT1, MMP28, SCA-1, SV2A, SEPP1, TIE1, TNFRSF21, LRP6, OPN3 mRNAs of Possible Extracellular Proteins
The present invention is further directed to mRNA potentially corresponding to secreted cell regulating marker structures.
Following mRNAs are also preferred as marker related to secreted glycoproteins:
CRHBP/CRH-BP, corticotropin-releasing hormone-binding protein
IGFBP7 (Insulin-like growth factor binding protein 7).
MMP28 is a secreted protein, which may exist in membrane associated form SEPP1 (selenoprotein P, plasma, 1),
Uromodulin-like 1, or
Collagen type V alpha 1, col5a1, A preferred matrix protein
Col5a1 mRNA appears to be novel marker for the preferred cell populations according to the invention.

Uromodulin-like 1, UMODL1
Present invention is specifically directed to UMODL1 mRNA, because the related protein uromodulin is strongly glycosylated protein with potential glycosylation associated functions. UMODL1 mRNA appears to be novel marker for the preferred cell populations according to the invention.

LT-Markers (Lrp6/Tcf7L2-Related) and Cell Junction-Type Signaling Related Marker Groups
The preferred LT-markers includes Lrp6, γ-catenin (JUP, plakoglobin), Tcf7L2/TFC4, HOXA9, HOXA10, MAP3K4 and IL-18, more preferably Lrp6, γ-catenin (JUP, plakoglobin), Tcf7L2/TFC4, MAP3K4 and IL-18. The background related material of markers other than HOXA9 and HOXA10 is represented with other groups bellow or above (transcription factors, cell adhesion IL-18).

HOXA9 and HOXA10
HOXA9 and -10 have been reported from cord blood CD34+ cells (Ferrell C M et al. (2005) Stem Cells 23 (5) 644-55). These appear to be novel markers for the preferred cell populations according to the invention.

Transcription Factors
The present invention is further directed markers related to specifically expressed transcription factors.

STAT5

The transcription factor has been implicated in connection with hematopoietic differentiation of cord blood cells (Buitenhuis M et al. (2003) Blood 101 (1) 134-43).

Pubmed search did not indicate CD133 association.

The invention is specifically directed to the marker of STAT5 for analysis of CD133-type cell populations, and/or from complete cell populations according to the invention, derived from mononuclear cells and/or cell populations of human cord blood.

GATA-2

This transcription factor has been indicated in some cord blood derived CD34+ cell preparations (Pan X et al. (2000) 127 (1) 105-12), GATA-2 has been also indicated in vasculogenesis from human embryonal stem cells (Gerecht-Nir S et al. (2005) Dev. Dyn. 232 (2) 487-97).

The invention is specifically directed to the marker of GATA-2 for analysis of CD133-type cell populations, and/or from complete cell populations according to the invention, derived from mononuclear cells and/or cell populations of human cord blood.

Tcf7L2/TFC4

This signaling pathway molecule was not found to be indicated for CD34+, CD133+ or human cord blood cells in PubMed.

HOXA5

In a background publication transfection of CD34+ cord blood cells with HOXA5 was used in studies of hematopoiesis indicating suppression of erythropoiesis and promotion of myelopoiesis (Crooks G M et al. (1999) 94 (2) 519-28). HOXA5 gene expression has not been indicated as specifically overexpressed marker of early human cells, especially preferred cell populations according to the present invention.

Mitogen-Activated Protein Kinase Kinase Kinase 4, MAP3K4

MAP3K4 mRNA appears to be novel marker for the preferred cell populations according to the invention.

Cell Cycle Related Markers

GATA2, N-MYC, DST, PLAGL1, NME1, CDK6, BCAT1, CDK4, BMI-1 MCM2, MCM5, MCM6, MCM7, CDK2AP1, SH3MD2, UHRF1, ZNRF1, EDD, SKB1, STAG1, ANAPC7 and MPHOSPH9. The invention is preferably further directed down regulated markers p18, and CDKN2D. Certain levels of cell cycle related markers are observed in connection with normal cell cycle in many types of cells. The present invention is in a preferred embodiment directed to analysis one or several, preferably at least 2, even more preferably at least 3 cell cycle related markers according to the invention in context of analyzing one or several other markers according to the invention. The analysis of part of the markers may be novel as such from the preferred cell types.

GATA2 is also preferred as a preferred transcription factor.

N-MYC

N-MYC mRNA expression has been reported from human fetal blood Lin-CD34+CD38− cells [Shojaei F et al. Blood (2004) 103 (7) 2430-40]. GATA2 and N-MYC showed 2-3 times higher levels of expression in peripheral blood than in bone marrow CD34+ cells, (Steidl U et al. Blood (2002) 99 (6) 2037-44). Pre-B cells do not have overexpressiion of N-Myc (Pathobiology (1992) 60 (2) 87-92, Wetherall And Vogler). Pubmed search did not indicated CD133 or cod blood association.

Dystonin DST

DST mRNA appears to be novel marker for the preferred cell populations according to the invention.

Pleiomorphic Adenoma Gene Like1, Plagl1 (Lot1/Zac1)

Plagl1 mRNA appears to be novel marker for the preferred cell populations according to the invention.

NME1

NME1 mRNA appears to be novel marker for the preferred cell populations according to the invention, and for stem cell populations in general.

CDKN2 (p16INK4a)

CDKN2 mRNA appears to be novel marker for the preferred cell populations according to the invention.

CDK4, Cyclin Dependent Kinase 4

CDK4 has been reported from cord blood mononuclear cells. TGF-beta1 inhibits its expression. This work does not indicate homogenous cell populations according to the invention (Zhonggou Shi Xan Xue Xe Xue Za Zhi (2004) 12 (5) 644-8 Shi B et al.). CKD4 has been indicated to be expressed, while other cyclins are not expressed in CD34+ bone marrow cells, status of cdk4 during hematopoiesis was no induction or stable expression, thus further indicating no specific analytical change with the cell populations quite different from the preferred cells according to the invention (Leuk Lymphoma (2002) 43 (2) 225-31 Furukawa Y et al.; Blood (2001) 97 (9) 2604-10, Lewis J L et al).

CDK4 mRNA appears to be novel marker for the preferred cell populations according to the invention.

CDK6

CDK6 has been reported from CD34+ hematopoietic cell lines and other hematopoietic cells (BBRC (1998) 231 (1) 73-6 Della Regione F et al.)

CDK4 mRNA appears to be novel marker for the preferred cell populations according to the invention.

CDK2AP1 (p12DOC-1)

CDK2AP1 mRNA appears to be novel marker for the preferred cell populations according to the invention.

BCAT-1

BCAT-1 mRNA appears to be novel marker for the preferred cell populations according to the invention.

BMI-1

BMI-1 has been reported from hematopoietic type cells developed from embryonic stem cells (Zhonggou Shi Xan Xue Xe Xue Za Zhi (2005) 13 (2) 222-8 Wang J et al.) and from CD34+ bone marrow cells with high expression in comparison to negative counterpart (Blood (1998) 91 (4) 1216-24 Lessard J et al. BMI-1 mRNA appears to be novel marker for the preferred cell populations according to the invention.

Minichromosome Maintenance Protein-2, MCM-2

MCM-2 mRNA appears to be novel marker for the preferred cell populations according to the invention, and for stem cells in general.

Minichromosome Maintenance Protein-5, MCM-5

MCM-5 mRNA appears to be novel marker for the preferred cell populations according to the invention.

The invention is specifically directed to the mRNA for analysis of mononuclear cells and/or cell populations from human cord blood, preferably CD133-type cell populations. The present invention is further directed to MCM-5 mRNA as a novel hematopoietic stem cell marker.

Minichromosome Maintenance Protein-6, MCM-6

MCM-6 mRNA appears to be novel marker for the preferred cell populations according to the invention, and for stem cells in general.

Minichromosome Maintenance Protein-7, MCM-7

MCM-7 mRNA appears to be novel marker for the preferred cell populations according to the invention, and for stem cells in general.

Anaphase Promoting Complex Subunit 7, ANAPC7

ANAPC7 mRNA appears to be novel marker for the preferred cell populations according to the invention, and for stem cells in general.

M-Phase Phosphoprotein 9, MPHOSPH9

MPHOSPH9 mRNA appears to be novel marker for the preferred cell populations according to the invention, and for stem cells in general.

Ubiquitin-Like, Containing PHD and RING Finger Domains, 1, UHRF1

UHRF1 mRNA appears to be novel marker for the preferred cell populations according to the invention, and for stem cells in general.

SH3 Multiple Domains 2, SH3MD2

SH3MD2 mRNA appears to be novel marker for the preferred cell populations according to the invention, and for stem cells in general.

Skb1

Skb1 mRNA appears to be novel marker for the preferred cell populations according to the invention, and for stem cells in general.

ZNRF1

ZNRF1 mRNA appears to be novel marker for the preferred cell populations according to the invention, and for stem cells in general.

STAG1/Stromal Antigen 1, Stro-1

Stro-1+ mesenchymal cells direct in NOD/SCID mouse to spleen muscles, BM, and kidneys while more Stro-1− directed to lungs. The cultivated mesenchymal cell populations were derived from cord blood but usefulness as a marker was not indicated nor presence in a homogenous cell populations, the cell may be different from CD34+ cells (Blood (2004) 103 (9) 3313-9 Besidhoum M et al.). In a preferred embodiment the invention is directed to primary cell populations without artificial cultivation or transfections.

Stro-1 mRNA appears to be novel marker for the preferred cell populations according to the invention.

EDD

EDD mRNA appears to be novel marker for the preferred cell populations according to the invention.

p18

Cyclin Dependent kinase inhibitors p18INK4c was reported to be highly expressed in CD34+ progenitor cells and in acute myeloid leukemia cells, but not in normal myeloid cells (Br J hematol. (1999 106 (3) 644-51 Tschan, M P et al).

p18 mRNA appears to be novel downregulated marker and cancer related marker for the preferred cell populations according to the invention.

Potential Cell Migration Function Related Markers

The present invention is specifically directed to markers selected from the group: SPINK2, CD133 and SEPP1; more preferably SPINK2 and SEPP1 and most preferably SPINK2; as potential cell migration associated markers. These molecules have been associated with sperm/microvillus development. The invention is directed to the use of the marker SPINK2 together with any other preferred markers for methods according to the invention, more preferably together with CD133 and/or SEPP1.

Markers Related to Potential Endothelial Development

The present invention is specifically directed to markers according to the present invention when these have connection to potential proteins associated with potential endothelial development. The markers potentially related to endothelial development include ADAM28, ANGP1, CRIM1, DSG2, EMP1, JUP, MAGI1, TIE1.

Preferred potential endothelial development associated mRNAs were selected by comparing expression between CD133+ and CD34+, the following marker were revealed to be associated with CD133+ type cells ANGP1, DESG2, CRIM1, EMP1, ADAM28, and MAG1.

Association preferred emdothelial development related markers with CD133-type cells.

The table indicates expression fold change in comparison with corresponding negative cell population.

|        | Mean fold change CD133+ | Mean fold change CD34+ |
|--------|-------------------------|------------------------|
| ANGPT1 | 18.7                    | 9.6                    |
| DESG2  | 10.7                    | 6.5                    |
| CRIM1  | 4.8                     | 1.8                    |
| EMP1   | 5.7                     | 4.2                    |
| ADAM1  | 14.4                    | 5.5                    |
| MAGI1  | 13.7                    | 5.5                    |

MAG1, membrane associated guanylated kinase inverted-1
MAGI1 mRNA appears to be novel marker for the preferred cell populations according to the invention.

ESC-Related Stem Cell Markers

The present invention is specifically directed to transcriptional analysis of embryonal stem cell related markers in the preferred cell populations. Preferred ESC-related stem cell markers, in a preferred embodiment are DNMT3B, DNMT3A, and DPPA4.

DNMT3B and DNMT3A

Background about DNMT3B and DNMT3A describes hematopoietic cells from murine fetal livel, yolk sac, and adult bone marrow. Due to difference between species and tissues this is not relevant with regard to present invention (Gene Epr. Patterns (2004) 5 (1) 43-9, Watanab D et al). Another study describes human leukemia and bone marrow cells which express DNMT3B, DNMT3A, but human cord blood, such as cord blood markers were not described (Blood (2001) 97 (5) 1172-9 Mizuno S et al.).

DNMT3B, and DNMT3A mRNA appear to be novel marker for the preferred cell populations according to the invention.

DPPA4

DPPA4 mRNA appears to be novel marker for the preferred cell populations according to the invention.

Markers with On-Off Change in Expression

Subgroup 1. Glycosyltransferases

Glucosaminyl (N-acetyl) transferase 2 I-branching enzyme GCNT2

UDP-Gal:betaGlcNAc beta 1,3-galactosyltransferase polypeptide 3,B3GALT3

CMP-sialic acid alpha2,3sialyltransferase III, ST3GalVI mRNA, SIAT10

Subgroup 2. Nucleotide metabolism enzyme:

Nudix (nucleoside diphosphate linked moiety X)-type motif 5, NUDT5;

Subgroup 3. Glycoprotein:

Synaptic vesicle glycoprotein 2A SV2A

Subgroup 4. Regulatory protein:

Zinc finger protein 117 (HPF9), ZNF117

SIAT10

SIAT10 has been reported to have hardly detectable expression in a cultivated hematopoietic cell line (JBC (274) (1999) 11479-86 Okajima T et al.).

SIAT10 mRNA appears to be novel marker for the preferred cell populations according to the invention, and for stem cells in general.

B3GALT3

Potential product of B3GALT3 globoside has been suggested for signal transduction in embryonal carcinoma cells through AP1 and CREB, no B3GALT3 mRNA expression was indicated in the model (Song Y et al JBC (1998) 273, 2517-25). The relevancy of the data with regard to non-cancer cells of present invention cannot be known with regard to the present invention.

B3GALT3 mRNA appears to be novel marker for the preferred cell populations according to the invention, and for stem cells in general.

GCNT2

Expression of GCNT2 has been reported from bone marrow CD34+ cells and cultivated differentiating cells thereof (Inaba N et al. Blood (2003) 101, 2870-6). The data does not indicate presence of the mRNA in human cord blood or in any preferred cell population according to the invention. The data does not indicate the usefulness of the marker for differentiation of hematopoietic stem cell types.

GCNT2 mRNA appears to be novel marker for the preferred cell populations according to the invention.

Nudix (Nucleoside Diphosphate Linked Moiety X), NUDT5

NUDT5 mRNA appears to be novel marker for the preferred cell populations according to the invention.

Zinc Finger Protein 117 (HPF9), ZNF117

ZNF117 mRNA appears to be novel marker for the preferred cell populations according to the invention.

Markers Associated with Chromosomal Alterations in Blood Cancers and Other Conditions Baalc (Brain and Acute Leukemia Cytoplasmic)

Baalc has been reported in another context as development related protein from CD34+ bone marrow cells (Baldus, C D et al. (2003) 31 (11) 1051-6) and associated with mesoderm and muscle development (Satoskar A A et al Gene Expr Patterns (2005) 5 (4) 463-73).

Baalc (brain and acute leukemia cytoplasmic) mRNA appears to be novel marker for the preferred cell populations according to the invention.

T-Cell Lymphoma Breakpoint Associated Target 1, TCBA1

TCBA1 alteration occurs at band 6q21 in T cell lymphomas/leukemias, it may be fusion of TCBA1-SUSP1, or aberrant non-chimeric transcript (Tagaw H. et al. (2002) 34 (2) 175-85)

TCBA1 mRNA appears to be novel marker for the preferred cell populations according to the invention, and for stem cells in general.

Wolf-Hirschhorn Syndrome Candidate 1, WHSC1

This gene is associated with a syndrome caused by deletion of short arm of chromosome 4 associated with a myelo dysplastic syndrome (MDS), possibly caused by allelic loss of WHSC1 (Sharathkuma A et al. Am J Med Genet A (2003) 119 (2) 194-9). In multiple myeloma translocation of t (4; 14) p(16.3; q32) probably deregulated WHSC1 gene (Finelli P et al. Blood (1999) 94 (2) 724-32).

WHSC1 mRNA appears to be novel marker for the preferred cell populations according to the invention, and for stem cells in general.

Antibody Target Structures

The present invention is further directed to cell surface marker structures, which can be recognized by antibodies. This group includes preferred plasma membrane proteins according to the invention, furthermore the invention is directed to molecules characterized by antibodies as cell markers. Preferably this group includes mRNA of serologically defined colon cancer antigen 8, SDCCAG8, and in another embodiment mRNA of Sarcoma antigen NY-SAR-79.

Serologically Defined Colon Cancer Antigen 8, SDCCAG8

SDCCAG8 mRNA appears to be novel marker for the preferred cell populations according to the invention.

Sarcoma Antigen NY-SAR-79

Sarcoma antigen NY-SAR-79 mRNA appears to be novel marker for the preferred cell populations according to the invention.

Islet Cell Autoantigen 1 69kDA, ICA1

ICA1 mRNA appears to be novel marker for the preferred cell populations according to the invention.

Furthermore, the inventors noted a very recent publication (He X et al. (2005) Stem cells and Development 14, 188-198) with a doubly selected cell populations of cord blood. The expression was compared to CD34− cell populations, so the actual relation of the more limited group of markers presented in the article, with regard to preferred cell populations according to the present invention was not indicated. The data appears to be more CD34 related in contrast to the most preferred embodiments of present invention.

The presence of less markers and different markers indicates difference in cell populations. It is also totable that the purification process used by He et al. would not allow to access to present type of cells or corresponding background cell populations The present invention is not directed to markers of the publication as novel stem cell marker if the markers with similar gene names actually do correspond to the specific markers of the present invention, it is realized that the publication uses different identification number system for the mRNAs.

The present invention is specifically directed to the markers possibly also noted by He et al. when these are analyzed form preferred complete and homogenous cell populations of cord blood selected with regard to single marker according to the present invention.

There is also an increasing need for methods for purification of cell population from various sample types. Purified cell populations are developed for various scientific products and research tools and/or therapeutic products or lead products for therapeutic development.

The samples, or sources of cell populations, are usually tissues, tissue cultures and/or cell cultures. The samples contain beside the target cell population, also other cellular material or other cellular materials. The other cellular material includes multiple different cell populations and/or cell like materials, which should be separated from the desired cell population. The major problems are to maintain the desired cell population intact and remove other cellular material with similarities with the desired cell population. Preferred sample is cell or tissue material containing free or easily mobilizable cells such as blood and/or blood derived materials.

It has been realized that various human tissues contain multipotent cells such as various progenitor cells, or stem cells, which are useful for scientific studies and developing therapeutics for animals and human. There is a need for purification of multipotent cells from various sample types.

The current cell purification methods include affinity methods such as affinity bead methods. The purification methods are not optimal especially for applications requiring highly pure cells. The present invention reveals a novel purification method, which allows effective purification of a cell population. The method yields especially complete cell populations. The complete cell populations are especially useful for scientific development, diagnostics development and cell culture and development thereof.

Hematopoietic stem cells (HSC), with their unique self-renewal and differentiation capacity, offer great potential for the treatment of hematological disorders, immunodeficiency and inborn errors of metabolism [51, 52]. HSCs can be collected from mobilized peripheral blood (PB), bone marrow (BM) and cord blood (CB). Lately CB has been increasingly utilized because it is readily available, HLA mismatch is better tolerated and there is a decreased risk of graft-versus-host disease when using CB-derived HSCs [53]. Even though the cell content of CB is limited, it has higher frequency of progenitors compared to PB or BM [53-55]. CB-derived CD34+ cells have also been shown to proliferate more rapidly than their counterparts from BM [56], and CB-derived HSCs possess increased engraftment potential when compared to cells from PB or BM [57, 58]. In addition, recent studies suggest that CB is a source of non-hematopoietic stem cells [59, 60].

Enrichment of HSCs is based on the surface expression of phenotypic markers or the lack of expression of lineage-specific markers. The most commonly used surface marker for HSC selection is CD34, a transmembrane glycoprotein expressed on HSCs. CD34 is also used to quantify the stem cell content of collected units in CB banks [61]. Most, if not all, CD34+ cells express CD133 glycoprotein on their surface. CD133 is appears to be expressed on more primitive cells and CD133+ grafts have been tested in stem cell transplantation [62-64]. Fluorescence-activated cell sorting and immunomagnetic selection system employ these cell surface antigens to enrich HSCs. However, a major challenge has been the difficulty to produce highly pure HSC fractions with good recovery. Furthermore, the handling of CB is challenging due to the relatively high content of thrombocytes and nucleated erythroid precursors. For these reasons, standardized protocols for PB sample handling and cell separation do not work well for CB. Only few studies have investigated the efficiency of the immunomagnetic selection method used to isolate CD34+ cells from CB. Belvedere et al. compared the results from 49 selections and reported mean CD34+ cell purities of 41% and 85% after first and second passage through the separation column, respectively [67]. Melnik et al. report an average purity of 60% for CB-derived CD34+ cells from 10 separations [68].

In this invention, different protocols were optimized to enrich HSCs with over 90% purity from fresh and cryopreserved CB. Cryopreserved CB cells have been considered especially challenging in selection procedures because of cell aggregation caused by cell damage during thawing. The used protocols were based on positive selection of cells expressing CD34 and CD133. The magnetic cell sorting system MACS was used due to its gentleness and time-effectiveness. Further, the clonogenic capacity of selected HSC populations was determined using colony-forming unit (CFU) assay.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DESCRIPTION OF THE INVENTION

Figure 1:
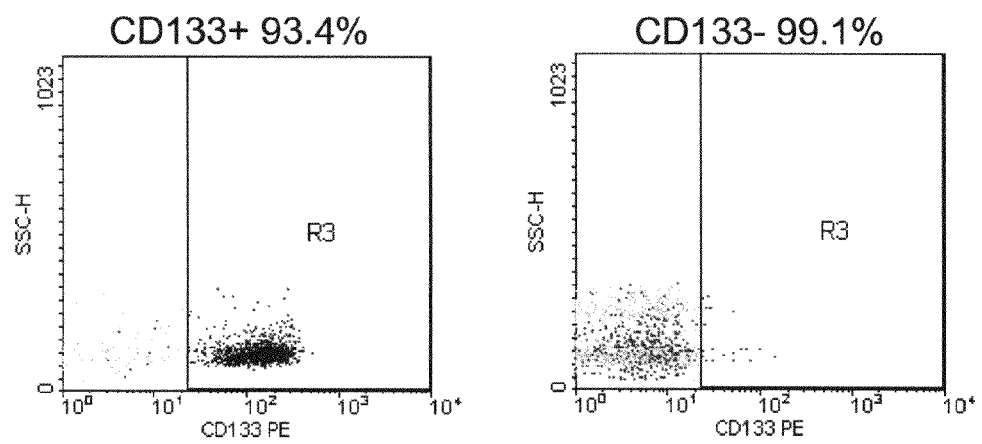
FIG. 1. Purity assessment of CD133+ and CD133− cell fractions by flow cytometry. Gates were set to exclude >99% of control cells labeled with isotype-specific antibody. Percentages indicating the purity of isolated cell fractions are shown for both plots.

Novel Markers for Human Cord Blood Cell Populations

The present invention revealed group of specific mRNA-level markers useful for the analysis of human cord blood cell populations. The mRNA markers can be used for defining the status of specific cell population for scientific evaluation and for cell populations used for cellular therapies. At the priority application level the present invention is specifically mRNA-level markers even though part of the application and description may refer more to corresponding protein or glycan structure implying a potential biological role associated with mRNA-level marker.

The inventors further revealed special cell surface markers for the human cord blood. The cell surface molecules are preferably correlated with the mRNA expression. Preferred novel cell surface markers are glycan markers, in preferred embodiment sialylated N-glycan markers. In a preferred embodiment the present invention is directed to a combined analysis of both cell surface markers and mRNA markers.

Complete Cell Populations for Novel Screening Methods

The invention produced for the first time complete cell population from human cord blood cells. It is realized that the purity of the cell population and the purity of the negative control cell population are especially useful for screening and selecting marker for further characterization, controlling the quality of and manipulation of the cell populations. The inventors also applied mRNA array technologies to reveal novel mRNA level markers. The invention further revealed and verified the presence of certain cell surface protein markers by using monoclonal antibodies The invention further revealed novel glycan array markers by novel and effective mass spectrometric screening technology. The invention revealed the total N-linked glycomes of the preferred cell populations. It is realised that the glycome comprises multide of glycan markers present in cell surface and correlating with certain glycosylation enzyme mRNA expression. It is also realized that the specific glycomes comprise glycan structures important for the structures of cell surface proteins and the glycan structures can be used as additional or complementary markers with cell surface transmembrane or cell surface associated proteins. The invention further revealed correlations between glycosylation enzyme data and cell surface structures produced by the enzymes encoded by the mRNA-markers. It is realized that the verified mRNA markers can be used as alternatives for the analysis of cell surface glycan structure expression.

Method for Combined mRNA Expression Analysis and Glycome Analysis

The invention is directed to further methods including the steps of

1) Producing pure, preferably complete, cell population according to the invention
2) Screening mRNA expression levels of the cell population and screening of glycans of the cell population by carbohydrate recognizing screening methods preferably by
   i) release of N-glycans
   ii) purification of N-glycan fractions, preferably non-derivatized N-glycans
   iii) analysis of the N-glycan fraction, preferably by mass spectrometric screening
   iv) optionally further analysing or verifying the structure by additional structural analysis, preferably by specific glycosidase or chemical digestion or derivatizations(s) and/or additional mass spectrometric analysis and/or NMR-spectrometric analysis of the fraction and/or screening by one or several glycan binding proteins and/or by tandem mass spectrometry, more preferably by specific glycosidase digestion and mass spectrometric analysis or by NMR analysis.
3) Correlating the glycan expression with mRNA expression, preferably
   a. correlating glycosylation enzyme expression with expressed glycans
   and/or
   b. assignment and/or correlation of glycan structures with expressed glycoproteins preferably transmembrane glycoproteins.
4) Selecting the structure correlated in step 3) as a marker structure The invention also discloses further correlation operation of step 3) directed to the present data of mRNA expression and glycan profiling according to the invention. It is realized that the data comprise several glycoproteins and transmembrane glycoproteins and glycosylation enzymes, which are not yet classified to preferred enzyme groups. This, the invention is directed to classifying these to obtain further glycan and/or mRNA level markers for uses according to the invention.

It is further realized that the data contains multiple mRNA targets, associated to expression of proteins which protein level structure and/or function is not well-known or not well-known in human or mammalian biology, part of which will be recognized as important protein level cell surface markers or receptors or other effector molecules such as cytokines or growth factors, which would be useful to assign with part of the glycome revealed by the present invention to obtain real biological target structure for recognition of specific binding molecules and specific glycan or carbohydrate binding molecules. The data further contain glycosylation enzymes and proteins, which will be assigned to glycosylation enzymes synthesising specific human structures, which can be correlated with expressed glycan structures and thus use the mRNA information for analysis of glycosylation status.

It is further realized that the present mRNA markers can be assigned to, or will be assignable to after status of yet unknown mRNA marker will have been revealed, to specific cell functions related to regulation, differentiation, cell adhesion and cell signalling or other preferred function described by the invention, and specific mRNA marker or markers selected from the mRNA markers or corresponding protein level or glycan level markers according to inventions can be selected for specific uses in context of the cells according to the invention.

The invention further realizes that it is possible to perform further mRNA screening for example by array or RT-PCR methods to further verify the current results and/or screen additional mRNA markers and the data can be assigned with present glycosylation data.

It is further realized that more glycan screening under different condition or optional further analysing, or verifying the structures by additional structural analysis by methods described above, can be performed and also analysis of other other glycan groups can be performed such as analysis of protein linked O-glycans and lipid linked glycans and the data can be correlated with present mRNA data.

The invention is further directed to method of verification of the presence of glycan or protein level markers by specific binding molecules by method comprising steps
1) obtaining a cell population according to the invention
2) contacting the cell population with a binding molecule specific for a preferred protein level and/or glycan level marker on the cells, preferably the binding molecule is a protein, such as an enzyme or antibody, more preferably a specific antibody
3) analysing the level of binding.

In preferred embodiments the method is applied for analysis antibodies specific for glycan structures, more preferably specific for structural epitopes obtained from glycome profiling and optionally by correlating the profiling result with mRNA expression marker of a glycosylation enzyme participating to the biosynthesis of the structure.

Verifying of Presence of Cell Surface Markers ALCAM (CD166) and FLT3(CD135)

In order to verify the presence of proteins identified as potential cell surface markers commercial monoclonal antibodies were used. The cell surface presence of both ALCAM and FLT3 could be verified by antibodies. In contrast the antibodies used for two other markers revealed not to be useful for the recognition of the marker glycoproteins from the present cells.

Uses of the Markers in Further Selecting Optimised Markers and Development of Specific Binding Molecules for the Markers The invention is specifically directed to the use of the novel markers of specific preferred cell types for further selecting most optimal markers and for development for specific binding molecules, which specifically recognize the marker substances for development of optimised analytical tools and/or materials for manipulation of the cells.

The manipulation of the cells includes selection of specific subpopulations by using specific binding pairs to the molecules to sort the cell subpopulations containing the selected marker of the cells for example by immunomagnetic bead selection or fluorescent activated cell sorting methods, or manipulation of cell growth or differentiation by cultivation.

Example of Preferred Glycan Level and Corresponding mRNA Markers

In a preferred embodiment the invention is directed to the use of specific glycan markers for recognition and characterization of preferred cell populations. For example it was revealed that α3-sialylation, and specific sialyalted N-glycan structures were increased in a preferred cell population according to the invention. A mRNA related to the synthesis of this structure was also revealed to be highly upregulated in contrast to background cord blood cell population. The glycan marker was reveled to characteristic marker for a cord blood stem cell population, especially cell population comprising mainly CD133 cells. It is realized that such markers can be used for analysis for cell populations for example for quality control of cell products. The cord blood cells and CD34 and CD133 cell populations and other cell populations are important candidates for, and under development to, therapeutic cell populations. It is further realized, that especially the sialyl markers and other markers, which are localized on cell surface, are especially useful for manipulation of the cells for example in cell culture methods and/or cell sorting methods.

The invention realized that it is possible to use a specific glycan recognition reagent binding to the sialylated structure such as α3-sialic acid, peferably on N-glycan-structures according to the invention by a specific sialidase enzyme, a lectin such as a MAA-lectin or specific mRNA-binding probe which binds to mRNA of SIAT10-enzyme to characterize cord blood cell populations more preferably cord blood stem cell populations such as CD133-cell populations or CD133 comprising cell populations. The invention is further directed to mass spectrometric and NMR-methods for the analysis of the presence of the marker and its level. In a preferred embodiment the mass spectrometric method is used in combination with digestion by specific glycosidase enzyme or enzymes.

Types of Specific Binding Molecules

The markers according to the invention can be recognized specific binding molecules (or binding pairs). The binding binding bind specifically to the target molecules or specifically enough for useful analysis against the background the cell materials are analysed or specifically enough for manipulation of cell population by sorting or by affecting cell growth conditions.

The binding molecules include various recognition molecules well-known in the art such as nucleic acids and aptamers, proteins, peptides and low molecular weight ligands. It is realized that specific binding pairs includes nucleic acids such as probes or primers hybridising with the preferred mRNA-markers. The specific binding molecules includes nucleic acid molecules for recognition of the novel mRNA markers. It is realized that the sequences used by the array/PCR studies in the examples represent on part of possible selective nucleic acid sequences and that various other probes or PCR-primers and other diagnostic nucleic acids or homologs (such as peptide nucleic acids) can be produced for similar analysis.

The binding molecules further includes specific binding proteins or binding domains thereof for the protein level markers and other molecules useful for recognition of proteins such as
a) specific ligand binding proteins such as growth factors/cytokines for growth factors/cytokines, growth factor/cytokine receptors (or soluble binding domains thereof) for growth/cytokines factors, specific counter receptors such as integrin counter receptors, collagen binding proteins,
b) immunological/artificial ligands such as antibodies or antibody domains, phage display peptides or aptamers developed to bind to a protein marker or glycan marker
c) specific metabolic ligands such as substrates/inhibitors for enzymes (preferably specific substrates or inhibitors of nucleotide modifying enzymes [such as ATPase substrates, nucleotidase substrate, metalloprotease substrates/inhibitors such as MMP28 ligands], and lower molecular weight binder/effector molecules such as nucleotides, nucleotide sugars, oligosaccharide sequences/glycans for lectins.
d) carbohydrate specific binding pairs such as lectins, glycan specific antibodies, enzymes (e.g sialidases) and/or non-enzymatic neolectins derived thereof.

It is realized that protein level markers according to the invention can be produced by recombinant protein expression using recombinant DNA-technologies well known in the art. The recombinant proteins can be further specifically modified to comprise preferred glycan structures by selecting a production host cell line which produces proper human type glycosylation including mammalian cells and possible in vitro modification of the glycans of the cells or by using specifically glycoengineered cells such as yeast cells developed and patented by Kirin Brewery (JP) or Glycofi (US) or glycoengineered insect or plant cells. It is further realized that purified protein or glycan marker can be used for production of specific binding molecules recognizing the marker structures. The specific binders of various types can be produced by known technologies such as technologies for production of monoclonal antibodies by immunization or library selection against the pure protein marker or by in selection of molecular libraries such as phage display peptide or protein such as antibody libraries or other molecular libraries such as combinatorial chemistry libraries, chemical peptide libraries or nucleic acid libraries such as aptamer libraries against the pure protein markers. Methods producing antibody binders includes various forms of antibodies including polyclonal, monoclonal, chimeric between species, humanized, hybrid time, single chain, Fab-fragment, and minimal domain structure comprising antibodies.

Isolated glycan structures can be released and purified from glycoproteins or produced by chemical and/or enzymaticsynthesis methods. For immunization glycans can be conjugated ot proteins such as keyhole limpet hemocyanin or bovinen serum albumin and for in vitro screening of peptide, aptamer or phage display libraries the glycan structures can be conjugated to solid phases and/or marker proteins.

Methods for Selecting Optimal Targets and their Specific Molecules

The invention is directed to the use of the target mRNAs and/or corresponding protein and/or glycan targets listed in the invention for further selection of a marker or markers for the binding of the cells or materials derived thereof preferably for analysis of the cells or for the manipulation of the cells. The invention preferably uses whole target lists and/or subgroups there in for effective selection of the optimised targets. It is realised that more optimal targets may be needed because the requirements of specific use such as analytical applications such as the assay formats and its requirement for example for specific types of monoclonal antibodies or for suitability for cell manipulation methods such as cell cultivation and/or cell selection and aim for specific manipulation of differentiation of the cell population to a specific direction such as to neuroectodermal or mesenchymal direction. It is further realized that the markers are preferably optimised/verified for the use in clinical context such as clinical trials and/or for larger populations of cell donors including further heterogeneity in the markers.

It is further realized that for practical use lower number of markers would be useful as long as the preferred activity/selectivity is obtained.

The preferred selection method preferably further includes use of data from other cell experiment for theoretical preselection of from a group according to the invention and use of the selected subgroup for selection of one or several optimised targets. The invention is preferably directed to use of group or subgroup of preferred markers comprising at least about 10 markers according to the invention, more preferably about 6 preferred markers according to the invention, more preferably about 4 preferred markers according to the invention, and most preferably 3 markers according to the invention for selection of 1-3 optimized markers according to the invention.

The selection of optimal markers for a stem cell population according to the invention preferably includes following steps:
1) producing pure, preferably complete, cell population according to the invention
2) selecting preferred marker for testing the cell population from markers listed in Tables
3) Producing specific binding molecule recognizing the marker
4) testing the binding of the binding molecule to the cell population or testing the manipulation of the cell population by the binding molecule
5) optionally repeating the test with multiple cell populations from different individuals and with a control cell population(s)
6) selecting the optimal binding protein based on the binding activity and/or specificity and/or reproducibility The specific binding molecules may be commercially available such as various antibody and ligand molecules. As an optional step the binding molecule can be controlled against pure protein, glycoprotein or glycan cell surface marker. Alternatively the specific binding molecules may be produced by immunization and/or library screening methods.

The invention is further directed to testing group of binding molecules against the specific marker protein on target cell materials according to the invention. It is realized that it is useful to optimise the binders to the preferred cell population as the presentation of the marker structures vary, especially the glycan structures may be different and affect also binding of cell surface protein epitope recognizing antibodies. Preferred selection of the binders for isolated pure proteins or for cell level analysis of the marker includes following steps:
1) Producing pure, preferably complete, cell population according to the invention
2) Producing specific binding molecule(s) recognizing the marker
3) Testing the binding of the binding molecule to the cell population or testing the manipulation of the cell population by the binding molecule
4) Optionally repeating the test with multiple cell populations from different individuals and with a control cell population(s)
5) Selecting the optimal binding protein or binding proteins based on the binding activity and/or specificity and/or reproducibility or clinical suitability or other preferred quality.

Combination of Protein and Glycan Marker Data

The present invention revealed specific glycan marker structures present on preferred cells according to the invention. The N-glycan structures on proteins allow recognition by specific carbohydrate binding pairs such as lectins or enzymes or neolectins. A preferred example of lectins is *Maacia amuriensis* agglutinin MAA, which was shown to recognize the preferred cord blood cell populations by binding the α3-sialylated glycan marker. The present invention further revealed mass spectrometric and NMR profiling methods for recognition of the glycan structures from glycoproteins.

The invention revealed upregulated cell surface proteins, part of which are cell associated matrix or cytokine proteins, and a preferred group is transmembrane proteins. The invention is specifically directed to cell surface protein which comprise N-glycosylation sites. The invention is directed to performing N-glycosylation site analysis to the protein peptide sequences and selecting markers comprising N-glycosylation sites (Asn-Xxx-Ser(Cys)) and optionally also for the analysis of the presence of transmembrane glycoproteins by analysis of transmembrane sequences by standard hydphobiscity analysis of protein sequence or by checking database information about the protein structure. Preferred marker protein group includes proteins It is realized that the potential cell surface N-glycoproteins may be recognized by specific carbohydrate binding probes or regents such as antibodies recognizing the protein part of the cell surface marker proteins.

Combination of Recognition of Glycan Markers and Glycoprotein Markers

In a preferred embodiment the invention is specifically directed to recognition of at least one cell surface glycoprotein marker and glycan marker according to the invention. The invention is specifically directed to recognition of the novel N-glycan structures revealed from the cells according to the invention in context of recognition of cell surface glycoproteins, more preferably cell surface transmembrane glycoproteins according to the invention.

Assignment of Glycan Structures with Specific Cell Surface Marker Proteins

In a preferred embodiment the invention is directed to the assignment of glycan structures to the specific cell surface glycoproteins, more preferably cell surface transmembrane glycoproteins, which carry the glycans on them. The present invention revealed the cell surface N-glycan glycome of the cells according to the invention comprising at least most of the glycans carried by the cell surface glycoprotein. The invention thus revealed potential glycan based tools for isolation of specifically glycosylated proteins. The potential membrane glycoprotein according to the invention can be isolated by specific monoclonal antibody or other specific isolation methods from the specific cell population and the glycans can be analysed. Alternatively the knowledge about the expressed glycans can be used for isolation of glycoprotein fraction comprising specific glycan structures by molecules binding the glycans and the identity of proteins and optionally also the glycan structures (about which partial information is obtained by the binding to glycan binding material) are analyzed.

It realized that the preferred assignment method includes following steps

1) Producing pure, preferably complete, cell population according to the invention
2) Affinity purification of material containing glycoprotein(s) and assignment of glycosylation and the glycoprotein. Specifically glycosylated glycoprotein fraction or a specific glycoprotein is purified by
   a) Specific glycoprotein is purified
      i. By specific monoclonal antibody binding to the specific protein structure, preferably by affinity methods such as imuunoprecipitation and
      ii. analysis of the glycosylation of the protein by glycosylationa analysis methods,
         preferably by release of glycans and analysis of the glycans by mass spectrometric methods and optionally the glycosylation is assigned to specific glycosylation sites
   b) Specific glycoprotein fraction is purified and analyzed by
      i. Isolating the glycoprotein fraction by specific carbohydrate binding proteins such as lectins, preferably by affinity chromatography,
      ii. the isolated protein(s) carrying the specific glycans is recognized by proteomics methods such as proteolysis and mapping peptides and/or tandem mass spectrometric methods for sequencing the peptides.
      iii. optionally the specific glycan structures are sequenced and/or assigned to specific glycosylation sites of the protein (are recognized by mass spectrometry Preferred carbohydrate recognizing protein such as lectin or antibody based method includes:
1) Producing pure, preferably complete, cell population according to the invention
2) a fraction of specifically glycosylated proteins is recognized and isolated by binding specific lectins and/or carbohydrate binding proteins to specific glycans on proteins from the cell fraction and
3) the isolated protein(s) carrying the specific glycans is recognized by proteomics methods such as proteolysis and mapping peptides and/or tandem mass spectrometric methods for sequencing the peptides.
4) Optionally the specific glycan structures are sequenced and/or assigned to specific glycosylation sites of the proteins are recognized by mass spectrometry It is further realized that in a preferred methods specific monoclonal antibodies can used for binding to the proteins and purification of the proteins for example by using immunoprecipitation and immunoaffinity methods and/or electrophoresis such as two dimensional gel electrophoresis methods and/or blotting recognition methods such as western blot methods. When the preferred cell surface proteins have been purified the glycan structures of the protein can be revealed by methods known in the art such as mass spectrometry, NMR-spectroscopy, specific enzymatic degradation and binding by carbohydrate binding reagents such as lectins.

Use of Cell Surface Verified Transmembrane, Glycosylation Site Comprising Proteins for Assignment of Glycans with Specific Glycan Structures Revealed by the Present Invention The invention is especially directed to assignment of glycosylation site comprising proteins, preferably transmembrane proteins, with specific glycan structures and preferred method of assignment comprise optionally a first target selection step of analysing the presence of transmembrane sequence and N-glycosylation site in the protein, preferably by analysis of the protein sequence by software designed for the analysis.

Preferably the method involves isolation of the protein by a specific binding molecule such as a specific antibody, preferably a monoclonal antibody.

The present invention is especially directed to assignment of specific preferred glycan structures according to the invention with the verified of cell surface marker ALCAM (CD166) and FLT3(CD135). The invention is especially directed to assignment of the proteins with glycans revealed to be expressed in the preferred cell populations according to the invention most preferably cord blood glycans and glycans of cord blood stem cells such as glycan of preferred CD133 cells.

The invention is specifically directed to assignment of ALCAM with N-glycans according to the invention, preferably complex type N-glycans, mannose type N-glycans and/or sialylated N-glycans such as α3-sialylated glycans and/or α6-sialylated glycans. The assignment is especially preferred for analysis and development of ALCAM as a cell type specific target and optimised binding molecules for its recognition.

The invention is specifically directed to assignment of FLT3 with N-glycans according to the invention, preferably complex type N-glycans, mannose type N-glycans and/or sialylated N-glycans such as α3-sialylated glycans and/or α6-sialylated glycans. The assignment is especially preferred for analysis and development of FLT3 as a cell type specific target and optimised binding molecules for its recognition.

The Preferred N-Glycan Structures According to the Invention

The present invention revealed preferred N-glycan structures useful as markers. The analysis by mass spectrometry and NMR and by mRNA expression of glycosylation enzymes revealed both complex type and mannose type N-glycans and presence of both α3- and α6-linked sialic acid in cord blood cell populations and significant differences in the proportions of the sialylation in different cord blood cell populations, the CD133 cells preferred α3-sialylation. The invention revealed that this type of glycans are present on average glycoproteins of cord blood cell population. The specific structures can modify the activities of proteins and it is useful the assign the specific structural types with glycoproteins.

The invention revealed by mass spectrometry, NMR, and correlation with biosynthetic enzymes mRNA expression specific structural elements of the cord blood glycans. The complex type N-glycans comprise mostly or substantially type II N-acetylactosamine, large amounts of both bi-antennary comple terminal mannose structures are present and the common N-glycan core structures essentially lack GlcNAc branching of the N-glycan core.

The N-glycan analysis of total profiles of released N-glycans revealed beside the glycans above, which were verified to comprise
1) complex biantennary N-glycans, such as Galβ4GlcNAcβ2Manα3(Galβ4GlcNAcβ2Manα6)Manβ4GlcNAcβ4(Fucα6)$_{0-1}$GlcNAcβ-, wherein the reminal N-acetylactosamines can be elongated from Gal with NeuNAcα3 and/or NeuNAcα6 and
2) terminal mannose containing N-glycans such as High-mannose glycans with formula Hex$_{5-9}$HexNAc$_2$ and degradation products thereof comprising low number of mannose residues Hex$_{1-4}$HexNAc$_2$.

The glycan share common core structure according to the Formula:

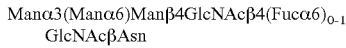
Manα3(Manα6)Manβ4GlcNAcβ4(Fucα6)$_{0-1}$GlcNAcβAsn wherein the non-reducing end terminal Man residues can be elongated to the complex type structures or to mannose type structures.

It was further analyzed that the N-glycan compositions contained only very minor amounts glycans of additional HexNAx in comparison to monosaccharide compositions the complex type glycan above, which could indicated presence of no or very low amounts of the N-glycan core linked GlcNAc-residues (not linked to αMan-residues) described by Stanley P M and Raju T S (JBC-publications 90's), the level of bisecting GlcNAc also appears to be low. The NMR-analysis further indicate that the cord blood N-glycan structures are essentially devoid of GlcNAcα6-linked to reducing end subterminal GlcNAcβ4 of the N-glycan core. The essentially devoid of indicates less than 10% of all the protein linked glycans, more preferably less than 8%.

Novel Purification Method for Human Cord Blood Cells

The inventors further discovered a novel method for purification of human cord blood cells. This method allows effective, and reproducible purification of complete cell populations with good yield. The invention is further directed to specific complete cell populations comprising approximately naturally occurring numbers of cells expressing either high and low levels of the specific marker used for purification of the cell population. The invention is further directed to use of the cell population for the analysis of the markers according to the invention.

Method for Purification of Mononuclear Cell Population

The present methods are further directed to a novel method for producing the highly purified cell populations from cord blood. The purification of a mononuclear cell population from human cord blood, especially cord blood or placental blood forms a special challenge. This appears to depend on the composition of human cord blood. In a few documented publications purification of mononuclear cell populations to level of purity of about 50-60% has been reported. The mononuclear cell population refers here to a subpopulation of the mononuclear cells.

Binding Molecule for the Methods According to the Invention

The method is based on the use of a specific binding molecule, which binds a marker structure on surface of a cell population. In a preferred embodiment the present invention is directed to use of a protein binding molecule, more preferably an antibody and most preferably a monoclonal antibody.

The present invention is further directed to glycan binding molecules, which recognize glycan marker structures on a cell surface. In a preferred embodiment the binding molecule is a protein, more preferably an enzyme, a lectin or a glycan binding antibody.

Novel Cell Purification Method

Two Step Process for Purification of a Cell Population

In a preferred purification method a binding molecule is used in a two-step process. In the preferred process a substrate preparation from human early blood is
1) handled in process for substrate preparation
2) put in contact with a specific binding molecule
3) processed in an affinity purification method by the specific binding molecule
4) recovered from the affinity purification
5) put in the second contact with a specific binding molecule
6) processed in an affinity purification method by the specific binding molecule
7) recovered from the affinity purification A Preferred Affinity Purification Method The affinity purification method is preferably a magnetic bead method, more preferably an immunomagnetic bead method. It is further realized that many other affinity methods can be used including methods containing immobilized affinity reagent. The preferred affinity reagent is antibody useful for purification of a mononuclear cell population, preferably CD133-type cell population, from human tissue material, most preferably from human cord blood. Preferred antibodies to for the purification method includes anti-CD34 and anti-CD133 antibodies.

Preferred Clean and Safe Process for Production of Substrate Preparation from Human Cord Blood A preferred substrate preparation of human cord blood is fraction of mononuclear cells prepared from human cord blood.

In the preferred substrate preparation process the blood is collected in sterile collection bags, preferably containing citrate phosphate-dextrose solution. The collected blood units are in a preferred embodiment tested negative for pathogens, which may be present in blood products. In a preferred process the blood units are tested at least for human immunodeficiency virus, hepatitis C virus, hepatitis B virus, human T-cell lymphotrophic virus and syphilis and unit with negative test results are used.

The sample of mononuclear cells is preferably produced by a density method, more preferably by Ficoll-Hypaque density method.

Analysis of Cell Purity

The present invention is directed to pure cell populations when the purity is assessed by cell counting method more preferably by FACS method. The present invention is preferably directed to purity of a cell preparation being a cell count based purity. The cell count based purity indicates the portion of number of pure from the total number of cells.

High Yield of Highly Purified Complete Cell Populations

The present invention is especially directed to obtain high yields of highly purified cell populations by the novel purification process. It is realized that production of cell with high yields is clear benefit in processes involving precious and scarce material such as human cord blood. It is further realized that complete cell populations with different types of positive cells offer a novel high yield raw material. The reproducibility of the process is further a beneficial factor in effective use of cell materials.

It is know in the art that highly purified cell populations may be obtained by increasing washing of cells contacted with magnetic beads. However this process will reduce the yield of the cells. Moreover the washing would release cell populations with weak binding to affinity matrix, creating a biased cell population which actually does not correspond to total cell population carrying the specific marker structure.

Figure 8:
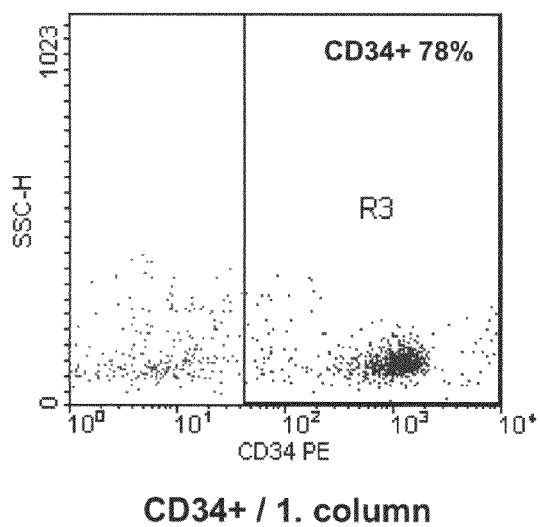
FIG. 8. Purity assessment of CD34+ cell fraction after one or two column separations. A) The CD34+ cell fraction was 78% pure after the first column separation. B) A 92% pure CD34+ cell faction was obtained by an additional labeling step in connection with a second column separation. CD34+ cell populations were defined by first gating on forward and side scatter properties excluding platelets and debris. Subsequent gates were set to exclude >99% of control cells labeled with isotype-specific antibody. Percentages indicating the purity of isolated cell fractions are shown for both plots. Abbreviations: SSC, side scatter; PE, phycoerythrin.
Figure 8:
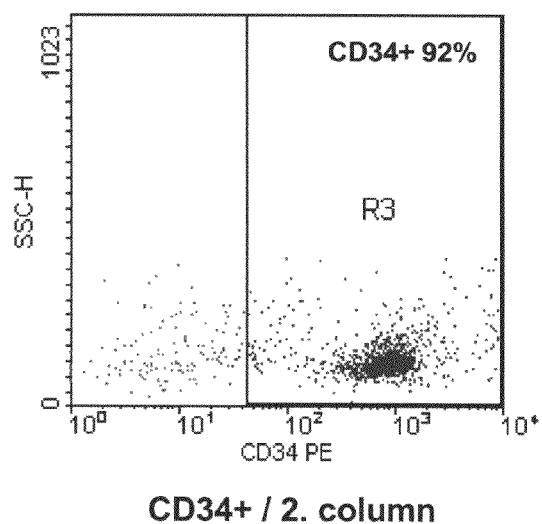
Figure 9:
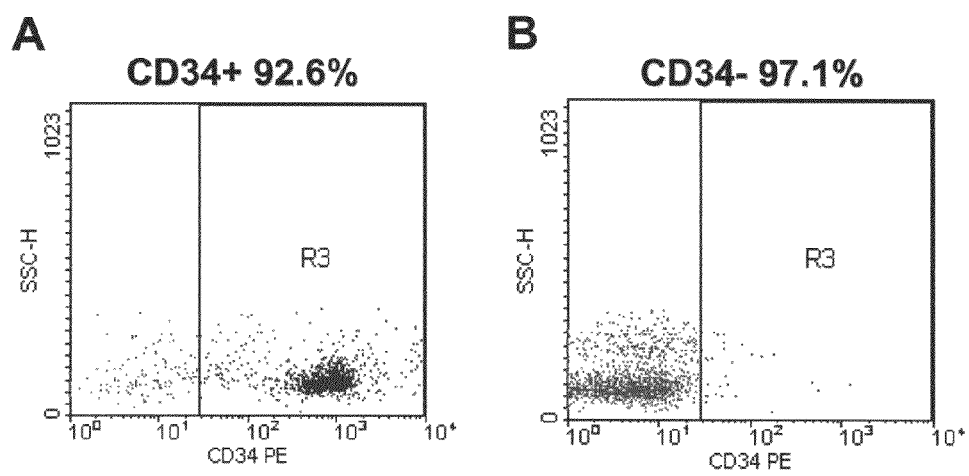
FIG. 9. Purity assessment of CD34+ and CD34− cell fractions after two column separations. A) Purity of CD34+ cell fraction is 92.6% after the first column separation, B) Purity of CD34− cell fraction is 97.1%.

The inventor compared traditional purification methods using one and two purification rounds in immunomagnetic methods. It was found out the purities and/or yields with cord blood were poor with both one and two column methods. Extensive washing released substantial amounts of cells from columns at each purification round. It is realized that the release of a specific cell depend on the affinity of the cell to immobilized affinity reagent and less avidly bound cells are more easily lost biasing the cell population. As shown in FIG. 8 the flow cytometric analysis pattern of the cell population in the middle and after the present purification are very reproducible.

Preferred Recovery % to be Obtained by the Method According to the Invention

The current methods producing highly purified cells especially by affinity methods such as magnetic bead methods usually fail to show any respectable yield from starting material. The measurement of the low amounts of cells in starting material is difficult making recovery %-estimates difficult. The optimised process according to the invention avoids the loss of materials and shows repducible and reasonable minimum recovery % values, The inventors were able to obtain highly purified cell from early blood with the yield of over 50%. This is high yield for highly purified cells. The present invention is especially directed to production of highly purified cell populations, preferably complete cell populations from human cord blood. The invention is directed to preferred highly purified complete cell populations produced according to the invention with the yields of at least about 70%, more preferably at least about 75% of purified cells, and even more preferably at least about 80%, and even more preferably at least about 90% from the preferred raw material preferably human cord blood.

Complete Cell Populations and Production Thereof

The present invention is specifically directed to the methods of isolating highly purified complete cell populations by the methods according to the present invention. The complete cell populations would contain both weakly and highly binding cells representing the original distribution of cells binding weakly and highly to a specific affinity reagent, preferably a monoclonal antibody, in the raw material from which the cell are produced, preferably cord blood.

The invention is further directed to highly purified complete cell population produced from cord blood, preferably the complete cell population is a mononuclear cell population from cord blood, and in a preferred embodiment CD34-positive and CD133-positive cells.

Reproducibility of the Purification of the Highly Purified Complete Cell Population The present invention is specifically directed to processes according to the present invention when the highly purified complete cell population is produced with less than 5%-unit variation from the mean purity % (for example mean 95% and variation less than +−5%), more preferably with less than 3%-unit variation from the mean purity. Alternatively the invention is directed to highly reproducible processes when the highly purified cell population is produced so that the differences of the purity figures from the mean purity are less than 3%, more preferably less than 2.5%, even more preferably less than 2%, in particular less than 1.5% and most preferably less than 1%. The inventors were able the to produce numerous cell populations (more than 10) with the reproducible yield.

Preferred Purity of Reproducibly Highly Purified Mononuclear Complete Cell Populations from Human Cord Blood The present invention is specifically directed to production of purified cell populations from human cord blood meaning neonatal blood, preferably from human cord blood and/human placental blood. As described above production of highly purified complete cell preparations from human cord blood has been a problem in the field. In the broadest embodiment the invention is directed to biological equivalents of human cord or placental blood as cord blood according to the invention, when these would comprise similar markers and which would yield similar cell populations when separated similarity as the CD133 cell population and equivalents according to the invention or when cells equivalent to the cord blood is contained in a sample further comprising other cell types. It is realized that characteristics similar to the cord blood can be at least partially present before the birth of an human. The inventors found out that it is possible to produce highly purified cell populations from with purity useful for exact gene profiling and biomarker analysis.

The preferred purity depends of the affinity of the antibody used. For purification using commercial CD34-antibody preferred purity of complete cell population is at least 90%, more preferably at least 93%, and most preferably at least 95%. In a purification process according to invention by anti-CD133 antibody preferred purity of complete cell population is at least 90%, more preferably at least 93%, and most preferably at least 95%.

The present invention is directed to complete cell populations from human early blood with purity of at least at least 85%, more preferably at least 90%, even more preferably with increasing preference 91%, 92%, 93%, 94%, 95% respectively and most preferably with increasing preference at least 95%, 96%, 97% or 98%. In a specific embodiment the present invention is directed to ultrapure complete cell population in which the level of impurities is less than 10%, more preferably less than 5% and most preferably less than 3%. The innovation is specifically directed to complete cell populations purified by anti CD34 and anti-CD133 antibodies.

In a specific embodiment the present invention is directed to highly purified human complete CD133+ and CD 34+ cell populations derived from cord blood.

Highly Viable Cell Populations

The present methods gives beside the unexpectedly high yields and recovery, completeness, purity and reproducibility also highly viable cells. The highly viable cells survived the purification intact and are capable of prolifetating. Preferably the complete cell population is at least 95% viable, more preferably at least 97% viable, even more preferably at least 98% viable, and most preferably at least 99% viable. It is realized that background data usually does not give any indication about the viability of the cells.

High Through Put Production

It is realized that the present method is suitable for production of relatively large scientific and even large scale industrial and/or therapeutic cell samples. The scientific level process produces about 100 000-1 000 000 cells from about $10^8$ of mononuclear raw material cells The method according to the invention can be upscaled 10-100 fold or even more with established separation technologies. It is realized that in microscale FACS type processes may produce highly pure cell populations, but currently these are not useful for production of larger amounts of cells from large amount of starting material, using FACS to produce larger amounts in numerous batches would be extremely expensive and the cell would suffer at least in terms of viability during lengthy process, probably affecting also recovery and purity. The present invention is preferably directed to preferred purified cell batches comprising about cell in range of 100 000-100 000 000, and in preferred embodiment in range of about 1 000 000 to 10 000 000 cells.

Highly Purified Cell Population Produced According to The Invention

The present invention is preferably directed to the process according to the invention for the production of the reproducible highly purified, preferably complete, viable cell populations according to the invention.

mRNA-Analysis to Reveal Specific Marker mRNAs of Cell Populations

Use of a Highly Purified Mononuclear Cell Population of Cord Blood for mRNA Analysis The present invention is specifically directed to use the highly purified cell populations from human cord blood for analysis of mRNA expression levels. It is realized that the gene expression analysis is highly sensitive and for example 10-30% contamination by cells with high expression levels of specific set of genes could bias the results of gene expression analysis. The gene expression analysis may be performed by any gene expression analysis method, preferably by a known gene expression analysis method.

mRNA-Analysis Methods

In a preferred embodiment the gene expression analysis is performed by at least one mRNA expression analysis method preferably selected from the group: a hydridization method a gene array method, RT-PCR-method, qRT-PCR-method or SAGE-method (serial analysis of gene expression). In an embodiment expression of one preferred mRNA species is performed. In a preferred embodiment mRNA expression analysis is performed for multiple mRNA species. Preferably multiple mRNA species are analysed in a profiling method. The profiling method is preferably directed to the analysis of the status of a cell population. In another embodiment the mRNA-profiling method is directed to or further directed to the analysis of the purity of a cell population.

Analysis of Common mRNA Markers Present in Several Individual Cell Populations

It was realized that even highly purified human cord blood cells population have differences in gene expression levels. The present invention is directed to analysis of mRNA-markers of several individual purified populations of human cord blood cells and comparing the expression profiles. In a preferred embodiment the invention is directed to mRNA markers, which are common for several individual cell populations. The common markers are especially useful for recognition of cell populations where individual variations exist. According to the invention the analysis of individual variation of mRNA-markers is especially useful for analysis of cell populations, especially mononuclear cell populations, of human cord blood.

Preferred Cell Populations

Inventors discovered mRNA markers present in purified cell populations of human cord blood. More preferably the cells have special differentiation capacity.

In a specific embodiment the present invention is directed to mRNA markers overexpressed in human CD133+ and/or CD 34+ cell populations derived from cord blood. In a preferred embodiment the present invention is directed to mRNA markers overexpressed in both human CD133+ and CD 34+ cell populations derived from cord blood.

In another preferred embodiment the present invention is directed to mRNA markers over-expressed in human CD133+ but less effectively expressed in CD 34+ cell populations derived from cord blood. This indicates mRNA markers, which are coexpressed with CD133. The present invention is specifically directed to methods for recognition of cell populations with weak association with CD34 mRNA expression but with high expression of CD133 co-expressed markers. The analysis of CD133 associated markers would be useful for analysis of status or purity of CD133 or CD34 cell populations.

The CD34 positive cell population is relatively large and heterogenous. It is not optimal for several applications aiming to produce specific cell products. The present invention is preferably directed to specifically selected non-CD34 populations, called homogenous cell populations. The homogenous cell populations are in generally smaller size mononuclear cell populations with size corresponding to CD133+ cell populations and being smaller than CD34+ cell populations. The homogenous cell population may a subpopulation of CD34+ cell population, but in preferred embodiment it is a CD133 cell population or CD133-type cell population. Preferably the homogenous cell populations are selected by binding a specific binder to a cell surface marker of the cell population. Preferably the homogenous cells are selected by a cell surface marker having correlation low correlation with CD34-marker and high correlation with CD133 on cell surfaces. Preferred cell surface markers include α3-sialylated structures according to the present invention enriched in CD133-type cells. Pure, preferably complete, CD133+ cell population are preferred for the analysis according to the present invention.

The present invention is directed to essential mRNA-markers, which would allow analysis or recognition of the cell populations from pure cord blood derived material. The present invention is specifically directed to markers specifically expressed early human cord blood cells.

The present invention is in a preferred embodiment directed to native cells, meaning non-genetically modified cells. Genetic modifications are known to alter cells and background from modified cells the present invention further directed in a preferred embodiment to fresh non-cultivated cells The invention is directed to use of the markers for analysis of cells of special differentiation capacity, the cells being preferably human blood cells or human more preferably cord blood cells.

In a specific embodiment the invention is directed to the analysis of presence of cord blood derived mononuclear cell populations by using the markers according to the present invention.

The invention further revealed novel markers for human multipotent cell or stem cells, the invention is specifically directed to the markers for the analysis of stem cells.

Preferred Cell Populations for the Uses According to the Invention

The present invention is preferably directed to complete cell populations selected with regard to a single marker.

The present invention is further directed to analysis of CD133-type cell populations, preferably complete cell populations on mRNA levels and their correlation with marker mRNAs.

The "CD133-type cell populations" according to the invention are similar to the CD133+ cell populations, but preferably selected with regard to another marker than CD133. The marker is preferably a CD133-coexpressed marker. In a preferred embodiment the invention is directed to CD133+ cell population or CD133+ subpopulation as CD133-type cell populations The invention is further directed to analysis of the marker levels by methods according to the present invention, and analysis of the preferred marker combinations according to the present invention.

Preferred Markers and Reagents with Regard to Novelty

The present invention is directed to novel markers and reagents for the methods according to invention. These have clear benefits on two levels 1) first these are patentable 2) there is less need for potential licensing fees related to earlier patents for using the products. The inventors did search potential background to reveal the novel markers. However, it is realized that the amount of potential background is exhaustive due to various genomics works and part of the potential background is not practically available for the search by the inventors.

The present invention disclaims the markers about which there is real novelty background to the level there is real relevant background, which would prevent the patenting of the specific marker on a specific region. It is realized background can be found searching various databases.

Preferred Markers for Specific Cell Populations

Highest Expression Levels

The present invention is specifically directed to markers of highest expression level in the preferred cell population. The markers of the highest expression are most effective in differentiating the cell populations from other cell populations not having equally high expression level of one or several of the mRNA-markers of the highest expression levels. The present invention is specifically directed to use of the mRNA markers of highest expression levels for methods according to the invention.

Hematopoietic Stem Cell Related Marker mRNAs

The present invention is directed to analysis from purified cell populations, preferably highly purified complete cell populations according to the present invention, when these are analysed with regard to enriched hematopoietic stem cell marker mRNAs as specific group or as specific subgroups or as individual markers selected from the group CD133, CD34, KIT, TIE, SCA-1, MEIS1 and ANGPT1. In a preferred embodiment the invention is directed to use of this group of marker mRNA, and preferred subgroups of it including KIT, TIE1, SCA-1, MEIS1 and ANGPT1, more preferably SCA-1, KIT, ANGPT1 and TIE; SCA-1, most preferably TIE1 and ANGPT1; or in separately preferred embodiments SCA-1 and TIE1; SCA-1 and ANGPT1. In a preferred embodiment the present invention is directed to analysis of early human cell population not selected by CD34 antibody, preferably a non-CD34+ cell population is a CD133 expressing homogenous cell population. In another preferred embodiment the invention is directed to methods involving combinations of a preferred marker group with CD133 preferably CD133 mRNA Preferably markers SCA-1, KIT, ANGPT1 or TIE1 (TIE), more preferably SCA-1, TIE1 or ANGPT1, and most preferably SCA-1 or ANGPT1 is analysed. In a preferred embodiment ANGPT1 is analysed from CD133-type cells. In another preferred embodiment SCA-1 is analysed from a preferred early human cell population.

The preferred hematopoietic stem cells related-markers includes CD133, CD34, KIT, TIE1, ANGPT1, SCA-1, and MEIS1.

The invention is further directed to each marker as individual marker. The specific scope of invention with regard to a specific marker is presented below or in other preferred marker groups.

ANGPT1

The present invention is specifically directed to ANGPT1 as a marker of CD133 positive complete cell populations, preferably complete blood derived cell populations, more preferably, complete cell populations derived from cord blood.

TIE1

The present invention shows TIE1 as an important marker of complete cell populations, especially from complete CD133 cell populations and in combination with other important markers.

SCA-1

The present invention is preferably directed to markers of human cells for which the background is not relevant. SCA-1 is preferred for all cells and methods according to the invention, most preferably for the preferred CD133 type cells.

MEIS1

MEIS1 is a preferred angiogenesis, especially capillary angiogenesis associated marker. MEIS1 is preferred for all cells and methods according to the invention, most preferably for the preferred CD133 type cells.

KIT (CD117)

The present invention shows KIT as an important marker of complete cell populations, especially from complete CD133 cell populations and in combination with other important markers.

Transcription Related Markers Especially for Hematopoietic Analysis

Genes upregulated in CD133 cells and supporting self-renewal, such as transcription factor GATA2, MPLV, transcription factor signal transducer and activator of transcription STAT5A, and Wnt-signalling pathway transcription factor TCF7L2 are preferred for the mRNA-directed methods according to the present invention. These genes are especially preferred with regard to analysis in context of hematopoiesis. Upregulated Hox (homeobox genes, transcription related) genes involved in HSC regulation and stem cell expansion such as HOXA9 (fold change 130), HOXA5 (fold change 10) and HOXA10 (fold change 3.7) are also preferred as separate group for analysis and methods according to the present invention. Fold changes indicate the change of expression level in CD133+ cell population in comparison to CD133− cells, similarity fold changes may be used for comparison other two cell populations, which are positive and negative with regard to a specific marker of a specific cell population.

Transcription Factors

The present invention is further directed markers related to specifically expressed transcription factors.

The invention is further directed to each marker as an individual marker. The specific scope of invention with regard to a specific marker is presented below or in other preferred marker groups.

STAT5

The invention is specifically directed to the marker of STAT5 for analysis of CD133-type populations, and/or from complete cell populations according to the invention, derived from mononuclear cells and/or cell populations of human cord blood.

GATA-2

The invention is specifically directed to the marker of GATA-2 for analysis of CD133-type cell populations, and/or from complete cell populations according to the invention, derived from mononuclear cells and/or cell populations of human cord blood.

Tcf7L2/TFC4

The invention is specifically directed to the mRNA for analysis of mononuclear cells and/or cell populations from human cord blood, preferably CD133-type cell populations. The present invention is further directed to Tcf7L2/TFC4 mRNA as a novel hematopoietic stem cell marker.

HOXA5

The invention is specifically directed to the mRNA for analysis of mononuclear cells and/or cell populations from human cord blood, preferably CD133-type cell populations. The present invention is further directed to HOXA5 mRNA as a novel hematopoietic stem cell marker.

Mitogen-Activated Protein Kinase Kinase Kinase 4, Map3K4

The invention is specifically directed to the mRNA for analysis of mononuclear cells and/or cell populations from human cord blood, preferably CD133-type cell populations. The present invention is further directed to MAP3K4 mRNA as a novel hematopoietic stem cell marker.

CD133 Specific Early Cell Markers

Baalc (brain and acute leukemia cytoplasmic) has been reported in another context as development related protein from CD34+ bone marrow cells and to be associated with muscle development (Satoskar A A et al Gene Expr Patterns (2005) 5 (4) 463-73). The inventors were able to find high specific expression of the gene in preferred homogenous cell populations according to invention. Cytoplasmic markers are especially useful for mRNA analysis but corresponding proteins are likely not useful as cell surface markers.

Intracellular transcription related molecules are not preferred for the analysis of extracellular marker structures. Their regulated expression patterns are very useful for mRNA-analytics. In a specific embodiment the invention is directed to the analysis of intracellular glycosylation of potential intracellular protein corresponding to a mRNA according to the preferred embodiment, more preferably intracellular O-GlcNAc glycosylation is analyzed from a protein of preferred cell population. More preferably O-GlcNAc is analyzed from potential STAT5-protein.

Overexpressed mRNA Corresponding to a Potential Extracellular Signal Transduction Molecule The overexpression of C17, a gene coding for an extracellular molecule with signal transduction activity, was 15-fold. The overexpressed mRNA is preferred for analysis according to the invention.

Additional Preferred mRNA Markers Especially for Hematopoiesis Related Analysis

The present invention is further directed to analysis of following hematopoiesis directed markers: preferably overexpression of AML1, downregulations of NFE2 and CD45, and lack of PAX5 and GATA1 and PU.1 and lack of the expression of lineage-determination markers, preferably glycophorin-A, CD38, CD7, CD33, CD56, CD16, CD3, or CD2. The invention is directed in a preferred embodiment to analysis of markers indicating the lineage negative status of cell populations from preferred cells. Preferred hematopoiesis directed assay would be directed to analysis of myeloid and/or lymphoid lineage potential.

Preferred Gene Clustering Methods Derived Markers

Genclustering methods revealed a group four associated mRNAs, a novel marker SPINK2 had similar expression pattern with known HSC markers CD133, CD34 and KIT. The association of SPINK2 and HSCs has not been described previously. The present invention is specifically directed to mRNA analysis of hematopoietic stem cells, and more preferably preferred cells according to the invention, when SPINK2 is used for the analysis. The present invention is further directed to analysis of SPINK2 together with at least one other preferred marker according to the present invention, more preferably with at least one marker selected from the group CD133, CD34 and KIT.

The gene clustering methods further revealed that FLT3, LAPTM4B, EBPL and CRIM1 had minor variance in all CD133+ samples, and are form a preferred target group for analysis according to the present invention, more preferably a novel marker LAPTM4B, EBPL or CRIM1 is analyzed, yet more preferably LAPTM4B or CRIM1 is analyzed. CRIM1 is also preferred as potential glycan expressing protein according to the invention. The CRIM1 is further preferred as an angiogenesis or endothelial directed mRNA.

Other very similarly expressed transcripts were ANKRD28, and several members of the HOX gene family and transcripts encoding hypothetical proteins, preferably the invention is further directed to mRNA analysis with regard to these genes. Moreover, DKC1, BAALC and JUP had minimal variation within CD133+ replicates, and are a preferred group for analysis according to the invention.

In contrast, slightly more variation was observed in the expression of KIT, a known stem cell marker. In another separate embodiment the invention is directed to the expression of KIT in a preferred cell population according to the invention, preferably with one or more preferred other mRNA or other preferred markers according to the invention.

Three groups of similarly expressed markers were obtained. The preferred markers includes SPINK2, CD133, CD34, KIT, FLT3, LAPTM4B, EBPL, CRIM1, ANKRD28, DKC1, BAALC and JUP. The preferred subgroups are group1: SPINK2, CD133, CD34, and KIT; group2 FLT3, LAPTM4B, EBPL and CRIM1; group3 ANKRD28, DKC1, BAALC and JUP.

The invention is further directed to each marker as individual marker. The specific scope of invention with regard to a specific marker is presented below or in other preferred marker groups.

Ankyrin Repeat Domain 28, ANKRD28

The invention is specifically directed to the mRNA for analysis of mononuclear cells and/or cell populations from human cord blood, preferably CD133-type cell populations. The present invention is further directed to ANKRD28 mRNA as a novel hematopoietic stem cell marker.

The present invention is further directed to ANKRD28 mRNA as a novel stem cell marker.

Baalc (Brain and Acute Leukemia Cytoplasmic)

The invention is specifically directed to the mRNA for analysis of mononuclear cells and/or cell populations from human cord blood, preferably CD133-type cell populations. The present invention is further directed to Baalc mRNA as a novel hematopoietic stem cell marker in human cord blood.

Dyskeratosis Congenita 1 Dyskerin, DKC1

The invention is specifically directed to the mRNA for analysis of mononuclear cells and/or cell populations from human cord blood, preferably CD133-type cell populations.

The present invention is further directed to DKC1 mRNA as a novel hematopoietic stem cell marker.

The present invention is further directed to ANKRD28 mRNA as a novel stem cell marker.

EBPL Emopamil Binding Protein

The invention is specifically directed to the mRNA for analysis of mononuclear cells and/or cell populations from human cord blood, preferably CD133-type cell populations. The present invention is further directed to EBPL mRNA as a novel hematopoietic stem cell marker.

The present invention is further directed to EBPL mRNA as a novel stem cell marker.

Serine Protease Inhibitor, Kazal Type 2 (Acrosin-Trypsin Inhibitor), SPINK2

The invention is specifically directed to the mRNA for analysis of mononuclear cells and/or cell populations from human cord blood, preferably CD133-type cell populations. The present invention is further directed to SPINK2 mRNA as a novel hematopoietic stem cell marker.

Cell Adhesion Related Molecules

The invention is further specifically directed 12 mRNA-markers that encode adhesion related molecules and were up-regulated in CD133+ cells.

The overexpression of these genes (ALCAM, CD34, COL5A1, DSG2, DST, IL-18, ITGA9, JUP, PKD2, SEPP1, TRO, VAV3, and VLA-4) was observed in CD133-type cell according to the invention. The invention is preferably directed to individual novel markers and subgroups thereof, the individual novel markers according to the invention includes ALCAM, COL5A1, DSG2, DST, IL-18, ITGA9, JUP, PKD2, SEPP1, TRO, VAV3, and VLA-4, more preferably COL5A1, DSG2, DST, IL-18, ITGA9, JUP, PKD2, SEPP1, TRO, VAV3, and VLA-4; and even more preferably COL5A1, DSG2, DST, IL-18, JUP, PKD2, SEPP1, TRO, VAV3.

Part of the markers are especially preferred as cell adhesion supportive factors, especially in connection with cell junctions and cytoskeleton, these are referred as group 1 (of cell adhesion related molecules): DSG2, DST, JUP, PKD2, VAV3.

Part of the molecules have roles as extracellular proteins supporting cell adhesion, referred under the embodiment as group 2, such as IL-18, COL5A1, SEPP1.

The third preferred group includes cell adhesion receptors ALCAM, ITGA9, and VLA-4.

The invention is further directed to each marker as individual marker. The specific scope of -invention with regard to a specific marker is presented below or in other preferred marker groups.

IL-18

IL-18 is cell adhesion related protein but as a cytokine not a direct cell adhesion receptor molecule.

The invention is specifically directed to the mRNA for analysis of mononuclear cells and/or cell populations from human cord blood, preferably CD133-type cell populations. The present invention is further directed to IL-18 mRNA as a novel hematopoietic stem cell marker.

The present invention is further directed to IL-18 mRNA as a novel stem cell marker.

JUP (Plakoglobin, Gamma-Catenin)

JUP may function as intracellular protein and its role is especially related to cell junctions and support of cell adhesion.

The invention is specifically directed to the mRNA for analysis of mononuclear cells and/or cell populations from human cord blood, preferably CD133-type cell populations. The present invention is further directed to JUP mRNA as a novel hematopoietic stem cell marker The present invention is further directed to JUP mRNA as a novel stem cell marker.

Polycystin-2 PKD2

PKD2 may function as intracellular protein and its role is especially related to cell junctions and support of cell adhesion.

The invention is specifically directed to the mRNA for analysis of mononuclear cells and/or cell populations from human cord blood, preferably CD133-type cell populations. The present invention is further directed to PKD2 mRNA as a novel hematopoietic stem cell marker.

The present invention is further directed to PKD2 mRNA as a novel stem cell marker.

VAV3

VAV3 may function as intracellular protein and its role is especially related to cell junctions and support of cell adhesion.

The invention is specifically directed to the mRNA for analysis of mononuclear cells and/or cell populations from human cord blood, preferably CD133-type cell populations. The present invention is further directed to VAV3 mRNA as a novel hematopoietic stem cell marker.

The present invention is further directed to VAV3 mRNA as a novel stem cell marker.

VLA4, (Very Late Activation Antigen 4), Integrin Alpha4Beta1

VLA4 is specifically preferred as an overexpressed marker in native CD133 type cells, and preferred homogenous cell populations according to the invention. VLA is further preferred as combination with novel markers according to the present invention. VLA is further preferred for analysis of cancer related markers or adult cell marker from the preferred cells according to the invention.

Preferred Receptor Molecules

The inventors revealed markers related to preferred receptor molecules. These includes preferred cell adhesion receptors (group 1 under the embodiment), regulatory receptors (group 2) and growth factor receptors (group 3).

Preferred cell adhesion receptors include ALCAM (Activated leukocyte cell adhesion molecule), ITGA9, and VLA-4.

Preferred growth and activating factor receptors include CRIM1 (cysteine-rich motor neuron 1), FLT-3, SCA-1, KIT, TIE1, LRP6 Low density lipoprotein receptor-related protein 6, and TNFRSF21 (tumor necrosis factor receptor superfamily, member 21).

Preferred regulatory receptors include: PTPRD (Protein tyrosine phosphatase, receptor type, D), PILRB (paired immunoglobin-like type 2 receptor beta), ADAM28. Under a specific embodiment SPINK2 with protease inhibitor domain is also considered as a member of this group.

Growth Factors and Cytokines

The inventors were able to define certain growth factors and cytokines being specifically associated with the preferred cell populations.

The invention is especially directed to one or several of the growth factor and cytokine markers according to the invention selected from the group consisting of: ANGPT1, AREG Amphiregulin (schwannoma-derived growth factor), IGFBP7 (Insulin-like growth factor binding protein 7, Angiomodulin/Mac25/tumor adhesion factor TAF, Insulin-like growth factor binding protein-related protein 1), and IL-18, The invention is further directed IGFBP7 (Insulin-like growth factor binding protein 7) as a special growth factor regulating protein.

The invention is further directed to the methods of testing the binding of the cytokine and growth factor markers alone or in combination with regard to the cells according to the invention. The invention is especially directed testing and optimisation of growth conditions of cell culture methods in which any stem cells or cells according to the invention is cultivated in presence of ANGPT1, AREG, IGFBP7, and/or IL-18 more preferably markers with angiogenesis/growth factor association are selected: ANGPT1, AREG and/or IGFBP7. It is realized that because there is specific expression of the factors in the stem cell fractions, the growth factors are related to the activities of the cells cultivated in the presence of these. In a preferred embodiment the cells are cultivated in the presence of one or several of the factors in order to control the differentiation of the cell population.

In a preferred embodiment ANGPT1 is selected for the cell growth experiments in order to accomplish/affect differentiation of cell polulation, preferably to mesenchymal and/or neuroectodermal direction. In a preferred embodiment IGFBP7 is selected for the cell growth experiments in order to accomplish/affect differentiation of cell polulation, preferably to mesenchymal and/or neuroectodermal direction. In a preferred embodiment AREG is selected for the cell growth experiments in order to accomplish/affect differentiation of cell population, preferably to mesenchymal and/or neuroectodermal direction.

Cell Matrix Related Markers

The invention is further specifically directed to extracellular matrix related markers col5a1 (collagen type V alpha 1), and MMP28, matrix metalloproteinase 28.

It is realized that cell matrix related markers would have major effects in cell growth and/or differentiation. The invention is further directed to the methods of testing the binding of the cell matrix related markers alone or in combination with regard to the cells according to the invention. The invention is especially directed testing and optimisation of growth conditions of cell culture methods in which any stem cells or cells according to the invention is cultivated in presence of col5a1, or MMP28 or an inhibitor of MMP28, more preferably col5a1. It is realized that inhibitor of MMP28 would likely also have major effect on the cell growth/differentiation, but likely to opposite direction in comparison to MMP28.

It is realized that because there is specific expression of the factors in the stem cell fractions, the cell matrix related factors are related to the activities of the cells cultivated in the presence of these. In a preferred embodiment the cells are cultivated in the presence of one or several of the factors in order to control the differentiation of the cell population.

In a preferred embodiment col5a1 is selected, as an important regulating cell matrix component, for the cell growth experiments in order to accomplish/affect differentiation of cell polulation, preferably to mesenchymal and/or neuroectodermal direction In a another preferred embodiment MMP28 or an inhibitor of MMP28 is selected for the cell growth experiments in order to accomplish/affect differentiation of cell polulation, preferably to mesenchymal and/or neuroectodermal direction. In a preferred embodiment MMP28 is selected for the cell growth experiments in order to accomplish/affect differentiation of cell population, preferably to mesenchymal and/or neuroectodermal direction.

Marker of Highest Weight Value in Gene Priorization Analysis

LAPTM4B got the highest weight value in gene prioritization. LAPTM4B is a preferred marker for the analysis of the cells according to the invention and preferred in for the use together with other preferred markers according to the invention.

LAPTM4B

The invention is specifically directed to the mRNA for analysis of mononuclear cells and/or cell populations from human cord blood, preferably CD133-type cell populations. The present invention is further directed to LAPTM4B mRNA as a novel hematopoietic stem cell marker.

Cell Cycle Related Markers

The invention is further directed to analysis of early human cells by using preferred overexpressed and underexpressed cell cycle related markers in the preferred cell populations.

The invention is further directed to the approximate levels of overexpression or underexpression of the preferred cell cycle related markers in the preferred cell populations according to the present invention, most preferably in a CD133+ cell population. Preferably the preferred marker has at least similar level of underexpression or overexpression in the preferred cell population when compared to cell population from which the preferred cell population is isolated from by selection by a marker such as CD133. The preferred cell cycle related markers includes: GATA2 N-MYC, DST, PLAGL1, NME1, CDK6, BCAT1, CDK4, BMI-1 MCM2, MCM5, MCM6, MCM7 CDK2AP1, SH3MD2, UHRF1, ZNRF1, EDD, SKB1, STAG1, ANAPC7 and MPHOSPH9. The invention is preferably further directed to down regulated markers p18, and CDKN2D.

Further preferred subgroups of cell cycle related markers include:

GATA2 (fold change 7.0 in CD133+ cells in comparison with CD133− cells of cord blood) and N-MYC (fold change 15 in CD133+ cells), DST (fold change 5.3) and PLAGL1 (fold change 9.1) and NME1 (overexpressed in CD133+ cells by 3.7-fold), CDK6 (fold change 10) and BCAT1 (fold change 19), CDK4 (fold change 3.9) and BMI-1 (overexpression by 2.8-fold). The invention is preferably further directed down regulated marker p18, (underexpressed by 5.1-fold in CD133+ cells in comparison with CD133− cells of cord blood). Furthermore preferred overexpressed cell cycle markers includes S-phase related markers: MCM2 (fold change 3.1), MCM5 (fold change 4.2), MCM6 (fold change 2.5) and MCM7 (fold change 2.8), were up-regulated; CDK2AP1 (overexpressed by 4-fold) and a down regulated marker CDKN2D (underexpressed by 20-fold). Additionally preferred cell cycle related markers include transcripts for molecules with ubiquitin-protein ligase activity, such as SH3MD2, UHRF1, ZNRF1, EDD and TIF1 (over-expressed more than 3-fold). Furthermore the invention is directed to specific over-expressed genes associated with mitosis, preferably SKB1, STAG1, ANAPC7 and MPHOSPH9 (overexpressed by 2.6-fold, 1.6-fold, 2.6-fold and 3.1-fold, respectively).

Cell Cycle Related Markers

GATA2, N-MYC, DST, PLAGL1, NME1, CDK6, BCAT1, CDK4, BMI-1 MCM2, MCM5, MCM6, MCM7, CDK2AP1, SH3MD2, UHRF1, ZNRF1, EDD, SKB1, STAG1, ANAPC7 and MPHOSPH9. The invention is preferably further directed to down regulated markers p18, and CDKN2D GATA2 is also preferred as a preferred transcription factor.

The invention is further directed to each marker as individual marker. The specific scope of invention with regard to a specific marker is presented below or in other preferred marker groups.

N-MYC

The invention is specifically directed to the marker of GATA-2 for analysis of CD133-type cell populations, and/or from complete cell populations according to the invention, derived from mononuclear cells and/or cell populations of human cord blood.

Dystonin DST

The invention is specifically directed to the mRNA for analysis of mononuclear cells and/or cell populations from human cord blood, preferably CD133-type cell populations. The present invention is further directed to DST mRNA as a novel hematopoietic stem cell marker.

Pleiomorphic Adenoma Gene Like1, Plagl1 (Lot1/Zac1)

The invention is specifically directed to the mRNA for analysis of mononuclear cells and/or cell populations from human cord blood, preferably CD133-type cell populations. The present invention is further directed to Plagl1 mRNA as a novel hematopoietic stem cell marker.

NME1

The invention is specifically directed to the mRNA for analysis of mononuclear cells and/or cell populations from human cord blood or subpopulations thereof. The present invention is further directed to NME1 mRNA as a novel hematopoietic stem cell marker.

The present invention is further directed to NME1 mRNA as a novel stem cell marker.

CDKN2 (p16INK4a)

The invention is specifically directed to the mRNA for analysis of mononuclear cells and/or cell populations from human cord blood, preferably CD133-type cell populations. The present invention is further directed to CDKN2 mRNA as a novel hematopoietic stem cell marker.

CDK4, Cyclin Dependent Kinase 4

CDK4 mRNA appears to be novel marker for the preferred cell populations according to the invention. The invention is specifically directed to the mRNA for analysis homogenous/complete cell populations from human cord blood, preferably CD133-type cell populations.

CDK6

The invention is specifically directed to the mRNA for analysis homogenous/complete cell populations from human cord blood, preferably CD133-type cell populations.

CDK2AP1 (p12DOC-1)

The invention is specifically directed to the mRNA for analysis of mononuclear cells and/or cell populations from human cord blood, preferably CD133-type cell populations. The present invention is further directed to CDK2AP1 mRNA as a novel hematopoietic stem cell marker.

BCAT-1

The invention is specifically directed to the mRNA for analysis of mononuclear cells and/or cell populations from human cord blood, preferably CD133-type cell populations. The present invention is further directed to BCAT-1 mRNA as a novel hematopoietic stem cell marker.

BMI-1

The invention is specifically directed to the mRNA for analysis of mononuclear cells and/or cell populations from human cord blood, preferably CD133-type cell populations. The present invention is further directed to BMI-1 mRNA as a novel hematopoietic stem cell marker.

Minichromosome Maintenance Protein-2, MCM-2

The invention is specifically directed to the mRNA for analysis of mononuclear cells and/or cell populations from human cord blood, preferably CD133-type cell populations. The present invention is further directed to MCM-2 mRNA as a novel hematopoietic stem cell marker.

The invention is further directed to MCM-2 mRNA as a novel stem cell marker.

Minichromosome Maintenance Protein-5, MCM-5

The invention is specifically directed to the mRNA for analysis of mononuclear cells and/or cell populations from human cord blood, preferably CD133-type cell populations. The present invention is further directed to MCM-5 mRNA as a novel hematopoietic stem cell marker.

Minichromosome maintenance protein-6, MCM-6

The invention is specifically directed to the mRNA for analysis of mononuclear cells and/or cell populations from human cord blood, preferably CD133-type cell populations. The present invention is further directed to MCM-6 mRNA as a novel hematopoietic stem cell marker.

The invention is further directed to MCM-6 mRNA as a novel stem cell marker.

Minichromosome Maintenance Protein-7, MCM-7

The invention is specifically directed to the mRNA for analysis of mononuclear cells and/or cell populations from human cord blood, preferably CD133-type cell populations. The present invention is further directed to MCM-7 mRNA as a novel hematopoietic stem cell marker.

The invention is further directed to MCM-7 mRNA as a novel stem cell marker

Anaphase Promoting Complex Subunit 7, ANAPC7

The invention is specifically directed to the mRNA for analysis of mononuclear cells and/or cell populations from human cord blood, preferably CD133-type cell populations. The present invention is further directed to ANAPC7 mRNA as a novel hematopoietic stem cell marker.

The invention is further directed to ANAPC7 mRNA as a novel stem cell marker.

M-Phase Phosphoprotein 9, MPHOSPH9

The invention is specifically directed to the mRNA for analysis of mononuclear cells and/or cell populations from human cord blood, preferably CD133-type cell populations. The present invention is further directed to MPHOSPH9 mRNA as a novel hematopoietic stem cell marker.

The invention is further directed to MPHOSPH9 mRNA as a novel stem cell marker.

Ubiquitin-Like, Containing PHD and Ring Finger Domains, 1, UHRF1

The invention is specifically directed to the mRNA for analysis of mononuclear cells and/or cell populations from human cord blood, preferably CD133-type cell populations. The present invention is further directed to UHRF1 mRNA as a novel hematopoietic stem cell marker.

The invention is further directed to UHRF1 mRNA as a novel stem cell marker.

SH3 Multiple Domains 2, SH3MD2

The invention is specifically directed to the mRNA for analysis of mononuclear cells and/or cell populations from human cord blood, preferably CD133-type cell populations. The present invention is further directed to SH3MD2 mRNA as a novel hematopoietic stem cell marker.

The invention is further directed to SH3MD2 mRNA as a novel stem cell marker.

Skb1

The invention is specifically directed to the mRNA for analysis of mononuclear cells and/or cell populations from human cord blood, preferably CD133-type cell populations. The present invention is further directed to Skb1 mRNA as a novel hematopoietic stem cell marker.

The invention is further directed to Skb1 mRNA as a novel stem cell marker.

ZNRF1

The invention is specifically directed to the mRNA for analysis of mononuclear cells and/or cell populations from human cord blood, preferably CD133-type cell populations. The present invention is further directed to ZNRF1 mRNA as a novel hematopoietic stem cell marker.

The invention is further directed to ZNRF1 mRNA as a novel stem cell marker.

STAG1/Stromal antigen 1, Stro-1

Stro-1 mRNA appears to be novel marker for the preferred cell populations according to the invention. The invention is specifically directed to the mRNA for analysis of mononuclear cells and/or cell populations from human cord blood, preferably CD133-type cell populations.

The present invention is further preferably directed to Stro-1 mRNA as a novel human hematopoietic stem cell marker.

EDD

The invention is specifically directed to the mRNA for analysis of mononuclear cells and/or cell populations from human cord blood, preferably CD133-type cell populations. The present invention is further directed to EDD mRNA as a novel hematopoietic stem cell marker.

p18, Cyclin Dependent Kinase Inhibitors p18INK4c

The invention is specifically directed to the mRNA for analysis of mononuclear cells and/or cell populations from human cord blood, preferably CD133-type cell populations. The present invention is further directed to p18 mRNA as a novel hematopoietic stem cell down-regulated marker from human cord blood.

Preferred Markers Associated with Non-Hematopoietic Early Cell Properties

The present invention is specifically directed to preferred markers, which are directed to general stem cell like differentiation capabilityor non-hematopoietic differentiation.

Potential Cell Migration Related Markers

The decreased expression of SPINK2 in testis has been shown to be associated with infertility. Similarly, CD133 has been suggested to have a role in the biogenesis of spermatozoa and the molecule may function in the formation and stabilization of epididymal stereocilia and tail of spermatozoa. CD133 expression is assumed to affect the formation of lamellipodia enabling HSC migration. Similarily selenoprotein P (SEPP1), also preferred as potential glycoprotein, has been associated with spem development and flagellar development (Olson G E, et al. Biol Reprod (2005) Mar. 2, 2005 ahead of print). The invention is specifically directed to SPINK2, CD133 and SEPP1 in analysis of early human cell populations according to the invention, more preferably in analysis of migratory early human cell populations, more preferably SPINK2 or SEPP1 is analyzed.

The present invention is specifically directed to markers selected from the group: SPINK2, CD133 and SEPP1; more preferably SPINK2 and SEPP1 and most preferably SPINK2; as potential cell migration associated markers. These molecules have been associated with sperm/microvillus development. The invention is directed to the use of the marker SPINK2 together with any other preferred markers for methods according to the invention, more preferably together with CD133 and/or SEPP1.

Markers Related to Potential Endothelial Development

The present invention is specifically directed to markers according to the present invention when these have connection to potential proteins associated with potential endothelial development. The markers potentially related to endothelial development include JUP, DSG2, TIE1, ANGP1 and CRIM1. Preferred subgroups of endothelial development associated markers includes adhesive junction related molecules, early endothelia related molecules and angiogenesis associated molecules. Preferred adhesive junction associated mRNAs include: mRNA of plakoglobin (JUP) and desmoglein 2 (DSG2). Preferred angiogenesis associated mRNA markers include TIE and angiopoietin1 (ANGP1). Preferred early endothelial related molecules includes CRIM1 mRNA.

The present invention is specifically directed to markers according to the present invention when these have connection to potential proteins associated with potential endothelial development. The markers potentially related to endothelial development include ADAM28, ANGP1, CRIM1, DSG2, EMP1, JUP, MAGI1, TIE1.

Preferred potential endothelial development associated mRNAs were selected by comparing expression between CD133+ and CD34+ cells, the following markers were revealed to be associated with CD133+ type cells ANGP1, DESG2, CRIM1, EMP1, ADAM28, and MAGI1.

The invention is further directed to each marker as individual marker. The specific scope of invention with regard to a specific marker is presented below or in other preferred marker groups.

MAGI1, Membrane Associated Guanylated Kinase Inverted-1

The invention is specifically directed to the mRNA for analysis of mononuclear cells and/or cell populations from human cord blood, preferably CD133-type cell populations. The present invention is further directed to MAGI1 mRNA as a novel hematopoietic stem cell marker.

Markers Related to Potential Neuronal Development

The present invention is specifically directed to markers according to the present invention when these have connection to potential proteins associated with potential early neuronal development.

Preferred early neuronal related molecules include mRNAs of CRIM1, SV2A (synaptic vesicle glycoprotein 2A).

ESC-Related Stem Cell Markers

The present invention is specifically directed to transcriptional analysis of embryonal stem cell related markers in the preferred cell populations. Preferred ESC-related stem cell markers, such as DNMT3B, DNMT3A, and DPPA4 were over-expressed in CD133+ cells. DNMT3B is especially preferred as potential de novo DNA-methylation related mRNA and DPPA4 as an embryonal development pluripotency associated gene.

The invention is further directed to each marker as individual marker. The specific scope of invention with regard to a specific marker is presented below or in other preferred marker groups.

DNMT3B and DNMT3A

DNMT3B, and DNMT3A mRNA appear to be novel markers for the preferred cell populations according to the invention.

The invention is specifically directed to the mRNA for analysis of mononuclear cells and/or cell populations from human cord blood, preferably CD133-type cell populations. The present invention is further directed to DNMT3B, and DNMT3A mRNA as a novel neonatal hematopoietic stem cell marker.

DPPA4

The invention is specifically directed to the mRNA for analysis of mononuclear cells and/or cell populations from human cord blood, preferably CD133-type cell populations. The present invention is further directed to DPPA4 mRNA as a novel hematopoietic stem cell marker.

Early CD133-Type Cell Population with Low CD34 Association

The inventors were able to observe markers of special early blood mononuclear cell populations which have low association with CD34 marker. As CD34 is associated with hematopoiesis and the low association markers are likely to be associated with development to other cell types. The inventors were able to observe differences between CD34+ cell populations and CD133-type homogenous cell populations. The following mRNA markers are preferred for the analysis of the homogenous CD133-type cell populations: SV2A, FLVCR, SLC16A14, ALCAM, DSG2 and FLT3.

Transmembrane and/or Membrane Associated Proteins

The present invention is preferably directed to following markers related to transmembrane and/or membrane associated proteins shown in Table. Additionally preferred membrane or membrane associated proteins includes human the receptor tyrosine kinase TIE1 and SCA-1.

The invention is further directed to each marker as individual marker. The specific scope of invention with regard to a specific marker is presented below or in other preferred marker groups.

ADAM28

The invention is specifically directed to the mRNA for analysis of mononuclear cells and/or cell populations from human cord blood, preferably CD133-type cell populations. The present invention is further directed to ADAM28 mRNA as a novel hematopoietic stem cell marker.

The present invention is further directed to ADAM28 mRNA as a novel stem cell -marker.

ALCAM, Activated Leukocyte Cell Adhesion Molecule (Mouse Dm-Grasp Protein; Rat MEMD Protein, HB2, SB-10 Antigen, KG-CAM)

The invention is specifically directed to the mRNA for analysis of mononuclear cells and/or cell populations from human cord blood, preferably CD133-type cell populations. The present invention is further directed to ALCAM mRNA as a novel neonatal hematopoietic stem cell marker.

Amphiregulin AREG

Actually in a preferred embodiment soluble glycoproteins growth factor at least in most cases, it is preferred also as a membrane associated protein, larger isoform is known.

The invention is specifically directed to the mRNA for analysis of mononuclear cells and/or cell populations from human cord blood, preferably CD133-type cell populations. The present invention is further directed to AREG mRNA as a novel hematopoietic stem cell marker.

The invention is further directed to AREG mRNA as a novel stem cell marker.

ATP9A (ATPase, Class II, Type 9A)

The invention is specifically directed to the mRNA for analysis of mononuclear cells and/or cell populations from human cord blood, preferably CD133-type cell populations. The present invention is further directed to ATP9A mRNA as a novel hematopoietic stem cell marker.

The invention is further directed to ATP9A mRNA as a novel stem cell marker.

CRHBP/CRH-BP, Corticotropin-Releasing Hormone-Binding Protein/ CRFBP/CRF-BP, corticotropin-releasing factor-binding protein The invention is specifically directed to the mRNA for analysis of mononuclear cells and/or cell populations from human cord blood, preferably CD133-type cell populations. The present invention is further directed to CRHBP mRNA as a novel hematopoietic stem cell marker.

The invention is further directed to CRHBP mRNA as a novel stem cell marker.

CRIM1

The invention is specifically directed to the mRNA for analysis of mononuclear cells and/or cell populations from human cord blood, preferably CD133-type cell populations. The present invention is further directed to CRIM1 mRNA as a novel hematopoietic stem cell marker.

The invention is further directed to CRIM1 mRNA as a novel human stem cell marker.

C14rf1 Chromosome 14 Open Reading Frame 1

The invention is specifically directed to the mRNA for analysis of mononuclear cells and/or cell populations from human cord blood, preferably CD133-type cell populations. The present invention is further directed to C14orf1 mRNA as a novel hematopoietic stem cell marker.

The invention is further directed to C14orf1 mRNA as a novel stem cell marker.

CYYR1 (Cysteine and Tyrosine-Rich 1)

The invention is specifically directed to the mRNA for analysis of mononuclear cells and/or cell populations from human cord blood, preferably CD133-type cell populations. The present invention is further directed to CYYR1 mRNA as a novel hematopoietic stem cell marker.

The invention is further directed to CYYR1 mRNA as a novel stem cell marker.

Desmoglein 2, DSG2

The invention is specifically directed to the mRNA for analysis of mononuclear cells and/or cell populations from human cord blood, preferably CD133-type cell populations. The present invention is further directed to DSG2 mRNA as a novel hematopoietic stem cell marker.

Epithelial Membrane Protein 1, EMP1

The invention is specifically directed to the mRNA for analysis of mononuclear cells and/or cell populations from human cord blood, preferably CD133-type cell populations. The present invention is further directed to EMP1 mRNA as a novel hematopoietic stem cell marker.

The invention is further directed to AREG mRNA as a novel human stem cell marker.

FLT3

The present invention is directed to FLT3 as an overexpressed marker in cord blood CD133 type cells and in homogeneous cell populations according to the invention. The invention is further directed to the use of the marker together of other preferred markers and marker groups.

FLVCR (Feline Leukemia Virus Subgroup C Cellular Receptor)

The invention is specifically directed to the mRNA for analysis of mononuclear cells and/or cell populations from human cord blood, preferably CD133-type cell populations. The present invention is further directed to FLVCR mRNA as a novel hematopoietic stem cell marker.

The invention is further directed to FLVCR mRNA as a novel stem cell marker.

GPR125 (G Protein-Coupled Receptor 125)

The invention is specifically directed to the mRNA for analysis of mononuclear cells and/or cell populations from human cord blood, preferably CD133-type cell populations. The present invention is further directed to GPR125 mRNA as a novel hematopoietic stem cell marker.

The invention is further directed to GPR125 mRNA as a novel stem cell marker.

IGFBP7 (Insulin-Like Growth Factor Binding Protein 7)

The invention is specifically directed to the mRNA for analysis of mononuclear cells and/or cell populations from human cord blood, preferably CD133-type cell populations. The present invention is further directed to IGFBP7 mRNA as a novel hematopoietic stem cell marker.

Integrin 9alpha, Alpha9beta1 Integrin, ITG9A

The invention is specifically directed to the mRNA for analysis of mononuclear cells and/or cell populations from human cord blood, preferably CD133-type cell populations. The present invention is further directed to ITG9A mRNA as a novel hematopoietic stem cell marker.

KIAA0286

The invention is specifically directed to the mRNA for analysis of mononuclear cells and/or cell populations from human cord blood, preferably CD133-type cell populations. The present invention is further directed to KIAA0286 mRNA as a novel hematopoietic stem cell marker.

The invention is further directed to KIAA0286 mRNA as a novel stem cell marker.

KIAA0152

The invention is specifically directed to the mRNA for analysis of mononuclear cells and/or cell populations from human cord blood, preferably CD133-type cell populations. The present invention is further directed to KIAA0152 mRNA as a novel hematopoietic stem cell marker.

The present invention is further directed to KIAA0152 mRNA as a novel stem cell marker.

LRP6

The invention is specifically directed to the mRNA for analysis of mononuclear cells and/or cell populations from human cord blood, preferably CD133-type cell populations. The present invention is further directed to LRP6 mRNA as a novel hematopoietic stem cell marker.

MMP28 Matrix Metalloproteinase 28

The invention is preferably directed to MMP28 as a membrane associated protein.

The invention is specifically directed to the mRNA for analysis of mononuclear cells and/or cell populations from human cord blood, preferably CD133-type cell populations. The present invention is further directed to MMP28 mRNA as a novel hematopoietic stem cell marker.

The invention is further directed to MMP28 mRNA as a novel stem cell marker.

PILRB (Paired Immunoglobin-Like Type 2 Receptor Beta)

PILRB mRNA appears to be novel marker for the preferred cell populations according to the invention. The invention is specifically directed to the mRNA for analysis of mononuclear cells and/or cell populations from human cord blood, preferably CD133-type cell populations. The present invention is further directed to PILRB mRNA as a novel neonatal hematopoietic stem cell marker.

PON2, paraoxonase2

The invention is specifically directed to the mRNA for analysis of mononuclear cells and/or cell populations from human cord blood, preferably CD133-type cell populations. The present invention is further directed to PON2 mRNA as a novel hematopoietic stem cell marker.

The present invention is further directed to PON2 mRNA as a novel stem cell marker.

PTPRD (Protein Tyrosine Phosphatase, Receptor Type, D)

The invention is specifically directed to the mRNA for analysis of mononuclear cells and/or cell populations from human cord blood, preferably CD133-type cell populations. The present invention is further directed to PTPRD mRNA as a novel hematopoietic stem cell marker.

The invention is further directed to PTPRD mRNA as a novel stem cell marker.

SLC16A14 (Solute Carrier Family 16 (Monocarboxylic Acid Transporters), Member 14)

The invention is specifically directed to the mRNA for analysis of mononuclear cells and/or cell populations from human cord blood, preferably CD133-type cell populations. The present invention is further directed to SLC16A14 mRNA as a novel hematopoietic stem cell marker.

The invention is further directed to SLC16A14 mRNA as a novel stem cell marker.

SEPP1 (Selenoprotein P, Plasma, 1)

The invention is specifically directed to SEPP1 as a membrane associated marker.

The invention is specifically directed to the mRNA for analysis of mononuclear cells and/or cell populations from human cord blood, preferably CD133-type cell populations. The present invention is further directed to SEPP1 mRNA as a novel hematopoietic stem cell marker.

The invention is further directed to SEPP1 mRNA as a novel stem cell marker.

SV2A

The invention is specifically directed to the mRNA for analysis of mononuclear cells and/or cell populations from human cord blood, preferably CD133-type cell populations. The present invention is further directed to SV2A mRNA as a novel hematopoietic stem cell marker.

The invention is further directed to SLC16A14 mRNA as a novel stem cell marker.

TM7SF3 (Transmembrane 7 Superfamily Member 3)

The invention is specifically directed to the mRNA for analysis of mononuclear cells and/or cell populations from human cord blood, preferably CD133-type cell populations. The present invention is further directed to TM7SF3 mRNA as a novel hematopoietic stem cell marker.

The invention is further directed to TM7SF3 mRNA as a novel stem cell marker.

Transmembrane 6 Superfamily Member 2 Isoform 2 TM6SF1

The invention is specifically directed to the mRNA for analysis of mononuclear cells and/or cell populations from human cord blood, preferably CD133-type cell populations. The present invention is further directed to TM6SF1 mRNA as a novel hematopoietic stem cell marker.

The present invention is further directed to TM6SF1 mRNA as a novel stem cell marker.

TNFRSF21 (Tumor Necrosis Factor Receptor Superfamily, Member 21)/DEATH Receptor 6, DR6

The invention is specifically directed to the mRNA for analysis of mononuclear cells and/or cell populations from human cord blood, preferably CD133-type cell populations. The present invention is further directed to TNFRSF21 mRNA as a novel hematopoietic stem cell marker.

The invention is further directed to TNFRSF21 mRNA as a novel stem cell marker.

Trophinin, TRO

The invention is specifically directed to the mRNA for analysis of mononuclear cells and/or cell populations from human cord blood, preferably CD133-type cell populations. The present invention is further directed to TRO mRNA as a novel hematopoietic stem cell marker.

The invention is further directed to TRO mRNA as a novel stem cell marker

Vezatin

The invention is specifically directed to the mRNA for analysis of mononuclear cells and/or cell populations from human cord blood, preferably CD133-type cell populations. The present invention is further directed to Vezatin mRNA as a novel hematopoietic stem cell marker.

The invention is further directed to Vezatin mRNA as a novel stem cell marker.

Transmembrane and/or Membrane Associated Glycoproteins

The present invention is in a preferred embodiment directed to glycoproteins of the preferred cell populations, most preferably CD133-type cells. The invention is further specifically directed to the analysis of potentially N-glycosylated proteins in connection with analysis of the preferred glycan markers, preferably N-glycan markers according to the invention. The preferred mRNAs corresponding to potential N-glycoproteins preferably include: AREG, ALCAM, ITGA9, FLT3, PTPRD, TM7SF3, PON2, DST, ADAM28, CRIM1, CRHBP, DSG2, EMP1, FSTL1, GPR125, IGFBP7, KIT, MMP28, PILRB, SCA-1, SV2A, SEPP1, TIE1, TNFRSF21, and LRP6 and VLA4.

The invention is further directed to following glycoproteins of higher membrane association, cell surface availability: ALCAM, ITGA9, FLT3, PTPRD, TM7SF3, PON2, ADAM28, CRIM1, CRHBP, DSG2, EMP1, FSTL1, GPR125, IGFBP7, KIT, PILRB, SCA-1, SV2A, SEPP1, TIE1, TNFRSF21, and LRP6 and VLA4.

A preferred group includes following glycoproteins AREG, ALCAM, ITGA9, FLT3, PTPRD, TM7SF3, PON2, DST, which belong to a subgroup of preferred transmembrane proteins and a growth factor AREG.

Another preferred group includes cell surface receptor type glycoproteins such as ADAM28, ALCAM, CRIM1, FLT3, ITGA9, KIT, LRP6, PILRB, PTPRD, TNFRSF21, and VLA4. The receptor type glycoproteins are further preferred as specific subgroups of receptor molecules according to the invention. Another preferred subgroup of the receptors includes novel adhesion related receptors ADAM28, CRIM1, ITGA9, LRP6, PILRB, PTPRD, TNFRSF21, and VLA4.

mRNAs of Possible Extracellular Proteins

The present invention is further directed to mRNA potentially corresponding to secreted cell regulating marker structures.

Following mRNAs are also preferred as marker related to secreted glycoproteins:
CRHBP/CRH-BP, corticotropin-releasing hormone-binding protein
IGFBP7 (Insulin-like growth factor binding protein 7).
MMP28 is a secreted protein, which may exist in membrane associated form
SEPP1 (selenoprotein P, plasma, 1),
Uromodulin-like 1,
or
Collagen Type V Alpha 1, Col5a1, a Preferred Matrix Protein The invention is specifically directed to the mRNA for analysis of mononuclear cells and/or cell populations from human cord blood, preferably CD133-type cell populations. The present invention is further directed to Col5a1 mRNA as a novel hematopoietic stem cell marker.

Uromodulin-like 1, UMODL1

Present invention is specifically directed to UMODL1 mRNA, because the related protein uromodulin is strongly glycosylated protein with potential glycosylation associated functions.

The invention is specifically directed to the mRNA for analysis of mononuclear cells and/or cell populations from human cord blood, preferably CD133-type cell populations. The present invention is further directed to UMODL1 mRNA as a novel hematopoietic stem cell marker.

LT-markers (Lrp6/Tcf7L2-Related) and Cell Junction-Type Signaling Related Marker Groups The preferred LT-markers includes Lrp6, γ-catenin (JUP, plakoglobin), Tcf7L2/TFC4, HOXA9, HOXA10, MAP3K4 and IL-18, more preferably Lrp6, γ-catenin (JUP, plakoglobin), Tcf7L2/TFC4, MAP3K4 and IL-18. The background related material of markers other than HOXA9 and HOXA10 is represented with other groups bellow or above (transcription factors, cell adhesion IL-18).

HOXA9 and HOXA10 Directed Markers

The present invention is specifically targeted to methods and reagents according to the invention when complete and/or homogenous cell populations are used with regard to HOXA9 and/or HOXA10, in a preferred embodiment the cell populations is a CD133 type cell populations, preferably from human cord blood.

LT-markers (Lrp6/Tcf7L2-Related) and Cell Junction-Type Signaling Related Marker Groups Lrp6 is a general signaling receptor, and Tcf7L2/TFC4 is a signaling component associated with Lrp6, revealed by the invention which are associated as proteins with cell biology and in regulatory processes several other markers revealed by the invention.

The present invention is preferably directed marker related to Lrp6 and/or Tcf7L2 associated markers, shortened as LT-markers, as separate preferred markers, as marker subgroups with other preferred properties and as preferred marker groups.

Lrp6 and TfcL2 is strongly associated to Wnt-signalling pathway. It is realized that the present invention may be considered as partial Wnt-related signaling pathway in homogenous human cord blood cell populations. The invention is specifically and separately directed to Lrp6 and TfcL2-related and Wnt-related signaling components and their associated markers revealed by the invention, preferably the preferred LT-signaling markers.

The LT-markers are further related to cell junction structures connecting extracellular structures to intracellular signaling.

The inventors were able to reveal a family of LT-markers in homogenous cell populations of human cord blood cells, in a preferred embodiment in CD133 cells. The combination of the overexpressed markers is new and several of the markers has not been previously known to be overexpressed in hematopoietic stem cells.

The inventors were able to reveal a family of mRNA LT-markers in homogenous cell populations of human cord blood cells, in a preferred embodiment in CD133 cells. The combination of the overexpressed markers is new and several of the markers has not been previously known to be overexpressed in hematopoietic stem cells.

The LT-markers are especially preferred in context of angiogenesis.

The preferred LT-markers pathway markers includes Lrp6, γ-catenin (JUP, plakoglobin), Tcf7L2/TFC4, HOXA9, HOXA10, MAP3K4 and IL-18, more preferably Lrp6, γ-catenin (JUP, plakoglobin), Tcf7L2/TFC4, MAP3K4 and IL-18

The invention is further directed to each marker as individual marker. The specific scope of invention with regard to a specific marker is presented below or in other preferred marker groups.

HOXA9 and HOXA10 Directed Markers

HOXA9 and -10 have been reported from cord blood CD34+ cells (Ferrell C M et al. (2005) Stem Cells 23 (5) 644-55).

The present invention is specifically targeted to methods and reagents according to the invention when complete and/or homogenous cell populations are used, in a preferred embodiment the cell populations is a CD133 type cell populations.

Markers with an on-Off Change in Expression

The present invention is in a preferred embodiment directed to following group of mRNAs which are overexpressed in CD133 type cell populations but not expressed in corresponding negative cell populations:

Subgroup 1. Glycosyltransferases
Glucosaminyl (N-acetyl) transferase 2 I-branching enzyme GCNT2

UDP-Gal:betaGlcNAc beta 1,3-galactosyltransferase polypeptide 3
CMP-sialic acid alpha2,3sialyltransferase III, ST3GalVI mRNA,
Subgroup 2. Nucleotide metabolism enzyme:
Nudix (nucleoside diphosphate linked moiety X)-type motif 5, NUDT5;
Subgroup 3. Glycoprotein:
Synaptic vesicle glycoprotein 2A SV2A
Subgroup 4. Regulatory protein:
Zinc finger protein 117 (HPF9), ZNF117

The 3 first preferred groups are all glycosylation associated and preferred as such. The group of glycosyltransferases is especially preferred and preferred in combination together with any other of the three groups. SVA2 is represented also with preferred membrane glycoproteins.

The invention is further directed to each marker as individual marker. The specific scope of invention with regard to a specific marker is presented below or in other preferred marker groups.

SIAT10

The invention is specifically directed to the mRNA for analysis of mononuclear cells and/or cell populations from human cord blood, preferably CD133-type cell populations. The present invention is further directed to SIAT10 mRNA as a novel hematopoietic stem cell marker.

The invention is further directed to SIAT10 mRNA as a novel stem cell marker.

B3GALT3

The invention is specifically directed to the mRNA for analysis of mononuclear cells and/or cell populations from human cord blood, preferably CD133-type cell populations. The present invention is further directed to B3GALT3 mRNA as a novel hematopoietic stem cell marker.

The invention is further directed to SIAT10 mRNA as a novel stem cell marker.

GCNT2

The invention is specifically directed to the mRNA for analysis of mononuclear cells and/or cell populations from human cord blood, preferably CD133-type cell populations. The present invention is further directed to B3GALT3 mRNA as a novel neonatal hematopoietic stem cell marker.

Nudix (Nucleoside Diphosphate Linked Moiety X), NUDT5

The invention is specifically directed to the mRNA for analysis of mononuclear cells and/or cell populations from human cord blood, preferably CD133-type cell populations. The present invention is further directed to NUDT5 mRNA as a novel hematopoietic stem cell marker.

Zinc Finger Protein 117 (HPF9), ZNF117

The invention is specifically directed to the mRNA for analysis of mononuclear cells and/or cell populations from human cord blood, preferably CD133-type cell populations. The present invention is further directed to ZNF117 mRNA as a novel hematopoietic stem cell marker.

Analysis of Changes Related to Diseases, Especially Cancer and Chromosomal Alterations, and Blood Malignancies (Leukemias/Lymphomas)

The present invention revealed several genes associated with blood cancers. It is important to reveal malignant changes in cell populations aimed for therapeutic, analytic or other uses.

The preferred marker mRNAs and/or other markers, preferably carbohydrate markers, to be used in analysis of leukemia and lymphoma presence are preferably selected so that markers differently expressed in blood malignancies and the preferred cell populations are analyzed, in another embodiment in certain cancer types markers potentially similarly expressed with the markers of preferred cell populations according to the present invention are analyzed.

It is noted that human cord blood is used as such or as mononuclear cells or as isolated cell populations for stem cell culture and/or isolation for further scientific and/or therapeutic uses. Especially when the human cord blood is used for therapeutic processes it is crucially important to control the quality of the transferred cell materials with regard to presence of potential cancer or malignant cells and other chromosomal/gene alterations, for example related to blood diseases. Even non-hematologic cancers may be release metastasing cells to blood. It is especially crucial to control childhood cancers from cord blood samples, though when the cell propagate in patient also later appearing malignancies would be serious problem.

It is especially noted that CD34+ and/or CD133 purified cell populations from cord blood may be associated with multiple disease cells like cancers containing the same markers. The invention is specifically directed to analysis of these cell populations and especially cord blood CD133 positive cell populations with regard to the disease markers Cells intended for therapeutic use in humans should be analyzed with regard to potential cancer markers when autologous stem cell transplantation is performed for treatment of leukemia or other disease. Special purging technologies have been developed for removal of defective cells from cellS to be transplanted. The present invention is specially directed to analysis of purged cells.

The present invention is preferably directed to analysis of cancer associated markers from preferred cells according to the invention. The invention is specifically directed to the mRNA for analysis of mononuclear cells and/or cell populations from human cord blood, preferably CD133-type cell populations.

The present invention is further directed to use of novel hematopoietic cell associated mRNAs as a novel hematopoietic stem cell marker for analysis of preferred cord blood cells and cell populations according to the invention.

Markers Associated with Chromosomal Alterations in Blood Cancers and Other Conditions The mRNA expression analysis revealed several targets, which are associated with chromosomal alterations in cancers especially in leukemias and/or lymphomas. It is realized that the alterations affect the expression levels in cancers and often lead to expression of non-natural fusion gene products. When mRNA analysis of a non-fusion mRNA is performed the over expressed corresponding early blood marker may be compared with expression levels of markers associated with chromosomal alteration in blood cancers. Preferably the analysis is performed together with markers not expressed in blood cancer cells. The information about the expression levels in human cord blood and preferred cell lines may be also used for selection of the marker gene group from analysis directed to search for non-altered cells.

It is realized that several inherited chromosomal and other alterations also cause hematologic and other diseases, which should be avoided in process of transplantation.

The invention is especially directed to analysis of blood cancer (lymphoma/leukemia) and brain cancer associated and other childhood cancer, more preferably myeloid leukemias and neuroblastoma, and in a specifically preferred embodiment acute myelogenous cancer (AML).

The invention is further under a specific embodiment directed to analysis of so called cancer stem cells with regard to markers according to present invention in order to reveal the potential relatedness of the cancer stem cells with regard to natural stem cell-types according to the present invention.

Preferred examples of markers according to the invention for analysis according to the invention, especially for analysis of cancer and other chromosomal alterations and pregnancy/neonatal condition related diseases with examples of preferred disease-types to be analyzed:

ALCAM is associated with poor survival from colorectal carcinoma
Baalc (brain and acute leukemia cytoplasmic), acute myeloid leukemia
BCAT-1, lymphoma
BMI-1, cancerous stem cells from brain tumors
CDK6 Cyclin dependent kinase 6, T cell lymphomas
CDKN2 (p16INK4a), downregulated in testicular germ cell tumors
CDK2AP1 (p12DOC-1), downregulated in human oral cancers
CRHBP, prediction of preeclapmsia, other pregnancy related conditions.
DKC1, Dyskeratosis congenita 1 dyskerin
DNMT3B and DNMT3A, human leukemia cells
EBPL, emopamil binding protein-like, X-chromosomal chondrodysplasia punctuata
EMP1, esophageal cancer deregulated gene
FLT3, acute myeloid leukaemia (AML), pediatric non-promyelocytic acute myeloid leukaemia
HOXA9, primary AML (acute myeloid leukemia)-cells
HOXA10, myeloid leukemia, defective lymphoid development
IGFBP7, inflammatory breast cancer and in plaeural mesothelioma
IL-18, periventricular leukomalacia (neonatal white matter damage), often leads to cerebral palsy
KIT, v-kit Hardy-Zuckerman 4 feline sarcoma viral oncogene homolog, AML and other cancers
JUP (Plakoglobin, gamma-catenin), expression with seminomas
MEIS1, AML-leukemia
Melanoma associated gene
MMP28, broad range of carcinomas
N-MYC is a gene marker for neuroblastoma
NME1, loss of NME1 in teratomas, embryonal carcinomas
NUDT5, cancer cells
NY-SAR-79, Sarcoma antigen
Plagl1, Pleiomorphic Adenoma gene like1, silenced in ovarian and breast cancer
SDCCAG8, Serologically defined colon cancer antigen 8
TCBA1, T-cell lymphoma breakpoint associated target 1, T cell lymphomas/leukemias,
TRO, testicular cell tumors
UHRF1, deregulated in cancer
VLA4, AML-leukemia, CD34+ chronic myeloid leukemia patients,
WHSC1, Wolf-Hirschhom syndrome candidate 1
p18, Cyclin Dependent kinase inhibitor p18INK4c myeloid leukemia cells
Further Markers Includes
CD133, Acute myeloid leukemia (AML), brain tumors, lung cancer, kidney cancer CD34, Acute myeloid leukemia (AML),
More Preferably CD133 is Used in Combination with Other Preferred Markers These are separately preferred as markers to be used in combination with any of the above markers, the marker may be specifically selected according to indication found most likely for the cell material to be studied.

The invention is further directed screening method, when several potential neonatal defects/diseases are analyzed, the preferred disease groups are selected from group: cancer, other chromosomal alterations and pregnancy/neonatal condition related diseases.

The invention is further directed to comparison of markers downregulated or deregulated in cancer with markers overexpressed in the preferred cell populations according to the invention.

The Invention is Further Directed to Specific Indication Subgroups of the Markers and Specific Subtypes of the Markers Preferably transmembrane and/or membrane associated markers, secreted markers,
transcription factors, and cell cycle related markers,
more preferably glycosylated protein related markers.
Leukemia /Lymphoma, Examples of Preferred Specific Indications Baalc (brain and acute leukemia cytoplasmic), acute myeloid leukemia
BCAT-1, lymphoma
CDK6 Cyclin dependent kinase 6, T cell lymphomas
DNMT3B and DNMT3A, human leukemia cells
FLT3, acute myeloid leukaemia (AML), pediatric non-promyelocytic acute myeloid leukaemia
HOXA9, primary AML (acute myeloid leukemia)-cells
HOXA10, myeloid leukemia, defective lymphoid development
KIT, v-kit Hardy-Zuckerman 4 feline sarcoma viral oncogene homolog, AML and other cancers
MEIS1, AML-leukemia
TCBA1, T-cell lymphoma breakpoint associated target 1, T cell lymphomas/leukemias,
VLA4, AML-leukemia, CD34+ chronic myeloid leukemia patients,
p18, Cyclin Dependent kinase inhibitor p18INK4c myeloid leukemia cells
Preferred Acute Myeloid Leukaemia
Baalc (Brain and Acute Leukemia Cytoplasmic)
FLT3
HOXA9, AML-leukemia
KIT, v-kit Hardy-Zuckerman 4 feline sarcoma viral oncogene homolog, AML and other cancers
MEIS1, AML-leukemia
VLA4 AML-leukemia, CD34+ chronic myeloid leukemia patients,
p18, Cyclin Dependent kinase inhibitor p18INK4c myeloid leukemia cells,
Downregulated in present CD133 cells
brain, Embryonal Carcinoma Type and Childhood
Bmi-1, cancerous stem cells from brain tumors
N-MYC is a gene marker for neuroblastoma
NME1, loss of NME1 in teratomas, embryonal carcinomas; expressed in unfavourable neuroblastomas
CDKN2 (p16INK4a), downregulated in testicular germ cell tumors
JUP (Plakoglobin, gamma-catenin), expression with seminomas
TRO, testicular cell tumors
Other Cancers,
ALCAM is associated with poor survival from colorectal carcinoma
CDK2AP1 (p12DOC-1), Downregulated in Human Oral Cancers
EMP1, esophageal cancer deregulated gene
IGFBP7, inflammatory breast cancer and in plaeural mesothelioma
ITG9A, renal, lung and breast carcinomas Melanoma associated gene
MMP28, broad range of carcinomas
NUDT5, cancer cells
NY-SAR-79, Sarcoma antigen
Plagl1, Pleiomorphic Adenoma gene like1, silenced in ovarian and breast cancer
SDCCAG8, Serologically defined colon cancer antigen 8
UHRF1, deregulated in cancer
Baalc (Brain and Acute Leukemia Cytoplasmic)

Baalc has been reported in another context as development related protein from CD34+ bone marrow cells (Baldus, C D et al. (2003) 31 (11) 1051-6) and associated with mesoderm and muscle development (Satoskar A A et al Gene Expr Patterns (2005) 5 (4) 463-73).

Baalc (brain and acute leukemia cytoplasmic) mRNA appears to be novel marker for the preferred cell populations according to the invention.

The invention is specifically directed to the mRNA for analysis of mononuclear cells and/or cell populations from human cord blood, preferably CD133-type cell populations. The present invention is further directed to Baalc mRNA as a novel hematopoietic stem cell marker from human cord blood.

T-Cell Lymphoma Breakpoint Associated Target 1, TCBA1

TCBA1 alteration occurs at band 6q21 in T cell lymphomas/leukemias, it may be fusion of TCBA1-SUSP1, or aberrant non-chimeric transcript (Tagaw H. et al. (2002) 34 (2) 175-85)

TCBA1 mRNA appears to be novel marker for the preferred cell populations according to the invention, and for stem cells in general.

The invention is specifically directed to the mRNA for analysis of mononuclear cells and/or cell populations from human cord blood, preferably CD133-type cell populations. The present invention is further directed to TCBA1 mRNA as a novel hematopoietic stem cell marker.

The present invention is further directed to TCBA1 mRNA as a novel stem cell marker.

Neonatal/Pregnancy Condition Diagnostic, Cord Blood

Under specific condition the present invention is directed to analysis of neonatal/pregnancy condition related markers from human cord blood, examples of preferred markers includes:

IL-18, periventricular leukomalacia (neonatal white matter damage), often leads to cerebral palsy
CRHBP, prediction of pre-eclampsia, other pregnancy related conditions.

Preferred Markers for Other Chromosomal Alterations
DKC1, Dyskeratosis congenita 1 dyskerin
EBPL, emopamil binding protein-like, X-chromosomal chondrodysplasia punctuata
N-MYC was reported a marker for partial 2p trisomy
Wolf-Hirschhom syndrome candidate 1, WHSC1
Wolf-Hirschhorn Syndrome Candidate 1, WHSC1

This gene is associated with a syndrome caused by deletion of short arm of chromosome 4 associated with a myelo dysplastic syndrome (MDS), possibly caused by allelic loss of WHSC1 (Sharathkuma A et al. Am J Med Genet A (2003) 119 (2) 194-9). In multiple myeloma translocation of t (4; 14) p (16.3; q32) probably deregulated WHSC1 gene (Finelli P et al. Blood (1999) 94 (2) 724-32).

WHSC1 mRNA appears to be novel marker for the preferred cell populations according to the invention, and for stem cells in general.

The invention is specifically directed to the mRNA for analysis of mononuclear cells and/or cell populations from human cord blood, preferably CD133-type cell populations. The present invention is further directed to WHSC1 mRNA as a novel hematopoietic stem cell marker.

The present invention is further directed to WHSC1 mRNA as a novel stem cell marker.

Antibody Target Structures

The present invention is further directed to cell surface marker structures, which can be recognized by antibodies. This group includes preferred plasma membrane proteins according to the invention, furthermore the invention is directed to molecules characterized by antibodies as cell markers. Preferebly this group includes mRNA of
Serologically defined colon cancer antigen 8, SDCCAG8, and in another embodiment mRNA of Sarcoma antigen NY-SAR-79.

Serologically Defined Colon Cancer Antigen 8, SDCCAG8

The invention is specifically directed to the mRNA for analysis of mononuclear cells and/or cell populations from human cord blood, preferably CD133-type cell populations. The present invention is further directed to SDCCAG8 mRNA as a novel hematopoietic stem cell marker.

Sarcoma Antigen NY-SAR-79

The invention is specifically directed to the mRNA for analysis of mononuclear cells and/or cell populations from human cord blood, preferably CD133-type cell populations. The present invention is further directed to Sarcoma antigen NY-SAR-79 mRNA as a novel hematopoietic stem cell marker.

Islet Cell Autoantigen 1 69 kDA, ICA1

The invention is specifically directed to the mRNA for analysis of mononuclear cells and/or cell populations from human cord blood, preferably CD133-type cell populations. The present invention is further directed to ICA1 mRNA as a novel hematopoietic stem cell marker.

mRNA Corresponding to Potentially Glycosylated, Preferably N-Glycosylated Protein The present invention is directed to search mRNAs corresponding to potentially glycosylated proteins. The present invention is further directed to method of searching for preferred mRNA-species corresponding to proteins containing potential glycosylation sites, in a preferred embodiment N-glycosylation sites. Presence of N-glycosylation indicates potential for carrying a glycan marker structure on cell surface. The group of mRNA-species corresponding to proteins containing potential N-glycosylation sites, briefly abbreviated here as N-glyco-protein mRNA, offers possibility for rational search and selection of extracellular markers of preferred cell populations.

Method for Searching mRNA Corresponding to Potentially Glycosylated Protein

The present invention is directed to search mRNAs corresponding to potentially glycosylated proteins. The search of potentially glycosylated methods is preferably performed by glycosylation comparison method or sequence search method. The preferred glycosylation comparison method involves search of glycosylation information about same or homologous corresponding gene product protein in another cell or tissue type. The preferred sequence search method includes search of glycosylation site signals from the protein sequences, preferred glycosylation site signal includes signals for conjugating glycan to protein, preferably signals for incorporations of O-glycan or N-glycan.

The present invention in search of mRNA-corresponding to N-glycosylated protein is directed to database search of the preferred mRNA-sequences translatable to Asn-Xxx-Ser/Cys, most preferably Asn-Xxx-Ser, wherein Xxx is any amino acid except proline.

Preferred N-Glyco-Protein mRNAs

The present invention is in a preferred embodiment directed over-expressed mRNA signals corresponding to a protein potentially carrying N-glycan. These mRNA-signals can be translated to proteins carrying amino acid sequence Asn-Xxx-Ser/Cys, most preferably Asn-Xxx-Ser, wherein Xxx is any amino acid except proline. The mRNA sequences can be obtained by genetic code. The present invention is directed to the preferred mRNA-sequences translatable to Asn-Xxx-Ser/Cys, most preferably Asn-Xxx-Ser, wherein Xxx is any amino acid except proline.

Methods for the Search of Potential Verified Glyco Proteins Corresponding to N-Glyco-Protein mRNA The inventors were able to find changes in cellular glycosylation, especially in N-glycosylation. It is now realized that many preferred glycan markers are carried by proteins. The present invention is directed to search of the proteins, which carry important glycan markers according to the invention and are overexpressed in the cells. The search of glycoprotein marker corresponding to N-glyco-protein mRNA can be performed by traditional method of analysing glycosylation of a specific protein. The preferred search of glycoprotein markers includes steps of recognition of a protein and recognition of the corresponding glycan marker together.

The recognition of the glycan marker and protein marker may be performed by binding agents, preferably by antibodies, or by other methods such as mass spectrometry, biochemical sequence and composition analysis, molecular size analysis and analysis by chromatographic or electrophoretic mobility connected with other data or functional analysis in case the protein has specific function such as enzymatic activity/specific ligand; glycan markers are preferably recognized by specific binding molecules described by the invention, The present invention is further directed to the verified glycoproteins discovered according to the invention and their use in processes involving recognition or binding to early human cells, preferably for the use in analytical or diagnostic binding to the glycocoproteins in order to observe early human cells or preferred cell populations according to the present invention.

mRNA Corresponding to Potential Glycosylation Enzymes, Preferably Glycosyltransferase Enzymes In a preferred embodiment the present invention is directed mRNA corresponding to potential glycosylation enzymes, preferably glycosyltransferase enzymes, potentially further involved in synthesis glycan level markers. The mRNA group is abbreviated as glyco-enzyme mRNA markers. The glycosylation enzymes do not directly correspond to other preferred classes of mRNAs, but possible products of the enzymes may be involved in synthesis of glycans on potential glycoproteins. The potential connection of the mRNA, enzyme protein level and glycan levels cannot be known from mRNA-expression. The mRNA corresponding to potentia glycosylation enzyme group is a preferred group of mRNA-markers because of useful expression levels and because of its nature as mRNA-group with separate nature when compared with the other preferred mRNA-groups.

Preferred mRNA Markers Corresponding to Potential Glycosylation Enzymes Specific for Human CORD Blood Cell Populations The present invention is preferably directed to glyco-enzyme mRNA markers specific for the CD133+ cell populations derived from human early blood. More preferably the present invention is directed to glyco-enzyme mRNA markers of human cord blood cell population cell populations with weak or low expression in CD34+ cells.

ST3GalVI mRNA

ST3GalVI mRNA has high expression level, for example, in CD133+ cell population but much lower expression in CD34 positive cells. The functional specificity of the potential corresponding gene product, the enzyme CMP-sialic acid Galβ4GlcNAc α2-3sialyltransferase VI is transfer of sialic acid from CMP-sialic acid type donors to Galβ4GlcNAc-type acceptors, the enzyme is directed to synthesis of structures SAα3Galβ4GlcNAc.

This specificity likely corresponds to α3-sialyltransferase activity synthesizing sialylated glycans in CD133+ cell population.

The inventors were able to observe substantial level of α3-sialylation in comparison to potential α6-sialylation on specific N-glycan structures in CD113+ cells while corresponding N-glycan marker CD133 negative cells contained practically no α3-sialidase releasable sialic acid, example 5.

mRNA of Glucosaminyl (N-Acetyl) Transferase 2 I-Branching Enzyme GCNT2

The mRNA codes potential β1-6 N-acetylglucosaminyltransferase.

mRNA Of UDP-Gal:BetaGlcNAc Beta 1,3-Galactosyltransferase Polypeptide 3

The mRNA codes potential β1-3 N-acetylgalactosaminyltransferase.

The invention is further directed to the following glycosyltransferase mRNAs as specific markers which have are expressed in CD133+ but not in CD133− cells: B3GALT3 GCNT2 and SIAT10.

ST6GalNAcIV

The invention is further directed to a glycosyltransferase mRNA marker downregulated in CD133+ cells: ST6GalNAcIV, affymetrix probe set ID 220937_s_at. The mRNA corresponds to a potential α6-sialyltranferase transferring to 6-position of a GalNAc residue.

Nucleotide Sugar Metabolim Enzymes

It is realized that glycan synthesis is partially regulated by nucleotide sugar synthesis and degradation enzymes. The preferred enzymes according to the present invention includes:

Nudix (Nucleoside Diphosphate Linked Moiety X), NUDT5

The invention is specifically directed to the mRNA for analysis of mononuclear cells and/or cell populations from human cord blood, preferably CD133-type cell populations. The present invention is further directed to NUDT5 mRNA as a novel hematopoietic stem cell marker.

CMAH, CMP-NeuNAc-Hydroxylase

The invention is further directed to a nucleotide methabolims mRNA, more specifically a nucleotide sugar synthesis mRNA marker upregulated in cord blood cells more preferably in CD133+ cells and CD34+ cells: CMAH, affymetrix probe set ID 205518_s_at. The mRNA corresponds to a potential CMP-NeuNAc hydroxylase related to synthesis of CMP-NeuNGc from CMP-NeuNAc. The mRNA corresponds to an enzyme, which has been reported to be potentially inactive in human due to mutations.

Methods for the Search of Potential Verified Glycoenzyme Products, Glycan Markers Correlating to Specific Glycoenzyme mRNA The present invention is specifically directed to analysis of expression of glycoenzymes, and even more preferably their potential products, glycan markers. The expression on the glycoenzyme on protein level is not obvious from mRNA levels as translation level expression control exists. Furthermore the carbohydrate level expression is controlled at several levels in cells, for example in the case of glycosyltransferases by regulation of enzyme activity, availability of donor and acceptor substrates, by cellular organization of the Golgi complex and association of the glycosyltransferase enzymes in Golgi, all of the four latter factors being in turn affected by multiple cell biological factors.

The present invention is directed to search of the glycan markers corresponding to mRNA markers by using the preferred glycan analysis methods according to the present invention.

Verified Glycan Marker Corresponding to Glycosylation Enzymes

The present invention is further directed to the verified glycan marker discovered according to the invention and their use in processes involving recognition or binding to early human cells, preferably for the use in analytical or diagnostic binding to the glycocoproteins in order to observe early human cells or preferred cell populations according to the present invention.

ST3GalVI mRNA Expression and Structures SAα3Galβ4GlcNAc

The inventors were able to identify increased sialylation of the early cell material expressing ST3GalVI mRNA. The data indicates especially synthesis of terminal structures SAα3Galβ4GlcNAc and more specifically SAα3Galβ4GlcNAcβ terminal structures. Analysis of the sialylated structures indicates that α3-sialyltransferase activity synthesizing sialylated glycans is correlated with ST3GalVI mRNA in CD133+ cell population.

The mRNA expression analysis further indicated that the ST3GalVI expression is more upregulated in CD133+ when compared with CD133− cells that in CD34+ when compared with CD34−. The ST3GalVI is thus more CD133+ cell population associated marker than CD34+ associated.

Indirect Analysis of mRNA-Level Marker

The present invention is further directed to indirect analysis of a mRNA level marker. The indirect analysis measures a factor correlating to the mRNA-expression. The factor is preferably a protein level or a glycan level marker. In a preferred embodiment the present invention is directed to
1. defining the potential protein level expression corresponding to a mRNA-level marker expression preferably mRNA coding the protein marker and
2. correlating it with the mRNA-level expression,
3. if correlation, preferably positive correlation, would exist use of the protein level marker with correlation to the mRNA-marker instead of the mRNA marker In another preferred embodiment the present invention is directed to
1. defining the potential glycan level expression corresponding to a mRNA-level marker expression preferably mRNA coding an enzyme, more preferably a glycosyltranferase involved in the synthesis of the glycan and
2. correlating it with the mRNA-level expression,
3. if correlation, preferably positive correlation, would exist, use of the glycan level marker, which correlates to the mRNA-marker, instead of the mRNA marker; or the use of mRNA marker and the glycan marker together.

The benefit of the use of the protein or glycan level marker is that these markers can be observed by common analytic and diagnostic methods including use of diagnostic antibodies and antibody based technologies.

Analysis of Glycan Markers from Early Human Cells

The present invention is under a preferred embodiment directed analysis of one or several expressed glycan markers together with the analysis of mRNA-markers.

The present invention is specifically directed to the analysis of glycan markers from human cord blood.

Glycan Marker Analysis to Reveal Markers Specific Marker Glycans of Cell Populations Use of a Highly Purified Mononuclear Cell Population of Cord Blood for Glycan Analysis The present invention is specifically directed to use the highly purified cell populations from human cord blood for analysis of glycan expression levels. It is realized that the glycan expression analysis is highly sensitive and for example 10-30% contamination by cells with high expression levels of specific glycan structures could bias the results of glycan expression analysis. The glycan expression analysis may be performed by any glycan expression analysis method, preferably by a known glycan expression analysis method.

Preferred Glycan Analysis Methods

In a preferred embodiment the glycan expression analysis is performed by a mass spectrometric method and/or a protein based glycan expression method or combination of a mass spectrometric and protein based glycan expression methods.

In a preferred embodiment the glycan expression analysis is performed by a mass spectrometric method. In an embodiment expression of one preferred glycan species is performed. In a preferred embodiment glycan expression analysis is performed for multiple glycan species. Preferably multiple glycan species are analysed by a mass spectrometric profiling method. The profiling method is preferably directed to the analysis of the status of a cell population. In another embodiment the glycan profiling method is directed to the analysis of the purity of a cell population.

Analysis of Common Glycan Markers Present in Several Individual Cell Populations It was realized that even highly purified human cord blood cells population may have differences in glycan expression levels. The present invention is directed to analysis of mRNA-markers of several individual purified populations of human cord blood and comparing the expression profiles. In a preferred embodiment the invention is directed to glycan markers, which are common for several individual cell populations. The common markers are especially useful for recognition of cell populations where individual variations exist. According to the invention the analysis of individual variation of glycan-markers is especially useful for analysis of cell populations, especially mononuclear cell populations, of human cord blood.

Preferred Cell Populations

Inventors discovered mRNA markers present in purified cell populations of human cord blood. More preferably the cells have special differentiation capacity.

In a specific embodiment the present invention is directed to glycan markers over-expressed in human CD133+ and/or CD 34+ cell populations derived from cord blood. In preferred embodiment the present invention is directed to mRNA markers over-expressed in both human CD133+ and CD 34+ cell populations derived from cord blood.

In another preferred embodiment the present invention is directed to glycan markers over-expressed in human CD133+ but less effectively expressed in CD 34+ cell populations derived from cord blood. This indicates glycan markers, which are co-expressed with CD133. The present invention is specifically directed to methods for recognition of cell populations with high expression of CD133 co-expressed glycan markers, which preferably have low association with CD34 expression. The analysis of CD133 associated markers would be useful for analysis of purity of CD133 or CD34 cell populations.

The present invention is directed to essential glycan-markers, which would allow recognition of the cell populations from pure cord blood derived material. The present invention is specifically directed to markers specifically expressed early human cells present in cord blood and equivalent materials.

The invention is directed to use of the markers for analysis of cells of special differentiation capacity, the cells being preferably human cord blood cells.

In a specific embodiment the invention is directed to the analysis of presence of human cord blood derived mononuclear cell populations by using the markers according to the present invention.

Preferred Glycan-Markers of Cell Populations
Sialylated Glycan Markers of Human Cord Blood Cells The present invention is directed to sialylated glycan markers from human early blood cells. It was found out that sialylation level is increased in certain cell populations. Furthermore increase of specific structures was revealed.

Specific Sialylated Cell Populations

The sialylation was increased in CD133+ cell population. The inventors were able to find correlation between ST3GalVI mRNA expression and presence of SAα3Galβ4GlcNAc-structures on cell surfaces. The structures correspond to published specificity of the sialyltransferase. The results show connection between the transferase mRNA expression and specific N-glycan structures. The present invention is further directed to homogenous and complete mononuclear cell populations of CD133 type from human cord blood according to the invention, preferably CD133+ cells comprising the preferred N-glycans with α3-sialylated structures. The invention is further directed to the complete CD133 type cells produced by the processes according to the invention comprising the α3-sialylated structures according to the invention.

Combination of the Glycan Marker and mRNA-Analysis
General Glycomics Technologies The present invention is specifically directed to the combined analysis of mRNA profile and glycan profile. The invention is specifically directed to methods of defining relative mRNA expression changes between at least two different cell samples, and defining relative differences of glycan expression of the same samples. The comparison may be performed between a baseline sample, for example CD133− cell sample and a cell population enriched with a specific marker such as CD133+ cells. The comparisons can be also made between samples from different human individuals, for examples between cord bloods from different individual humans.

In a preferred embodiment relatively at least one relatively overexpressed marker and/or at least one underexpressed marker are defined, more preferably both at least one overexpressed marker and at least one underexpressed marker are defined. In another preferred embodiment only over-expressed markers are defined.

The invention is specifically directed to methods of combined use of mRNA markers and glycans for analytics and diagnostics. These method increases the number of possible variables to be analysed. These variables are partially independent as expression of glycan markers is regulated on multiple levels. The mRNA level analysis of a specific glycan associated marker may be correlated with expression of a glycan structure.

Glycan Markers

The glycan markers according to the invention are oligosaccharides or polysaccharides releasable from cells. More preferably the glycan markers consist of at least two types of monosaccharide units selected from the group: Hex, HexNAc, HexA, Pen, DeoxyHex, sialic acids, wherein Hex is hexose, preferably glucose, galactose or mannose, deoxyHex is fucose, Pen is pentose, preferably xylose, HexA is a hexuronic acid preferably glucuronic acid, HexNAc is N-acetylhexosamine, preferably N-acetylglucosamine of N-acetylgalactosamine, and sialic acid is preferably N-acetylneuraminic acid, the monosaccharide units further include preferably natural derivatives thereof. More preferably the monosaccharide units are selected from the group glucose, galactose or mannose, fucose, xylose, glucuronic acid, N-acetylglucosamine or N-acetylgalactosamine, and N-acetylneuraminic acid. The preferred glycan markers are preferably protein linked O-glycans, preferably serine/threeonine linked O-glycans, even more preferably these are linked through GalNAc; or N-glycans.

Preferred Uses of the Analysis Methods and Cell Materials of Invention

The present invention is specifically directed to methods and cell materials according to the invention for differentiating human cord blood populations from other cell populations preferably from adult peripheral blood. For example because human cord blood is used therapeutically, methods for verification of the material are needed.

The invention is further directed to the use of the method according to the any of the claims for differentiating human cord blood populations from hematologic malignancy. The markers according to the present invention are useful for various diagnostics methods involving human cord blood according to the present invention, when the material may be contaminated by malignant cells. This method is especially preferred for analysis of transplantable cord blood materials.

Culture or Maintenance of Specific Cell Types and their Analysis

The inventors were able to show that the highly pure complete cell populations according to the present invention, preferably CD133+ cells, can be useful as source of effectively cultivable cell types.

Present invention is specifically directed to the cultivation of the preferred cells according to the invention, and cells produced by the preferred methods according to the invention. In a preferred embodiment the invention is directed to production of non-hematopoietice cells.

The invention is directed to effective production of specific hematopoietic cell populations shown to be effectively produced in examples, more preferably CFU-GM colonies and CFU-GEMM colonies. The invention is further directed to methods according to and described by the invention to be used in context of cultivation of the preferred cells.

The invention is further in a preferred embodiment directed to the analysis of the cultivated cells, preferably cultivated cells being produced according to the invention, when the cultivated cells are compared with the data or cells according to the present invention.

Combined Detection of a Cell Surface Marker and a mRNA Marker

The inventors were able to reveal novel mRNA-markers for human cord blood CD133-cells. The mRNA markers have altered expression, preferably increased expression according in the specific cells according to the invention. It is realized that the reproducibly expressed markers are useful for determining the status of the cells. The mRNA-markers may be used for profiling cells and analysing their purity or status as described by the invention. Preferred subgroups of mRNA markers are related to potential cell surface markers such as plasma membrane linked or associated proteins and/or cell surface glycan structures. The invention is specifically directed to subgroups of mRNAs referred as glycan related mRNAs, which are related to specific glycan structures.

The inventors are further able describe certain protein and glycan markers as preferred cell surface markers. The cell surface markers are especially useful for analysis of intact cells by known technologies involving agents specifically recognizing the cells surface markers.

The inventors further revealed that it is useful to analyze at least one cell surface marker and at least one mRNA marker according to the invention. The invention is further specifically directed to cell analysis using at least one cell surface glycan marker and at least one mRNA marker, when the cell surface marker(s) is correlated with the mRNA-marker(s), and analysis for studying such correlation, the mRNA marker being more preferably a glycan related mRNA.

Expression of a specific cell surface glycan marker α3-linked sialic acid on a specific N-glycan was correlated and verified with the expression of specific α3-sialyltransferase mRNA.

Combined Detection of a Cell Surface Glycan Marker and a mRNA Marker

The inventors realized is especially useful to profile at least two type of markers:
1) a specific glycan structure, which is correlated with the specific nature of the cells, preferably correlated with the stem cell type nature of the cell type,
2) presence or absence of a mRNA-marker, which is diagnostic for the status of the cells. This provides novel method for analysis cells, especially stem cells, and more preferably the preferred cells and cell populations according to the invention.

The method provides especially useful information, because the markers are on different biosynthetic levels. In a preferred embodiment the invention detects markers, which are specifically expressed or over expressed in context of a cell type.

Biosynthetic Levels

The mRNA-marker is on the level of transferring information for the protein synthesis of potential marker protein, while the glycan structures are biosynthetic end product with biological communication functions on cell surfaces. In case a marker protein verified to correlated with mRNA expression is analysed, the glycan marker as a secondary gene product is still at different biosynthetic level. The glycan structures are not encoded directly by genes but produced by glycosyltransferase enzymes in highly organized Golgi apparatus utilizing specific acceptor and donor structures involving complex regulation is all aspects. The analysis of markers of different biosynthetic level provides novel perspective to a specific cell population, providing more accurate information about the status of cells and potential changes in it. It is know that changes in status of a cell line may not be observed when detecting single or few mRNA or protein level markers. Due to complex regulatory status of glycan synthesis involving for example cell biology of Golgi transport, carbohydrate energy metabolism and nucleotide synthesis, intracellular transport of nucleotides and other precursors, gene regulation and translation regulation, during usually multiple steps in synthesis of linear or branched oligosacccharide glycan, the glycan markers are preferred sensors of cell status and type. Combination this with specifically selected mRNA marker(s) or corresponding protein markers, which are under limited but strong regulation, allows correlation of the glycan marker change usually affected by multiple factors, with a more specific regulation route(s) of mRNA and/or protein regulation.

Glycan Marker and Glycan Related mRNA Marker

Due to special nature of the glycan markers the invention is further directed to an especially useful group of marker mRNAs, which are related to glycan structure. The glycan related mRNA are selected as a special group from the preferred mRNA markers according to the invention. The glycan marker and glycan related mRNA marker to be used according to the invention may be further selected so that these would have at least some level of correlation. Correlations can be found between expression of multiple mRNA-markers and glycan markers.

The preferred "glycan related mRNA-markers" includes at least four major types of markers potentially directed to production of a protein of following types of groups 1-4 and thus having correlation with expression of potential glycan markers:
1. Glycoproteins carrying specific glycan structures. Preferred subgroups of glycoproteins include N-glycosylated proteins, O-glycosylated proteins, and proteoglycans.
2. Glycosynthese proteins including Glycan biosynthetic and biodegradative proteins involved in reactions forming the glycans, preferably glycosyltransferases and nucleotide sugar synthesis/transports proteins and glycosidases
3. Glycosylation regulating protein is selected from the group consisting of transcription factors, cell cycle related proteins, receptor proteins and growth factors and
4. Glycan binding proteins. This group includes protein binding carbohydrate proteins, without enzymatic activity of group 2, also known as lectins. A preferred subgroup of the lectins includes glycosaminoglycan binding proteins.

In a preferred embodiment the invention is directed to groups 1. Glycoproteins and 2. Glycan biosynthetic and biodegradative proteins as preferred "primarily glycan related mRNA markers". These are especially preferred because of direct relation of the functional glycan and the potential protein, the Glycoproteins carry glycan structures and Glycan biosynthetic and biodegradative proteins produce the glycan structures. Multiple factors such as close association of the biosynthetic pathways and synthetic enzymes and the regulation of the enzymes creates relation and correlations between glycan structures even when these belong to partially separated biosynthetic pathways of glycan structures.

In a specific embodiment correlation of specific glycan related mRNA and glycan marker is not established. The method according to the present invention measuring the mRNA and the glycan structure can be performed to establish potential correlation or non-correlation of the expressions of the markers. In case of non-correlation important information of the regulatory status and potential alternative biosynthesis in cells is obtained. In case of correlation the knowledge of correlation would allow detection of change in connection between the specific markers. The measurement of the potentially correlated markers without establishing the exact connection(s) is also useful method to obtain additional perspective for analysis of cell populations.

Search of Additional Cell Surface Markers

The present invention is specifically directed to the analysis to reveal if the potential glycan and/or protein markers correlating mRNA markers according to the invention would be useful as novel cell surface markers of the cells. A specifically preferred group to be analysed in search of the cell surface markers would be the transmembrane or membrane associated proteins, especially glycoproteins, potentially encoded by the preferred mRNA markers according to the invention.

It was further realized that more novel surface markers may be revealed by searching correlation between the mRNA markers and corresponding protein/glycan markers. Under a specific embodiment the expression of cell surface marker may be analysed by mRNA marker, or vice versa, when the correlation of the mRNA and cell surface markers would be revealed. The analysis according to the present invention may be performed by analysis of two novel cell surface protein markers described by the invention or at least two mRNAs according to the invention, so that at least one of the markers is novel.

The present invention is specifically directed to profiling multipotent cells or stem cells, more preferably the preferred cell populations according to the present invention by detecting presence or absence of at least two biological markers in said cell population, wherein at least one of said markers is a cell surface marker, and at least one of said markers is a mRNA marker. Preferably the method does not primarily involve use of known markers cell surface or mRNA markers such CD133 or CD34. The known markers may be used as additional marker. The present invention is further directed to analysis of glycosylation according to the invention in connection with CD34 and CD133 markers.

Comparison of Cord Blood CD34+ and CD133+ Specific Constitutive Gene Expression

Analysis of mRNAs present in all four CD133+ samples but absent in CD133− cells gave 257 (Venn1 CD133+) mRNAs, similar analysis of all three CD34+ cell populations against CD34− cells gave 207 genes (Venn1 CD34+).

In a preferred embodiment the present invention is directed to the analysis and methods according to the invention directed to the specific marker mRNA transcripts specific for the CD34+ cells (in Tables 17 and 19).

Comparison of the present mRNAs gave 85 mRNA transcripts common for (all) CD34+ and (all) CD133+ cells but absent in corresponding CD34− and CD133− samples (Table 17). It is realized that these 85 mRNAs form a group of specifically and constitutively expressed stem cell type genes in two different stem cell type populations of cord blood. Thus, the invention represents here constitutively expressed and specific markers common to cord blood CD34+ and CD133+ cells. The markers in the list are especially preferred for the analysis of primitive or stem cell like status of human cord blood cells and related and derived cell populations thereof.

The marker group is further useful in profiling of cancer related markers according to the invention or cancer related markers which can be selected from the markers according to the invention; and especially for profiling of stem cell and cancer specific markers, more preferably stem cell or stem cell population or specific cord blood cell population markers and blood cell cancer markers especially leukaemia related markers.

From this group of 10 markers related to potential membrane proteins based on annotation of the mRNA markers was selected as a more preferred group, shown in Table 18, it is further realized that other preferred groups of potential membrane, glycoproteins and other preferred markers according to invention are preferred when selected from the Table 17.

The comparison the specific and constitutive mRNA expression in CD34+ and CD133+ cell populations further revealed specific and constitutive mRNA population of 122 mRNAs, Table 19, specific for CD34+ but not for CD133+ cells. The invention represents here constitutively expressed and specific markers common to CD34+ but not to CD133+ type cell populations, especially cord blood cell populations. The CD34+ cells are common cell population developed for therapeutics and other uses and constitutively expressed markers of this type are useful according to the invention for analysis of CD34+ cells, especially cord blood cells and related or derived cell populations.

The comparison of the specific and constitutive mRNA expression in CD34+ and CD133+ cell populations further revealed specific and constitutive mRNA population of 172 mRNAs, Table 20, specific for CD133+ but not for CD34+ cells. The invention represents here constitutively expressed and specific markers common to CD133+ but not to CD34+ type cell populations, especially cord blood cell populations. The CD133+ cells are common cell population developed for therapeutics and other uses and constitutively expressed markers of this type are useful according to the invention for analysis of CD133+ cells, especially cord blood cells and related or derived cell populations.

The marker groups of Tables 19 and/or 20 are further useful in comparison of cancer related markers according to the invention or cancer related markers which can be selected from the markers according to the invention; and especially for comparison of stem cell and cancer specific markers, more preferably stem cell or stem cell population or specific cord blood cell population markers and blood cell cancer markers especially leukaemia related markers. It is further realized that other preferred groups of potential membrane proteins, glycoproteins, glycosylation enzyme related markers and other preferred markers according to invention are more preferred, especially in the specific contexts described, when selected from the Table 19 and/or 20.

Comparison of Cord Blood CD34+ and CD133+ Present Gene Expression

Analysis of present mRNAs in all three cord blood CD34+ cell populations and in all four CD133+ cell populations, without comparison of expression in corresponding CD34− and CD133− cell populations, was also performed. Comparison of the present mRNAs revealed 36 mRNAs present in CD34+ cells, Table 21, but not present in all of CD133+ cells. This mRNA population show unique markers present in CD34+ cell populations. The invention is specifically directed to use of group of mRNAs for studies of difference of CD34+ and CD133+ type cell populations.

Analysis of present mRNAs in cord blood CD34+ and CD133+ cell populations without comparison of expression in corresponding CD34− and CD133− cell populations was also performed. Comparison of the present mRNAs revealed 250 mRNAs present in CD133+ cells, Table 22 but not present in all CD34+ cells. This mRNA population show unique markers present in CD133+ cell populations. The invention is specifically directed to use of group of mRNAs for studies of difference of CD34+ and CD133+ type cell populations.

The marker groups of Tables 21 and/or 22 are further useful in comparison of cancer related markers according to the invention or cancer related markers which can be selected from the markers according to the invention; and especially for comparison of stem cell and cancer specific markers, more preferably stem cell or stem cell population or specific cord blood cell population markers and blood cell cancer markers especially leukaemia related markers. It is further realized that other preferred groups of potential membrane proteins, glycosylation enzyme related markers, glycoproteins and other preferred markers according to invention are more preferred, especially in the specific contexts described, when selected from the Table 21 and/or 22.

The inventors have also discovered a method for purification of cell populations, especially from human cord blood. This method allows effective, and reproducible purification of complete cell populations with good yield. The invention is further directed to specific complete cell populations comprising approximately naturally occurring numbers of cells expressing either high and low levels of the specific marker used in the purification process of the cell population.

The present invention provides a method for purification of a cell population from a sample or raw material containing multiple cell populations, comprising the following subsequent steps:
- a) contacting said sample with a cell-type-specific binding reagent linked to a polyvalent matrix by mixing said reagent with the sample so that a complex of said binding reagent and a cell population of interest forms;
- b) immobilizing the complex obtained from step a);
- c) removing the material that is not immobilized;
- d) releasing the immobilized complex;
- e) contacting the sample obtained from step d) with an additional amount of the specific binding reagent linked to a polyvalent matrix by mixing the additional amount of binding reagent with said sample;
- f) immobilizing the complex obtained from step e);
- g) removing the material that is not immobilized;
- h) releasing the immobilized complex; and
- i) recovering a cell population bound to the binding reagent.

Method for Purification of Mononuclear Cell Populations

The present method is further directed to producing highly purified cell populations from cord blood. The purification of specific mononuclear cell populations from human cord blood, especially cord blood or placental blood forms a special challenge. This appears to depend on the composition of human cord blood. In a few documented publications purification of mononuclear cell populations to level of purity of about 50-60% has been reported. The mononuclear cell population refers here to a subpopulation of the mononuclear cells.

Binding Molecules

The method is based on the use of a specific binding molecule, which binds to a marker structure, such as a protein, on the surface of a cell belonging to a certain cell population. In a preferred embodiment the present invention is directed to the use of a protein-binding molecule, which preferably is an antibody and most preferably a monoclonal antibody.

The present invention is further directed to glycan binding molecules, which recognize glycan marker structures on a cell surface. In a preferred embodiment the binding molecule is a protein, more preferably an enzyme, a lectin or a glycan binding antibody.

Two Step Process for Purification of a Cell Population

In a preferred purification method, a binding molecule is used in a two-step process. In the preferred process a substrate preparation from a sample is
1) handled in process for substrate preparation;
8) put in contact with a specific binding molecule;
9) processed in an affinity purification method by the specific binding molecule;
10) recovered from the affinity purification;
11) put in the second contact with a specific binding molecule;
12) processed in an affinity purification method by the specific binding molecule; and
13) recovered from the affinity purification A Preferred Affinity Purification Method The affinity purification method is preferably a magnetic bead method, more preferably an immunomagnetic bead method. It is further realized that many other affinity methods can be used including methods containing immobilized affinity reagent. The preferred affinity reagent is an antibody useful for purification of a mononuclear cell population, preferably CD133-type cell population, from human tissue material, most preferably from human cord blood. Preferred antibodies for the purification method includes anti-CD34 and anti-CD133 antibodies.

Preferred Clean and Safe Process for Production of Human Cord Blood Sample

A preferred sample or substrate preparation of human cord blood is a fraction of mononuclear cells prepared from human cord blood.

In the preferred substrate preparation process the blood is collected in sterile collection bags, preferably containing citrate phosphate-dextrose solution. The collected blood units can be tested for pathogens, which may be present in blood products. In a preferred and regular process the blood units are tested at least for human immunodeficiency virus, hepatitis C virus, hepatitis B virus, human T-cell lymphotrophic virus, and syphilis, and only units with negative test results are used.

The sample of mononuclear cells is preferably produced by a density gradient method, more preferably by Ficoll-Hypaque density method.

There is increasing need for methods for purification cell population from various sample types. Purified cell populations are developed for various scientific products and research tools and/or therapeutic products or lead products for therapeutic development.

Sample Materials

The samples, or sources of cell populations, are preferably tissues, tissue cultures and/or cell cultures. The samples contain, beside the target cell population, also other cellular material or other cellular materials. The other cellular material indicates multiple different cell populations, and/or cell like materials, which should be separated from the desired cell population. The invention is directed to the maintaining the desired cell population intact and remove other cellular material with similarities with the desired cell population. Preferred sample is cell or tissue material containing free or easily mobilizable cells such as blood and/or blood derived materials.

The other cell like materials mean here degraded cells and materials derived from cells and tissues. Cell purification, cell culturing and cell storage methods may yield contaminating other cell like materials. Especially storage in lower temperatures and freezing/cryopreservation cause increase of other cell like material in sample. The invention is especially directed to purification of cell population containing other cell like materials, more preferably cryopreserved cells, and most preferably cryopreserved cord blood cell.

The invention reveals additional methods useful for the handling of cells aimed for cryopreservation or use in the purification involving cryopreserved cells, especially for prevention of aggregation of cryopreserved cells. The invention is directed to selection of anticoagulant solution for handling of cells preventing the aggregation of cryopreserved cells. It was revealed that the ethylenediamine tetraacetic acid (EDTA, Merck, Darmstadt, Germany)/its concentration in standard solution was not useful while the anticoagulant citrate dextrose solution, formula A (ACD/A, Baxter Healthcare, Lessines, Belgium) was revealed to be effective in preventing the aggregation, the invention is especially directed to the citrate dextrose solution and like for the handling of the cells aimed for cryopreservation and purification, especially purification by magnetic bead methods, and preferably according to the invention. The invention further revealed that DNAse solution is useful for prevention of the aggregation, and the invention is directed to the use of DNAse in the handling of cell for the purification, preferably for the purification of the cord blood cells by magnetic beads, especially for the handling of cells for the purification according to the present invention.

Cell Populations

Cell population is according to invention functionally and/or structurally homogenous population of cells. Preferably the cell population comprise at least one specific marker structure, which can be recognized by specific binding reagent according to the invention. The most preferred cell populations according to the invention are CD34+ and CD133+ cell populations, especially when purified from human cord blood or equivalent. The cell population may be homogenous or heterogenous with regard to the level of expression of the marker.

The preferred cell population may represent a minor fraction of the cells in the sample. Purification of such low proportion of cells is especially challenging. The invention is especially directed to purification of cell population representing less than 10%, more preferably less than 5%, even more preferably about 0.05-1% and most preferably about 0.1-0.5% of the total number of the cells in the sample.

Preferred "Negative Cell Populations"

The present invention is further directed to corresponding "negative cell populations", which means highly pure multiple cell population containing sample materials from which a specific cell population has been removed by the method according to the invention. Most preferred negative cell populations are CD34− and CD133− cell from human cord blood. The negative cell populations are especially useful materials e.g. for controlling and standardising scientific experiments studying the positive cell populations. The invention is especially directed to the use of a specific cell population and its corresponding negative cell population for the comparison with each other in structural and/or functional analysis, preferably by preferred profiling method(s).

Preferred Purification of Multipotent Cells

It has been realized that various human tissues contain multipotent cells such as various progenitor cells, or stem cells, which are useful for scientific studies and developing therapeutics for animals and human. There is a need for purification of multipotent cells from various sample types.

Most preferably the invention is directed to purification of multipotent cell populations from cord blood, such as CD34+ and CD133+ cell populations.

Uses of the Cell Populations

The cell populations according to the invention, especially complete cell populations, are especially useful for scientific development and studies including analytical development of complete and pure cell population, diagnostics development, and for studies and production of therapeutic cells and cell culture and development thereof.

Preferred Analysis of the Cell Populations by Profiling of Complete Cell Population The invention is especially directed to profiling of marker molecules of cell populations purified according to the invention, especially complete cells populations. The preferred profiling methods includes mRNA-profiling for example by mRNA-cip tecgene expression profiling methods and novel glycomics profiling of expressed glycans on cells.

Analysis of Cell Purity

The present invention is directed to the preparation of pure cell populations, wherein the purity can be assessed, e.g., by cell counting method, such as FACS method.

High Yield of Highly Purified Complete Cell Populations

It is known in the art that highly purified cell populations may be obtained by increasing washing of cells contacted with magnetic beads. However this process will reduce the yield of the cells. Moreover, the washing would release cell populations with weak binding to affinity matrix, creating a biased cell population which actually does not correspond to total cell population carrying the specific marker structure.

The inventors compared traditional purification methods using one and two purification rounds in immunomagnetic methods. It was found out that the purities and/or yields with cord blood were poor with both one and two column methods. Extensive washing released substantial amounts of cells from columns at each purification round. It is realized that the release of a specific cell depend on the affinity of the cell to immobilized affinity reagent and less avidly bound cells are more easily lost biasing the cell population. The present data including the flow cytometric analysis patterns indicates that the process and the purified cell populations are very reproducible.

Preferred Recovery % to be Obtained by the Method According to the Invention

The current methods producing highly purified cells especially by affinity methods such as magnetic bead methods usually fail to show any respectable yield from starting material. The measurement of the low amounts of cells in starting material is difficult making recovery %-estimates difficult. The optimised process according to the invention avoids the loss of materials and shows reproducible and reasonable approximate minimum recovery levels. The method can allow, under optimal conditions, the yield of about 50% or more of highly purified cells from cord blood. This is relatively good yield level for highly purified cells. The present invention is especially directed to production of highly purified cell populations, preferably complete cell populations from human cord blood. The invention is directed to highly purified complete cell populations obtainable by the method according to the invention with the yields of at least about 70%, preferably at least about 75% of purified cells, and even more preferably at least about 80%, and even most preferably at least about 90% from the raw material such as human cord blood.

Complete Cell Populations and Production Thereof

The present invention is specifically directed to the methods of isolating highly purified complete cell populations by the methods according to the present invention. The complete cell populations would contain both weakly and highly binding cells representing the original distribution of cells in the raw material from which the cells are isolated. The weakly binding and highly binding cells indicate the binding efficiency of the desired cell population with regard to the binding reagent. The binding efficiency is in preferred embodiment measured by FACS analysis.

The present invention is especially directed to complete cell population and production thereof, when the cell population to be purified from a sample, that contains substantial amount of weakly binding cells. The preferred substantial amounts includes ranges of relatively low amount of weakly binding cells amounts, preferably observable by FACS analysis, above about 0.1% preferably at least about 1%, more preferably at least about 3%, even more preferably about 0.5-5% and most preferably about 1-10%. Including the low amounts of weakly binding cells are useful for many application as the minor population have effect of analytics and function, especially in biological use and/or cell culture. The preferred substantial amounts further includes ranges of relatively high amount of weakly binding cells amounts, preferably observable by FACS analysis, above about 5% preferably at least about 8%, more preferably at least about 10%, even more preferably about 5-15%, even more preferably about 5-35%, and most preferably about 5-50%. The methods are especially preferred for CD34+ cells according to the invention. These comprise varying amounts CD34+ dim cells (estimated to vary between depending on the sample 0-40%). The FACS analysis of CD133+ populations reveal only scattered cells outside of the main population indicating very low amount of CD133+ dim cells in the population.

The invention is further directed to highly purified complete cell population produced from cord blood, preferably the complete cell population is a mononuclear cell population from cord blood, and in a more preferred embodiment said mononuclear cell population consists of CD34-positive or CD133-positive cells.

Reproducibility of the Purification of the Highly Purified Complete Cell Population The present invention is specifically directed to processes according to the present invention wherein a highly purified complete cell population is produced with less than 5%-unit variation from the mean purity % (for example mean 95% and variation less than +−5%), more preferably with less than 3%-unit variation from the mean purity. Alternatively, the invention is directed to highly reproducible processes, when the highly purified cell population is produced so that the differences of the purity figures from the mean purity are less than 3%, preferably less than 2.5%, more preferably less than 2%, even more preferably less than 1.5%, and most preferably less than 1%. The inventors were able to produce numerous cell populations (more than 10) with the reproducible yield.

Preferred Purity of Reproducibly Highly Purified Mononuclear Complete Cell Populations from Human Cord Blood The present invention is especially directed to production of purified cell populations from cord blood, preferably from human cord blood and/human placental blood and corresponding materials. As described above production of highly purified complete cell preparations from human cord blood has been a problem in the field. In the broadest embodiment the invention is directed to biological equivalents of human cord or placental blood as cord blood according to the invention, when these would comprise similar markers and which would yield similar cell populations when separated similarity as the CD133+ cell population and equivalents according to the invention or when cells equivalent to the cord blood is contained in a sample further comprising other cell types. It was revealed that it is possible to produce highly purified cell populations from cord blood with purity useful e.g. for exact gene expression profiling and biomarker analysis.

The preferred purity depends of the affinity of the antibody used. For commercial CD34-antibody, the preferred purity of a complete cell population is at least 90%, more preferably at least 93%, and most preferably at least 95%. For anti-CD133 antibody, preferred purity of a complete cell population is at least 90%, more preferably at least 93%, and most preferably at least 95%.

The present invention is directed to complete cell populations from human early blood with purity of at least 85%, more preferably at least 90%, 91%, 92%, 93%, 94%, or 95%, and most preferably at least 95%, 96%, 97% or 98%. In a specific embodiment, the present invention is directed to an ultrapure complete cell population in which the level of impurities is less than 10%, more preferably less than 5%, and most preferably less than 3%. The invention is specifically directed to complete cell populations purified by anti-CD34 and anti-CD133 antibodies.

In a specific embodiment the present invention is directed to highly purified human complete CD133+ and CD 34+ cell populations derived from cord blood.

Highly Viable Cell Populations

The present methods gives beside the high yields and recovery, completeness, purity and reproducibility also highly viable cells. The highly viable cells survived the purification step intact and are capable of proliferating. Preferably, the complete cell population is at least 95% viable, more preferably at least 97% viable, even more preferably at least 98% viable, and most preferably at least 99% viable.

High Throughput Production

It is realized that the present method is suitable for production of relatively large scientific and even large scale industrial and/or therapeutic cell samples. The scientific level process produces about 100 000-1 000 000 cells from about $1-2\times10^8$ of mononuclear raw material cells The method according to the invention can be upscaled 10-100 fold or even more with established separation technologies. It is realized that in microscale FACS type processes highly pure cell populations may be produced, but currently these are not useful for production of larger amounts of cells from large amount of starting material, using FACS to produce larger amounts in numerous batches would be extremely expensive and cells would suffer at least in terms of viability during the lengthy process, probably affecting recovery and purity, as well. The present invention is preferably directed to the purified cell batches of CD34+ or CD133+ cells comprising cells in range of $10^5$-$10^8$, and in preferred embodiment in range of about $10^6$ to $10^7$ cells.

Highly Purified Cell Population Obtainable by the Method Disclosed

The present invention is preferably directed to the process according to the invention for the production of the reproducible highly purified, preferably complete, viable cell populations according to the invention.

It is noted that the sequences of the target or marker genes listed in the tables and figures are available in the public databases such as in GenBank. The tables provide accession numbers, the Affymetrix probe set ID, and name for each of the sequences. The sequences of the genes in public databases, such as GenBank, are herein expressly incorporated by reference in their entirety as of the filing date of this application (see www.ncbi.nim.nih.gov).

EXPERIMENTAL SECTION

Example 1

Summary and Introduction of a mRNA Array Analysis

Human cord blood (CB)-derived CD133+ cells carry characteristics of primitive hematopoietic cells and proffer an alternative for CD34+ cells in hematopoietic stem cell (HSC) transplantations. To characterize the CD133+ cell population on genetic level, a global expression analysis of CD133+ cells was performed using oligonucleotide microarrays. CD133+ cells were purified from 4 fresh CB units by immunomagnetic selection. All 4 CD133+ samples showed significant similarity in their gene expression pattern, whereas they differed clearly from the CD133− control samples.

In all, 690 transcripts were differentially expressed between CD133+ and CD133− cells. Of these, 393 were increased and 297 were decreased in CD133+ cells. The highest overexpression was noted in genes associated to metabolism, cellular physiological processes, cell communication and development. A set of 257 transcripts expressed solely in the CD133+ cell population was recognized. The results demonstrate that CD133+ cells express primitive markers and they possess clonogenic progenitor capacity.

This study provides a gene expression profile for human CD133+ cells. It presents a set of genes that may be utilized to unravel the properties of the CD133+ cell population, assumed to be highly enriched in HSCs.

Introduction

The HSCs, possessing self-renewing and differentiation potential, are required for the lifelong sustenance of a functional blood system. Hematological malignancies have been successfully treated with stem cell transplantations for decades. Recently, stem cell transplantations have been used as a therapy for many non-hematological disorders, such as immunodeficiency syndromes, inborn errors of metabolism and autoimmune diseases[1, 2, 3]. More specific transplants consisting of selected HSCs are required for novel indications of stem cell transplantations and especially when human leukocyte antigen-identical sibling donors are not available. The use of T and B cell depletion facilitates the prevention of graft versus host disease and Epstein-Barr virus lymphoproliferative disease[4, 5]. The number of primitive cells and their proliferation capacity are considered preferable parameters for the engraftment potential as compared to nucleated cellularity[6]. To increase the number of cells used in transplantations and to promote ex vivo expansion of HSCs, a greater understanding of profitable cell populations is required.

CB is an excellent source of HSCs. Rapidly available CB serves as an alternative for patients without potential bone marrow (BM) donor. Lower risk of graft versus host disease and cytomegalovirus infection are associated with CB transplantations. The comparison of the gene expression profiles of HSCs from peripheral blood (PB), BM and CB suggests that CB-derived HSCs also carry the potential to differentiate into cells of nonhematopoietic lineages[7]. The HSCs from different sources display unique characteristics in terms of key transcription factors and genes associated to cell cycle, homing and apoptosis[7, 8, 9]. HSCs from CB express a large number of transcription factors not seen in HSCs from other sources. The expression of these transcription factors may inhibit differentiation and might explain the higher proliferation rate observed in CB-derived HSCs[7].

The CD34 antigen has been the most widely used marker for HSC enrichment. Although the reconstruction of adaptive immune system has been demonstrated with human CB-derived CD34+ progenitor cells in mice[10], the CD34+ cell fraction is apparently quite heterogeneous. The CD133 antigen provides a promising single selection marker for HSC enrichment. The CD133+ cells are considered to be highly non-committed with the capacity to self-renew and differentiate. In addition, CD133+ cells have been shown to have higher clonogenic capacity than CD34+/CD133− cells[11]. Most of the CD133+ cells are CD34+ bright, whereas CD34+ dim cells are CD133−. A small population of CD34−/CD133+ cells (0.2%) has been found in CB, demonstrating that CD133 expression is not necessarily associated with CD34 expression[12].

The CD133 molecule has been found on the surface of hematopoietic, neuronal and embryonal stem cells (ESC). Moreover, the expression of CD133 is related to several solid organ malignancies such as lung, prostate and brain cancers[13, 14, 15]. A recent study demonstrates that only CD133+ cancer stem cells are capable of brain tumor initiation while they sustain the ability to self-renew and proliferate[15]. CB-derived CD133+ cells uphold hematopoietic development. In addition, they are able to differentiate into endothelial and neuronal cells[16].

The aim of this study was to characterize CB-derived CD133+ cells on genomic level, and to provide the first gene expression profile of CD133+ cells. A global gene expression analysis of CD133+ cells was performed using Affymetrix microarray system. The clonogenic progenitor capacity of CD133+ cells was demonstrated showing that they are highly non-committed and hold potential to differentiate into all cell types of the hematopoietic system. The expression analysis presented in this study focuses on transcripts that are associated with hematopoiesis, cell cycle and cell adhesion. The gene expression data bank of the CD133+ cells may be utilized to study the pathogenesis of hematological diseases deriving from HSCs.

Example 2

Materials and Methods Useful for mRNA-Array Expression Analysis

Cells

Umbilical CB was obtained from the Helsinki University Central Hospital, Department of Obstetrics and Gynecology, and Helsinki Maternity Hospital. All donors gave the informed consent and the study protocol was accepted by the ethical review board of the Helsinki University Central Hospital and Finnish Red Cross Blood Service. CB was collected in sterile collection bags (Cord Blood Collection system, Medsep Corporation, Covina, USA) containing citrate phosphate dextrose solution, and processed within 4-20 hours. All CB units tested negative for human immunodeficiency virus, hepatitis C virus, hepatitis B virus, human T-cell lymphotropic virus and syphilis. Mononuclear cells (MNC) were isolated by Ficoll-Hypaque density gradient (Amersham Biosciences, Piscataway, USA). CD133+ cells were enriched through positive immunomagnetic selection using CD133 Cell Isolation Kit and MACS affinity columns (Miltenyi Biotec, Bergisch Gladbach, Germany). CD133+ cells were subjected to 2 rounds of separation. CD133− cells from the same CB unit were collected for control purposes. Microarray analysis was performed using 4 separate CB units. In addition, 6 CB units were processed for quantitative real-time polymerase chain reaction (qRT-PCR) analysis.

Flow Cytometry

Immunomagnetically selected cells were labeled with phycoerythrin (PE)- and fluorescein isothiocyanate (FITC)-conjugated monoclonal antibodies (mAbs) to evaluate the purity of cell fractions. Labeling was carried out using CD133/2-PE (clone 293C3, Miltenyi Biotec) and CD45-FITC (clone 2D1, Becton Dickinson, Franklin Lakes, USA) in 50 µl of phosphate-buffered saline (PBS) at room temperature for 20 minutes. Isotype-identical monoclonal antibodies $IgG_{2b}$-PE and $IgG_1$-FITC (Becton Dickinson) served as controls. Flow cytometry analysis was performed on Becton Dickinson FACSCalibur™ with a 488 nm blue argon laser. Fluorescence was measured using 530/30 nm (FITC) and 585/42 nm (PE) bandpass filters. Data were analyzed using the ProCOUNT™ software (BD Biosciences, San Jose, USA) and Windows Multiple Document Interface for Flow Cytometry, WinMDI version 2.8 (http://facs.scripps.edu/software.html).

Colony-forming Unit Assay

Colony-forming unit (CFU) assay was performed using methylcellulose, MethoCult GF H4434 with recombinant cytokines and erythropoietin (StemCell Technologies, Vancouver, Canada). A total of $2 \times 10^3$ CD133+ cells, $1 \times 10^5$ CD133− cells or $1 \times 10^5$ MNCs were plated in duplicate and cultured for 14 days at 37° C. with 5% carbon dioxide in a humidified atmosphere. Colonies were counted according to their morphological characteristics.

RNA Isolation

Total RNA from up to $2 \times 10^7$ pelleted cells was purified with RNeasy Mini Kit (Qiagen GmbH, Hilden, Germany) according to the manufacturer's instructions. Yield and quality of the RNA was measured by spectrophotometric analysis with GeneQuant pro (Amersham Pharmacia Biotech). Each sample, 1 µg of total RNA, was assessed for the integrity of RNA by discrimination of 18S and 28S ribosomal RNA on 1% agarose using Ethidium Bromide for visualization.

Microarray Analysis

Total RNA from each sample was used to prepare biotinylated target RNA, with minor modifications from the manufacturer's recommendations (http://www.affymetrix.com/support/technical/manual/expression_manual.affx). In brief, first-strand cDNA was generated from 100 ng of total RNA using a T7-linked oligo(dT) primer. After the first cDNA synthesis cycle, in vitro transcription was performed with unlabeled ribonucleotides. A second round of cDNA synthesis was then performed followed by in vitro transcription with biotinylated UTP and CTP (Enzo Diagnostics, Farmingdale, USA). Cleanup of double-stranded cDNA was performed using Pellet Paint® Co-Precipitant (Novagen, Madison, USA) instead of Glycogen. Standard Affymetrix hybridization cocktail was added to 15 µg fragmented cRNA. After overnight hybridization using Affymetrix GeneChip Instrument System (Affymetrix, Santa Clara, USA), arrays were washed, stained with streptavidin-phycoerythrin and scanned on Affymetrix GeneChip Scanner 3000. All experiments were performed using Affymetrix Human Genome U133 Plus 2.0 oligonucleotide arrays (http://www.affymetrix.com/products/arrays/specific/hgu133plus.affx). The replicate results of hybridization data for CD133+ and CD133− cells were obtained from 4 individual CB units. Sample labeling and hybridization was carried out at the Finnish DNA Microarray Centre at Turku Centre for Biotechnology, Turku, Finland.

Statistical Analysis

Pearson correlation coefficient (m=8, n=54 612) was calculated for each sample pair using original signals values obtained from Operating Software detection algorithm.

The Pearson correlation coefficient, $r_{ik}$, between $i^{th}$ and $k^{th}$ samples, say $\{y_{1i}, y_{2j}, \ldots, y_{ni}\}$ and $\{y_{1k}, y_{2k}, \ldots, y_{nk}\}$, respectively, is defined by $$r_{ik} = \frac{\sum_{j=1}^{n}(y_{ji} - \overline{y_i})(y_{jk} - \overline{y_k})}{(n-1)s_i s_k}, \text{ for } i \neq k \text{ and } 1 \leq i, k \leq m,$$

where $$\overline{y_k} = \sum_{j=1}^{n} y_{jk}/n \text{ and } s_k = \sqrt{\sum_{j=1}^{n}(y_{jk} - \overline{y_k})/(n-1)}$$

are the mean and standard deviation of the $k^{th}$ sample, respectively.

Pre-processing and Filtering of Microarray Data

The Affymetrix GeneChip Operating Software detection algorithm was used to determine the presence or absence of expression for each transcript. A transcript with either the detection call present or marginal was considered expressed. To define differential gene expression, the CD133+ data were compared against the CD133− data. The transcripts assigned with change call increased, decreased, marginally increased or marginally decreased were considered differentially expressed. The direction of change (increased or decreased) was to be the same in all CD133+ samples and the fold change cut-off value was set to 3.

Clustering and Annotation

In order to identify and visualize the differences between the CD133+ and CD133− samples, 2 clustering algorithms, hierarchical clustering and self-organizing maps (SOM) with the component plane representation, were applied[17, 18, 19]. In hierarchical clustering, average and correlation were used as linkage and distance metric, respectively. Hierarchical clustering was performed for all 8 CD133+ and CD133− samples. The SOM algorithm clusters transcripts having similar expression profile in the same neuron of the component plane. Accordingly, transcripts clustered close to each other are similar, while topologically distant transcripts have dissimilar expression pattern. The component plane representation includes also an unified-matrix (U-matrix) representation, which can be used to identify robust clusters consisting of several neurons[19]. For the SOM, the mean expression across 4 CD133+ and 4 CD133− samples resulting in 2 component planes were used. The SOM toolbox with Euclidean distance function, Gaussian neighborhood function, sheet SOM map with 15×9 neurons and batch learning algorithm was applied for the SOM analysis[20]. Affymetrix GO Ontology Mining tool was employed to obtain molecular functions, biological processes and cellular components for the transcripts in the clusters. The statistically significant hits were defined by chi-squared test and the associated P value with the significance level at 5% (P<0.05).

Gene Prioritization

To order the genes according to their discriminatory power, a stepwise gene selection algorithm was used[21]. Briefly, the algorithm computes mean and standard deviation across CD133+ samples (µ+, σ+) and across CD133− samples (µ−, σ−). The weight for ith gene is computed using signal-to-noise ratio[22]:

$$w_i = \frac{(\mu_{i+} - \mu_{i-})}{\sigma_{i+} + \sigma_{i-}}.$$

If a gene has large magnitude weight, then the gene is strongly differentially expressed between CD133+ and CD133− samples, and variation in CD133+ and CD133− is low.

Quantitative qRT-PCR Analysis

To further confirm the information obtained from the microarray data, 10 genes (CD133, CD34, KIT, SPINK2, Notch1, SOX4, TIE, CD2, CD14 and CD45) were subjected to qRT-PCR analysis using pools with 3 samples in each. Analysis was performed on 2 biological replicates. Total RNA was DNase-treated with DNA-free™ Kit (Ambion Inc., Austin, USA), and reverse transcription was performed using High-Capacity cDNA Archive Kit with RNase Inhibitor Mix (Applied Biosystems, Foster City, USA) in a final volume of 100 µl. Thermal cycling conditions for reverse transcription were 25° C. for 10 minutes and 37° for 120 minutes on GeneAmp® PCR System 9700 (Applied Biosystems).

For the polymerase chain reaction (PCR), the template was added to PCR mix consisting of 12.5 µl TaqMan Universal PCR Master Mix containing Uracil N-glycosylase for PCR carry-over prevention, 1.25 µl of TaqMan Assays-On-Demand Gene expression probe (Hs00195682_m1, Hs01040181_m1, Hs00156373_m1, Hs00174029_m1, Hs00413187_m1, Hs00268388_s1, Hs00178500_m1, Hs0069122_g1, Hs00365634_g1, Hs99999905_m1) and diethyl pyrocarbonate-treated water (Ambion Inc.). Samples were assayed in triplicate in a total volume of 25 µl. The qRT-PCR thermal cycling conditions were as follows: an initial step at 50° C. for 2 min for Uracil N-glycosylase activation; 95° C. for 10 min; and 40 cycles of 15 s at 95° C. and 1 min at 60° C.

A standard curve for serial dilutions of GAPDH rRNA was similarly constructed. GAPDH was chosen to internal control because its expression levels had no variance between the samples in the microarray analysis. Changes in fluorescence were monitored using the ABI PRISM 7000 Sequence Detection System, and raw data were analyzed by Sequence Detection System 1.1 Software (Applied Biosystems). The relative standard curve method was used to balance the variation in the amount of cDNA and to compensate for different levels of inhibition during reverse transcription and PCR.

Example 3

Results and Discussion of mRNA-analysis

Quality Assessment

The purity of positively selected CD133+ cells was over 90%, and the CD133− cell population was nearly 100% pure (FIG. 1). Generally $10^5$-$10^6$ CD133+ cells were recovered from a CB unit and the viability of selected cells was 99% at the least. The integrity of total RNA was confirmed by spectrophotometry and agarose gel electrophoresis.

To ensure the uniformity and comparability of the biological replicates, their pair-wise relationships were defined by Pearson correlation coefficients. The Pearson correlation coefficients were calculated for all the data points excluding Affymetrix control samples, thus 54 609 transcripts per array became compared. The consistency in all cases was high, but the correlation within CD133+ samples was stronger than correlation between CD133+ and CD133− samples. The correlation coefficients between CD133+ replicates had a mean of 0.98 (range 0.95-1.00). The correlation coefficients indicated significant similarity of the CD133+ samples. The correlation coefficients between CD133+ and CD133− samples reached an average of 0.78. In hierarchical clustering, the CD133+ and CD133− samples clustered at the opposite ends of the dendrogram. These results demonstrate that the CD133+ cells are much more similar to one another than to the CD133− cells from the same individual.

The differential expression of 10 genes was confirmed by qRT-PCR analysis. The average fold change was calculated for each gene and compared to the result from microarray analysis. The values were comparable and the qRT-PCR analysis confirmed the microarray results (Table 1).

The Expression Profile of CD133+ Cells

Figure 2:
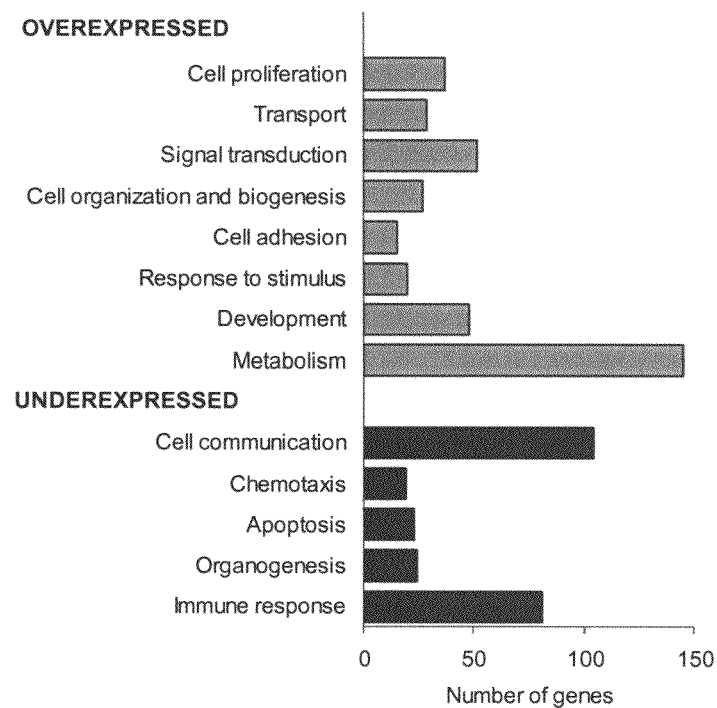
FIG. 2. Biological processes represented by the differentially expressed genes in CD133+ and CD133− cells.

The comparison of CD133+ and CD133− data sets resulted in 690 transcripts that were differentially expressed at least 3-fold (supplement data 1). In CD133+ cells, 393 of the transcripts were up-regulated, and 297 were down-regulated. The differentially expressed genes encode proteins involved in diverse biological processes ranging from cell communication and development to response to stimulus and metabolism (FIG. 2). Annotation was found for 214 (54%) up-regulated transcripts, while the remaining 179 had no associated biological function. Annotation was found for 215 (72%) of the down-regulated transcripts.

Figure 3:
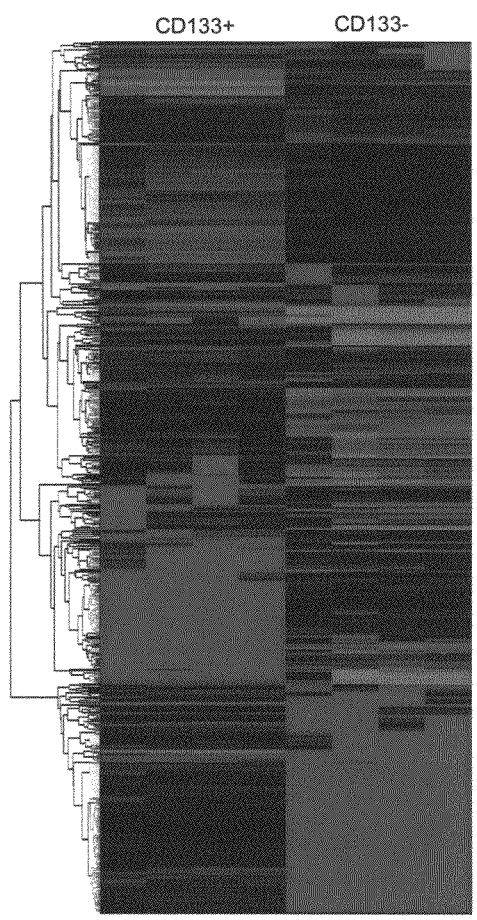
FIG. 3. Hierarchical clustering of 690 differentially expressed transcripts between CD133+ and CD133− samples.

Two different clustering methods was applied to the set of 690 transcripts passing the initial screening filter. Hierarchical cluster analysis showed moderate variation in expression within a transcript between replicates (FIG. 3). The expression of genes encoding CD133, CD34 and other transmembrane proteins such as FLT3, LAPTM4B, EBPL and CRIM1 had minor variance in all 4 CD133+ samples. Other very similarly expressed transcripts were ANKRD28, several members of the HOX gene family and transcripts encoding hypothetical proteins. Moreover, DKC1, BAALC and JUP had minimal variation within CD133+ replicates. In contrast, slightly more variation was observed in the expression of KIT, a known stem cell marker.

Figure 4:
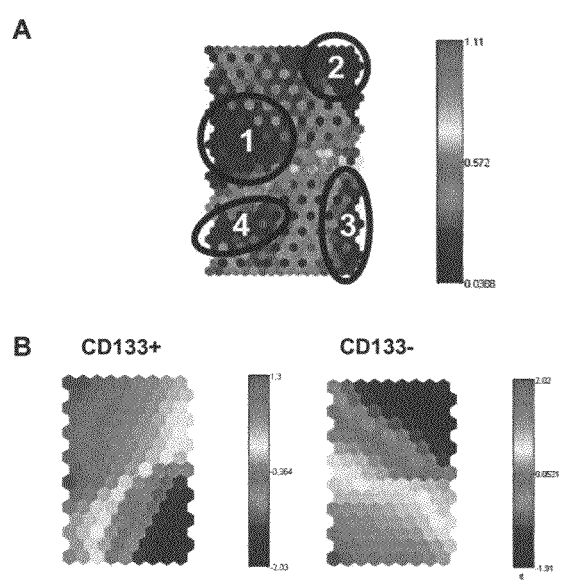
FIG. 4. Classification of CD133+ and CD133− samples by mean SOM analysis. (A) The 4 clusters determined by U-matrix. (B) Mean SOM component planes for CD133+ and CD133− samples.

The SOM was constructed using mean values of 690 differentially expressed genes between the CD133+ and CD133− samples (FIG. 4). The mean value was used to determine the similar expression behavior common to all CD133+ samples. The SOM revealed 4 prominent clusters of genes distinguishing CD133+ and CD133− cell populations. The clusters are illustrated by the U-matrix.

SOM clusters 1 and 2 represented up-regulated genes, and clusters 3 and 4 comprised down-regulated genes. In cluster 1, the association to a biological process was attained for 88 (57%) of the transcripts. The significantly represented biological processes were cell growth and maintenance, cell proliferation and regulation of cell cycle. In cluster 2, a functional role was found for 69 (59%) of the transcripts. The most significant functional category was cell organization and biogenesis. Cluster 3 contained a group of down-regulated genes associated to cell communication, metabolism and immune response. Annotation was found for 86 (76%) of the genes in cluster 3. In addition, cluster 4 contained a number of genes whose protein products participate in cell communication and response to stimulus. Moreover, the phosphorylation and phosphate metabolism-related genes were abundant. Cluster 4 contained 64 (70%) transcripts with known biological function.

In the SOM component plane, the most prominent finding was that known HSC markers CD133, CD34 and KIT had similar expression patterns and they clustered into the same neuron (Table 4). Interestingly, this neuron also contained the gene for SPINK2. The role of SPINK2 is poorly understood but its expression is seen in human BM CD34+ cells and testicle tissues (http://genome.ucsc.edu/cgi-bin/hgNear).

CD133+ Cell Enriched Genes

Altogether, 22 764 (42%) of the 54 675 transcripts on the arrays were expressed in one or more of the CD133+ samples. On each CD133+ array, similar number of transcripts was expressed with maximum variance of 0.8%. Up-regulation was seen in 6178 (11%) transcripts in at least one CD133+ sample. Each individual CD133+ sample had similar number of unique gene expression. The common expression pattern for all 4 CD133+ samples encompassed 2285 up-regulated transcripts. Of these, 2034 (89%) transcripts were overexpressed at least 2-fold. The transcripts were prioritized based on their degree of increased expression and the magnitude of standard deviation. Gene prioritization was performed in order to identify the genes that best discriminate CD133+ and CD133− cells.

The 2285 transcripts common for all CD133+ samples included genes whose protein products participate in cell communication, development, response to endogenous stimulus, chromosome organization and biogenesis. Also genes associated to RNA processing and mRNA metabolism were significantly overexpressed. Annotated biological process was found for 1399 (61%) of the transcripts.

Figure 5:
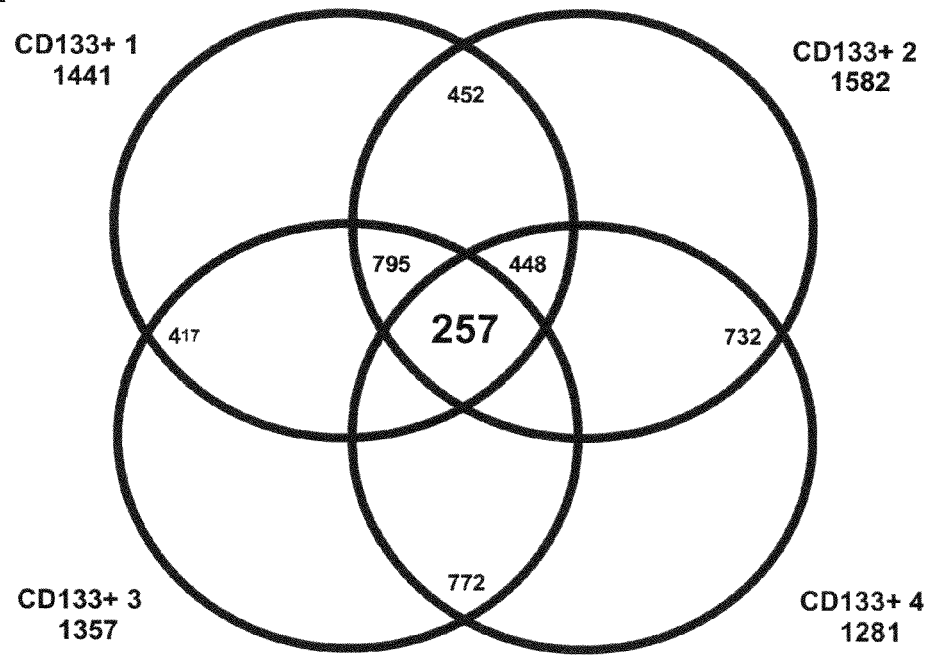
FIG. 5. Common transcripts expressed in CD133+ cells. (A) Schematic representation of intersections and differences in CD133+ cells. Only transcripts expressed in CD133+ cells but absent in CD133− cells were included. (B) Categorization of common genes expressed in CD133+ cells based on Gene Ontology annotation.
Figure 5:
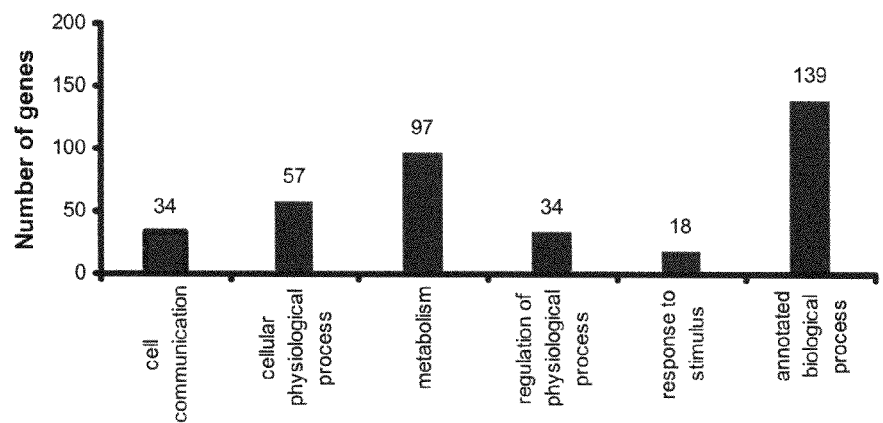

The expression of 257 transcripts was seen in CD133+ samples only (FIG. 5A, Supplement data 2). These transcripts were absent in CD133− control samples. The annotation was found for 155 (60%) transcripts (FIG. 5B). A great number of transcripts were involved in DNA metabolism (17 transcripts), and cell proliferation (17 transcripts). The 257 transcripts expressed in CD133+ cells only contained 31 genes encoding potential integral membrane proteins that may serve as markers for HSCs (Table 2). In gene prioritization, the gene coding for transmembrane protein LAPTM4B got the highest weight value. In CD133+ cells, LAPTM4B expression was 26-fold.

Cell Cycle

The expression data were surveyed to establish the cell cycle state of CD133+ cells. The expression of GATA2 (fold change 7.0) and N-MYC (fold change 15) that keep the HSCs in undifferentiated state was significantly elevated in CD133+ cells. The down-regulation of these genes would initiate the cell cycle. DST (fold change 5.3) and PLAGL1 (fold change 9.1) which support cell cycle arrest were up-regulated as well. A cell cycle inhibitor and negative regulator of proliferation, NME1, was overexpressed in CD133+ cells by 3.7-fold.

Majority of CB-derived HSCs have been shown to be in quiescent phase[23]. However, factors promoting the $G_1$ phase, such as CDK6 (fold change 10) and BCAT1 (fold change 19), were overexpressed along with CDK4 (fold change 3.9) that acts in the $G_1$/S transition. The negative regulator of CDK4 and CDK6, p18, was underexpressed by 5.1-fold. Moreover, the overexpression of BMI-1 was observed by 2.8-fold. BMI-1 enhances cell cycle by inhibiting p16, the negative regulator of cell cycle. As expected, p16 was not expressed in CD133+ cells.

The S phase was demonstrated by high expression of genes encoding minichromosome maintenance proteins crucial in DNA replication. Known S phase inducers, MCM2 (fold change 3.1), MCM5 (fold change 4.2), MCM6 (fold change 2.5) and MCM7 (fold change 2.8), were up-regulated. Interestingly, CDK2AP1, a suppressor of DNA replication, was overexpressed by 4-fold and CDKN2D, needed in S phase, was underexpressed by 20-fold. However, the low expression of CDKN2D refer to $G_1$ phase[24]. No known transcripts encoding molecules acting in $G_2$ phase or $G_2$/M transition were seen. Many transcripts for molecules with ubiquitin-protein ligase activity, such as SH3MD2, UHRF1, ZNRF1, EDD and TIF1, were overexpressed more than 3-fold. Many cell cycle regulatory molecules are controlled by ubiquitin-mediated proteolysis to allow a rapid transition between cell cycle stages, and to regulate the number of cells entering cell cycle[25]. Genes associated with mitosis, such as SKB1, STAG1, ANAPC7 and MPHOSPH9, were overexpressed by 2.6-fold, 1.6-fold, 2.6-fold and 3.1-fold, respectively. These data suggest that a portion of CD133+ cells are cycling.

Hematopoiesis

The expression of genes associated to self-renewal and differentiation was studied to unravel the hematopoietic state of CD133+ cells. Several HSC-associated genes were overexpressed: CD133 by 60-fold, CD34 by 13-fold, KIT by 26-fold, TIE by 3.2-fold, SCA-1 by 2.1-fold, MEIS1 by 10-fold and ANGPT1 by 12-fold. Genes supporting self-renewal such as GATA2, MPLV, STAT5A and TCF7L2 were up-regulated by 7.0-fold, 12-fold, 1.9-fold and 3.3-fold, respectively. Hox genes, thought to be involved in HSC regulation, were also highly up-regulated. The expression of HOXA9 (fold change 130) induces stem cell expansion, HOXA5 (fold change 10) and HOXA10 (fold change 3.7) are specific for the long-term repopulating population of HSCs[26]. Up-regulation of GATA2 and other transcription factors supporting self-renewal may account for the differentiation arrest and the more primitive nature of CB-derived HSCs[7]. The previously reported early markers for hematopoeitic progenitors, BAALC and C17[27, 28, 29], were expressed in CD133+ cells only. The BAALC gene was overexpressed by 33-fold. The expression of BAALC has been shown in brain tissue, yet its functional role is unknown[28]. The overexpression of C17, a gene coding for an extracellular molecule with signal transduction activity, was 15-fold.

AML1, overexpressed by 2.5-fold in CD133+ cells, may also support HSC self-renewal albeit it has been characterized as an early differentiation marker of the myeloid lineage. The other early myeloid differentiation gene PU.1 was absent. GATA1 affecting erythropoiesis and PAX5 promoting B-precursor development were both absent. No change in expression of GFI1 leading to T-lymphoid differentiation was detected. NFE2, required for HSCs determination to megakaryocyte and erythrocyte lineage, was down-regulated.

The expression of lineage-determination markers glycophorin-A, CD38, CD7, CD33, CD56, CD16, CD3, or CD2 was undetected in CD133+ cells. The expression of CD45 was seen in CD133+ cells but it was down-regulated. The CD45 antigen is abundant in lymphoid cells covering about 10% of the cell surface. The gene expression results suggest a naive state for the CD133+ cell population containing long-term and short-term repopulating HSCs as well as early progenitors with myeloid and lymphoid lineage potential.

Figure 6:
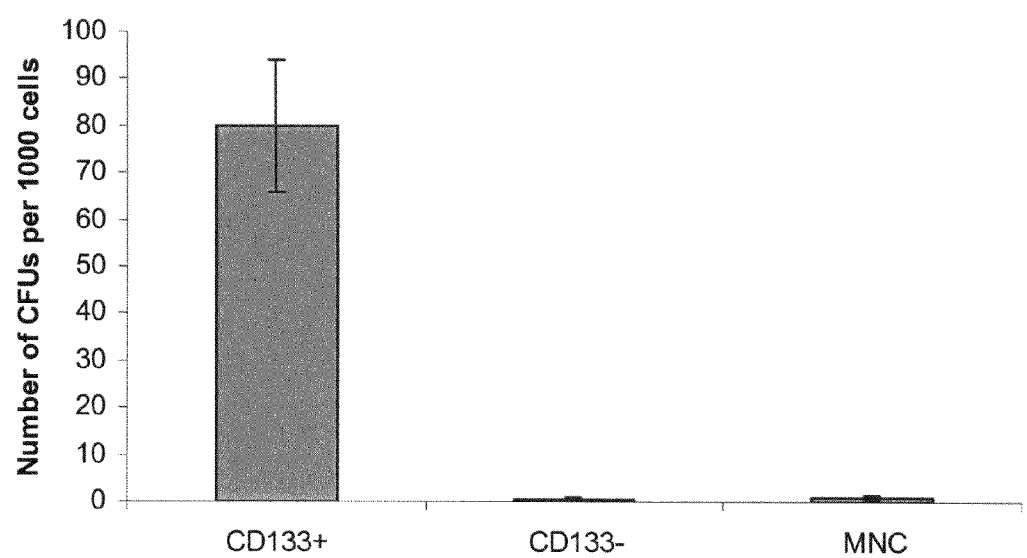
FIG. 6. Clonogenic progenitor cell capacity of CD133+, CD133− and MNC populations.
Figure 7:
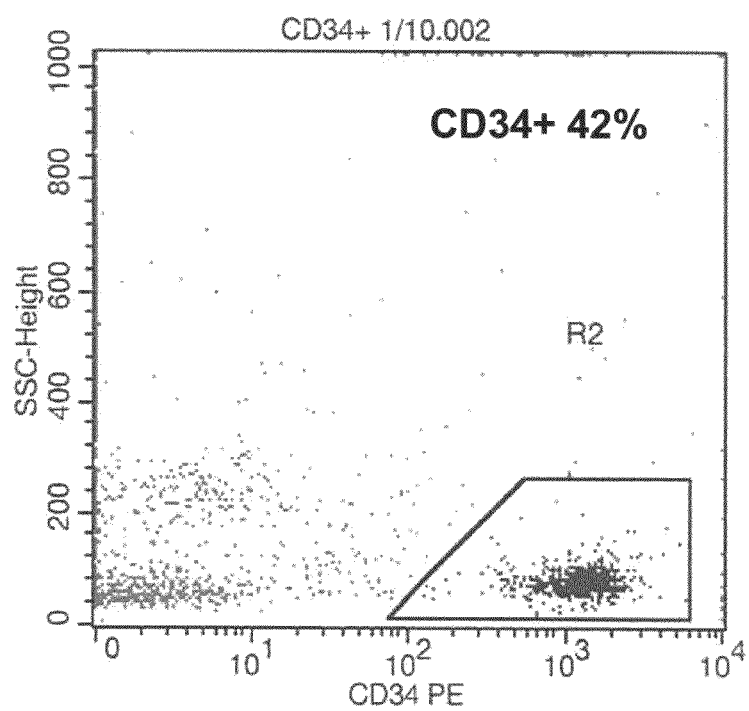
FIG. 7. Purity assessment of CD34+ cell fraction by flow cytometry. Purity of CD34+ cells (green) is 42% when using one column separation.

CFU assay was used to measure the clonogenic progenitor capacity of CD133+ and CD133− cells as well as MNCs (Table 3). Total CFU (CFU-TOT) number was determined as the sum of granulocyte-erythroid-macrophage-megakaryocyte (CFU-GEMM), granulocyte-macrophage (CFU-GM), erythroid (CFU-E) and burst-forming erythroid (BFU-E) colonies (FIG. 6). CFU-TOT counts were 80, 0.58 and 1.09 per 1000 cells for CD133+, CD133− and MNC populations, respectively. The highest proportion of CD133+ cells formed CFU-GM colonies (58%) and CFU-GEMM colonies (38%). BFU-Es represented 4.2% of the colonies, yet CFU-E colonies were not observed. Taken together, CD133+ is a valid selection marker for HSC-enrichment. The clonogenic progenitor capacity of CD133+ cells demonstrates that they are highly non-committed and hold potential to differentiate into all cells in the hematopoietic system.

Discussion

The gene expression profile of human HSCs, especially CD34+ cells, has been reported from various sources[7, 8, 9, 26, 30, 31, 32]. The aim of this study was to characterize the gene expression profile of CB-derived cells selected using CD133, a marker thought to be specific for HSCs. Altogether, 42% of the transcripts on the arrays were expressed in one or more of the CD133+ samples. The large number of expressed transcripts in CD133+ cells may be due to the open reading frame structure of HSCs[8, 33, 34, 35]. In all, 690 transcripts were found to be differentially expressed between CD133+ and CD133− cells. Among these were many genes encoding known stem cell markers and genes coding for hematopoietic regulators. The genes encoding mature hematopoietic markers were not expressed in CD133+ cells, whereas their expression was detected in CD133− cells.

Hierarchical cluster analysis presented a set of 537 transcripts with differential expression between CD133+ and CD133− cells. The expression pattern of these transcripts was similar within all CD133+ samples and CD133− samples, and the level of expression was uniform. Some transcripts showed variation in their expression level between biological replicates even though the direction of change was the same. The variance of expression level in CB-derived HSCs is known to be higher than in HSCs from other sources[7]. The higher individual variance may be explained by the unique birth event in each case.

SOM analysis was performed to the 690 differentially expressed genes. It revealed that SPINK2 had similar expression pattern with known HSC markers CD133, CD34 and KIT. The association of SPINK2 and HSCs has not been described previously. The markedly high expression of SPINK2 was confirmed by qRT-PCR. The decreased expression of SPINK2 in testis has been shown to be associated with infertility[36]. Similarly, CD133 has been suggested to have a role in the biogenesis of spermatozoa and the molecule may function in the formation and stabilization of epididymal stereocilia and tail of spermatozoa[37]. CD133 expression is assumed to affect the formation of lamellipodia enabling HSC migration[30].

SOM clustering demonstrated that the biological processes associated with up-regulated or down-regulated genes were divergent. Cluster 1 encompasses differentially expressed genes encoding proteins involved in cell growth and maintenance, cell proliferation and regulation of cell cycle. The high proliferation activity deduced from the expression pattern of CD133+ cells may reflect the existence of long-term repopulating HSCs in the CD133+ cell fraction. According to literature, most of the CD133+ cells reside in the $G_0/G_1$ state of cell cycle[23, 38]. Genes associated to cell cycle regulation were highly up-regulated in CD133+ cells. In contrast, the CD133− cell fraction displayed significantly elevated number of genes whose protein products participate in immune response and reaction to stimulus, corresponding to the expression pattern of mature blood cells.

In this study, the main focus was on expressed genes related to hematopoiesis and cell cycle. Moreover, the expression of genes encoding cell adhesion molecules that are related to functionally important processes in HSC migration and homing was examined. Among the 690 differentially expressed genes, 11 that encode adhesion molecules were up-regulated in CD133+ cells. The overexpression of these genes (CD34, IL-18, JUP, DST, COL5A1, TRO, DSG2, ITGA9, SEPP1, PKD2, VAV3) is also associated with cell cycle arrest and response to external stress. The 16 down-regulated genes associated to cell adhesion encoded known mature cell markers, such as CD2 and CD36. Several genes encoding chemokines and integrins were down-regulated. The low or undetectable expression of genes associated to migration probably relates to CB as the source of the CD133+ cells, as the CB microenvironment differs from BM. The engraftment potential of CB-derived HSCs is known to be delayed compared to other sources of HSCs[39]. The gene coding for VLA-4, needed for HSC homing, was up-regulated. The up-regulation of VLA-4 has been shown to be crucial to HSC engraftment in mice[40]. CB-derived HSCs have higher long-term engraftment capacity and their engraftment potential is significantly greater as compared to BM and PB[41, 7].

A set of 257 transcripts, expressed solely in CD133+ cells, was found. This set encompassed several genes coding for putative integral membrane proteins. The expression and localization of these proteins can not be deduced from the present data, and it is a subject of further investigations. Of the common genes expressed in CD133+ cells, LAPTM4B got the highest weight value in gene prioritization. The expression of LAPTM4B has been detected in mouse and human ESCs, HSCs and neuronal stem cells by several independent studies[26, 34, 42]. LAPTM4B has no know biological function but some observations link its up-regulation to certain cancer cell lines and poor differentiation of human hepatocellular carcinoma tissues[43]. For 125 of the 257 transcripts, a biological function could not be found. These novel genes may serve as basis for further studies on HSC regulation.

When comparing the CD133+ expression data with published data on human HSCs, the highest similarity was seen with slow dividing fraction of CB-derived CD34+CD38− cells[8, 26, 30]. Also, CB-derived CD34+CD38− cells and CD34+CD38-Lin-cells showed similarity to CD133+ cells[8, 30]. A few ESC-related stem cell markers, such as DNMT3B, DNMT3A, and DPPA4 were overexpressed in CD133+ cells as well[34, 44, 45, 46, 47, 48]. DNA methylation by DNMT3B is vital for de novo methylation in embryonic cells and is strongly down-regulated during ESC differentiation[49]. The mouse homolog for DPPA4, an embryonal development pluripotency associated gene, is related with Oct4 expression that has an essential role in the control of developmental pluripotency of embryonic cells[50]. Transcriptional evidence of ESC-related genes is a sign of the primitive nature of CB-derived CD133+ cells. CB-derived CD133+ cells have been shown to have non-hematopoietic differentiation potential with the capacity to develop into endothelial and neuronal cells[16].

This study provides a gene expression profile for CD133+ cells with an analysis focusing on genes associated to hematopoiesis and cell cycle. The microarray analysis results have been confirmed by qRT-PCR for several selected genes, and the clonogenic progenitor activity of CD133+ cells has been demonstrated. These results show that CD133+ cell fraction is an excellent source of HSCs with ability to self-renew and differentiate. The gene expression profile of CD133+ cells may be utilized to study the pathogenesis of hematological disorders and development of malignancies. An improved understanding of CB-derived CD133+ cells furthers their use in therapeutic applications. The present study provides additional information on the knowledge gathered from previous HSC gene expression analyses. Combining all published data would bring the scientific community closer to unraveling the riddle of HSCs.

Example 4a

Immunomagnetic Separation of CD34+/CD133+ Cells from Cord Blood

Preparation of Mononuclear Cells

Cord blood is diluted 1:4 with PBS-2 mMEDTA and 35 ml of diluted cord blood is carefully layered over 15 ml of Ficoll-Paque®. Tubes are centrifuged for 40 minutes at 400×g without brake. Mononuclear cell layer at the interphase is collected and washed twice in PBS-2 mM EDTA. Tubes are centrifuged for 10 minutes at 300×g. Cell pellet is resuspended in a final volume of 300 μl of PBS-2 mM EDTA-0.5% BSA per $10^8$ total cells.

Labeling of CD34+/CD133+ Cells

100 μl of FcR Blocking Reagent and 100 μl of CD34 or CD133 Microbeads are added per $10^8$ total cells. Suspension is incubated for 30 minutes at 6-12° C. Cells are washed with PBS-2 mMEDTA-0.5% BSA and resuspended in 500 μl of PBS-2 mM EDTA-0.5% BSA per $10^8$ cells.

Magnetic Separation

Column type is chosen according to the number of total cells: MS column for $<2\times10^8$ cells and LS column for $2\times10^8$-$2\times10^9$ cells. The column is placed in the magnetic field and rinsed with PBS-2 mMEDTA-0.5% BSA. Labeled cell suspension is applied to the column and the cells passing through the column are collected as the negative cell fraction. The column is then washed four times with PBS-2 mMEDTA-0.5% BSA. The column is removed from the magnetic field and the retained positive cells are eluted with PBS-2 mMEDTA-0.5% BSA using a plunger.

Additional Labeling of CD34+/CD133+ Cells

The eluted positive cells are centrifuged for 5 minutes at 300×g and resuspended in 300 μl PBS-2 mM EDTA-0.5%

BSA. 25 µl of FcR Blocking Reagent and 25 µl of CD34 or CD133 Microbeads are added. Suspension is incubated for 15 minutes at 6-12° C. Cells are washed with PBS-2 mM EDTA-0.5% BSA and resuspended in 500 µl of PBS-2 mM EDTA-0.5% BSA.

Additional Magnetic Separation

A MS column is placed in the magnetic field and rinsed with PBS-2 mMEDTA-0.5% BSA. Labeled cell suspension is applied to the column. The column is washed four times with PBS-2 mMEDTA-0.5% BSA. The column is then removed from the magnetic field and the retained positive cells are eluted with PBS-2 mMEDTA-0.5% BSA using a plunger.

Results

The low level of purity of cell populations isolated from cord blood is a problem known in the field. In general, the current level of purity is not good enough for analytics with gene expression arrays or the like. A reason for the problem is the composition of other cellular materials in cord blood and low amount cells in the target cell population. Furthermore the part of positive of the cells can be lost in extensive washings of the sample during the isolation process, which would reduce yield and enrichment of positive cells. Moreover, the methods involving extensive washings produced cell populations, which contain major amount of marker positive cells in the negative cell population, for example in CD34− or CD133− cell fractions, this would bias the control(baseline) cell population used for example in gene expression analysis. The methods involving extensive washing require large amount of material and the cell populations are easily biased so that part of the cells with low affinity towards the binding reagent are lost more easily than the cells with high expression of the specific marker. Furthermore, the washing may cause stress to cells and reduces the amount of alive and viable cells. Preferably, the method of the invention involve up to 1-5 washing steps, more preferably 3-5 and most preferably 4 washing steps during the steps c) and g).

Single Column Method

Figure 12:
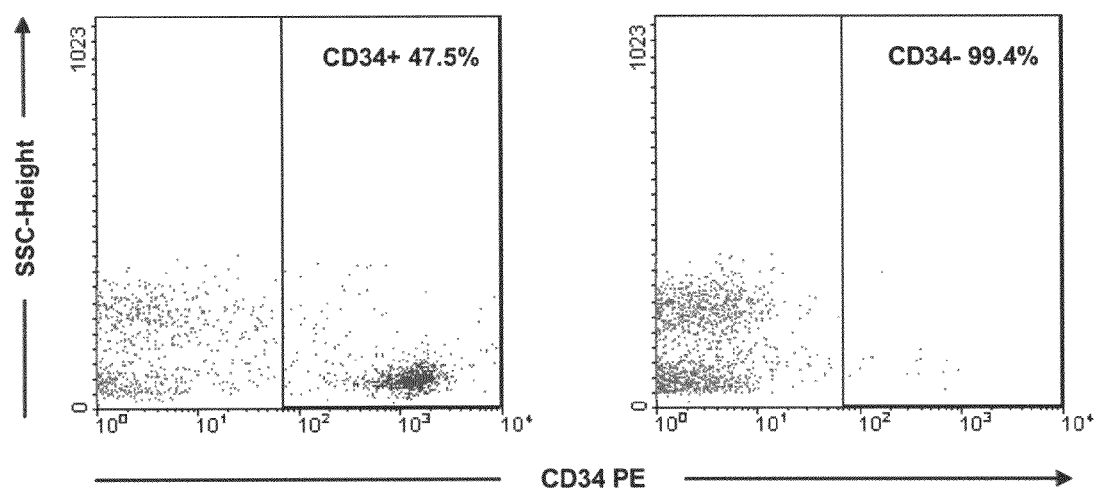
FIG. 12. Purity assessment of the CD34+ cell fraction by flow cytometry. The initial purity of CD34+ cells after separation through single column was 47.5%. The CD34− fraction was 99.4% pure. CD34+ and CD34− cell populations were defined by first gating on forward and side scatter properties excluding platelets and debris. Subsequent gates were set to exclude >99% of control cells labeled with isotype-specific antibody. Percentages indicating the purity of isolated cell fractions are shown for both plots. Abbreviations: SSC, side scatter; PE, phycoerythrin.

FIG. 12 shows one example of purity (47%) of CD34+ cells from one purification round using immunomagnetic separation (Miltenyi Biotech). This method gave 81% purity for CD133+ cells. The purifications from human cord blood with regard to CD34 are especially difficult, so the process was first developed for CD34+ cell population.

Effect of Extensive Washing and Using Two Column Method

Table 24 shows increased release of CD34+ cells from columns of immunomagnetic beads containing anti-CD34 antibody. It is realized that the process increases the purity of cells but at the same time reduces effectively the recovery of the cells, the purity for CD34+ cells is still under 80%. Table 25 shows the increase of cell purity in a column method. Using two column rounds increased the yield but did not give special benefit with regard to one column method. High amount of CD34+ cells (19%) were observed in the flow through of the second column.

Using Additional Labeling Between Purification Rounds Using Two Column System

Figure 13:
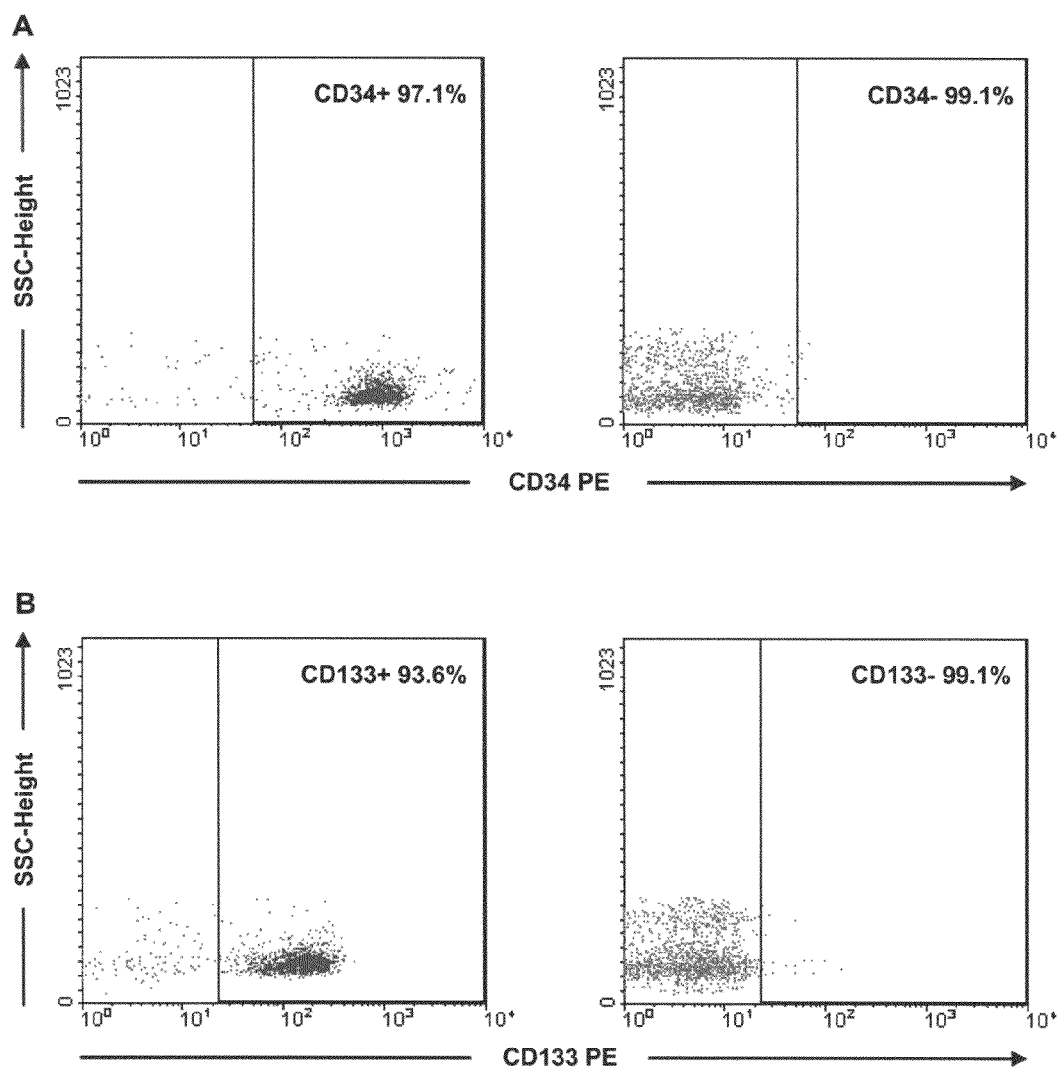
FIG. 13. Purity assessment of CD34+/−, and CD133+/−. A) Purities for CD34+ and CD34− cell factions were 97.1% and 99.1%, respectively. B) Purities for CD133+ and CD133− fractions were 93.6% and 99.1%, respectively. CD34+/−, CD133+/−cell populations were defined by first gating on forward and side scatter properties excluding platelets and debris. Subsequent gates were set to exclude >99% of control cells labeled with isotype-specific antibody. Percentages indicating the purity of isolated cell fractions are shown for both plots. Abbreviations: SSC, side scatter; IgG, immunoglobulin; PE, phycoerythrin.

FIG. 8. shows the purities of CD34+ cells in the novel two column process. FIG. 8A shows the purity of CD34+ cells after first column separation (78%). Additional labeling and second column purification increased the purity to 92% as seen in FIG. 8B. FIG. 13 shows additional example of highly purified cord blood CD34+ or CD133+ cells using two column separations, and the negative flow through fraction from (CD34− or CD133−) the first column.

Characteristic Yield and Recovery of the Novel Purification Method

The purification may be performed for example from about $1 \times 10^8$ mononuclear cells purified by Ficoll gradient from one unit of cord blood cells (approximately 80 ml, the amounts vary from experiment to experiment and reagents were adjusted with regard to starting material). Cord blood contains about 1-2% of CD34+ cells, the average yield of CD34+ cells in various experiment is about $0.5-1 \times 10^6$ cells (0.97%), from this recovery can be estimated to be between about 50-75%. The unit contains about 1% (or less) of CD133+ cells. The uncertainty of the measurement from the low amount of positive cells is substantial. The yield of CD133+ cells in the individual experiments was $0.5-1 \times 10^5$ cells corresponding to about 0.29% of the mononuclear cells used. The estimated recovery is about 30%.

Example 4b

Materials and Methods

Cord Blood Units

Umbilical cord blood (CB) was obtained from informed and consenting donors at the Helsinki University Central Hospital, Department of Obstetrics and Gynecology. Permit to collect and use donated stem cells has been obtained from the ethics board of the Helsinki University Central Hospital (550/E8/02) and the ethics board of the Finnish Red Cross Blood Service (40/02).

The umbilical cord was clamped according to standard hospital procedure and CB collections were performed ex utero. CB was collected into a sterile collection bag (Cord Blood Collection system, Medsep Corporation, Covina, USA) containing 25 ml of Citrate Phosphate Dextrose solution. The collection volume varied between 45-105 ml. Some CB units were volume reduced and cryopreserved in a BioArchive system at the Finnish Red Cross Blood Service, Cord Blood Bank as previously described [69] and some units were processed freshly within hours from collection. Altogether, 8 cryopreserved and 12 fresh CB units were used to optimize the protocols. In addition, 10 cryopreserved and 9 fresh CB units were used to test the optimized protocols.

Handling of Cord Blood Units

Cryopreserved CB unit was taken from the BioArchive system and kept for two minutes in the gas face of liquid nitrogen, 3-5 min at room temperature and in 37° C. water bath until completely thawed. CB was transferred from the freezing bag into 50 ml tubes containing 10 ml freezing solution: 2.5% albumin (Finnish Red Cross, Blood Service, Helsinki, Finland), 50% NaCl (Baxter Healthcare) and 50% Gentran40 (Baxter Healthcare). Freezing bag was rinsed with 15 ml of freezing solution and combined in the same tube. Cells were pelleted by centrifugation 600 g, 10 min and supernatant was discarded. When cell clumping occurred cell pellet was resuspended in 200 µl 1 mg/ml DNaseI (Sigma-Aldrich, Steinheim, Germany). Cells were then suspended carefully in 100 ml phosphate-buffered saline (PBS, pH 7.4) supplemented with 0.6% ACD/A. Fresh CB was diluted 1:4 with balanced salt solution, PBS, supplemented with 2 mM EDTA, to reduce the size and number of cell aggregates and to give better lymphocyte/mononuclear cell (MNC) yield in density gradient centrifugation.

MNCs were isolated by density gradient using 15 ml of Ficoll-Paque reagent (Amersham Biociences, Piscataway, USA) and 35 ml of diluted CB. The two-phase system was centrifuged at 400×g for 40 minutes. MNCs, collected from the interface between the two phases, were then washed twice with balanced salt solution using centrifugation of 300×g for 10 minutes. MNC counting was performed by automatic cell counter Sysmex K-1000 (Sysmex Corporation, Kobe, Japan).
Separation of CD34+/CD133+ Cells CD34+ and CD133+ cells were enriched through positive selection using the MiniMACS or MidiMACS separation system (Miltenyi Biotec). For the labeling of CD34+ cells, Direct CD34 progenitor Cell Isolation Kit was used, whereas CD133+ cell were labeled using the CD133 Cell Isolation Kit. 100 µl of FcR Blocking Reagent, to inhibit unspecific or Fc-receptor mediated binding, and 100 µl of CD34/CD133 MicroBeads for magnetic labeling of cells were added per $10^8$ cells, as per manufacturer's recommendations.

MS or LS MACS affinity columns were used depending on the number of MNCs. MS column was used for up to $2\times10^8$ MNCs, and LS column was used for $2\times10^8$ to $2\times10^9$ of total MNCs. Labeled cell suspension was subjected to immunomagnetic separation, where magnetically labeled cells retain in the column and unlabeled cells pass through the column. After several washes, the column was removed from the magnet and the retained CD34+ or CD133+ cells were eluted with 1-5 ml of PBS supplemented with 0.5% bovine serum albumin and 2 mM EDTA, using a plunger. CD34+ and CD133+ cells were subjected to one or two rounds of separation and their negative counterparts were collected for control purposes. In the two-column system, an additional labeling step between the column separations was tested, using 25 µl of both FcR Blocking Reagent and MicroBeads. The optimum purity and yield was obtained when using the additional labeling in connection with the two column system.

Purity

To determine the purity of column purified CD34 and CD133 cell fractions, $1\times10^5$ cells in PBS supplemented with 1% bovine serum albumin (BSA) were incubated with fluorescein isothiocyanate (FITC)-conjugated CD45 (clone 2D1, Becton Dickinson, Franklin Lakes, USA) or FITC-conjugated CD34 (clone AC136, Miltenyi Biotec) and phycoerythrin (PE)-conjugated CD34 (clone 345802 Becton Dickinson) or PE-conjugated CD133 (clone 293C3, Miltenyi Biotec) monoclonal mouse anti-human antibody at 4° for 15 min. Platelets were detected with PE-conjugated mouse anti-human CD41a monoclonal antibody. Isotype-identical monoclonal antibodies IgG2-PE and IgG1-FITC (Becton Dickinson) served as controls. After washing with PBS-1% BSA, cells were analyzed using Becton Dickinson FACSCalibur™ with a 488 nm blue argon laser. Fluorescence was measured using 530/30 nm (FITC) and 585/42 nm (PE) bandpass filters. Data were analyzed using the ProCOUNT™ software (BD Biosciences) or Windows Multiple Document Interface for Flow Cytometry, WinMDI version 2.8 (http://facs.scripps.edu/software.html). CD34+, and CD133+ cell populations were defined by first gating on forward and side scatter properties excluding platelets and debris. Subsequent gates were set to exclude >99% of control cells labeled with isotype-specific antibody.

Colony Forming Unit Assay

MNCs ($1\times10^5$) and enriched HSCs ($2\times10^3$) suspended in 300 µl Iscove's Modified Dulbecco's medium supplemented with 2% fetal bovine serum (Gibco/Invitrogen, Paisley, United Kingdom) were mixed vigorously with 3 ml of MethoCult GF H4434 containing recombinant cytokines and erythropoietin (StemCell Technologies). The cells in MethoCult medium were plated in duplicate into sterile 35 mm petri dishes, and colonies were scored according to their morphological characteristics by light microscopy after a 14-day culture. The assay was performed in triplicate for each cell type (CD34+, CD133+ and MNC).

Results and Discussion
Handling of Cord Blood (CB) Cells

The isolation of pure mononuclear cell (MNC) fractions from CB, and subpopulations thereof, brings about a special challenge. This appears to be due to the large number of thrombocytes and erythroid progenitors in CB. In Ficoll-Paque gradient, all erythroid cells do not sediment to the bottom layer, but are retained in the interphase of plasma and Ficoll-Paque. The erythroid cells remaining in the interphase are nucleated progenitors that hamper the subsequent immunomagnetic selection of HSC populations. The unusually slow sedimentation of erythroid cells is not seen when working with peripheral blood.

When handling cryopreserved CB, aggregation was observed. Aggregation was reduced by replacing ethylenediamine tetraacetic acid (EDTA, Merck, Darmstadt, Germany) with anticoagulant citrate dextrose solution, formula A (ACD/A, Baxter Healthcare, Lessines, Belgium) in the sample buffer. In some cases aggregation was so substantial that the cells needed to be resuspended in DNaseI containing buffer. DNase digests the DNA released from dead cells and prevents the aggregation. No aggregation was seen when handling fresh CB cells. DNase treatment did not affect on the viability or colony-forming potential of selected CB cells.

MNC Fraction

In cryopreserved CB, the mean MNC concentration was $5.14\times10^9$/l (range 0.96-10.0, SD=3.43) (FIG. 11), and the mean platelet concentration was $8.30\times10^9$/l (range 0-17, SD=5.46). Cryopreserved CB contained a mean of $0.14\times10^{12}$/l erythrocytes (range 0.02-0.67, SD=0.20), and mean hematocrit was 2%.

Figure 11:
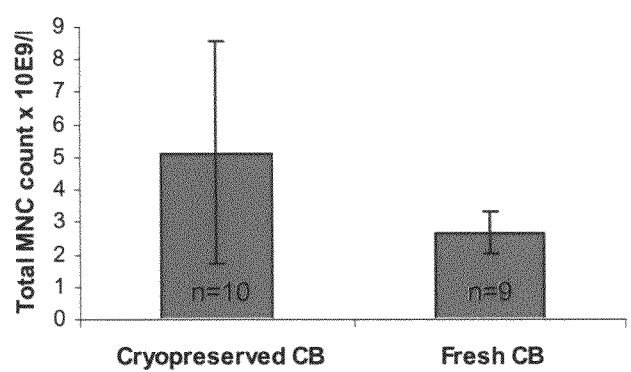
FIG. 11. MNC count in cryopreserved and fresh CB. The mean MNC concentration for cryopreserved and fresh CB was $5.1 \times 10^9/l$ (range 0.96-10.0, SD=3.43) and $2.7 \times 10^9/l$ (range 1.24-3.62, SD=0.64), respectively. The difference was not statistically significant (P=0.06). Abbreviations: MNC, mononuclear cells; CB, cord blood.

Fresh CB contained a mean of $2.68\times10^9$/l MNCs (range 1.24-3.62, SD=0.64) (FIG. 11). The difference in MNC concentration between cryopreserved and fresh samples was not statistically significant (P=0.06). The remarkably high disparity in the standard deviation of MNC concentration between cryopreserved and fresh CB may be due to the processing and freezing of cells performed to bank the CB units [69]. The mean concentration was $205.89\times10^9$/l (range 84-505, SD=130.58) for platelets and $0.12\times10^{12}$/l (range 0.03-0.50, SD=0.14) for erythrocytes. The mean hematocrit was 1%.

Immunomagnetic Separation of HSC Populations

When using the Direct CD34 progenitor Cell Isolation Kit with single column separation and the protocol recommended by the manufacturer (Miltenyi Biotec, Bergisch Gladbach, Germany), a purity of less than 50% was reached for CD34+ cells was reached (FIG. 12). To obtain highly pure CD34+ cells, the immunomagnetic selection method was optimized. Several washing steps (3-10) was tested for single column separation. A purity of 80% was achieved with extensive washing, but the yield was poor (less than 50% of the expected yield). Two successive column separations resulted in 77% purity, but a great number of CD34+ cells were still lost during the process. An additional labeling between the two column separations increased the purity to >90% (FIG. 8) and resulted in acceptable yield as well. The optimized two-column method with additional labeling proved reliable and was applied to the separation of both CD34+ and CD133+ cells. The purity of positively selected CD34+/CD133+ cells was reproducibly over 90% and their negative counterparts were nearly 100% pure.

Generally 0.86% of CD34+ cells (range 0.56-1.45, SD=0.36) and 0.21% of CD133+ cells (range 0.04-0.41, SD=0.12) were recovered from CB MNCs. The recovery of CD34+ cells was higher from fresh CB (1.0%) when compared to cryopreserved CB (0.78%), although the difference was not statistically significant (P=0.54). The results are consistent with the study by Almici et al. showing no significant difference in yield or in purity for fresh CB CD34+ cells in comparison to cryopreserved cells [70]. This was the case with CD133+ cells as well, the recovery being 0.29% for fresh CB and 0.12% for cryopreserved CB (P=0.11). The purities were not affected by the initial percentage of HSC populations in CB. The results of the purity assessment for representative samples of CD34+/−, and CD133+/−cells are shown in FIG. 13.

With the optimized protocols, a purity of 90% at least was achieved for CD34+, and CD133+ cells. Fresh CB was easier to handle and the recovery of HSC was higher from fresh CB. However, the viability was 99% at least for all the selected cell types from fresh and cryopreserved CB. This demonstrates that the optimized protocols work well in HSC enrichment for both fresh and cryopreserved CB. HSCs, enriched by the protocols described here, have been used in gene expression studies with great reproducibility and consistency [71].

It has been suggested that the binding of an antibody to the surface of a HSC may influence proliferation and differentiation through intracellular signaling pathways [64]. Anti-CD34 antibody has been shown to induce tyrosine phosphorylation in BM-derived CD34+ cells [72]. Further studies on the effect of the interaction between HSCs and the antibodies used for their selection as well as the possible impact of this contact on HSC graft potency are awaited.

Colony Forming Unit Assay

CFU assay was used to measure the clonogenic capacity of CD34+, and CD133+ cells as well as MNCs. Total CFU (CFU-TOT) number was determined as the sum of granulocyte-erythroid-macrophage-megakaryocyte (CFU-GEMM), granulocyte-macrophage (CFU-GM), erythroid (CFU-E) and burst-forming erythroid (BFU-E) colonies. CFU-TOT counts were 84.5, 80, and 0.47 per 1000 cells for CD34+, CD133+, and MNCs, respectively. CD34− and CD133− cell populations have shown very limited colony forming potential in our previous studies with CFU-TOT counts of 0.1 and 0.58 per 1000 cells, respectively.

The highest proportion of CB-derived HSCs formed CFU-GM colonies (mean 57.8%) and CFU-GEMM colonies (mean 35.8%). The proportion of individual colony types for CD34+, CD133+, Lin− and MNCs is represented in Table 23. BFU-Es represented a mean of 5.8% of the HSC colony content. This may be due to the inefficient removal of erythroid progenitors during the depletion. Very little CFU-E colonies were observed In HSC (mean 0.7%). The high proportion of BFU-E (15.4%) and CFU-E (5.5%) colonies formed by the MNC population reflects the unusual sedimentation of erythroid progenitors in CB. The results show that all the selected HSC populations have substantial clonogenic potential and are highly non-committed. Taken together, the markers traditionally used to separate HSC populations are useful until more specific markers are found.

Conclusions

Immunomagnetic cell sorting enables fast and gentle separation of HSCs. However, the previously reported protocols are not optimal for CB and result in unsatisfactory purity and yield, indicating a need for optimization of the procedures. With the modified protocols presented here, over 90% pure HSC fractions can be reproducibly obtained. This is essential for the use of specific hematopoietic progenitor cell types in research and therapeutic applications.

The single most important factor influencing engraftment in HSC transplantation appears to be the nucleated cell content. Even though the cell content is limited in CB and there is no possibility to obtain an additional graft from the same donor, the increased engraftment potential of CB-derived HSCs makes them an appealing alternative for HSCs from PB or BM. It remains to be seen whether the total nucleated cell content or a population of highly pure and specific hematopoietic progenitor cells will prove to be more important for graft potency.

Example 5

Glycosylation and Sialylation Linkage Analysis of Cord Blood Cell N-Glycans

EXPERIMENTAL PROCEDURES

N-glycan isolation from cord blood cell populations. Human cord blood mononuclear cells were isolated and divided into $CD133^+$ and $CD133^-$ cell populations as described above. N-linked glycans were detached from cellular glycoproteins by *F. meningosepticum* N-glycosidase F digestion (Calbiochem, USA) essentially as described previously (Nyman et al., 1998), after which the released glycans were purified for analysis by solid-phase extraction methods, including ion exchange separation, and divided into sialylated and non-sialylated fractions.

Mass spectrometric N-glycan analysis. MALDI-TOF mass spectrometry was performed with a Bruker Ultraflex TOF/TOF instrument, essentially as described previously (Saarinen et al., 1999; Harvey et al., 1993). Relative molar abundancies of sialylated glycan components were assigned based on their relative signal intensities (Papac et al., 1996).

α2,3-sialidase digestion. Sialylated N-glycans were treated with *S. pneumoniae* α2,3-sialidase (Glyko, UK) essentially as described previously (Saarinen et al., 1999). The sialic acid linkage specificity was controlled with synthetic oligosaccharides in parallel control reactions, and it was confirmed that in the reaction conditions the enzyme hydrolyzed α2,3-linked but not α2,6-linked sialic acids. After the enzymatic reaction, the glycans were purified and divided into sialylated and non-sialylated fractions and analyzed by mass spectrometry as described above.

Results

Mass spectrometric analysis of cord blood $CD133^+$ and $CD133^-$ cell N-glycans. Sialylated N-glycans were isolated from cord blood $CD133^+$ and $CD133^-$ cell fractions and analyzed by MALDI-TOF mass spectrometry as described under Experimental procedures, allowing for relative quantitation of individual N-glycan signals.

Figure 10:
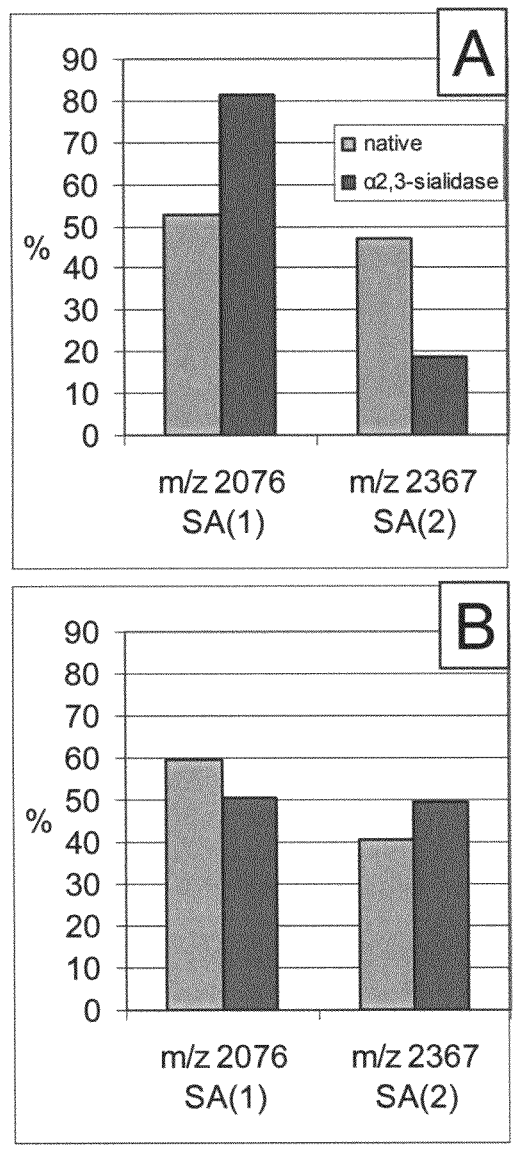
FIG. 10. α2,3-sialidase analysis of sialylated N-glycans isolated from A. cord blood CD133$^+$ cells and B. CD133$^-$ cells. The columns represent the relative proportions of a monosialylated glycan signal at m/z 2076 ($SA_1$) and the corresponding disialylated glycan signal at m/z 2367 ($SA_2$), as described in the text. In cord blood CD133$^-$ cells, the relative proportions of the $SA_1$ and $SA_2$ glycans do not change markedly upon α2,3-sialidase treatment (B), whereas in CD133$^+$ cells the proportion of α2,3-sialidase resistant $SA_2$ glycans is significantly smaller than α2,3-sialidase resistant $SA_1$ glycans (A).

Cord blood $CD133^+$ and $CD133^-$ cell N-glycans are differentially α2,3-sialylated. Sialylated N-glycans from cord blood $CD133^+$ and $CD133^-$ cells were treated with α2,3-sialidase, after which the resulting glycans were divided into sialylated and non-sialylated fractions, as described under Experimental procedures. Both α2,3-sialidase resistant and sensitive sialylated N-glycans were observed, i.e. after the sialidase treatment sialylated glycans were observed in the sialylated N-glycan fraction and desialylated glycans were observed in the neutral N-glycan fraction. The results indicate that cord blood $CD133^+$ and $CD133^-$ cells are differentially α2,3-sialylated. For example, after α2,3-sialidase treatment the relative proportions of monosialylated ($SA_1$) glycan signal at m/z 2076, corresponding to the $[M-H]^-$ ion of $NeuAc_1Hex_5HexNAc_4dHex_1$, and the disialylated ($SA_2$) glycan signal at m/z 2367, corresponding to the $[M-H]^-$ ion of $NeuAc_2Hex_5HexNAc_4dHex_1$, indicate that α2,3-sialidase resistant disialylated N-glycans are relatively more abundant in $CD133^-$ than in $CD133^+$ cells, when compared to α2,3-sialidase resistant monosialylated N-glycans (FIG. 10). It is concluded that N-glycan α2,3-sialylation in relation to other sialic acid linkages including especially α2,6-sialylation, is more abundant in cord blood CD133$^+$ cells than in CD133$^-$ cells.

The N-glycan analysis of total profiles of released N-glycans revealed beside the glycans above, which were verified to comprise
1) complex biantennary N-glycans, such as Galβ4GlcNAcβ2Manα3(Galβ4GlcNAcβ2Manα6) Manβ4GlcNAcβ4(Fucα6)$_{0-1}$GlcNAcβ-, wherein the reminal N-acetylactosamines can be elongated from Gal with NeuNAcα3 and/or NeuNAcα6 and
2) terminal mannose containing N-glycans such as High-mannose glycans with formula Hex$_{5-9}$HexNAc$_2$ and degradation products thereof comprising low number of mannose residues Hex$_{1-4}$HexNAc$_2$.

The glycan share common core structure according to the Formula:

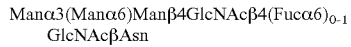
Manα3(Manα6)Manβ4GlcNAcβ4(Fucα6)$_{0-1}$ GlcNAcβAsn wherein the non-reducing end terminal Man residues can be elongated to the complex type structures of to mannose type structures.

It was further analyzed that the N-glycan compositions contained only very minor amounts glycans of additional HexNAx in comparison to monosaccharide compositions the complex type glycan above, which could indicated presence of no or very low amounts of the N-glycan core linked GlcNAc-residues described by Stanley P M and Raju T S (JBC-publications 90's). The NMR-analysis further indicate that the cord blood N-glyca structures are essentially devoid of GlcNAcα6-linked to reducing end subterminal GlcNAcβ4 of the N-glycan core. The essentially devoid of indicates less than 10% of all the protein linked N-glycans.

Preferred Structures of Terminal Mannose Type Structures

Based on enzymatic analysis, NMR and biosynthetic knowledge following structures could be assigned to terminal mannos glycans.

Preferred high- and low mannose type structures with GN2-core structure are according to the Formula M2:

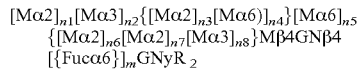
[Mα2]$_{n1}$[Mα3]$_{n2}${[Mα2]$_{n3}$[Mα6]}$_{n4}$][Mα6]$_{n5}$ {[Mα2]$_{n6}$[Mα2]$_{n7}$[Mα3]$_{n8}$}Mβ4GNβ4 [{Fucα6}]$_m$GNyR$_2$ wherein p, n1, n2, n3, n4, n5, n6, n7, n8, and m are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0;
M is Man and GN is GlcNAc, Fuc is L-fucose;
[ ] indicates determinant either being present or absent depending on the value of n1, n2, n3, n4, n5, n6, n7, n8, and m; and
{ } indicates a branch in the structure.

The high mannose structures lack part of the non-reducing end terminal mannoses so that There is at least preferably 6 or 5 mannose residue, most preferably 5.
yR$_2$-structures indicates the linkage to protein β-N-Asn.
Preferred General Molecular Structural Features of Low Man Glycans According to the present invention, low-mannose structures are preferentially identified by mass spectrometry, preferentially based on characteristic Hex$_{1-4}$HexNAc$_2$dHex$_{0-1}$ monosaccharide composition. The low-mannose structures are further preferentially identified by sensitivity to exoglycosidase digestion, preferentially α-mannosidase (Hex$_{2-4}$HexNAc$_2$dHex$_{0-1}$) or β-mannosidase (Hex$_1$HexNAc$_2$dHex$_{0-1}$) enzymes, and/or to endoglycosidase digestion, preferentially N-glycosidase F detachment from glycoproteins, Endoglycosidase H detachment from glycoproteins (only Hex$_{1-4}$HexNAc$_2$ liberated as Hex$_{1-4}$HexNAc$_1$), and/or Endoglycosidase F2 digestion (only Hex$_{1-4}$HexNAc$_2$dHex$_1$ digested to Hex$_{1-4}$HexNAc$_1$). The low-mannose structures are further preferentially identified in NMR spectroscopy based on characteristic resonances of the Manβ4GlcNAcβ4GlcNAc N-glycan core structure and Manα residues attached to the Manβ4 residue.

Several preferred low Man glycans described above can be presented in a single Formula:

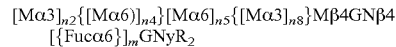
[Mα3]$_{n2}${[Mα6)]$_{n4}$}[Mα6]$_{n5}${[Mα3]$_{n8}$}Mβ4GNβ4 [{Fucα6}]$_m$GNyR$_2$ wherein p, n2, n4, n5, n8, and m are either independently 0 or 1; with the proviso that when n2 is 0, also n1 is 0; when n4 is 0, also n3 is 0; when n5 is 0, also n1, n2, n3, and n4 are 0; when n7 is 0, also n6 is 0; when n8 is 0, also n6 and n7 are 0; the sum of n1, n2, n3, n4, n5, n6, n7, and n8 is less than or equal to (m+3); [ ] indicates determinant either being present or absent depending on the value of n2, n4, n5, n8, and m; and
{ } indicates a branch in the structure;
Low mannose glycans preferably lack one of the terminal Man units so that
The glycan comprises 4 mannose residues;
M is Man and GN is GlcNAc, Fuc is L-fucose;
y and R2 indicates to b-N-glycosidic linkage to protein.
Preferred non-fucosylated low-mannose glycans are according to the formula:

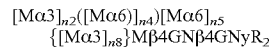
[Mα3]$_{n2}$([Mα6)]$_{n4}$)[Mα6]$_{n5}$ {[Mα3]$_{n8}$}Mβ4GNβ4GNyR$_2$ wherein p, n2, n4, n5, n8, and m are either independently 0 or 1,
with the proviso that when n5 is 0, also n2 and n4 are 0, and preferably either n2 or n4 is 0,
[ ] indicates determinant either being present or absent depending on the value of, n2, n4, n5, n8,
{ } and ( ) indicates a branch in the structure,
y and R2 are as indicated above.
Preferred Individual Structures of Non-Fucosylated Low-mannose Glycans
Special Small Structures Small non-fucosylated low-mannose structures are especially unusual among known N-linked glycans and characteristic glycans group useful for separation of cells according to the present invention. These include:

Mβ4GNβ4GNyR$_2$

Mα6Mβ4GN04GNyR$_2$

Mα3Mβ4GNβ4GNyR$_2$ and

Mα6{Mα3}Mβ4GNβ4GNyR$_2$.

Mβ4GNβ4GNyR$_2$ trisaccharide epitope is a preferred common structure alone and together with its mono-mannose derivatives Mα6Mβ4GNβ4GNyR$_2$ and/or Mα3Mβ4GNβ4GNyR$_2$, because these are characteristic structures commonly present in glycomes according to the invention. The invention is specifically directed to the glycomes comprising one or several of the small non-fucosylated low-mannose structures. The tetrasaccharides are in a specific embodiment preferred for specific Relations of N-glycan Types in Primitive Stem Cells, Especially Cord Blood Stem Cells The amounts of neutral terminal mannose containing glycans and neutral (non-sialylated) complex type glycans were quantified. The quantitation revealed that the total amount of terminal Mannose containing glycans was higher in comparison to neutral complex type glycans in more primitive/non-differentiated cells, such as cord blood CD34 and CD133 cells, which can be referred as stem cells. It was also realized that the ratio of neutral mannose terminal glycans to complex neutral glycans was even higher in CD133 positive cells in comparison to CD34 positive cells indicating also known more primitive status of CD133 cells in comparison to CD34 cells. Further more the paucimannose N-glycans were reduced in amount in comparison to complex type glycans in the more primitive cells.

Example 6

Presence of Cell Surface Molecules

Gene expression profile of CD133+ cells showed expression of several transcripts encoding plasma membrane proteins, of which the presence of CD135, CD166, DSG and SV2 on cell surface was studied by flow cytometry analysis. In addition, the presence of four embryonic stem cell markers SSEA3, SSEA4, TRA-1-60 and TRA-1-81 were studied. These related genes encoding for these protein products were not represented in Affymetrix HU133 Plus 2.0 chip used for gene expression profiling of CD133+ cells.
Materials and Methods
Cells Mononuclear cells (MNC) isolated from fresh cord blood units by Ficoll-Hypaque density gradient. Ten cord blood units were used for flow cytometric analysis.
Flow Cytometry MNCs were double-labeled with phycoerythrin (PE)-conjugated CD135 (FLT3)/CD166 (ALCAM) monoclonal antibodies (mAbs) (BD Biosciences Pharmingen, San Diego, Calif., USA) and CD45-fluorescein isothiocyanate (FITC)/ CD34-FITC mAbs. Isotype controls IgG1, k PE/FITC were used. Purified SV2, DSG2, SSEA3, SSEA4, TRA-1-60 and TRA-180 mAbs were used with secondary FITC-conjugated mAbs: anti-mouse IgG1, anti-rat IgM, anti-mouse IgM and anti-mouse IgG3. Flow cytometry analysis was performed on Becton Dickinson FACSCalibur™ and fluorescence was measured using 530/30 nm bandpass filters.
Results Presence of CD135 and CD166 markers was verified on cell surface. CD135 and CD166 mAbs labeled on average 11% and 20% of MNCs, respectively. Most of the CD34 labeled cells are also labeled with CD135 and CD166. CD135 and CD166 also label some of the CD41 and CD14 labeled cells. SV2, DSG, SSEA3, SSEA4, TRA-1-60 and TRA-1-81 mAbs did not label MNCs. This may be due to no marker on cell surface or because of poor reactivity of the antibody.

Example 7

N-glycans were isolated from the cells by N-glycosidase F digestion, fractionated into neutral and sialylated N-glycan fractions, purified, and subjected to $^1$H-NMR analysis (Fu, D. et al. (1994) *Carbohydr. Res.* 261, 173-86; Damm, J. B. L. et al. (1989) *Eur. J. Biochem.* 180, 101-10; Hård, K. et al. (1990) *Eur. J. Biochem.* 193, 263-71).

The $^1$H-NMR spectrum of the neutral N-glycan fraction showed that it contained high-mannose type N-glycans including the Man$_9$GlcNAc$_2$ high-mannose type N-glycan. For example, the spectrum contained the signals arising from H-1 of the β1,4-linked GlcNAc residue at 4.591 ppm (4.596 ppm, Fu et al., 1994, supra), H-2 of the β1,4-linked Man residue at 4.234 ppm (4.238 ppm, Fu et al., 1994, supra), and H-1 of the α1,2-linked Man residue in position 2,6,6,4,4 at 5.041 ppm (5.047 ppm, Fu et al., 1994, supra).

The $^1$H-NMR spectrum of the sialylated N-glycan fraction showed that it contained complex-type N-glycans including the biantennary complex-type N-glycan core sequence Galβ4GlcNAcβ2Manα3(Galβ4GlcNAcβ2Manα6) Manβ4GlcNAcβ4GlcNAc, with or without core α1,6-fucosylation, and with either α2,3- or α2,6-sialylation of the N-glycan antennae. For example, the spectrum contained the signals arising from H-1 of the α1,3-linked Man residue in position 3,4,4 at 5.135 ppm (5.135 ppm, Damm et al., 1989, supra), H-1 of β1,4-linked Gal residue at 4.545 ppm (4.544 ppm, Hård et al., 1990, supra), H-3 (axial) of α2,3-linked Neu5Ac residue at 1.804 ppm (1.797 ppm, Hård et al., 1990, supra), H-3 (axial) of α2,6-linked Neu5Ac residue at 1.723 ppm (1.719 ppm, Damm et al., 1989, supra), and H-1 of α1,6-linked Fuc residue at 4.895 ppm (4.892 ppm, Hård et al., 1990, supra).

Example 8

Biological Roles and Background Related to the mRNA Markers

Table 26 shows potential biological roles of various markers according to the invention. The invention is specifically directed to analysis of the specific marker groups for Signal transduction, DNA-matabolism, Response to stimulus, Cell proliferation, Transport and Development as specifically preferred groups for markers according to the invention. It is realized that the indications of the specifica The Table 26 show Unigene codes for the markers, which define the preferred markers most specifically. It is realized that the naming system of the mRNA array provider comprises mistakes with trivial names of the genes. The preferred codes to be used for specification of a marker includes the probe set id of Affymetrix company and especially the unigene code as in Table 26.

Reference Nos. 51-72. Shows some background related to analysis of different cord blood cell populations such as background for genomic profiling of CD34 cells or a cell population doubly selected with both CD34 and CD133 markers. These publications form some level background for CD34 type cord blood cell populations. However these markers do not create background for CD133 (single marker selected cell population or for complete CD133 population according to the invention. In a preferred embodiment the invention is directed to very general CD133 cell markers when markers of He et al are removed from the list. It is realized that due to various technical reasons He et al was unable to find major part of the present markers and the association of He-markers for pure CD133 population was not clear before present works. It is realized that the other works have used different cell populations and the selection population does not always give essentially clean selection marker negative cell populations. The present invention is specifically directed to markers for the analysis of pure and/or complete cell populations, preferably with the markers according to the invention.

The present invention is also directed to the specific groups of markers of Table 26 and other preferred groups according to the invention as markers for stem cells, when markers with background related to stem cells are removed from the groups. The present invention is also directed to the specific groups of markers of Table 26 and other preferred groups according to the invention as markers for cord blood cells, when markers with background related to cord blood cells are removed from the groups.

TABLE 1

Fold change of gene expression assessed by microarray and qRT-PCR-analysis

| Gene | Microarray fold change | qRT-PCR fold change |
|---|---|---|
| CD133 | 60 | * |
| CD34 | 13 | * |
| KIT | 26 | 38 |
| SPINK2 | 77 | 196 |
| SOX4 | 3.5 | 4.5 |
| NOTCH1 | 1.5 | 1.5 |
| TIE | 3.2 | 8.8 |
| CD2 | −20 | −50 |
| CD14 | −34 | −18 |
| CD45/PTPRC | −2.7 | −2.3 |

* The expression was abundant in CD133+ cells, but the very low expression in CD133− cells prevented the calculation of fold change.

TABLE 2

Transmembrane and/or membrane associated molecules (Affymetrix probe ID number)

| | | |
|---|---|---|
| ADAM28 | 205997_at | a disintegrin and metalloproteinase domain 28 |
| ALCAM | 201951_at | Activated leukocyte cell adhesion molecule |
| AREG | 1557285_at | Amphiregulin (schwannoma-derived growth factor) |
| ATP9A | 212062_at | ATPase, Class II, type 9A |
| C14orf1 | 202562_s_at | chromosome 14 open reading frame 1 |
| CRIM1 | 202551_s_at | cysteine-rich motor neuron 1 |
| CYYR1 | 235044_at | cysteine and tyrosine-rich 1 |
| DSG2 | 217901_at | Desmoglein 2 |
| DST | 215016_x_at | dystonin |
| EMP1 | 201324_at | epithelial membrane protein 1 |
| FLT3 | 206674_at | fms-related tyrosine kinase 3 |
| FLVCR | 222906_at | feline leukemia virus subgroup C cellular receptor |
| FSTL1 | 208782_at | follistatin-like 1 |
| GCNT2 | 230788_at | glucosaminyl (N-acetyl) transferase 2, I-branching enzyme |
| GPR125 | 210473_s_at | G protein-coupled receptor 125 |
| ITGA9 | 206009_at | integrin, alpha 9 |
| KIAA0152 | 200616_s_at | KIAA0152 gene product |
| KIAA0286 | 212621_at | KIAA0286 protein |
| KIT | 205051_s_at | v-kit Hardy-Zuckerman 4 feline sarcoma viral oncogene homolog |
| LAPTM4B | 208029_s_at | lysosomal associated protein transmembrane 4 beta |
| LRP6 | 225745_at | low density lipoprotein receptor-related protein 6 |
| MMP28 | 239272_at | matrix metalloproteinase 28 |
| NUP93 | 202188_at | nucleoporin 93 kDa |
| PILRB | 220954_s_at | paired immunoglobin-like type 2 receptor beta |
| PON2 | 210830_s_at | paraoxonase 2 |
| PTPRD | 213362_at | Protein tyrosine phosphatase, receptor type, D |
| SLC16A14 | 238029_s_at | solute carrier family 16 (monocarboxylic acid transporters), member 14 |
| SV2A | 203069_at | synaptic vesicle glycoprotein 2A |
| TM6SF1 | 1558102_at | Transmembrane 6 superfamily member 1 |
| TM7SF3 | 217974_at | transmembrane 7 superfamily member 3 |
| TNFRSF21 | 218856_at | tumor necrosis factor receptor superfamily, member 21 |
| TRO | 210882_s_at | trophinin |
| VEZATIN | 223089_at | transmembrane protein vezatin |
| VLA4 | 213416_at | very late activation antigen 4 |

TABLE 3

Frequency of different CFU colonies within CD133+, CD133− and MNC populations

| Cell population | CFU-GM (%) | CFU-GEMM (%) | BFU-E (%) | CFU-E (%) |
|---|---|---|---|---|
| CD133+ | 57.5 | 38.3 | 4.2 | 0.0 |
| CD133− | 14.7 | 17.4 | 64.4 | 3.5 |
| MNC | 44.8 | 44.8 | 5.6 | 4.8 |

TABLE 4

Preferred group of gene clustering derived markers

| Probe set ID | Gene Symbol | Gene title |
|---|---|---|
| 204304_s_at | PROM1/CD133 | prominin 1, CD133 antigen |
| 209543_s_at | CD34 | CD34 antigen |
| 205051_s_at | KIT | v-kit Hardy-Zuckerman 4 feline sarcoma viral oncogene homolog |
| 206310_at | SPINK2 | serine protease inhibitor, Kazal type 2 (acrosin-trypsin inhibitor) |

TABLE 5

393 transcripts up-regulated (Affymetrix probe set ID, see http://www.affymetrix.com) in CB-derived CD133+ cells

| | |
|---|---|
| 1 | 235142_at |
| 2 | 218899_s_at |
| 3 | 209905_at |
| 4 | 204753_s_at |
| 5 | 231982_at |

TABLE 5-continued 393 transcripts up-regulated (Affymetrix probe set ID, see http://www.affymetrix.com) in CB-derived CD133+ cells

| | |
|---|---|
| 6 | 225962_at |
| 7 | 206310_at |
| 8 | 227923_at |
| 9 | 219054_at |
| 10 | 216212_s_at |
| 11 | 209488_s_at |
| 12 | 223708_at |

TABLE 5-continued 393 transcripts up-regulated (Affymetrix probe set ID, see http://www.affymetrix.com) in CB-derived CD133+ cells

| | |
|---|---|
| 13 | 226676_at |
| 14 | 214651_s_at |
| 15 | 204304_s_at |
| 16 | 205984_at |
| 17 | 225782_at |
| 18 | 206298_at |
| 19 | 221286_s_at |
| 20 | 226517_at |
| 21 | 206674_at |
| 22 | 207836_s_at |
| 23 | 238484_s_at |
| 24 | 202890_at |
| 25 | 206660_at |
| 26 | 229437_at |
| 27 | 230698_at |
| 28 | 1559477_s_at |
| 29 | 226677_at |
| 30 | 231851_at |
| 31 | 225790_at |
| 32 | 205051_s_at |
| 33 | 1566482_at |
| 34 | 227692_at |
| 35 | 238444_at |
| 36 | 227688_at |
| 37 | 235287_at |
| 38 | 212489_at |
| 39 | 239280_at |
| 40 | 215294_s_at |
| 41 | 218051_s_at |
| 42 | 213541_s_at |
| 43 | 222780_s_at |
| 44 | 200986_at |
| 45 | 217901_at |
| 46 | 226210_s_at |
| 47 | 219479_at |
| 48 | 208029_s_at |
| 49 | 225086_at |
| 50 | 1553808_a_at |
| 51 | 228054_at |
| 52 | 227235_at |
| 53 | 226545_at |
| 54 | 225285_at |
| 55 | 204754_at |
| 56 | 205997_at |
| 57 | 241926_s_at |
| 58 | 201427_s_at |
| 59 | 1558871_at |
| 60 | 201015_s_at |
| 61 | 227370_at |
| 62 | 226985_at |
| 63 | 229002_at |
| 64 | 219789_at |
| 65 | 210410_s_at |
| 66 | 206683_at |
| 67 | 212686_at |
| 68 | 229461_x_at |
| 69 | 206478_at |
| 70 | 212775_at |
| 71 | 209781_s_at |
| 72 | 228692_at |
| 73 | 235109_at |
| 74 | 209493_at |
| 75 | 209487_at |
| 76 | 230896_at |
| 77 | 203688_at |
| 78 | 210432_s_at |
| 79 | 204798_at |
| 80 | 229307_at |
| 81 | 221935_s_at |
| 82 | 214039_s_at |
| 83 | 1554250_s_at |
| 84 | 230158_at |
| 85 | 235044_at |
| 86 | 239552_at |
| 87 | 1553183_at |
| 88 | 201431_s_at |
| 89 | 235324_at |
| 90 | 212186_at |
| 91 | 235333_at |
| 92 | 204069_at |
| 93 | 212746_s_at |
| 94 | 218397_at |
| 95 | 242002_at |
| 96 | 209576_at |
| 97 | 222799_at |
| 98 | 220038_at |
| 99 | 209543_s_at |
| 100 | 219837_s_at |
| 101 | 225308_s_at |
| 102 | 239364_at |
| 103 | 229530_at |
| 104 | 205609_at |
| 105 | 225240_s_at |
| 106 | 203069_at |
| 107 | 226134_s_at |
| 108 | 206009_at |
| 109 | 222258_s_at |
| 110 | 242051_at |
| 111 | 207002_s_at |
| 112 | 212062_at |
| 113 | 212013_at |
| 114 | 210145_at |
| 115 | 218844_at |
| 116 | 213258_at |
| 117 | 201215_at |
| 118 | 229199_at |
| 119 | 226025_at |
| 120 | 228011_at |
| 121 | 239080_at |
| 122 | 224847_at |
| 123 | 1558105_a_at |
| 124 | 217975_at |
| 125 | 203875_at |
| 126 | 235521_at |
| 127 | 227798_at |
| 128 | 224848_at |
| 129 | 209763_at |
| 130 | 207943_x_at |
| 131 | 209318_x_at |
| 132 | 1557285_at |
| 133 | 203633_at |
| 134 | 210571_s_at |
| 135 | 238002_at |
| 136 | 224851_at |
| 137 | 217894_at |
| 138 | 207550_at |
| 139 | 227297_at |
| 140 | 226473_at |
| 141 | 215388_s_at |
| 142 | 203178_at |
| 143 | 229572_at |
| 144 | 235564_at |
| 145 | 222891_s_at |
| 146 | 209524_at |
| 147 | 213094_at |
| 148 | 202600_s_at |
| 149 | 212012_at |
| 150 | 232424_at |
| 151 | 209676_at |
| 152 | 205518_s_at |
| 153 | 205624_at |
| 154 | 230624_at |
| 155 | 232383_at |
| 156 | 218694_at |
| 157 | 238732_at |
| 158 | 221942_s_at |
| 159 | 222240_s_at |
| 160 | 222603_at |
| 161 | 210664_at |
| 162 | 202371_at |
| 163 | 225764_at |
| 164 | 202016_at |
| 165 | 238488_at |
| 166 | 202551_s_at |

TABLE 5-continued 393 transcripts up-regulated (Affymetrix probe set ID, see http://www.affymetrix.com) in CB-derived CD133+ cells

| | |
|---|---|
| 167 | 236995_x_at |
| 168 | 205239_at |
| 169 | 224996_at |
| 170 | 208396_s_at |
| 171 | 212254_s_at |
| 172 | 210830_s_at |
| 173 | 215016_x_at |
| 174 | 212488_at |
| 175 | 202599_s_at |
| 176 | 203373_at |
| 177 | 213638_at |
| 178 | 225589_at |
| 179 | 204749_at |
| 180 | 219654_at |
| 181 | 224428_s_at |
| 182 | 222668_at |
| 183 | 201310_s_at |
| 184 | 227481_at |
| 185 | 228904_at |
| 186 | 212126_at |
| 187 | 220952_s_at |
| 188 | 223306_at |
| 189 | 202946_s_at |
| 190 | 239647_at |
| 191 | 219651_at |
| 192 | 213301_x_at |
| 193 | 212651_at |
| 194 | 220668_s_at |
| 195 | 212981_s_at |
| 196 | 235411_at |
| 197 | 201013_s_at |
| 198 | 203896_s_at |
| 199 | 213035_at |
| 200 | 204521_at |
| 201 | 225595_at |
| 202 | 226546_at |
| 203 | 212526_at |
| 204 | 228084_at |
| 205 | 239272_at |
| 206 | 223565_at |
| 207 | 228988_at |
| 208 | 218858_at |
| 209 | 209160_at |
| 210 | 213844_at |
| 211 | 202039_at |
| 212 | 225481_at |
| 213 | 209710_at |
| 214 | 236945_at |
| 215 | 204918_s_at |
| 216 | 225237_s_at |
| 217 | 202552_s_at |
| 218 | 228155_at |
| 219 | 218856_at |
| 220 | 238458_at |
| 221 | 201462_at |
| 222 | 209094_at |
| 223 | 225421_at |
| 224 | 218585_s_at |
| 225 | 228397_at |
| 226 | 228423_at |
| 227 | 201841_s_at |
| 228 | 206295_at |
| 229 | 203139_at |
| 230 | 204755_x_at |
| 231 | 226344_at |
| 232 | 209129_at |
| 233 | 223503_at |
| 234 | 223268_at |
| 235 | 1555888_at |
| 236 | 222906_at |
| 237 | 224827_at |
| 238 | 213129_s_at |
| 239 | 202345_s_at |
| 240 | 227231_at |
| 241 | 59631_at |
| 242 | 204030_s_at |
| 243 | 235056_at |
| 244 | 228280_at |
| 245 | 218718_at |
| 246 | 201162_at |
| 247 | 213056_at |
| 248 | 223475_at |
| 249 | 225613_at |
| 250 | 218807_at |
| 251 | 221004_s_at |
| 252 | 200806_s_at |
| 253 | 222761_at |
| 254 | 226265_at |
| 255 | 1557383_a_at |
| 256 | 204663_at |
| 257 | 212274_at |
| 258 | 203874_s_at |
| 259 | 233255_s_at |
| 260 | 227542_at |
| 261 | 224435_at |
| 262 | 1557132_at |
| 263 | 222587_s_at |
| 264 | 203787_at |
| 265 | 205608_s_at |
| 266 | 200832_s_at |
| 267 | 232231_at |
| 268 | 224710_at |
| 269 | 230127_at |
| 270 | 1555630_a_at |
| 271 | 204068_at |
| 272 | 205769_at |
| 273 | 212224_at |
| 274 | 217853_at |
| 275 | 204165_at |
| 276 | 201036_s_at |
| 277 | 209267_s_at |
| 278 | 209135_at |
| 279 | 226869_at |
| 280 | 212328_at |
| 281 | 229687_s_at |
| 282 | 229402_at |
| 283 | 227908_at |
| 284 | 227792_at |
| 285 | 221290_s_at |
| 286 | 211137_s_at |
| 287 | 205210_at |
| 288 | 201876_at |
| 289 | 210829_s_at |
| 290 | 221580_s_at |
| 291 | 1555872_a_at |
| 292 | 228941_at |
| 293 | 226721_at |
| 294 | 202804_at |
| 295 | 232636_at |
| 296 | 206726_at |
| 297 | 204866_at |
| 298 | 212428_at |
| 299 | 218772_x_at |
| 300 | 208767_s_at |
| 301 | 213222_at |
| 302 | 1552623_at |
| 303 | 202246_s_at |
| 304 | 201163_s_at |
| 305 | 201923_at |
| 306 | 220643_s_at |
| 307 | 205349_at |
| 308 | 225959_s_at |
| 309 | 217988_at |
| 310 | 1554298_a_at |
| 311 | 212397_at |
| 312 | 201970_s_at |
| 313 | 236798_at |
| 314 | 201260_s_at |
| 315 | 200994_at |
| 316 | 205768_s_at |
| 317 | 202336_s_at |
| 318 | 210473_s_at |
| 319 | 227213_at |
| 320 | 201014_s_at |

TABLE 5-continued 393 transcripts up-regulated (Affymetrix probe set ID, see http://www.affymetrix.com) in CB-derived CD133+ cells

| | |
|---|---|
| 321 | 211701_s_at |
| 322 | 203474_at |
| 323 | 213506_at |
| 324 | 225655_at |
| 325 | 238029_s_at |
| 326 | 202330_s_at |
| 327 | 201549_x_at |
| 328 | 228654_at |
| 329 | 235342_at |
| 330 | 218966_at |
| 331 | 232693_s_at |
| 332 | 212145_at |
| 333 | 225384_at |
| 334 | 200783_s_at |
| 335 | 213150_at |
| 336 | 229899_s_at |
| 337 | 231947_at |
| 338 | 207781_s_at |
| 339 | 225681_at |
| 340 | 201577_at |
| 341 | 225633_at |
| 342 | 227388_at |
| 343 | 204671_s_at |
| 344 | 225010_at |
| 345 | 208799_at |
| 346 | 224367_at |
| 347 | 235309_at |
| 348 | 201938_at |
| 349 | 201063_at |
| 350 | 201540_at |
| 351 | 221543_s_at |
| 352 | 1554679_a_at |
| 353 | 225295_at |
| 354 | 218490_s_at |
| 355 | 213122_at |
| 356 | 217221_x_at |
| 357 | 226521_s_at |
| 358 | 55872_at |
| 359 | 201479_at |
| 360 | 214501_s_at |
| 361 | 206544_x_at |
| 362 | 212153_at |
| 363 | 222750_s_at |
| 364 | 212609_s_at |
| 365 | 218313_s_at |
| 366 | 222735_at |
| 367 | 208051_s_at |
| 368 | 203404_at |
| 369 | 225082_at |
| 370 | 232985_s_at |
| 371 | 201459_at |
| 372 | 204807_at |
| 373 | 1564520_s_at |
| 374 | 218788_s_at |
| 375 | 209550_at |
| 376 | 243957_at |
| 377 | 238465_at |
| 378 | 218641_at |
| 379 | 234994_at |
| 380 | 201900_s_at |
| 381 | 201324_at |
| 382 | 203989_x_at |
| 383 | 216237_s_at |
| 384 | 230298_at |
| 385 | 202540_s_at |
| 386 | 234304_s_at |
| 387 | 203405_at |
| 388 | 208025_s_at |
| 389 | 1559534_at |
| 390 | 1553247_a_at |
| 391 | 203372_s_at |
| 392 | 204689_at |
| 393 | 218792_s_at |

TABLE 6

297 transcripts down-regulated (Affymetrix probe set ID, see http://www.affymetrix.com) in CB-derived CD133+ cells

| | |
|---|---|
| 1 | 211560_s_at |
| 2 | 205495_s_at |
| 3 | 206676_at |
| 4 | 210321_at |
| 5 | 206366_x_at |
| 6 | 231688_at |
| 7 | 202018_s_at |
| 8 | 212768_s_at |
| 9 | 207979_s_at |
| 10 | 226218_at |
| 11 | 205033_s_at |
| 12 | 214567_s_at |
| 13 | 203535_at |
| 14 | 205488_at |
| 15 | 214470_at |
| 16 | 37145_at |
| 17 | 212538_at |
| 18 | 210164_at |
| 19 | 217143_s_at |
| 20 | 208450_at |
| 21 | 210031_at |
| 22 | 209396_s_at |
| 23 | 238066_at |
| 24 | 205863_at |
| 25 | 230489_at |
| 26 | 226725_at |
| 27 | 213539_at |
| 28 | 205898_at |
| 29 | 218918_at |
| 30 | 1555759_a_at |
| 31 | 223836_at |
| 32 | 209840_s_at |
| 33 | 205728_at |
| 34 | 215049_x_at |
| 35 | 205237_at |
| 36 | 226685_at |
| 37 | 229070_at |
| 38 | 215646_s_at |
| 39 | 204971_at |
| 40 | 206545_at |
| 41 | 1555745_a_at |
| 42 | 211820_x_at |
| 43 | 209116_x_at |
| 44 | 206666_at |
| 45 | 218454_at |
| 46 | 214617_at |
| 47 | 205798_at |
| 48 | 217232_x_at |
| 49 | 214370_at |
| 50 | 202917_s_at |
| 51 | 210140_at |
| 52 | 213915_at |
| 53 | 222895_s_at |
| 54 | 205837_s_at |
| 55 | 210088_x_at |
| 56 | 211207_s_at |
| 57 | 210279_at |
| 58 | 206337_at |
| 59 | 240336_at |
| 60 | 213534_s_at |
| 61 | 204890_s_at |
| 62 | 241871_at |
| 63 | 240413_at |
| 64 | 202207_at |
| 65 | 203413_at |
| 66 | 215894_at |
| 67 | 203234_at |
| 68 | 201739_at |
| 69 | 220646_s_at |
| 70 | 204995_at |
| 71 | 214467_at |
| 72 | 204891_s_at |
| 73 | 204122_at |
| 74 | 231124_x_at |
| 75 | 1405_i_at |
| 76 | 202833_s_at |
| 77 | 201743_at |

TABLE 6-continued 297 transcripts down-regulated (Affymetrix probe set ID, see http://www.affymetrix.com) in CB-derived CD133+ cells

| | |
|---|---|
| 78 | 224356_x_at |
| 79 | 206150_at |
| 80 | 202201_at |
| 81 | 229247_at |
| 82 | 1557733_a_at |
| 83 | 205174_s_at |
| 84 | 231078_at |
| 85 | 210948_s_at |
| 86 | 219528_s_at |
| 87 | 208949_s_at |
| 88 | 211795_s_at |
| 89 | 211429_s_at |
| 90 | 226811_at |
| 91 | 227266_s_at |
| 92 | 211005_at |
| 93 | 216945_x_at |
| 94 | 206177_s_at |
| 95 | 39248_at |
| 96 | 206785_s_at |
| 97 | 205856_at |
| 98 | 204620_s_at |
| 99 | 236782_at |
| 100 | 211571_s_at |
| 101 | 206647_at |
| 102 | 221731_x_at |
| 103 | 203973_s_at |
| 104 | 204959_at |
| 105 | 201422_at |
| 106 | 219672_at |
| 107 | 211699_x_at |
| 108 | 220088_at |
| 109 | 209458_x_at |
| 110 | 230464_at |
| 111 | 203936_s_at |
| 112 | 201506_at |
| 113 | 205114_s_at |
| 114 | 205831_at |
| 115 | 221558_s_at |
| 116 | 211745_x_at |
| 117 | 204848_x_at |
| 118 | 205592_at |
| 119 | 205786_s_at |
| 120 | 205590_at |
| 121 | 209949_at |
| 122 | 224724_at |
| 123 | 202704_at |
| 124 | 214433_s_at |
| 125 | 203922_s_at |
| 126 | 202206_at |
| 127 | 211696_x_at |
| 128 | 204232_at |
| 129 | 211821_x_at |
| 130 | 211339_s_at |
| 131 | 224583_at |
| 132 | 202208_s_at |
| 133 | 205789_at |
| 134 | 201393_s_at |
| 135 | 219947_at |
| 136 | 205119_s_at |
| 137 | 205291_at |
| 138 | 202295_s_at |
| 139 | 216191_s_at |
| 140 | 205758_at |
| 141 | 204619_s_at |
| 142 | 204655_at |
| 143 | 227867_at |
| 144 | 213193_x_at |
| 145 | 206834_at |
| 146 | 226818_at |
| 147 | 1553177_at |
| 148 | 209555_s_at |
| 149 | 202007_at |
| 150 | 205821_at |
| 151 | 210395_x_at |
| 152 | 229029_at |
| 153 | 219812_at |
| 154 | 206488_s_at |
| 155 | 221059_s_at |
| 156 | 223280_x_at |
| 157 | 204018_x_at |
| 158 | 207072_at |
| 159 | 230550_at |
| 160 | 201110_s_at |
| 161 | 219580_s_at |
| 162 | 204777_s_at |
| 163 | 202643_s_at |
| 164 | 227265_at |
| 165 | 206420_at |
| 166 | 217414_x_at |
| 167 | 233371_at |
| 168 | 213093_at |
| 169 | 210429_at |
| 170 | 204698_at |
| 171 | 216834_at |
| 172 | 208438_s_at |
| 173 | 219700_at |
| 174 | 203502_at |
| 175 | 230690_at |
| 176 | 212400_at |
| 177 | 208018_s_at |
| 178 | 226625_at |
| 179 | 204007_at |
| 180 | 206390_x_at |
| 181 | 223809_at |
| 182 | 213906_at |
| 183 | 205685_at |
| 184 | 228170_at |
| 185 | 234987_at |
| 186 | 226841_at |
| 187 | 225798_at |
| 188 | 223454_at |
| 189 | 206682_at |
| 190 | 214054_at |
| 191 | 218723_s_at |
| 192 | 210240_s_at |
| 193 | 214696_at |
| 194 | 214146_s_at |
| 195 | 202693_s_at |
| 196 | 221698_s_at |
| 197 | 236081_at |
| 198 | 35626_at |
| 199 | 1558972_s_at |
| 200 | 204714_s_at |
| 201 | 226272_at |
| 202 | 210426_x_at |
| 203 | 209841_s_at |
| 204 | 204141_at |
| 205 | 204466_s_at |
| 206 | 1555355_a_at |
| 207 | 235964_x_at |
| 208 | 202803_s_at |
| 209 | 201887_at |
| 210 | 205950_s_at |
| 211 | 210915_x_at |
| 212 | 1555349_a_at |
| 213 | 223922_x_at |
| 214 | 207815_at |
| 215 | 224833_at |
| 216 | 203485_at |
| 217 | 228109_at |
| 218 | 216054_x_at |
| 219 | 213975_s_at |
| 220 | 204834_at |
| 221 | 229041_s_at |
| 222 | 220306_at |
| 223 | 210479_s_at |
| 224 | 212657_s_at |
| 225 | 203561_at |
| 226 | 235670_at |
| 227 | 213716_s_at |
| 228 | 225606_at |
| 229 | 227449_at |
| 230 | 228766_at |
| 231 | 206515_at |

TABLE 6-continued 297 transcripts down-regulated (Affymetrix probe set ID, see http://www.affymetrix.com) in CB-derived CD133+ cells

| | |
|---|---|
| 232 | 237753_at |
| 233 | 205559_s_at |
| 234 | 202448_s_at |
| 235 | 215838_at |
| 236 | 219371_s_at |
| 237 | 204912_at |
| 238 | 214032_at |
| 239 | 218872_at |
| 240 | 201695_s_at |
| 241 | 204467_s_at |
| 242 | 221210_s_at |
| 243 | 212077_at |
| 244 | 217147_s_at |
| 245 | 207980_s_at |
| 246 | 218638_s_at |
| 247 | 221841_s_at |
| 248 | 221011_s_at |
| 249 | 33304_at |
| 250 | 210222_s_at |
| 251 | 221081_s_at |
| 252 | 208146_s_at |
| 253 | 203305_at |
| 254 | 234165_at |
| 255 | 206145_at |
| 256 | 1552309_a_at |
| 257 | 212188_at |
| 258 | 202436_s_at |
| 259 | 1560034_a_at |
| 260 | 221541_at |
| 261 | 204103_at |
| 262 | 230972_at |
| 263 | 226682_at |
| 264 | 224789_at |
| 265 | 206698_at |
| 266 | 205900_at |
| 267 | 224707_at |
| 268 | 208869_s_at |
| 269 | 243764_at |
| 270 | 201008_s_at |
| 271 | 229040_at |
| 272 | 204731_at |
| 273 | 205098_at |
| 274 | 227645_at |
| 275 | 208868_s_at |
| 276 | 202437_s_at |
| 277 | 212192_at |
| 278 | 202499_s_at |
| 279 | 230492_s_at |
| 280 | 213006_at |
| 281 | 204614_at |
| 282 | 211458_s_at |
| 283 | 212830_at |
| 284 | 230942_at |
| 285 | 201059_at |
| 286 | 211962_s_at |
| 287 | 220112_at |
| 288 | 200866_s_at |
| 289 | 210075_at |
| 290 | 210504_at |
| 291 | 217274_x_at |
| 292 | 200838_at |
| 293 | 1553681_a_at |
| 294 | 57082_at |
| 295 | 242939_at |
| 296 | 219243_at |
| 297 | 205927_s_at |

TABLE 7

257 transcripts (Affymetrix probe set ID, see http://www.affymetrix.com) expressed in CB-derived CD133+ cells, but not in CD133− cells

| | |
|---|---|
| 1 | 208029_s_at |
| 2 | 225782_at |
| 3 | 209905_at |
| 4 | 231982_at |
| 5 | 213035_at |
| 6 | 206674_at |
| 7 | 218899_s_at |
| 8 | 222640_at |
| 9 | 201841_s_at |
| 10 | 205984_at |
| 11 | 209487_at |
| 12 | 223708_at |
| 13 | 222780_s_at |
| 14 | 227279_at |
| 15 | 221861_at |
| 16 | 221286_s_at |
| 17 | 227923_at |
| 18 | 219837_s_at |
| 19 | 204663_at |
| 20 | 226985_at |
| 21 | 201162_at |
| 22 | 204755_x_at |
| 23 | 202890_at |
| 24 | 212488_at |
| 25 | 202179_at |
| 26 | 210983_s_at |
| 27 | 206445_s_at |
| 28 | 204753_s_at |
| 29 | 212775_at |
| 30 | 212686_at |
| 31 | 202562_s_at |
| 32 | 203853_s_at |
| 33 | 223100_s_at |
| 34 | 229572_at |
| 35 | 226676_at |
| 36 | 206660_at |
| 37 | 222240_s_at |
| 38 | 216212_s_at |
| 39 | 1557910_at |
| 40 | 203633_at |
| 41 | 204454_at |
| 42 | 229002_at |
| 43 | 235109_at |
| 44 | 204178_s_at |
| 45 | 217786_at |
| 46 | 215016_x_at |
| 47 | 212153_at |
| 48 | 216199_s_at |
| 49 | 225554_s_at |
| 50 | 216035_x_at |
| 51 | 226473_at |
| 52 | 207836_s_at |
| 53 | 204866_at |
| 54 | 212062_at |
| 55 | 213645_at |
| 56 | 217901_at |
| 57 | 204754_at |
| 58 | 208107_s_at |
| 59 | 219553_at |
| 60 | 224513_s_at |
| 61 | 208782_at |
| 62 | 206298_at |
| 63 | 239364_at |
| 64 | 208984_x_at |
| 65 | 212875_s_at |
| 66 | 201115_at |
| 67 | 205997_at |
| 68 | 200986_at |
| 69 | 219173_at |
| 70 | 212126_at |
| 71 | 226291_at |
| 72 | 201932_at |
| 73 | 230424_at |
| 74 | 209493_at |
| 75 | 204669_s_at |
| 76 | 212013_at |

TABLE 7-continued 257 transcripts (Affymetrix probe set ID, see http://www.affymetrix.com) expressed in CB-derived CD133+ cells, but not in CD133− cells

| | |
|---|---|
| 77 | 213452_at |
| 78 | 218856_at |
| 79 | 212856_at |
| 80 | 225308_s_at |
| 81 | 201755_at |
| 82 | 200616_s_at |
| 83 | 212387_at |
| 84 | 201459_at |
| 85 | 205210_at |
| 86 | 202003_s_at |
| 87 | 203372_s_at |
| 88 | 225962_at |
| 89 | 208117_s_at |
| 90 | 230158_at |
| 91 | 210473_s_at |
| 92 | 218457_s_at |
| 93 | 231049_at |
| 94 | 203875_at |
| 95 | 228538_at |
| 96 | 223056_s_at |
| 97 | 210463_x_at |
| 98 | 225237_s_at |
| 99 | 227481_at |
| 100 | 1568597_at |
| 101 | 217221_x_at |
| 102 | 1558871_at |
| 103 | 221427_s_at |
| 104 | 202188_at |
| 105 | 209488_s_at |
| 106 | 215714_s_at |
| 107 | 217974_at |
| 108 | 212186_at |
| 109 | 209094_at |
| 110 | 230481_at |
| 111 | 230698_at |
| 112 | 226331_at |
| 113 | 213147_at |
| 114 | 201431_s_at |
| 115 | 213355_at |
| 116 | 235287_at |
| 117 | 209550_at |
| 118 | 230788_at |
| 119 | 205321_at |
| 120 | 212489_at |
| 121 | 221833_at |
| 122 | 218452_at |
| 123 | 227703_s_at |
| 124 | 1559477_s_at |
| 125 | 212609_s_at |
| 126 | 205768_s_at |
| 127 | 208975_s_at |
| 128 | 229333_at |
| 129 | 230624_at |
| 130 | 205769_at |
| 131 | 207949_s_at |
| 132 | 239848_at |
| 133 | 212651_at |
| 134 | 235721_at |
| 135 | 203069_at |
| 136 | 223565_at |
| 137 | 225790_at |
| 138 | 205647_at |
| 139 | 238890_at |
| 140 | 239413_at |
| 141 | 226869_at |
| 142 | 203919_at |
| 143 | 225743_at |
| 144 | 221221_s_at |
| 145 | 225745_at |
| 146 | 202326_at |
| 147 | 216944_s_at |
| 148 | 202293_at |
| 149 | 210882_s_at |
| 150 | 203404_at |
| 151 | 201951_at |
| 152 | 212746_s_at |
| 153 | 242064_at |
| 154 | 242002_at |
| 155 | 232693_s_at |
| 156 | 204835_at |
| 157 | 210410_s_at |
| 158 | 227601_at |
| 159 | 208396_s_at |
| 160 | 232424_at |
| 161 | 210830_s_at |
| 162 | 224015_s_at |
| 163 | 239272_at |
| 164 | 220954_s_at |
| 165 | 241926_s_at |
| 166 | 222799_at |
| 167 | 49452_at |
| 168 | 225113_at |
| 169 | 1554280_a_at |
| 170 | 229899_s_at |
| 171 | 209461_x_at |
| 172 | 232227_at |
| 173 | 230175_s_at |
| 174 | 203895_at |
| 175 | 230069_at |
| 176 | 228084_at |
| 177 | 242028_at |
| 178 | 238029_s_at |
| 179 | 227230_s_at |
| 180 | 209902_at |
| 181 | 1553605_a_at |
| 182 | 239280_at |
| 183 | 228692_at |
| 184 | 206205_at |
| 185 | 236562_at |
| 186 | 235044_at |
| 187 | 227908_at |
| 188 | 1566482_at |
| 189 | 236918_s_at |
| 190 | 233255_s_at |
| 191 | 201324_at |
| 192 | 216952_s_at |
| 193 | 227785_at |
| 194 | 203557_s_at |
| 195 | 43427_at |
| 196 | 1558102_at |
| 197 | 213894_at |
| 198 | 201427_s_at |
| 199 | 239552_at |
| 200 | 233543_s_at |
| 201 | 212621_at |
| 202 | 227822_at |
| 203 | 223089_at |
| 204 | 36830_at |
| 205 | 209053_s_at |
| 206 | 218844_at |
| 207 | 235603_at |
| 208 | 213638_at |
| 209 | 1565951_s_at |
| 210 | 222906_at |
| 211 | 218051_s_at |
| 212 | 203896_s_at |
| 213 | 213362_at |
| 214 | 213306_at |
| 215 | 235365_at |
| 216 | 1554298_a_at |
| 217 | 210571_s_at |
| 218 | 235079_at |
| 219 | 203869_at |
| 220 | 228297_at |
| 221 | 206009_at |
| 222 | 225833_at |
| 223 | 209485_s_at |
| 224 | 1553808_a_at |
| 225 | 1556061_at |
| 226 | 228054_at |
| 227 | 236945_at |
| 228 | 232098_at |

TABLE 7-continued 257 transcripts (Affymetrix probe set ID, see http://www.affymetrix.com) expressed in CB-derived CD133+ cells, but not in CD133− cells

| | |
|---|---|
| 229 | 227688_at |
| 230 | 231851_at |
| 231 | 230127_at |
| 232 | 211379_x_at |
| 233 | 225481_at |
| 234 | 238444_at |
| 235 | 235324_at |
| 236 | 203762_s_at |
| 237 | 228011_at |
| 238 | 227542_at |
| 239 | 225946_at |
| 240 | 1565830_at |
| 241 | 215294_s_at |
| 242 | 1553247_a_at |
| 243 | 229159_at |
| 244 | 204005_s_at |
| 245 | 235226_at |
| 246 | 236358_at |
| 247 | 235564_at |
| 248 | 236917_at |
| 249 | 206862_at |
| 250 | 235411_at |
| 251 | 206500_s_at |
| 252 | 206683_at |
| 253 | 1558605_at |
| 254 | 1557285_at |
| 255 | 1553183_at |
| 256 | 242358_at |
| 257 | 239080_at |

TABLE 8

Hematopoietic stem cell related markers

| | | |
|---|---|---|
| ANGPT1 | 205608_s_at | angiopoietin 1 |
| Meis1 | 204069_at | Meis1, myeloid ecotropic viral integration site 1 homolog (mouse) |
| SCA-1/ CASP3 | 202763_at | spinocerebellar ataxia 1/caspase 3, apoptosis-related cysteine protease |

TABLE 8-continued

Hematopoietic stem cell related markers

| | | |
|---|---|---|
| TIE1 | 204468_s_at | tyrosine kinase with immunoglobulin-like and EGF-like domains 1 |

TABLE 9

Transcription related markes especially for hematopoietic analysis

| | | |
|---|---|---|
| GATA2 | 209710_at | GATA binding protein 2 |
| HOXA10 | 213150_at | homeo box A10 |
| HOXA5 | 213844_at | homeo box A5 |
| HOXA9 | 214651_s_at | homeo box A9 |
| MAP3K4 | 216199_s_at | mitogen-activated protein kinase kinase kinase 4 |
| MPLV | 207550_at | myeloproliferative leukemia virus oncogene |
| STAT5A | 203010_at | signal transducer and activator of transcription 5A |
| TCF7L2 | 216035_x_at | transcription factor 7-like 2 (T-cell specific, HMG-box) |

TABLE 10

Preferred cluster analysis derived markers

| | | |
|---|---|---|
| ANKRD28 | 226025_at | ankyrin repeat domain 28 |
| BAALC | 218899_s_at | brain and acute leukemia, cytoplasmic |
| CD34 | 209543_s_at | CD34 antigen |
| CRIM1 | 202551_s_at | cysteine-rich motor neuron 1 |
| DKC1 | 201479_at | dyskeratosis congenita 1, dyskerin |
| EBPL | 223306_at | emopamil binding protein-like |
| FLT3 | 206674_at | fms-related tyrosine kinase 3 |
| JUP | 201015_s_at | junction plakoglobin |
| KIT | 205051_s_at | v-kit Hardy-Zuckerman 4 feline sarcoma viral oncogene homolog |
| LAPTM4B | 208029_s_at | lysosomal associated protein transmembrane 4 beta |
| PROM1 | 204304_s_at | prominin 1 |
| SPINK2 | 206310_at | serine protease inhibitor, Kazal type 2 (acrosin-trypsin inhibitor) |

TABLE 11

Cell cycle related markers

| | | |
|---|---|---|
| ANAPC7 | 225521_at | anaphase promoting complex subunit 7 |
| BCAT1 | 225285_at | branched chain aminotransferase 1, cytosolic |
| Bmi-1/PCGF4 | 202265_at | polycomb group ring finger 4 |
| CDK2AP1 | 201938_at | CDK2-associated protein 1 |
| CDK4 | 202246_s_at | cyclin-dependent kinase 4 |
| CDK6 | 235287_at | cyclin-dependent kinase 6 |
| CDKN2D | 210240_s_at | cyclin-dependent kinase inhibitor 2D (p19, inhibits CDK4) |
| DST | 212254_s_at | dystonin |
| EDD | 1555888_at | E3 identified by differential display |
| GATA2 | 209710_at | GATA binding protein 2 |
| MCM2 | 202107_s_at | MCM2 minichromosome maintenance deficient 2, mitotin (*S. cerevisiae*) |
| MCM5 | 216237_s_at | MCM5 minichromosome maintenance deficient 5, cell division cycle 46 |
| MCM6 | 201930_at | MCM6 minichromosome maintenance deficient 6 (MIS5 homolog, *S. pombe*) |
| MCM7/CDC47 | 210983_s_at | MCM7 minichromosome maintenance deficient 7 (*S. cerevisiae*) |
| MPHOSPH9 | 1558369_at | M-phase phosphoprotein 9 |
| NME1 | 201577_at | non-metastatic cells 1, protein (NM23A) expressed in |
| N-MYC/MYCNOS | 234376_at | v-myc myelocytomatosis viral related oncogene |
| p18/CDKN2C | 204159_at | cyclin-dependent kinase inhibitor 2C (p18, inhibits CDK4) |
| PLAGL1 | 207002_s_at | pleiomorphic adenoma gene-like 1 |
| SH3MD2 | 225589_at | SH3 multiple domains 2 |
| SKB1 | 1564520_s_at | SKB1 homolog (*S. pombe*) |
| STAG1 | 232588_at | stromal antigen 1 |
| UHRF1 | 225655_at | ubiquitin-like, containing PHD and RING finger domains, 1 |
| ZNRF1 | 225959_s_at | zinc and ring finger 1 |

TABLE 12

Endothelial development

| | | |
|---|---|---|
| ADAM28 | 205997_at | a disintegrin and metalloproteinase domain 28 |
| ANGP1 | 205608_s_at | Angiopoietin 1 |
| CRIM1 | 202551_s_at | cysteine-rich motor neuron 1 |
| DSG2 | 217901_at | Desmoglein 2 |
| EMP1 | 201324_at | epithelial membrane protein 1 |
| JUP | 201015_s_at | junction plakoglobin |
| MAGI1 | 227481_at | membrane associated guanylate kinase interacting protein-like 1 |
| TIE1 | 204468_s_at | tyrosine kinase with immunoglobulin-like and EGF-like domains 1 |

TABLE 13

ESC related markers

| | | |
|---|---|---|
| DNMT3A | 218457_s_at | DNA (cytosine-5-)-methyltransferase 3 alpha |
| DNMT3B | 220668_s_at | DNA (cytosine-5-)-methyltransferase 3 beta |
| DPPA4 | 232985_s_at | developmental pluripotency associated 4 |

TABLE 14

Secreted glycoproteins

| | | |
|---|---|---|
| Col5a1 | 212488_at | Collagen type V alpha 1 |
| CRHBP | 205984_at | Corticotropin releasing hormone binding protein |
| IGFBP7 | 201162_at | Insulin-like growth factor binding protein 7 |
| MMP28 | 239272_at | Matrix metalloproteinase 28 |
| SEPP1 | 201427_s_at | Selenoprotein P plasma 1 |
| UMODL1 | 1553182_at | Uromodulin-like 1 |

TABLE 15 markers with on-off change

Glycosyltransferases

| | | |
|---|---|---|
| B3GALT3 | 211379_x_at | UDP-Gal:betaGlcNAc beta 1,3-galactosyltransferase polypeptide 3 |
| GCNT2 | 230788_at | Glucosaminyl (N-acetyl) transferase 2 I-branching enzyme |
| ST3GalVI | 210942_s_at | CMP-sialic acid alpha2,3sialyltransferase III |

Nucleotide metabolism enzyme

| | | |
|---|---|---|
| NUDT5 | 223100_s_at | nudix (nucleoside diphosphate linked moiety X)-type motif 5 |

Glycoprotein

| | | |
|---|---|---|
| SV2A | 203069_at | synaptic vesicle glycoprotein 2A |

Regulatory protein

| | | |
|---|---|---|
| ZNF117 | 235564_at | Krueppel-related zinc finger protein 117 |

TABLE 16a

Single column purification method, CD34+cell purity in fractions.

| Cell fraction | CD34 purity |
|---|---|
| MNC | 1% |
| CD34− | 0.34% |
| Wash 1-4 | 0.41% |
| Wash 5-6 | 1% |
| Wash 7-8 | 3% |
| CD34+ | 78% |

TABLE 16b

Traditional two column purification method, CD34+cell purity in fractions.

| Cell fraction | CD34 purity |
|---|---|
| MNC | 0.79% |
| CD34−/1. column | 0.38% |
| Wash 1-2 | 0.32% |
| Wash 3-4 | 0.46% |
| Wash 5-6 | 0.51% |
| CD34+/1. column | 68% |
| CD34−/2. column | 19% |
| Wash 1-3 | 13% |
| CD34+/2. column | 77% |

TABLE 17

Transcripts common for CD34+ and CD133+ but absent in CD34− and CD133− samples

| Probe Set ID | Gene Symbol | Gene Title |
|---|---|---|
| 1553247_a_at | FLJ38281 | hypothetical protein FLJ38281 |
| 1554298_a_at | FLJ33620 | hypothetical protein FLJ33620 |
| 1557910_at | HSPCB | heat shock 90 kDa protein 1, beta |
| 1558871_at | — | *Homo sapiens*, clone IMAGE: 4105785, mRNA |
| 1559477_s_at | MEIS1 | Meis1, myeloid ecotropic viral integration site 1 homolog (mouse) |
| 200986_at | SERPING1 | serine (or cysteine) proteinase inhibitor, clade G (C1 inhibitor), member 1, (angioedema, hereditary) |
| 201115_at | POLD2 | polymerase (DNA directed), delta 2, regulatory subunit 50 kDa |
| 201324_at | EMP1 | epithelial membrane protein 1 |
| 201841_s_at | HSPB1 | heat shock 27 kDa protein 1 |
| 201951_at | ALCAM | Activated leukocyte cell adhesion molecule |
| 202179_at | BLMH | bleomycin hydrolase |
| 202562_s_at | C14orf1 | chromosome 14 open reading frame 1 |
| 202890_at | MAP7 | microtubule-associated protein 7 |
| 203372_s_at | SOCS2 | suppressor of cytokine signaling 2 |
| 203633_at | CPT1A | carnitine palmitoyltransferase 1A (liver) |
| 203875_at | SMARCA1 | SWI/SNF related, matrix associated, actin dependent regulator of chromatin, subfamily a, member 1 |
| 203895_at | PLCB4 | phospholipase C, beta 4 |
| 204005_s_at | PAWR | PRKC, apoptosis, WT1, regulator |
| 204454_at | LDOC1 | leucine zipper, down-regulated in cancer 1 |
| 204663_at | ME3 | malic enzyme 3, NADP(+)-dependent, mitochondrial |
| 204753_s_at | HLF | hepatic leukemia factor |

TABLE 17-continued

Transcripts common for CD34+ and CD133+ but absent in CD34– and CD133– samples

| Probe Set ID | Gene Symbol | Gene Title |
|---|---|---|
| 204754_at | HLF | Hepatic leukemia factor |
| 204755_x_at | HLF | hepatic leukemia factor |
| 204866_at | PHF16 | PHD finger protein 16 |
| 205210_at | TGFBRAP1 | transforming growth factor, beta receptor associated protein 1 |
| 205647_at | RAD52 | RAD52 homolog (S. cerevisiae) |
| 205769_at | SLC27A2 | solute carrier family 27 (fatty acid transporter), member 2 |
| 205984_at | CRHBP | corticotropin releasing hormone binding protein |
| 206298_at | ARHGAP22 | Rho GTPase activating protein 22 |
| 206660_at | IGLL1 | immunoglobulin lambda-like polypeptide 1 |
| 206674_at | FLT3 | fms-related tyrosine kinase 3 |
| 207836_s_at | RBPMS | RNA binding protein with multiple splicing |
| 208029_s_at | LAPTM4B | lysosomal associated protein transmembrane 4 beta |
| 208107_s_at | LOC81691 | exonuclease NEF-sp |
| 208396_s_at | PDE1A | phosphodiesterase 1A, calmodulin-dependent |
| 208984_x_at | RBM10 | RNA binding motif protein 10 |
| 209487_at | RBPMS | RNA binding protein with multiple splicing |
| 209493_at | PDZK3 | PDZ domain containing 3 |
| 209905_at | HOXA9 | homeo box A9 |
| 210463_x_at | FLJ20244 | hypothetical protein FLJ20244 |
| 212062_at | ATP9A | ATPase, Class II, type 9A |
| 212387_at | TCF4 | Transcription factor 4 |
| 212488_at | COL5A1 | Collagen, type V, alpha 1 |
| 212609_s_at | AKT3 | V-akt murine thymoma viral oncogene homolog 3 (protein kinase B, gamma) |
| 212651_at | RHOBTB1 | Rho-related BTB domain containing 1 |
| 212686_at | PPM1H | Protein phosphatase 1H (PP2C domain containing) |
| 216212_s_at | DKC1 | dyskeratosis congenita 1, dyskerin |
| 217901_at | DSG2 | Desmoglein 2 |
| 217974_at | TM7SF3 | transmembrane 7 superfamily member 3 |
| 218899_s_at | BAALC | brain and acute leukemia, cytoplasmic |
| 219837_s_at | C17 | cytokine-like protein C17 |
| 221286_s_at | PACAP | proapoptotic caspase adaptor protein |
| 222240_s_at | ISYNA1 | myo-inositol 1-phosphate synthase A1 |
| 222780_s_at | BAALC | brain and acute leukemia, cytoplasmic |
| 223089_at | VEZATIN | transmembrane protein vezatin |
| 225237_s_at | MSI2 | musashi homolog 2 (Drosophila) |
| 225308_s_at | TANC | TPR domain, ankyrin-repeat and coiled-coil-containing |
| 225782_at | LOC253827 | hypothetical protein LOC253827 |
| 225962_at | ZNRF1 | zinc and ring finger 1 |
| 226676_at | ZNF521 | zinc finger protein 521 |
| 226985_at | FGD5 | FYVE, RhoGEF and PH domain containing 5 |
| 227703_s_at | SYTL4 | synaptotagmin-like 4 (granuphilin-a) |
| 227923_at | SHANK3 | SH3 and multiple ankyrin repeat domains 3 |
| 228297_at | — | — |
| 228692_at | — | CDNA FLJ13569 fis, clone PLACE1008369 |
| 229002_at | MGC20262 | hypothetical protein MGC20262 |
| 229572_at | — | — |
| 230158_at | FLJ32949 | hypothetical protein FLJ32949 |
| 230424_at | C5orf13 | chromosome 5 open reading frame 13 |
| 230624_at | SLC25A27 | solute carrier family 25, member 27 |
| 230698_at | — | MRNA; cDNA DKFZp434H205 (from clone DKFZp434H205) |
| 231851_at | KIAA1579 | hypothetical protein FLJ10770 |
| 231982_at | — | Similar to HSPC323 |
| 235044_at | CYYR1 | cysteine and tyrosine-rich 1 |
| 235109_at | ZBED3 | Zinc finger, BED domain containing 3 |
| 235287_at | CDK6 | cyclin-dependent kinase 6 |
| 236918_s_at | MGC27085 | hypothetical protein MGC27085 |
| 239272_at | MMP28 | matrix metalloproteinase 28 |
| 239280_at | — | — |
| 239552_at | FLJ14712 | Hypothetical protein FLJ14712 |
| 241926_s_at | ERG | v-ets erythroblastosis virus E26 oncogene like (avian) |
| 242002_at | TCBA1 | T-cell lymphoma breakpoint associated target 1 |
| 242028_at | FLJ38281 | hypothetical protein FLJ38281 |
| 36830_at | MIPEP | mitochondrial intermediate peptidase |
| 49452_at | LOC283445 | hypothetical protein LOC283445 |

TABLE 18

Putative membrane proteins common for both CD34+ and CD133+ samples

| Probe Set ID | Gene Symbol | Gene Title |
|---|---|---|
| 202562_s_at | C14orf1 | chromosome 14 open reading frame 1 |
| 206674_at | FLT3 | fms-related tyrosine kinase 3 |
| 208029_s_at | LAPTM4B | lysosomal associated protein transmembrane 4 beta |
| 201951_at | ALCAM | Activated leukocyte cell adhesion molecule |
| 201324_at | EMP1 | epithelial membrane protein 1 |
| 212062_at | ATP9A | ATPase, Class II, type 9A |
| 217901_at | DSG2 | Desmoglein 2 |
| 223089_at | VEZATIN | transmembrane protein vezatin |
| 235044_at | CYYR1 | cysteine and tyrosine-rich 1 |
| 217974_at | TM7SF3 | transmembrane 7 superfamily member 3 |

TABLE 19

Transcripts present in all CD34+ samples but absent in CD34− and CD133+ samples

| Probe Set ID | Gene Symbol | Gene Title |
|---|---|---|
| 1557132_at | WDR17 | WD repeat domain 17 |
| 1558105_a_at | — | *Homo sapiens*, Similar to LOC169932, clone IMAGE: 4499203, mRNA |
| 1558369_at | MPHOSPH9 | M-phase phosphoprotein 9 |
| 1564520_s_at | SKB1 | SKB1 homolog (*S. pombe*) |
| 200707_at | PRKCSH | protein kinase C substrate 80K-H |
| 200771_at | LAMC1 | laminin, gamma 1 (formerly LAMB2) |
| 201015_s_at | JUP | junction plakoglobin |
| 201037_at | PFKP | phosphofructokinase, platelet |
| 201397_at | PHGDH | phosphoglycerate dehydrogenase |
| 201825_s_at | CGI-49 | CGI-49 protein |
| 202039_at | TIAF1/MYO18A | TGFB1-induced anti-apoptotic factor 1/myosin XVIIIA |
| 202540_s_at | HMGCR | 3-hydroxy-3-methylglutaryl-Coenzyme A reductase |
| 202551_s_at | CRIM1 | cysteine-rich motor neuron 1 |
| 202552_s_at | CRIM1 | cysteine-rich motor neuron 1 |
| 202766_s_at | FBN1 | fibrillin 1 (Marfan syndrome) |
| 202809_s_at | FLJ21919 | hypothetical protein FLJ21919 |
| 203281_s_at | UBE1L | ubiquitin-activating enzyme E1-like |
| 203343_at | UGDH | UDP-glucose dehydrogenase |
| 203678_at | KIAA1018 | KIAA1018 protein |
| 203690_at | TUBGCP3 | tubulin, gamma complex associated protein 3 |
| 203701_s_at | FLJ20244 | hypothetical protein FLJ20244 |
| 203981_s_at | ABCD4 | ATP-binding cassette, sub-family D (ALD), member 4 |
| 204538_x_at | NPIP | nuclear pore complex interacting protein |
| 204749_at | NAP1L3 | nucleosome assembly protein 1-like 3 |
| 204771_s_at | TTF1 | transcription termination factor, RNA polymerase I |
| 205051_s_at | KIT | v-kit Hardy-Zuckerman 4 feline sarcoma viral oncogene homolog |
| 205395_s_at | MRE11A | MRE11 meiotic recombination 11 homolog A (*S. cerevisiae*) |
| 205413_at | C11orf8 | chromosome 11 open reading frame 8 |
| 205527_s_at | GEMIN4 | gem (nuclear organelle) associated protein 4 |
| 206233_at | B4GALT6 | UDP-Gal:betaGlcNAc beta 1,4-galactosyltransferase, polypeptide 6 |
| 206295_at | IL18 | interleukin 18 (interferon-gamma-inducing factor) |
| 206310_at | SPINK2 | serine protease inhibitor, Kazal type 2 (acrosin-trypsin inhibitor) |
| 206316_s_at | KNTC1 | kinetochore associated 1 |
| 207871_s_at | ST7 | suppression of tumorigenicity 7 |
| 208682_s_at | MAGED2 | melanoma antigen family D, 2 |
| 208962_s_at | FADS1 | fatty acid desaturase 1 |
| 209014_at | MAGED1 | melanoma antigen family D, 1 |
| 209129_at | TRIP6 | thyroid hormone receptor interactor 6 |
| 209360_s_at | RUNX1 | runt-related transcription factor 1 (acute myeloid leukemia 1; aml1 oncogene) |
| 209543_s_at | CD34 | CD34 antigen |
| 209576_at | GNAI1 | guanine nucleotide binding protein (G protein), alpha inhibiting activity polypeptide 1 |
| 209627_s_at | OSBPL3 | oxysterol binding protein-like 3 |
| 209935_at | ATP2C1 | ATPase, Ca++ transporting, type 2C, member 1 |
| 210299_s_at | FHL1 | four and a half LIM domains 1 |
| 210387_at | HIST1H2BG | histone 1, H2bg |
| 210487_at | DNTT | deoxynucleotidyltransferase, terminal |
| 211701_s_at | TRO | trophinin |
| 211709_s_at | CLEC11A | C-type lectin domain family 11, member A |
| 212139_at | GCN1L1 | GCN1 general control of amino-acid synthesis 1-like 1 (yeast) |
| 212259_s_at | PBXIP1 | pre-B-cell leukemia transcription factor interacting protein 1 |
| 212608_s_at | NUDT3 | Nudix (nucleoside diphosphate linked moiety X)-type motif 3 |
| 212893_at | ZZZ3 | zinc finger, ZZ domain containing 3 |
| 213150_at | HOXA10 | homeo box A10 |
| 213156_at | — | *Homo sapiens*, clone IMAGE: 4214654, mRNA |
| 213258_at | TFPI | Tissue factor pathway inhibitor (lipoprotein-associated coagulation inhibitor) |
| 213506_at | F2RL1 | coagulation factor II (thrombin) receptor-like 1 |
| 213541_s_at | ERG | v-ets erythroblastosis virus E26 oncogene like (avian) |
| 213939_s_at | RIPX | rap2 interacting protein x |
| 214437_s_at | SHMT2 | serine hydroxymethyltransferase 2 (mitochondrial) |

TABLE 19-continued

Transcripts present in all CD34+ samples but absent in CD34− and CD133+ samples

| Probe Set ID | Gene Symbol | Gene Title |
|---|---|---|
| 214494_s_at | SPG7 | spastic paraplegia 7, paraplegin (pure and complicated autosomal recessive) |
| 214870_x_at | NPIP/LOC339047/LOC440341 | nuclear pore complex interacting protein, hypothetical protein LOC339047 |
| 215030_at | GRSF1 | G-rich RNA sequence binding factor 1 |
| 215388_s_at | CFH/CFHL1 | complement factor H, complement factor H-related 1 |
| 218164_at | SSP411 | sperm protein SSP411 |
| 218235_s_at | CGI-94 | comparative gene identification transcript 94 |
| 218503_at | KIAA1797 | KIAA1797 |
| 218710_at | FLJ20272 | hypothetical protein FLJ20272 |
| 218792_s_at | BSPRY | B-box and SPRY domain containing |
| 219174_at | CCDC2 | coiled-coil domain containing 2 |
| 219498_s_at | BCL11A | B-cell CLL/lymphoma 11A (zinc finger protein) |
| 219871_at | FLJ13197 | hypothetical protein FLJ13197 |
| 220416_at | ATP8B4 | ATPase, Class I, type 8B, member 4 |
| 221501_x_at | LOC339047 | hypothetical protein LOC339047 |
| 221506_s_at | TNPO2 | transportin 2 (importin 3, karyopherin beta 2b) |
| 221515_s_at | LCMT1 | leucine carboxyl methyltransferase 1 |
| 221834_at | LONP | Peroxisomal lon protease |
| 222258_s_at | SH3BP4 | SH3-domain binding protein 4 |
| 222369_at | — | — |
| 222489_s_at | WRNIP1 | Werner helicase interacting protein 1 |
| 223491_at | COMMD2 | COMM domain containing 2 |
| 224185_at | FLJ10385 | Hypothetical protein FLJ10385 |
| 224634_at | GPATC4 | G patch domain containing 4 |
| 224646_x_at | — | — |
| 224710_at | RAB34 | RAB34, member RAS oncogene family |
| 224722_at | MIB1 | mindbomb homolog 1 (*Drosophila*) |
| 224804_s_at | C15orf17 | chromosome 15 open reading frame 17 |
| 225045_at | KIAA1212 | KIAA1212 |
| 225095_at | SPTLC2 | serine palmitoyltransferase, long chain base subunit 2 |
| 225178_at | TTC14 | tetratricopeptide repeat domain 14 |
| 225223_at | SMAD5 | SMAD, mothers against DPP homolog 5 (*Drosophila*) |
| 225335_at | ZNF496 | zinc finger protein 496 |
| 225421_at | ACY1L2 | Aminoacylase 1-like 2 |
| 225595_at | — | MRNA; cDNA DKFZp566P1124 (from clone DKFZp566P1124) |
| 225655_at | UHRF1 | ubiquitin-like, containing PHD and RING finger domains, 1 |
| 225681_at | CTHRC1 | collagen triple helix repeat containing 1 |
| 225802_at | TOP1MT | topoisomerase (DNA) I, mitochondrial |
| 225901_at | PLIP | PTEN-like phosphatase |
| 226043_at | GPSM1 | G-protein signalling modulator 1 (AGS3-like, *C. elegans*) |
| 226602_s_at | LOC440820 | similar to breakpoint cluster region isoform 1 |
| 226677_at | ZNF521 | zinc finger protein 521 |
| 226691_at | KIAA1856 | KIAA1856 protein |
| 226784_at | TWISTNB | TWIST neighbor |
| 227297_at | ITGA9 | Integrin, alpha 9 |
| 227952_at | FLJ90036 | Hypothetical protein FLJ90036 |
| 228012_at | MATR3 | Matrin 3 |
| 228156_at | — | *Homo sapiens*, clone IMAGE: 4346533, mRNA |
| 229231_at | LOC114659 | KIAA0563-related gene |
| 229623_at | — | Similar to hypothetical protein LOC231503 |
| 230434_at | PHOSPHO2 | phosphatase, orphan 2 |
| 230815_at | — | Similar to KIF27C |
| 231864_at | — | — |
| 231899_at | KIAA1726 | KIAA1726 protein |
| 235142_at | ZBTB8 | zinc finger and BTB domain containing 8 |
| 237105_at | — | MRNA; cDNA DKFZp686G1498 (from clone DKFZp686G1498) |
| 238043_at | ARID1B | AT rich interactive domain 1B (SWI1-like) |
| 238484_s_at | — | — |
| 241505_at | — | — |
| 243816_at | ZNF70 | Zinc finger protein 70 (Cos17) |
| 243957_at | LOC400464 | similar to FLJ43276 protein |
| 37384_at | PPM1F | protein phosphatase 1F (PP2C domain containing) |
| 38157_at | DOM3Z | dom-3 homolog Z (*C. elegans*) |
| 59631_at | TXNRD3 | thioredoxin reductase 3 |

TABLE 20

Transcripts present in all CD133+ samples but absent in CD133− and CD34+ samples

| Probe Set ID | Gene Symbol | Gene Title |
|---|---|---|
| 1553183_at | UMODL1 | uromodulin-like 1 |
| 1553605_a_at | ABCA13 | ATP-binding cassette, sub-family A (ABC1), member 13 |
| 1553808_a_at | NKX2-3 | NK2 transcription factor related, locus 3 (*Drosophila*) |

TABLE 20-continued

Transcripts present in all CD133+ samples but absent in CD133− and CD34+ samples

| Probe Set ID | Gene Symbol | Gene Title |
|---|---|---|
| 1554280_a_at | C9orf43 | chromosome 9 open reading frame 43 |
| 1556061_at | LOC283012 | hypothetical protein LOC283012 |
| 1557285_at | AREG | Amphiregulin (schwannoma-derived growth factor) |
| 1558102_at | TM6SF1 | Transmembrane 6 superfamily member 1 |
| 1558605_at | — | *Homo sapiens*, clone IMAGE: 4819775, mRNA |
| 1565830_at | KIAA1731 | KIAA1731 protein |
| 1565951_s_at | CHML | choroideremia-like (Rab escort protein 2) |
| 1566482_at | — | Hypothetical LOC400047 |
| 1568597_at | — | LOC442522 |
| 200616_s_at | KIAA0152 | KIAA0152 |
| 201162_at | IGFBP7 | insulin-like growth factor binding protein 7 |
| 201427_s_at | SEPP1 | selenoprotein P, plasma, 1 |
| 201431_s_at | DPYSL3 | dihydropyrimidinase-like 3 |
| 201459_at | RUVBL2 | RuvB-like 2 (*E. coli*) |
| 201755_at | MCM5 | MCM5 minichromosome maintenance deficient 5, cell division cycle 46 (*S. cerevisiae*) |
| 201932_at | MUF1 | MUF1 protein |
| 202003_s_at | ACAA2 | acetyl-Coenzyme A acyltransferase 2 (mitochondrial 3-oxoacyl-Coenzyme A thiolase) |
| 202188_at | NUP93 | nucleoporin 93 kDa |
| 202293_at | STAG1 | Stromal antigen 1 |
| 202326_at | BAT8 | HLA-B associated transcript 8 |
| 203069_at | SV2A | synaptic vesicle glycoprotein 2A |
| 203404_at | ARMCX2 | armadillo repeat containing, X-linked 2 |
| 203557_s_at | PCBD1 | 6-pyruvoyl-tetrahydropterin synthase/dimerization cofactor of hepatocyte nuclear factor 1 alpha (TCF1) |
| 203762_s_at | D2LIC | dynein 2 light intermediate chain |
| 203853_s_at | GAB2 | GRB2-associated binding protein 2 |
| 203869_at | USP46 | ubiquitin specific protease 46 |
| 203896_s_at | PLCB4 | phospholipase C, beta 4 |
| 203919_at | TCEA2 | transcription elongation factor A (SII), 2 |
| 204178_s_at | RBM14 | RNA binding motif protein 14 |
| 204669_s_at | RNF24 | ring finger protein 24 |
| 204835_at | POLA | polymerase (DNA directed), alpha |
| 205321_at | EIF2S3 | eukaryotic translation initiation factor 2, subunit 3 gamma, 52 kDa |
| 205768_s_at | SLC27A2 | solute carrier family 27 (fatty acid transporter), member 2 |
| 205997_at | ADAM28 | a disintegrin and metalloproteinase domain 28 |
| 206009_at | ITGA9 | integrin, alpha 9 |
| 206205_at | MPHOSPH9 | M-phase phosphoprotein 9 |
| 206445_s_at | HRMT1L2 | HMT1 hnRNP methyltransferase-like 2 (*S. cerevisiae*) |
| 206500_s_at | C14orf106 | chromosome 14 open reading frame 106 |
| 206683_at | ZNF165 | zinc finger protein 165 |
| 206862_at | ZNF254/ZNF539 | zinc finger protein 254/539 |
| 207949_s_at | ICA1 | islet cell autoantigen 1, 69 kDa |
| 208117_s_at | LAS1L | LAS1-like (*S. cerevisiae*) |
| 208782_at | FSTL1 | follistatin-like 1 |
| 208975_s_at | KPNB1 | karyopherin (importin) beta 1 |
| 209053_s_at | WHSC1 | Wolf-Hirschhorn syndrome candidate 1 |
| 209094_at | DDAH1 | dimethylarginine dimethylaminohydrolase 1 |
| 209461_x_at | WDR18 | WD repeat domain 18 |
| 209485_s_at | OSBPL1A | oxysterol binding protein-like 1A |
| 209488_s_at | RBPMS | RNA binding protein with multiple splicing |
| 209550_at | NDN | necdin homolog (mouse) |
| 209902_at | ATR | ataxia telangiectasia and Rad3 related |
| 210410_s_at | MSH5 | mutS homolog 5 (*E. coli*) |
| 210473_s_at | GPR125 | G protein-coupled receptor 125 |
| 210571_s_at | CMAH | Cytidine monophosphate-N-acetylneuraminic acid hydroxylase (CMP-N-acetylneuraminate monooxygenase) |
| 210830_s_at | PON2 | paraoxonase 2 |
| 210882_s_at | TRO | trophinin |
| 210983_s_at | MCM7 | MCM7 minichromosome maintenance deficient 7 (*S. cerevisiae*) |
| 211379_x_at | B3GALT3 | UDP-Gal:betaGlcNAc beta 1,3-galactosyltransferase, polypeptide 3 |
| 212013_at | D2S448 | Melanoma associated gene |
| 212126_at | CBX5 | Chromobox homolog 5 (HP1 alpha homolog, *Drosophila*) |
| 212153_at | POGZ | pogo transposable element with ZNF domain |
| 212186_at | ACACA | acetyl-Coenzyme A carboxylase alpha |
| 212489_at | COL5A1 | Collagen, type V, alpha 1 |
| 212621_at | KIAA0286 | KIAA0286 protein |
| 212746_s_at | KAB | KARP-1-binding protein |
| 212775_at | KIAA0657 | KIAA0657 protein |
| 212856_at | KIAA0767 | KIAA0767 protein |
| 212875_s_at | C21orf25 | chromosome 21 open reading frame 25 |
| 213035_at | ANKRD28 | ankyrin repeat domain 28 |
| 213147_at | HOXA10 | homeo box A10 |
| 213306_at | MPDZ | multiple PDZ domain protein |
| 213355_at | ST3GAL6 | ST3 beta-galactoside alpha-2,3-sialyltransferase 6 |
| 213362_at | PTPRD | Protein tyrosine phosphatase, receptor type, D |
| 213452_at | ZNF184 | zinc finger protein 184 (Kruppel-like) |

TABLE 20-continued

Transcripts present in all CD133+ samples but absent in CD133– and CD34+ samples

| Probe Set ID | Gene Symbol | Gene Title |
|---|---|---|
| 213638_at | PHACTR1 | phosphatase and actin regulator 1 |
| 213645_at | ENOSF1 | enolase superfamily member 1 |
| 213894_at | KIAA0960 | KIAA0960 protein |
| 215016_x_at | DST | dystonin |
| 215294_s_at | SMARCA1 | SWI/SNF related, matrix associated, actin dependent regulator of chromatin, subfamily a, member 1 |
| 215714_s_at | SMARCA4 | SWI/SNF related, matrix associated, actin dependent regulator of chromatin, subfamily a, member 4 |
| 216035_x_at | TCF7L2 | transcription factor 7-like 2 (T-cell specific, HMG-box) |
| 216199_s_at | MAP3K4 | mitogen-activated protein kinase kinase kinase 4 |
| 216944_s_at | ITPR1 | inositol 1,4,5-triphosphate receptor, type 1 |
| 216952_5_at | LMNB2 | lamin B2 |
| 217221_x_at | RBM10 | RNA binding motif protein 10 |
| 217786_at | SKB1 | SKB1 homolog (S. pombe) |
| 218051_s_at | FLJ12442 | hypothetical protein FLJ12442 |
| 218452_at | SMARCAL1 | SWI/SNF related, matrix associated, actin dependent regulator of chromatin, subfamily a-like 1 |
| 218457_s_at | DNMT3A | DNA (cytosine-5-)-methyltransferase 3 alpha |
| 218844_at | FLJ20920 | hypothetical protein FLJ20920 |
| 218856_at | TNFRSF21 | tumor necrosis factor receptor superfamily, member 21 |
| 219173_at | MYO15B | myosin XVB, pseudogene |
| 219553_at | NME7 | non-metastatic cells 7, protein expressed in (nucleoside-diphosphate kinase) |
| 220954_s_at | PILRB | paired immunoglobin-like type 2 receptor beta |
| 221221_s_at | KLHL3 | kelch-like 3 (Drosophila) |
| 221427_s_at | CCNL2 | cyclin L2 |
| 221833_at | LONP | Peroxisomal Ion protease |
| 221861_at | — | MRNA; cDNA DKFZp762M127 (from clone DKFZp762M127) |
| 222640_at | DNMT3A | DNA (cytosine-5-)-methyltransferase 3 alpha |
| 222799_at | HSPC049 | HSPC049 protein |
| 222906_at | FLVCR | feline leukemia virus subgroup C cellular receptor |
| 223056_s_at | XPO5 | exportin 5 |
| 223100_s_at | NUDT5 | nudix (nucleoside diphosphate linked moiety X)-type motif 5 |
| 223565_at | PACAP | proapoptotic caspase adaptor protein |
| 223708_at | C1QTNF4 | C1q and tumor necrosis factor related protein 4 |
| 224015_s_at | MRPS25 | mitochondrial ribosomal protein S25 |
| 224513_s_at | UBQLN4 | ubiquilin 4 |
| 225113_at | AGPS | Alkylglycerone phosphate synthase |
| 225481_at | — | — |
| 225554_s_at | ANAPC7 | anaphase promoting complex subunit 7 |
| 225743_at | RPUSD3 | RNA pseudouridylate synthase domain containing 3 |
| 225745_at | LRP6 | Low density lipoprotein receptor-related protein 6 |
| 225790_at | MSRB3 | methionine sulfoxide reductase B3 |
| 225833_at | LOC221955 | KCCR13L |
| 225946_at | C12orf2 | Chromosome 12 open reading frame 2 |
| 226291_at | ALS2 | amyotrophic lateral sclerosis 2 (juvenile) |
| 226331_at | BBX | Bobby sox homolog (Drosophila) |
| 226473_at | CBX2 | chromobox homolog 2 (Pc class homolog, Drosophila) |
| 226869_at | — | Full length insert cDNA clone ZD77F06 |
| 227230_s_at | KIAA1211 | KIAA1211 protein |
| 227279_at | TCEAL3 | transcription elongation factor A (SII)-like 3 |
| 227481_at | MAGI1 | membrane associated guanylate kinase interacting protein-like 1 |
| 227542_at | SOCS6 | Suppressor of cytokine signaling 6 |
| 227601_at | KIAA1627 | KIAA1627 protein |
| 227688_at | LRCH2 | leucine-rich repeats and calponin homology (CH) domain containing 2 |
| 227785_at | SDCCAG8 | serologically defined colon cancer antigen 8 |
| 227822_at | ZNF605 | zinc finger protein 605 |
| 227908_at | KIAA1171 | KIAA1171 protein |
| 228011_at | LOC137392 | similar to CG6405 gene product |
| 228054_at | TMEM44 | transmembrane protein 44 |
| 228084_at | — | Full-length cDNA clone CS0DF027YF17 of Fetal brain of Homo sapiens (human) |
| 228538_at | FLJ45880 | FLJ45880 protein |
| 229159_at | — | — |
| 229333_at | — | Transcribed locus, moderately similar to NP_055301.1 neuronal thread protein AD7c-NTP [Homo sapiens] |
| 229899_s_at | — | Similar to RPE-spondin |
| 230069_at | SFXN1 | sideroflexin 1 |
| 230127_at | — | Transcribed locus |
| 230175_s_at | — | — |
| 230481_at | ACY3 | aspartoacylase (aminocyclase) 3 |
| 230788_at | GCNT2 | glucosaminyl (N-acetyl) transferase 2, I-branching enzyme |
| 231049_at | LMO2 | LIM domain only 2 (rhombotin-like 1) |
| 232098_at | DST | dystonin |
| 232227_at | — | — |
| 232424_at | PRDM16 | PR domain containing 16 |
| 232693_s_at | ZNF395/FBXO16 | zinc finger protein 395/F-box protein 16 |
| 233255_s_at | BIVM | basic, immunoglobulin-like variable motif containing |
| 233543_s_at | FLJ13614 | hypothetical protein FLJ13614 |
| 235079_at | — | HepG2 partial cDNA, clone hmd1a08m5. |
| 235226_at | CDC2L6 | cell division cycle 2-like 6 (CDK8-like) |

TABLE 20-continued

Transcripts present in all CD133+ samples but absent in CD133− and CD34+ samples

| Probe Set ID | Gene Symbol | Gene Title |
|---|---|---|
| 235324_at | — | Transcribed locus |
| 235365_at | — | — |
| 235411_at | PGBD1 | piggyBac transposable element derived 1 |
| 235564_at | ZNF117 | Krueppel-related zinc finger protein |
| 235603_at | HNRPU | Heterogeneous nuclear ribonucleoprotein U (scaffold attachment factor A) |
| 235721_at | DTX3 | deltex 3 homolog (*Drosophila*) |
| 236358_at | — | — |
| 236562_at | ZNF439 | zinc finger protein 439 |
| 236917_at | MGC27085 | hypothetical protein MGC27085 |
| 236945_at | C9orf93 | chromosome 9 open reading frame 93 |
| 238029_s_at | SLC16A14 | solute carrier family 16 (monocarboxylic acid transporters), member 14 |
| 238444_at | ZNF618 | zinc finger protein 618 |
| 238890_at | — | Transcribed locus |
| 239080_at | UNQ9438 | TIMM9 |
| 239364_at | — | — |
| 239413_at | Cep152 | KIAA0912 protein |
| 239848_at | GA17 | Dendritic cell protein |
| 242064_at | SDK2 | Sidekick homolog 2 (chicken) |
| 242358_at | — | CDNA FLJ35666 fis, clone SPLEN2017781 |
| 43427_at | LOC283445 | hypothetical protein LOC283445 |

TABLE 21

Transcripts present (expressed) in all CD34+ samples but absent in CD133+ samples

| Probe Set ID | Gene Symbol | Gene Title |
|---|---|---|
| 1553708_at | MGC16075 | hypothetical protein MGC16075 |
| 1557700_at | POLH | Polymerase (DNA directed), eta |
| 1561271_at | — | *Homo sapiens*, clone IMAGE: 5299049, mRNA, partial cds |
| 1561573_at | — | *Homo sapiens*, clone IMAGE: 5528716, mRNA |
| 1569729_a_at | ASZ1 | ankyrin repeat, SAM and basic leucine zipper domain containing 1 |
| 200878_at | EPAS1 | endothelial PAS domain protein 1 |
| 201743_at | CD14 | CD14 antigen |
| 203065_s_at | CAV1 | caveolin 1, caveolae protein, 22 kDa |
| 204588_s_at | SLC7A7 | solute carrier family 7 (cationic amino acid transporter, y+ system), member 7 |
| 205103_at | CROC4 | transcriptional activator of the c-fos promoter |
| 205978_at | KL | klotho |
| 206207_at | CLC | Charcot-Leyden crystal protein |
| 206834_at | HBD | hemoglobin, delta |
| 207067_s_at | HDC | histidine decarboxylase |
| 211565_at | SH3GL3 | SH3-domain GRB2-like 3 |
| 211743_s_at | PRG2 | proteoglycan 2, bone marrow (natural killer cell activator, eosinophil granule major basic protein) |
| 214023_x_at | RP11-506K6.1 | tubulin, beta polypeptide paralog |
| 214247_s_at | DKK3 | dickkopf homolog 3 (*Xenopus laevis*) |
| 215056_at | — | Clone 23695 mRNA sequence |
| 215775_at | THBS1 | Thrombospondin 1 |
| 218541_s_at | C8orf4 | chromosome 8 open reading frame 4 |
| 218625_at | NRN1 | neuritin 1 |
| 224724_at | SULF2 | sulfatase 2 |
| 227952_at | FLJ90036 | Hypothetical protein FLJ90036 |
| 230572_at | FLJ30277 | hypothetical protein FLJ30277 |
| 231598_x_at | — | — |
| 232212_at | PLEKHA8 | pleckstrin homology domain containing, family A (phosphoinositide binding specific) member 8 |
| 233722_at | ZNF638 | Zinc finger protein 638 |
| 234548_at | HSPC117 | Hypothetical protein HSPC117 |
| 236422_at | FLJ22662 | Hypothetical protein FLJ22662 |
| 237422_at | ARL6IP2 | ADP-ribosylation factor-like 6 interacting protein 2 |
| 238264_at | — | — |
| 238447_at | RBMS3 | RNA binding motif, single stranded interacting protein |
| 241252_at | ESCO2 | Establishment of cohesion 1 homolog 2 (*S. cerevisiae*) |
| 243858_at | STS | Steroid sulfatase (microsomal), arylsulfatase C, isozyme S |
| 823_at | CX3CL1 | chemokine (C—X3—C motif) ligand 1 |

TABLE 22

Transcripts present (expressed) in all CD133+ samples but absent in CD34+ samples

| Probe Set ID | Gene Symbol | Gene Title |
|---|---|---|
| 1552286_at | ATP6V1E2 | ATPase, H+ transporting, lysosomal 31 kDa, V1 subunit E isoform 2 |
| 1552344_s_at | CNOT7 | CCR4-NOT transcription complex, subunit 7 |
| 1552787_at | HELB | helicase (DNA) B |
| 1553117_a_at | STK38 | serine/threonine kinase 38 |
| 1554934_at | RCBTB1 | regulator of chromosome condensation (RCC1) and BTB (POZ) domain containing protein 1 |
| 1555464_at | IFIH1 | interferon induced with helicase C domain 1 |
| 1556059_s_at | SPEN | spen homolog, transcriptional regulator (*Drosophila*) |
| 1556249_a_at | — | Hypothetical gene supported by AK057627; BC031275; BC045736 |
| 1557100_s_at | HECTD1 | HECT domain containing 1 |
| 1557193_at | PTPN2 | Protein tyrosine phosphatase, non-receptor type 2 |
| 1557400_at | — | CDNA FLJ38935 fis, clone NT2NE2014681 |
| 1557458_s_at | SHB | SHB (Src homology 2 domain containing) adaptor protein B |
| 1558014_s_at | MLSTD2 | male sterility domain containing 2 |
| 1558310_s_at | FLJ90723 | hypothetical protein FLJ90723 |
| 1558371_a_at | — | Hypothetical gene supported by AK127852 |
| 1559404_a_at | HMGN3 | High mobility group nucleosomal binding domain 3 |
| 1559881_s_at | ZNF12 | zinc finger protein 12 (KOX 3) |
| 1559957_a_at | — | *Homo sapiens*, clone IMAGE: 4157625, mRNA |
| 1560021_at | RPS20 | Ribosomal protein S20 |
| 1564212_at | — | CDNA FLJ40807 fis, clone TRACH2009268 |
| 1564238_a_at | WDR49 | WD repeat domain 49 |
| 1564474_at | — | Hypothetical LOC285711 |
| 1568639_a_at | LOC90246 | Hypothetical protein LOC90246 |
| 1569005_at | — | CDNA clone IMAGE: 4654330, partial cds |
| 1569106_s_at | FLJ10707 | hypothetical protein FLJ10707 |
| 1569189_at | MGC29649 | hypothetical protein MGC29649 |
| 1569240_at | LOC114977 | Hypothetical protein BC014148 |
| 1569277_at | ZNF91 | Zinc finger protein 91 (HPF7, HTF10) |
| 200755_s_at | CALU | calumenin |
| 201564_s_at | FSCN1 | fascin homolog 1, actin-bundling protein (*Strongylocentrotus purpuratus*) |
| 201799_s_at | OSBP | oxysterol binding protein |
| 201822_at | TIMM17A | translocase of inner mitochondrial membrane 17 homolog A (yeast) |
| 202003_s_at | ACAA2 | acetyl-Coenzyme A acyltransferase 2 (mitochondrial 3-oxoacyl-Coenzyme A thiolase) |
| 202111_at | SLC4A2 | solute carrier family 4, anion exchanger, member 2 (erythrocyte membrane protein band 3-like 1) |
| 202254_at | SIPA1L1 | Signal-induced proliferation-associated 1 like 1 |
| 202328_s_at | PKD1 | polycystic kidney disease 1 (autosomal dominant) |
| 202444_s_at | SPFH1 | SPFH domain family, member 1 |
| 202578_s_at | DDX19L | DEAD (Asp-Glu-Ala-As) box polypeptide 19-like |
| 202725_at | POLR2A | polymerase (RNA) II (DNA directed) polypeptide A, 220 kDa |
| 203015_s_at | SSX2IP | synovial sarcoma, X breakpoint 2 interacting protein |
| 203035_s_at | PIAS3 | protein inhibitor of activated STAT, 3 |
| 203254_s_at | TLN1 | talin 1 |
| 203329_at | PTPRM | protein tyrosine phosphatase, receptor type, M |
| 203417_at | MFAP2 | microfibrillar-associated protein 2 |
| 203756_at | ARHGEF17 | Rho guanine nucleotide exchange factor (GEF) 17 |
| 203767_s_at | STS | steroid sulfatase (microsomal), arylsulfatase C, isozyme S |
| 203853_s_at | GAB2 | GRB2-associated binding protein 2 |
| 204055_s_at | CTAGE5 | CTAGE family, member 5 |
| 204756_at | MAP2K5 | mitogen-activated protein kinase kinase 5 |
| 205018_s_at | MBNL2 | muscleblind-like 2 (*Drosophila*) |
| 205107_s_at | EFNA4 | ephrin-A4 |
| 205225_at | ESR1 | estrogen receptor 1 |
| 205248_at | C21orf5 | chromosome 21 open reading frame 5 |
| 205929_at | GPA33 | glycoprotein A33 (transmembrane) |
| 206060_s_at | PTPN22 | protein tyrosine phosphatase, non-receptor type 22 (lymphoid) |
| 206577_at | VIP | vasoactive intestinal peptide |
| 206618_at | IL18R1 | interleukin 18 receptor 1 |
| 206960_at | GPR23 | G protein-coupled receptor 23 |
| 207722_s_at | BTBD2 | BTB (POZ) domain containing 2 |
| 208159_x_at | DDX11 | DEAD/H (Asp-Glu-Ala-Asp/His) box polypeptide 11 (CHL1-like helicase homolog, *S. cerevisiae*) |
| 208934_s_at | LGALS8 | lectin, galactoside-binding, soluble, 8 (galectin 8) |
| 209163_at | CYB561 | cytochrome b-561 |
| 209499_x_at | TNFSF13 | tumor necrosis factor (ligand) superfamily, member 13 |
| 209582_s_at | CD200 | CD200 antigen |
| 210249_s_at | NCOA1 | nuclear receptor coactivator 1 |
| 210298_x_at | FHL1 | four and a half LIM domains 1 |
| 210543_s_at | PRKDC | protein kinase, DNA-activated, catalytic polypeptide |
| 210571_s_at | CMAH | cytidine monophosphate-N-acetylneuraminic acid hydroxylase (CMP-N-acetylneuraminate monooxygenase) |
| 210678_s_at | AGPAT2 | 1-acylglycerol-3-phosphate O-acyltransferase 2 (lysophosphatidic acid acyltransferase, beta) |
| 210720_s_at | APBA2BP | amyloid beta (A4) precursor protein-binding, family A, member 2 binding protein |
| 210733_at | — | — |
| 210811_s_at | DDX49 | DEAD (Asp-Glu-Ala-Asp) box polypeptide 49 |
| 211370_s_at | MAP2K5 | mitogen-activated protein kinase kinase 5 |
| 211593_s_at | MAST2 | microtubule associated serine/threonine kinase 2 |

TABLE 22-continued

Transcripts present (expressed) in all CD133+ samples but absent in CD34+ samples

| Probe Set ID | Gene Symbol | Gene Title |
| --- | --- | --- |
| 212065_s_at | USP34 | ubiquitin specific protease 34 |
| 212080_at | MLL | Myeloid/lymphoid or mixed-lineage leukemia (trithorax homolog, Drosophila) |
| 212186_at | ACACA | acetyl-Coenzyme A carboxylase alpha |
| 212235_at | PLXND1 | plexin D1 |
| 212385_at | TCF4 | Transcription factor 4 |
| 212667_at | SPARC | secreted protein, acidic, cysteine-rich (osteonectin) |
| 212755_at | — | — |
| 212957_s_at | LOC92249 | hypothetical protein LOC92249 |
| 213199_at | DKFZP586P0123 | DKFZP586P0123 protein |
| 213271_s_at | KIAA1117 | KIAA1117 |
| 213306_at | MPDZ | multiple PDZ domain protein |
| 213634_s_at | TRMT1 | tRNA (5-methylaminomethyl-2-thiouridylate)-methyltransferase 1 |
| 214558_at | GPR12 | G protein-coupled receptor 12 |
| 214748_at | LOC88523 | CG016 |
| 214761_at | ZNF423 | zinc finger protein 423 |
| 214976_at | RPL13 | ribosomal protein L13 |
| 215043_s_at | SMA3/SMA5 | SMA3/SMA5 |
| 215172_at | PTPN20 | protein tyrosine phosphatase, non-receptor type 20 |
| 215706_x_at | ZYX | zyxin |
| 217027_x_at | KPNB1 | karyopherin (importin) beta 1 |
| 217777_s_at | HSPC121 | butyrate-induced transcript 1 |
| 217881_s_at | CDC27 | cell division cycle 27 |
| 217935_s_at | C20orf44 | chromosome 20 open reading frame 44 |
| 218094_s_at | C20orf35 | chromosome 20 open reading frame 35 |
| 218325_s_at | DATF1 | death associated transcription factor 1 |
| 218494_s_at | SLC2A4RG | SLC2A4 regulator |
| 218498_s_at | ERO1L | ERO1-like (S. cerevisiae) |
| 218608_at | ATP13A2 | ATPase type 13A2 |
| 218664_at | CGI-63 | nuclear receptor binding factor 1 |
| 218868_at | ARP3BETA | actin-related protein 3-beta |
| 218903_s_at | MGC2731 | hypothetical protein MGC2731 |
| 218928_s_at | SLC37A1 | solute carrier family 37 (glycerol-3-phosphate transporter), member 1 |
| 218965_s_at | RBM21 | RNA binding motif protein 21 |
| 218971_s_at | HSPC049 | HSPC049 protein |
| 218992_at | C9orf46 | chromosome 9 open reading frame 46 |
| 219343_at | CDC37L1 | cell division cycle 37 homolog (S. cerevisiae)-like 1 |
| 219352_at | HERC6 | hect domain and RLD 6 |
| 219594_at | NINJ2 | ninjurin 2 |
| 220039_s_at | CDKAL1 | CDK5 regulatory subunit associated protein 1-like 1 |
| 220168_at | CASC1 | cancer susceptibility candidate 1 |
| 220183_s_at | NUDT6 | nudix (nucleoside diphosphate linked moiety X)-type motif 6 |
| 220305_at | MGC3260 | hypothetical protein MGC3260 |
| 220735_s_at | SENP7 | SUMO1/sentrin specific protease 7 |
| 220744_s_at | WDR10 | WD repeat domain 10 |
| 220885_s_at | CENPJ | centromere protein J |
| 220911_s_at | KIAA1305 | KIAA1305 |
| 221595_at | DKFZP564O0523 | hypothetical protein DKFZp564O0523 |
| 221894_at | ADCK2 | aarF domain containing kinase 2 |
| 221906_at | TXNRD3 | thioredoxin reductase 3 |
| 222250_s_at | DKFZP434B168 | DKFZP434B168 protein |
| 222801_s_at | FLJ13195 | hypothetical protein FLJ13195 similar to stromal antigen 3 |
| 223150_s_at | PTPN23 | protein tyrosine phosphatase, non-receptor type 23 |
| 223264_at | MESDC1 | mesoderm development candidate 1 |
| 223452_s_at | DKFZP564J0863 | DKFZP564J0863 protein |
| 223498_at | HCMOGT-1 | sperm antigen HCMOGT-1 |
| 223575_at | KIAA1549 | KIAA1549 protein |
| 223852_s_at | MGC4796 | Ser/Thr-like kinase |
| 223888_s_at | LARS | leucyl-tRNA synthetase |
| 224304_x_at | NIN | ninein (GSK3B interacting protein) |
| 224509_s_at | RTN4IP1 | reticulon 4 interacting protein 1 |
| 224745_x_at | DKFZp761A052 | hypothetical protein DKFZp761A052 |
| 224767_at | RPL37 | ribosomal protein L37 |
| 224931_at | SLC41A3 | solute carrier family 41, member 3 |
| 225009_at | CKLFSF4 | chemokine-like factor super family 4 |
| 225257_at | MGC20255 | hypothetical protein MGC20255 |
| 225286_at | ARSD | arylsulfatase D |
| 225329_at | LOC348262 | hypothetical protein LOC348262 |
| 225377_at | C9orf86 | chromosome 9 open reading frame 86 |
| 225529_at | CENTB5 | centaurin, beta 5 |
| 225577_at | HCG18 | HLA complex group 18 |
| 225615_at | LOC126917 | hypothetical protein LOC126917 |
| 225627_s_at | KIAA1573 | KIAA1573 protein |
| 225653_at | TGFBRAP1 | Transforming growth factor, beta receptor associated protein 1 |
| 225671_at | LOC124976 | hypothetical protein LOC124976 |
| 225930_at | NKIRAS1 | NFKB inhibitor interacting Ras-like 1 |
| 226082_s_at | SFRS15 | splicing factor, arginine/serine-rich 15 |

TABLE 22-continued

Transcripts present (expressed) in all CD133+ samples but absent in CD34+ samples

| Probe Set ID | Gene Symbol | Gene Title |
| --- | --- | --- |
| 226125_at | SLC9A3 | Solute carrier family 9 (sodium/hydrogen exchanger), isoform 3 |
| 226289_at | M11S1 | membrane component, chromosome 11, surface marker 1 |
| 226376_at | ZC3HDC5 | zinc finger CCCH type domain containing 5 |
| 226586_at | SAMD6 | sterile alpha motif domain containing 6 |
| 226793_at | LOC283267 | hypothetical protein LOC283267 |
| 226869_at | — | Full length insert cDNA clone ZD77F06 |
| 226872_at | RFX2 | regulatory factor X, 2 (influences HLA class II expression) |
| 227079_at | DHX8 | DEAH (Asp-Glu-Ala-His) box polypeptide 8 |
| 227159_at | LGP1 | homolog of mouse LGP1 |
| 227237_x_at | ATAD3B | ATPase family, AAA domain containing 3B |
| 227331_at | LOC283337 | Hypothetical protein LOC283337 |
| 227412_at | PPP1R3E | protein phosphatase 1, regulatory (inhibitor) subunit 3E |
| 227515_at | STAMBP | STAM binding protein |
| 227632_at | KIAA1171 | KIAA1171 protein |
| 227675_at | LRSAM1 | leucine rich repeat and sterile alpha motif containing 1 |
| 227822_at | ZNF605 | zinc finger protein 605 |
| 227854_at | FANCL | Fanconi anemia, complementation group L |
| 227859_at | RBJ | Ras-associated protein Rap1 |
| 227972_at | TOR2A | torsin family 2, member A |
| 228054_at | TMEM44 | transmembrane protein 44 |
| 228144_at | ZNF300 | zinc finger protein 300 |
| 228301_x_at | NDUFB10 | NADH dehydrogenase (ubiquinone) 1 beta subcomplex, 10, 22 kDa |
| 228346_at | — | Transcribed locus, moderately similar to NP_055301.1 neuronal thread protein AD7c-NTP [*Homo sapiens*] |
| 228358_at | SOX12 | SRY (sex determining region Y)-box 12 |
| 228913_at | — | LOC440135, *Homo sapiens*, clone IMAGE: 2900578, mRNA, partial cds |
| 229005_at | MCTP2 | Multiple C2-domains with two transmembrane regions 2 |
| 229251_s_at | TPCN2 | two pore segment channel 2 |
| 229444_at | — | — |
| 229506_at | — | CDNA clone IMAGE: 5263177, partial cds |
| 229509_at | MGC33302 | hypothetical protein MGC33302 |
| 229604_at | CMAH | Cytidine monophosphate-N-acetylneuraminic acid hydroxylase (CMP-N-acetylneuraminate monooxygenase) |
| 229876_at | PHKA1 | Phosphorylase kinase, alpha 1 (muscle) |
| 230093_at | TSGA2 | testis specific A2 homolog (mouse) |
| 230209_at | MGC11349 | Hypothetical protein MGC11349 |
| 230230_at | — | — |
| 230516_at | C7orf30 | Chromosome 7 open reading frame 30 |
| 230534_at | MGC15634 | hypothetical protein MGC15634 |
| 230543_at | — | Similar to Chloride intracellular channel protein 4 (Intracellular chloride ion channel protein p64H1) |
| 230571_at | TM4SF11 | Transmembrane 4 superfamily member 11 (plasmolipin) |
| 230968_at | — | Full-length cDNA clone CS0DF032YA11 of Fetal brain of *Homo sapiens* (human) |
| 231101_at | PPP2R5E | Protein phosphatase 2, regulatory subunit B (B56), epsilon isoform |
| 231489_x_at | — | Transcribed locus, weakly similar to NP_061913.2 elongation protein 4 homolog (*S. cerevisiae*) [*Homo sapiens*] |
| 231610_at | — | *Homo sapiens*, clone IMAGE: 5272626, mRNA |
| 231829_at | KIAA1271 | KIAA1271 protein |
| 232262_at | PIGL | phosphatidylinositol glycan, class L |
| 232553_at | PCYT1B | phosphate cytidylyltransferase 1, choline, beta isoform |
| 232921_at | LOC286025 | hypothetical protein LOC286025 |
| 233375_at | MGC12458 | Hypothetical protein MGC12458 |
| 233543_s_at | FLJ13614 | hypothetical protein FLJ13614 |
| 233787_at | C6orf163 | chromosome 6 open reading frame 163 |
| 234106_s_at | FLYWCH1 | FLYWCH-type zinc finger 1 |
| 234299_s_at | NIN | ninein (GSK3B interacting protein) |
| 235131_at | RHOJ | ras homolog gene family, member J |
| 235200_at | ZNF561 | Zinc finger protein 561 |
| 235259_at | MGC29898 | hypothetical protein MGC29898 |
| 235260_s_at | MGC29898 | hypothetical protein MGC29898 |
| 235318_at | — | Transcribed locus |
| 235359_at | LRRC33 | leucine rich repeat containing 33 |
| 235449_at | LRSAM1 | leucine rich repeat and sterile alpha motif containing 1 |
| 235581_at | — | Transcribed locus, weakly similar to NP_990417.1 ferritin H chain [*Gallus gallus*] |
| 235661_at | — | Transcribed locus |
| 235747_at | SLC25A16 | Solute carrier family 25 (mitochondrial carrier; Graves disease autoantigen), member 16 |
| 235888_at | — | Transcribed locus |
| 235974_at | SEC8L1 | SEC8-like 1 (*S. cerevisiae*) |
| 236032_at | DNM1L | Dynamin 1-like |
| 236358_at | — | — |
| 236476_at | VBP1 | Von Hippel-Lindau binding protein 1 |
| 236537_at | DRG1 | Developmentally regulated GTP binding protein 1 |
| 236641_at | KIF14 | Kinesin family member 14 |
| 237367_x_at | CFLAR | CASP8 and FADD-like apoptosis regulator |
| 237431_at | — | — |
| 237663_at | — | Transcribed locus |
| 237825_x_at | — | Transcribed locus |

TABLE 22-continued

Transcripts present (expressed) in all CD133+ samples but absent in CD34+ samples

| Probe Set ID | Gene Symbol | Gene Title |
|---|---|---|
| 238117_at | PPOX | protoporphyrinogen oxidase |
| 238459_x_at | SPATA6 | spermatogenesis associated 6 |
| 238550_at | RUFY2 | RUN and FYVE domain containing 2 |
| 238728_at | — | Transcribed locus, moderately similar to NP_055301.1 neuronal thread protein AD7c-NTP [*Homo sapiens*] |
| 238729_x_at | SAV1 | Salvador homolog 1 (*Drosophila*) |
| 238752_at | MRS2L | MRS2-like, magnesium homeostasis factor (*S. cerevisiae*) |
| 238882_at | SVIL | Supervillin |
| 238996_x_at | ALDOA | aldolase A, fructose-bisphosphate |
| 239080_at | UNQ9438 | TIMM9 |
| 239556_at | — | *Homo sapiens*, clone IMAGE: 5276804, mRNA |
| 239754_at | — | — |
| 239797_at | CEPT1 | Choline/ethanolamine phosphotransferase 1 |
| 239849_at | EMCN | Endomucin |
| 241399_at | FAM19A2 | family with sequence similarity 19 (chemokine (C-C motif)-like), member A2 |
| 242251_at | — | Transcribed locus |
| 242343_x_at | ZNF518 | Zinc finger protein 518 |
| 242851_at | KIAA1919 | KIAA1919 |
| 243264_s_at | FLJ11267 | hypothetical protein FLJ11267 |
| 243452_at | B4GALT6 | UDP-Gal:betaGlcNAc beta 1,4-galactosyltransferase, polypeptide 6 |
| 243619_at | FGFR1OP2 | FGFR1 oncogene partner 2 |
| 243948_at | EML5 | Echinoderm microtubule associated protein like 5 |
| 243964_at | SHPRH | SNF2 histone linker PHD RING helicase |
| 244761_at | — | Hypothetical gene supported by AK126569 |
| 244783_at | YAF2 | VY1 associated factor 2 |
| 37586_at | ZNF142 | zinc finger protein 142 (clone pHZ-49) |
| 40612_at | KIAA1117 | KIAA1117 |
| 45714_at | HCFC1R1 | host cell factor C1 regulator 1 (XPO1 dependant) |

TABLE 23

Frequency of different types of CFU colonies within CD34+, CD133+, Lin- and MNC populations.

| Cell type | CFU-GM | CFU-GEMM | BFU-E | CFU-E |
|---|---|---|---|---|
| CD34+ | 58.2% | 33.2% | 7.2% | 1.4% |
| CD133+ | 57.4% | 38.3% | 4.3% | 0.0% |
| MNC | 37.8% | 41.3% | 15.4% | 5.5% |

TABLE 24

Single column purification method, CD34+cell purity in fractions.

| Cell fraction | CD34 purity |
|---|---|
| MNC | 1% |
| CD34− | 0.34% |
| Wash 1-4 | 0.41% |
| Wash 5-6 | 1% |
| Wash 7-8 | 3% |
| CD34+ | 78% |

TABLE 25

Traditional two column purification method, CD34+cell purity in fractions.

| Cell fraction | CD34 purity |
|---|---|
| MNC | 0.79% |
| CD34−/1. column | 0.38% |
| Wash 1-2 | 0.32% |
| Wash 3-4 | 0.46% |
| Wash 5-6 | 0.51% |
| CD34+/1. column | 68% |
| CD34−/2. column | 19% |
| Wash 1-3 | 13% |
| CD34+/2. column | 77% |

TABLE 26

The genes representing the most significant biological processes in CD133+ cells.

| Symbol | Name | Unigene ID |
|---|---|---|
| Signal transduction | | |
| DPYSL3 | Dihydropyrimidinase-like 3 | 519659 |
| ALCAM | Activated leukocyte cell adhesion molecule | 150693 |
| SOCS2 | Suppressor of cytokine signaling 2 | 485572 |
| PLCB4 | Phospholipase C, beta 4 | 472101 |
| RBM14 | RNA binding motif protein 14 | 11170 |

TABLE 26-continued

The genes representing the most significant biological processes in CD133+ cells.

| Symbol | Name | Unigene ID |
|---|---|---|
| TGFBRAP1 | Transforming growth factor, beta receptor associated protein 1 | 446350 |
| CRHBP | Corticotropin releasing hormone binding protein | 115617 |
| ITGA9 | Integrin, alpha 9 | 113157 |
| HRMT1L2 | HMT1 hnRNP methyltransferase-like 2 (*S. cerevisiae*) | 20521 |
| FLT3 | Fms-related tyrosine kinase 3 | 507590 |
| PDE1A | Phosphodiesterase 1A, calmodulin-dependent | 416061 |
| DDAH1 | Dimethylarginine dimethylaminohydrolase 1 | 379858 |
| GPR125 | G protein-coupled receptor 125 | 99195 |
| AKT3 | V-akt murine thymoma viral oncogene homolog 3 (protein kinase B, gamma) | 498292 |
| RHOBTB1 | Rho-related BTB domain containing 1 | 148670 |
| PTPRD | Protein tyrosine phosphatase, receptor type, D | 446083 |
| TCF7L2 | Transcription factor 7-like 2 (T-cell specific, HMG-box) | 501080 |
| MAP3K4 | Mitogen-activated protein kinase kinase kinase 4 | 390428 |
| ITPR1 | Inositol 1,4,5-triphosphate receptor, type 1 | 374613 |
| TNFRSF21 | Tumor necrosis factor receptor superfamily, member 21 | 443577 |
| CYTL1 | Cytokine-like 1 | 13872 |
| PILRB | Paired immunoglobin-like type 2 receptor beta | 530084 |
| LRP6 | Low density lipoprotein receptor-related protein 6 | 210343 |
| C12orf2 | Chromosome 12 open reading frame 2 | 269941 |
| MAGI1 | Membrane associated guanylate kinase interacting protein-like 1 | 16064 |
| SOCS6 | Suppressor of cytokine signaling 6 | 44439 |
| DST | Dystonin | 485616 |
| ERG | V-ets erythroblastosis virus E26 oncogene like (avian) | 473819 |
| DNA metabolism | | |
| POLD2 | Polymerase (DNA directed), delta 2, regulatory subunit 50 kDa | 306791 |
| RUVBL2 | RuvB-like 2 (*E. coli*) | 515846 |
| MCM5 | MCM5 minichromosome maintenance deficient 5, cell division cycle 46 (*S. cerevisiae*) | 517582 |
| BAT8 | HLA-B associated transcript 8 | 520038 |
| SMARCA1 | SWI/SNF related, matrix associated, actin dependent regulator of chromatin, subfamily a, member 1 | 152292 |
| POLA | Polymerase (DNA directed), alpha | 495880 |
| RAD52 | RAD52 homolog (*S. cerevisiae*) | 525220 |
| ATR | Ataxia telangiectasia and Rad3 related | 271791 |
| MSH5 | MutS homolog 5 (*E. coli*) | 371225 |
| MCM7 | MCM7 minichromosome maintenance deficient 7 (*S. cerevisiae*) | 438720 |
| CBX5 | Chromobox homolog 5 (HP1 alpha homolog, *Drosophila*) | 349283 |
| SMARCAL1 | SWI/SNF related, matrix associated, actin dependent regulator of chromatin, subfamily a-like 1 | 516674 |
| DNMT3A | DNA (cytosine-5-)-methyltransferase 3 alpha | 515840 |
| CBX2 | Chromobox homolog 2 (Pc class homolog, *Drosophila*) | 368410 |
| Responce to stimulus | | |
| HSPCB | Heat shock 90 kDa protein 1, beta | 509736 |
| CHML | Choroideremia-like (Rab escort protein 2) | 170129 |
| SERPING1 | Seine (or cysteine) proteinase inhibitor, clade G (C1 inhibitor), member 1, (angioedema, hereditary) | 384598 |
| SEPP1 | Selenoprotein P, plasma, 1 | 275775 |
| HSPB1 | Heat shock 27 kDa protein 1 | 520973 |
| TCEA2 | Transcription elongation factor A (SII), 2 | 505004 |
| IGLL1 | Immunoglobulin lambda-like polypeptide 1 | 348935 |
| D2S448 | Melanoma associated gene | 332197 |
| Cell proliferation | | |
| AREG | Amphiregulin (schwannoma-derived growth factor) | 270833 |
| IGFBP7 | Insulin-like growth factor binding protein 7 | 479808 |
| EMP1 | Epithelial membrane protein 1 | 436298 |
| STAG1 | Stromal antigen 1 | 412586 |
| PAWR | PRKC, apoptosis, WT1, regulator | 406074 |
| LDOC1 | Leucine zipper, down-regulated in cancer 1 | 45231 |
| MPHOSPH9 | M-phase phosphoprotein 9 | 507175 |
| NDN | Necdin homolog (mouse) | 50130 |
| DKC1 | Dyskeratosis congenita 1, dyskerin | 4747 |
| SKB1 | SKB1 homolog (*S. pombe*) | 367854 |
| CCNL2 | Cyclin L2 | 515704 |
| ANAPC7 | Anaphase promoting complex subunit 7 | 529280 |
| CDK6 | Cyclin-dependent kinase 6 | 119882 |
| Transport | | |
| NUP93 | Nucleoporin 93 kDa | 276878 |
| SV2A | Synaptic vesicle glycoprotein 2A | 516153 |
| CPT1A | Carnitine palmitoyltransferase 1A (liver) | 503043 |
| ICA1 | Islet cell autoantigen 1, 69 kDa | 487561 |
| KPNB1 | Karyopherin (importin) beta 1 | 532793 |
| OSBPL1A | Oxysterol binding protein-like 1A | 370725 |
| ATP9A | ATPase, Class II, type 9A | 368002 |

TABLE 26-continued

The genes representing the most significant biological processes in CD133+ cells.

| Symbol | Name | Unigene ID |
|---|---|---|
| COL5A1 | Collagen, type V, alpha 1 | 210283 |
| FLVCR | Feline leukemia virus subgroup C cellular receptor | 7055 |
| SYTL4 | Synaptotagmin-like 4 (granuphilin-a) | 522054 |
| SFXN1 | Sideroflexin 1 | 369440 |
| SLC25A27 | Solute carrier family 25, member 27 | 40510 |
| SLC16A14 | Solute carrier family 16 (monocarboxylic acid transporters), member 14 | 504317 |
| UNQ9438 | TIMM9 | 534663 |
| MIPEP | Mitochondrial intermediate peptidase | 507498 |
| | Development | |
| MAP7 | Microtubule-associated protein 7 | 486548 |
| HLF | Hepatic leukemia factor | 196952 |
| ADAM28 | A disintegrin and metalloproteinase domain 28 | 528304 |
| WHSC1 | Wolf-Hirschhorn syndrome candidate 1 | 113876 |
| HOXA9 | Homeo box A9 | 127428 |
| TRO | Trophinin | 434971 |
| HOXA10 | Homeo box A10 | 110637 |
| GCNT2 | Glucosaminyl (N-acetyl) transferase 2, I-branching enzyme | 519884 |
| LMO2 | LIM domain only 2 (rhombotin-like 1) | 34560 |

REFERENCES

Harvey, D. J., et al. (1993) *Rapid Commun. Mass Spectrom.* 7(7):614-9

Nyman, T. A., et al. (1998) *Eur. J. Biochem.* 253(2):485-93

Papac, D., et al. (1996) *Anal. Chem.* 68(18):3215-23

Saarinen, J., et al. (1999) *Eur. J. Biochem.* 259(3):829-40

References for mRNA Analysis Examples:

1. Bielorai B, Trakhtenbrot L, Amariglio N et al. Multilineage hematopoietic engraftment after allogeneic peripheral blood stem cell transplantation without conditioning in SCID patients. Bone Marrow Transplant. 2004; 34:317-320.
2. Saccardi R, Tyndall A, Coghlan G et al. Consensus statement concerning cardiotoxicity occurring during haematopoietic stem cell transplantation in the treatment of autoimmune diseases, with special reference to systemic sclerosis and multiple sclerosis. Bone Marrow Transplant. 2004; 34:877-881.
3. Grigull L, Beilken A, Schrappe M et al. Transplantation of allogeneic CD34-selected stem cells after fludarabine-based conditioning regimen for children with mucopolysaccharidosis 1H (M. Hurler). Bone Marrow Transplant. 2005; 35:265-269.
4. Lang P, Handgretinger R, Niethammer D et al. Transplantation of highly purified CD34+ progenitor cells from unrelated donors in pediatric leukemia. Blood. 2003; 101:1630-1636.
5. Handgretinger R, Klingebiel T, Lang P, Gordon P, Niethammer D. Megadose transplantation of highly purified haploidentical stem cells: current results and future prospects. Pediatr Transplant. 2003; 7 Suppl 3:51-5.:51-55.
6. Migliaccio A R, Adamson J W, Stevens C E et al. Cell dose and speed of engraftment in placental/umbilical cord blood transplantation: graft progenitor cell content is a better predictor than nucleated cell quantity. Blood. 2000; 96:2717-2722.
7. Ng Y Y, van Kessel B, Lokhorst H M et al. Gene-expression profiling of CD34+ cells from various hematopoietic stem-cell sources reveals functional differences in stem-cell activity. J Leukoc Biol. 2004; 75:314-323.
8. Georgantas R W, III, Tanadve V, Malehorn M et al. Microarray and serial analysis of gene expression analyses identify known and novel transcripts overexpressed in hematopoietic stem cells. Cancer Res. 2004; 64:4434-4441.
9. Steidl U, Kronenwett R, Rohr U P et al. Gene expression profiling identifies significant differences between the molecular phenotypes of bone marrow-derived and circulating human CD34+ hematopoietic stem cells. Blood. 2002; 99:2037-2044.
10. Traggiai E, Chicha L, Mazzucchelli L et al. Development of a human adaptive immune system in cord blood cell-transplanted mice. Science. 2004; 304:104-107.
11. de Wynter E A, Emmerson A J, Testa N G. Properties of peripheral blood and cord blood stem cells. Baillieres Best Pract Res Clin Haematol. 1999; 12:1-17.
12. Gallacher L, Murdoch B, Wu D M et al. Isolation and characterization of human CD34(−)Lin(−) and CD34(+)Lin(−) hematopoietic stem cells using cell surface markers AC133 and CD7. Blood. 2000; 95:2813-2820.
13. Hilbe W, Dirnhofer S, Oberwasserlechner F et al. CD133 positive endothelial progenitor cells contribute to the tumour vasculature in non-small cell lung cancer. J Clin Pathol. 2004; 57:965-969.
14. Richardson G D, Robson C N, Lang S H et al. CD133, a novel marker for human prostatic epithelial stem cells. J Cell Sci. 2004; 117:3539-3545.
15. Singh S K, Hawkins C, Clarke I D et al. Identification of human brain tumour initiating cells. Nature. 2004; 432:396-401.
16. Baal N, Reisinger K, Jahr H et al. Expression of transcription factor Oct-4 and other embryonic genes in CD133 positive cells from human umbilical cord blood. Thromb Haemost. 2004; 92:767-775.
17. Eisen M B, Spellman P T, Brown P O, Botstein D. Cluster analysis and display of genome-wide expression patterns. Proc Natl Acad Sci USA. 1998; 95:14863-14868.
18. Kohonen, T. Self-organizing maps. 3rd edn. 2001. Springer.
19. Hautaniemi S, Yli-Harja O, Astola J et al. Analysis and visualization of gene expression microarray data in human cancer using self-organizing maps. Machine Learning. 2003; 52:45-66.
20. Vesanto, J., Himberg, J., Alhoniemi, E., and Parhankangas, J. SOM toolbox for Matlab 5. Technical Report A57. 2000. Finland, Helsinki University of Technology.

21. Kauraniemi P, Hautaniemi S, Autio R et al. Effects of Herceptin treatment on global gene expression patterns in HER2-amplified and nonamplified breast cancer cell lines. Oncogene. 2004; 23:1010-1013.
22. Golub T R, Slonim D K, Tamayo P et al. Molecular classification of cancer: class discovery and class prediction by gene expression monitoring. Science. 1999; 286: 531-537.
23. Grskovic B, Ruzicka K, Karimi A, Qujeq D, Muller M M. Cell cycle analysis of the CD133+ and CD133− cells isolated from umbilical cord blood. Clin Chim Acta. 2004; 343:173-178.
24. Okuda T, Hirai H, Valentine V A et al. Molecular cloning, expression pattern, and chromosomal localization of human CDKN2D/INK4d, an inhibitor of cyclin D-dependent kinases. Genomics. 1995; 29:623-630.
25. Hershko A, Ganoth D, Pehrson J, Palazzo R E, Cohen L H. Methylated ubiquitin inhibits cyclin degradation in clam embryo extracts. J Biol Chem. 1991; 266:16376-16379.
26. Ivanova N B, Dimos J T, Schaniel C et al. A stem cell molecular signature. Science. 2002; 298:601-604.
27. Baldus C D, Tanner S M, Kusewitt D F et al. BAALC, a novel marker of human hematopoietic progenitor cells. Exp Hematol. 2003; 31:1051-1056.
28. Tanner S M, Austin J L, Leone G et al. BAALC, the human member of a novel mammalian neuroectoderm gene lineage, is implicated in hematopoiesis and acute leukemia. Proc Natl Acad Sci USA. 2001; %20; 98:13901-13906.
29. Liu X, Rapp N, Deans R, Cheng L. Molecular cloning and chromosomal mapping of a candidate cytokine gene selectively expressed in human CD34+ cells. Genomics. 2000; 65:283-292.
30. Wagner W, Ansorge A, Wirkner U et al. Molecular evidence for stem cell function of the slow-dividing fraction among human hematopoietic progenitor cells by genome-wide analysis. Blood. 2004; 104:675-686.
31. Zhou G, Chen J, Lee S et al. The pattern of gene expression in human CD34(+) stem/progenitor cells. Proc Natl Acad Sci USA. 2001; %20; 98:13966-13971.
32. Shojaei F, Gallacher L, Bhatia M. Differential gene expression of human stem progenitor cells derived from early stages of in utero human hematopoiesis. Blood. 2004; 103:2530-2540.
33. Akashi K, He X, Chen J et al. Transcriptional accessibility for genes of multiple tissues and hematopoietic lineages is hierarchically controlled during early hematopoiesis. Blood. 2003; 101:383-389.
34. Ramalho-Santos M, Yoon S, Matsuzaki Y, Mulligan R C, Melton D A. "Stemness": transcriptional profiling of embryonic and adult stem cells. Science. 2002; 298:597-600.
35. Terskikh A V, Miyamoto T, Chang C, Diatchenko L, Weissman I L. Gene expression analysis of purified hematopoietic stem cells and committed progenitors. Blood. 2003; 102:94-101.
36. Rockett J C, Patrizio P, Schmid J E, Hecht N B, Dix D J. Gene expression patterns associated with infertility in humans and rodent models. Mutat Res. 2004; 549:225-240.
37. Fargeas C A, Joester A, Missol-Kolka E et al. Identification of novel Prominin-1/CD133 splice variants with alternative C-termini and their expression in epididymis and testis. J Cell Sci. 2004; 117:4301-4311.
38. Summers Y J, Heyworth C M, de Wynter E A et al. AC133+ G0 cells from cord blood show a high incidence of long-term culture-initiating cells and a capacity for more than 100 million-fold amplification of colony-forming cells in vitro. Stem Cells. 2004; 22:704-715.
39. Rocha V, Wagner J E, Jr., Sobocinski K A et al. Graft-versus-host disease in children who have received a cord-blood or bone marrow transplant from an HLA-identical sibling. Eurocord and International Bone Marrow Transplant Registry Working Committee on Alternative Donor and Stem Cell Sources. N Engl J. Med. 2000; 342:1846-1854.
40. Peled A, Kollet O, Ponomaryov T et al. The chemokine SDF-1 activates the integrins LFA-1, VLA-4, and VLA-5 on immature human CD34(+) cells: role in transendothelial/stromal migration and engraftment of NOD/SCID mice. Blood. 2000; 95:3289-3296.
41. Frassoni F, Podesta M, Maccario R et al. Cord blood transplantation provides better reconstitution of hematopoietic reservoir compared with bone marrow transplantation. Blood. 2003; 102:1138-1141.
42. Abeyta M J, Clark A T, Rodriguez R T et al. Unique gene expression signatures of independently-derived human embryonic stem cell lines. Hum Mol Genet. 2004; 13:601-608.
43. Liu X R, Zhou R L, Zhang Q Y et al. Structure analysis and expressions of a novel tetratransmembrane protein, lysosoma-associated protein transmembrane 4 beta associated with hepatocellular carcinoma. World J. Gastroenterol. 2004; 10:1555-1559.
44. Bhattacharya B, Miura T, Brandenberger R et al. Gene expression in human embryonic stem cell lines: unique molecular signature. Blood. 2004; 103:2956-2964.
45. Richards M, Tan S P, Tan J H, Chan W K, Bongso A. The transcriptome profile of human embryonic stem cells as defined by SAGE. Stem Cells. 2004; 22:51-64.
46. Sperger J M, Chen X, Draper J S et al. Gene expression patterns in human embryonic stem cells and human pluripotent germ cell tumors. Proc Natl Acad Sci USA. 2003; 100:13350-13355.
47. Sato N, Sanjuan I M, Heke M et al. Molecular signature of human embryonic stem cells and its comparison with the mouse. Dev Biol. 2003; 260:404-413.
48. Tanaka T S, Kunath T, Kimber W L et al. Gene expression profiling of embryo-derived stem cells reveals candidate genes associated with pluripotency and lineage specificity. Genome Res. 2002; 12:1921-1928.
49. Okano M, Xie S, Li E. Cloning and characterization of a family of novel mammalian DNA (cytosine-5) methyltransferases. Nat Genet. 1998; 19:219-220.
50. Bortvin A, Eggan K, Skaletsky H et al. Incomplete reactivation of Oct4-related genes in mouse embryos cloned from somatic nuclei. Development. 2003; 130:1673-1680.

References for Cell Purification Method:
51. Bhattacharya A, Slatter M A, Chapman C E, Barge D, Jackson A, Flood T J et al.: Single centre experience of umbilical cord stem cell transplantation for primary immunodeficiency. *Bone Marrow Transplant* 2005, 36: 295-299.
52. Peters C, Steward C G: Hematopoietic cell transplantation for inherited metabolic diseases: an overview of outcomes and practice guidelines. *Bone Marrow Transplant* 2003, 31: 229-239.
53. Grewal S S, Barker J N, Davies S M, Wagner J E: Unrelated donor hematopoietic cell transplantation: marrow or umbilical cord blood? *Blood* 2003, 101: 4233-4244.
54. Broxmeyer H E, Douglas G W, Hangoc G, Cooper S, Bard J, English D et al.: Human umbilical cord blood as a potential source of transplantable hematopoietic stem/progenitor cells. *Proc Natl Acad Sci USA* 1989, 86: 3828-3832.

55. Broxmeyer H E, Hangoc G, Cooper S, Ribeiro R C, Graves V, Yoder M et al.: Growth characteristics and expansion of human umbilical cord blood and estimation of its potential for transplantation in adults. *Proc Natl Acad Sci USA* 1992, 89: 4109-4113.
56. Hao Q L, Shah A J, Thiemann F T, Smogorzewska E M, Crooks G M: A functional comparison of CD34+CD38− cells in cord blood and bone marrow. *Blood* 1995, 86: 3745-3753.
57. Vormoor J, Lapidot T, Pflumio F, Risdon G, Patterson B, Broxmeyer H E et al.: Immature human cord blood progenitors engraft and proliferate to high levels in severe combined immunodeficient mice. *Blood* 1994, 83: 2489-2497.
58. Hogan C J, Shpall E J, McNulty O, McNiece I, Dick J E, Shultz L D et al.: Engraftment and development of human CD34(+)-enriched cells from umbilical cord blood in NOD/LtSz-scid/scid mice. *Blood* 1997, 90: 85-96.
59. Tondreau T, Meuleman N, Delforge A, Dejeneffe M, Leroy R, Massy M et al.: Mesenchymal Stem Cells Derived from CD133-Positive Cells in Mobilized Peripheral Blood and Cord Blood: Proliferation, Oct4 Expression, and Plasticity. *Stem Cells* 2005, 23: 1105-1112.
60. Yang C, Zhang Z H, Li Z J, Yang R C, Qian G Q, Han Z C: Enhancement of neovascularization with cord blood CD133+ cell-derived endothelial progenitor cell transplantation. *Thromb Haemost* 2004, 91: 1202-1212.
61. Aroviita P, Teramo K, Hiilesmaa V, Kekomaki R: Cord blood hematopoietic progenitor cell concentration and infant sex. *Transfusion* 2005, 45: 613-621.
62. Yin A H, Miraglia S, Zanjani E D, Almeida-Porada G, Ogawa M, Leary A G et al.: AC133, a novel marker for human hematopoietic stem and progenitor cells. *Blood* 1997, 90: 5002-5012.
63. Pasino M, Lanza T, Marotta F, Scarso L, De Biasio P, Amato S et al.: Flow cytometric and functional characterization of AC133+ cells from human umbilical cord blood. *Br J Haematol* 2000, 108: 793-800.
64. Lang P, Bader P, Schumm M, Feuchtinger T, Einsele H, Fuhrer M et al.: Transplantation of a combination of CD133+ and CD34+ selected progenitor cells from alternative donors. *Br J Haematol* 2004, 124: 72-79.
67. Belvedere O, Feruglio C, Malangone W, Bonora M L, Donini A, Dorotea L et al.: Phenotypic characterization of immunomagnetically purified umbilical cord blood CD34+ cells. *Blood Cells Mol Dis* 1999, 25: 140-145.
68. Melnik K, Nakamura M, Comella K, Lasky L C, Zborowski M, Chalmers J J: Evaluation of eluents from separations of CD34+ cells from human cord blood using a commercial, immunomagnetic cell separation system. *Biotechnol Prog* 2001, 17: 907-916.
69. Aroviita P, Teramo K, Westman P, Hiilesmaa V, Kekomaki R: Associations among nucleated cell, CD34+ cell and colony-forming cell contents in cord blood units obtained through a standardized banking process. *Vox Sang* 2003, 84: 219-227.
70. Almici C, Carlo-Stella C, Wagner J E, Mangoni L, Garau D, Re A et al.: Clonogenic capacity and ex vivo expansion potential of umbilical cord blood progenitor cells are not impaired by cryopreservation. *Bone Marrow Transplant* 1997, 19: 1079-1084.
71. Jaatinen T, Hemmoranta H, Hautaniemi S, Niemi J, Nicorici D, Laine J et al.: Global gene expression profile of human cord blood-derived CD133+ cells. Stem Cells, published online Oct. 6, 2005: doi: 10.1634/stemcells.2005-0185.
72. Tada J, Omine M, Suda T, Yamaguchi N: A common signaling pathway via Syk and Lyn tyrosine kinases generated from capping of the sialomucins CD34 and CD43 in immature hematopoietic cells. *Blood* 1999, 93: 3723-3735.

We claim:
1. A method for purification of a cell population from a sample containing multiple cell populations, comprising the following sequential steps:
   a) contacting a sample with a cell-type-specific binding reagent linked to a polyvalent matrix by mixing said reagent with the sample so that a complex of said binding reagent and a cell population of interest forms;
   b) immobilizing the complex obtained from step a);
   c) removing the material that is not immobilized;
   d) releasing the immobilized complex;
   e) contacting the sample obtained from step d) with an additional amount of the specific binding reagent linked to a polyvalent matrix by mixing the additional amount of binding reagent with said sample;
   f) immobilizing the complex obtained from step e);
   g) removing the material that is not immobilized;
   h) releasing the immobilized complex; and
   i) recovering a cell population bound to the binding reagent.
2. The method according to claim 1, wherein said polyvalent matrix is selected from the group consisting of: a solid phase, a solid phase which comprises magnetic material, and a solid phase which comprises a magnetic bead, and said magnetic bead is applied to a magnetic field.
3. The method according to claim 1, wherein the cell population of step i) is recovered as a complex of the binding reagent and the cell population, and said cell population is released from the binding reagent.
4. The method according to claim 1, wherein the binding reagent is a monoclonal antibody.
5. The method according to claim 1, wherein the cells in said sample are labeled with a marker and the binding reagent is a labeled antibody applicable for an immunoassay or FACS analysis.
6. The method according to claim 1, wherein the washing in steps c) and g) involve up to 1-5 washing steps.
7. The method according to claim 1, wherein the cell population is a stem cell population.
8. The method according to claim 1, wherein said cord blood cell population contains CD34 or CD133 antigen.
9. The method according to claim 8 further comprising the step of profiling the obtained cell population by detecting the presence or absence of at least one mRNA marker listed in Table 1, 2, 4-15, 17, 18, 20, 22, or 26 in said cell population.
10. The method according to claim 8 further comprising the step of detecting expression of sialyltransferase ST3Ga1VI and amount of α3-linked sialic acids on N-glycans in said cell population.
11. A purified cord blood cell population containing CD34 antigen obtained by the method according to claim 8, wherein said cells are CD34+ cells with a purity of at least 90% as assessed by flow cytometry and wherein said sample of cells comprises above 5% CD34+ dim cells as observable by flow cytometry.
12. The purified cord blood cell population according to claim 11, wherein the cells show expression of at least one mRNA marker listed in Table 17 or 19.
13. The purified cord blood cell population according to claim 11, wherein total CFU count for the CD34+ cells is about 80/1000 cells.
14. The method of claim 1, wherein the cell population is a cord blood cell population.

\* \* \* \* \*